US012054495B2

(12) United States Patent
Pennington et al.

(10) Patent No.: US 12,054,495 B2
(45) Date of Patent: *Aug. 6, 2024

(54) SUBSTITUTED MACROCYCLIC COMPOUNDS AND RELATED METHODS OF TREATMENT

(71) Applicant: Alkermes, Inc., Waltham, MA (US)

(72) Inventors: Lewis D. Pennington, Arlington, MA (US); Younggi Choi, Stow, MA (US); Hoan Huynh, Waltham, MA (US); Brian M. Aquila, Marlborough, MA (US); Ingo Andreas Mugge, Waltham, MA (US); Yuan Hu, Waltham, MA (US); James R. Woods, Waltham, MA (US); Roman A. Valiulin, Cambridge, MA (US); Brian Kenneth Raymer, Holliston, MA (US); Jörg Martin Bentzien, White Plains, NY (US); Michael R. Hale, Bedford, MA (US); Jonathan Ward Lehmann, Burlington, MA (US); Daljit Matharu, Lexington, MA (US); Srinivasa Karra, Pembroke, MA (US)

(73) Assignee: Alkermes, Inc., Waltham, MA (US)

( * ) Notice: Subject to any disclaimer, the term of this patent is extended or adjusted under 35 U.S.C. 154(b) by 35 days.

This patent is subject to a terminal disclaimer.

(21) Appl. No.: 17/991,899

(22) Filed: Nov. 22, 2022

(65) Prior Publication Data

US 2023/0339969 A1   Oct. 26, 2023

Related U.S. Application Data

(63) Continuation of application No. 17/104,993, filed on Nov. 25, 2020, now Pat. No. 11,542,276.

(60) Provisional application No. 63/030,979, filed on May 28, 2020, provisional application No. 62/939,825, filed on Nov. 25, 2019.

(51) Int. Cl.
| | | |
|---|---|---|
| C07D 498/04 | (2006.01) |
| A61K 31/395 | (2006.01) |
| A61P 25/26 | (2006.01) |
| A61P 43/00 | (2006.01) |
| C07D 498/08 | (2006.01) |
| C07D 498/14 | (2006.01) |
| C07D 498/18 | (2006.01) |
| C07D 498/22 | (2006.01) |

(52) U.S. Cl.
CPC ............ *C07D 498/08* (2013.01); *A61P 25/26* (2018.01); *C07D 498/18* (2013.01); *C07D 498/22* (2013.01); *C07B 2200/05* (2013.01)

(58) Field of Classification Search
CPC .. C07D 498/04; C07D 498/08; C07D 498/14; C07D 498/18; C07D 498/22; C07B 2200/05; A61K 31/395; A61P 25/26; A61P 43/00
See application file for complete search history.

(56) References Cited

U.S. PATENT DOCUMENTS

| | | |
|---|---|---|
| 5,635,599 A | 6/1997 | Pastan et al. |
| 6,428,985 B1 | 8/2002 | Bromberg et al. |
| 6,492,492 B1 | 12/2002 | Stayton et al. |
| 6,808,902 B1 | 10/2004 | Treuheit et al. |
| 7,211,253 B1 | 5/2007 | Way |
| 7,271,149 B2 | 9/2007 | Glaesner et al. |
| 7,696,322 B2 | 4/2010 | Bleck et al. |
| 7,829,679 B2 | 11/2010 | Ushida et al. |
| 7,928,074 B2 | 4/2011 | Khare |
| 8,063,182 B1 | 11/2011 | Brockhaus et al. |
| 8,163,522 B1 | 4/2012 | Brockhaus et al. |
| 8,258,163 B2 | 9/2012 | Yanagisawa et al. |
| 8,765,669 B2 | 7/2014 | Kajihara et al. |
| 8,933,197 B2 | 1/2015 | Stemmer et al. |
| 9,527,807 B2 | 12/2016 | Fukumoto et al. |
| 9,611,262 B2 | 4/2017 | Shireman et al. |
| 9,815,787 B2 | 11/2017 | Nagase et al. |
| 10,017,481 B2 | 7/2018 | Obrecht et al. |
| 10,287,305 B2 | 5/2019 | Fujimoto et al. |
| 10,351,522 B2 | 7/2019 | Nagase et al. |
| 10,428,023 B2 | 10/2019 | Kajita et al. |
| 10,508,083 B2 | 12/2019 | Fujimoto et al. |
| 10,584,097 B2 | 3/2020 | Kajita et al. |
| 10,898,737 B2 | 1/2021 | Fujimoto et al. |
| 11,479,552 B2 | 10/2022 | Yoshida et al. |
| 2002/0127227 A1 | 9/2002 | Holmes et al. |
| 2002/0159969 A1 | 10/2002 | Agrawal et al. |
| 2003/0073822 A1 | 4/2003 | Lofling et al. |

(Continued)

FOREIGN PATENT DOCUMENTS

| | | |
|---|---|---|
| CN | 101962413 A | 2/2011 |
| EP | 2836485 B1 | 1/2018 |

(Continued)

OTHER PUBLICATIONS

Cox, C. D., et al., "Conformational analysis of N,N-disubstituted-1,4-diazepane orexin receptor antagonists and implications for receptor binding", Bioorganic & Medicinal Chemistry Letters, 19(11)DOI:10. 1016/J.BMCL.2009. 04.026, 2009, 2997-3001.

Irukayama-Tomobe, Y. , et al., "Nonpeptide orexin type-2 receptor agonist ameliorates narcolepsy-cataplexy symptoms in mouse models", PNAS, 2017, vol. 114, No. 22, 5731-5736.

McGaughey, G. , et al., "Shaping suvorexant: application of experimental and theoretical methods for driving synthetic designs", J. Comput. Aided Mol. Des., 2014, 28, 5-12.

(Continued)

*Primary Examiner* — Brenda L Coleman

(74) *Attorney, Agent, or Firm* — Elmore Patent Law Group, P.C.; Joseph C. Zucchero; Carolyn S. Elmore

(57) ABSTRACT

The present invention provides compounds useful for the treatment of narcolepsy or cataplexy in a subject in need thereof. Related pharmaceutical compositions and methods are also provided herein.

51 Claims, No Drawings

(56) References Cited

U.S. PATENT DOCUMENTS

| | | |
|---|---|---|
| 2003/0229226 A1 | 12/2003 | Okamoto et al. |
| 2004/0137580 A1 | 7/2004 | Holgersson et al. |
| 2005/0069552 A1 | 3/2005 | Bleck et al. |
| 2005/0260222 A1 | 11/2005 | Gupta et al. |
| 2005/0265995 A1 | 12/2005 | Tomlinson et al. |
| 2006/0110429 A1 | 5/2006 | Reiff et al. |
| 2007/0105767 A1 | 5/2007 | Kharbanda et al. |
| 2008/0045493 A1 | 2/2008 | Drescher et al. |
| 2008/0286211 A1 | 11/2008 | Barker et al. |
| 2009/0054489 A1 | 2/2009 | Hauske |
| 2010/0016547 A1 | 1/2010 | Ito et al. |
| 2010/0227394 A1 | 9/2010 | Bleck et al. |
| 2010/0285014 A1 | 11/2010 | Cox et al. |
| 2013/0217864 A1 | 8/2013 | Cho et al. |
| 2013/0295084 A1 | 11/2013 | Hunter et al. |
| 2013/0316404 A1 | 11/2013 | Roers et al. |
| 2013/0336925 A1 | 12/2013 | Alvarez et al. |
| 2014/0024650 A1 | 1/2014 | Fukumoto et al. |
| 2014/0056895 A1 | 2/2014 | Baurin et al. |
| 2014/0072581 A1 | 3/2014 | Dixit et al. |
| 2014/0234962 A1 | 8/2014 | Alvarez et al. |
| 2015/0071948 A1 | 3/2015 | Lazar et al. |
| 2016/0068583 A1 | 3/2016 | McCauley et al. |
| 2016/0175458 A1 | 6/2016 | Alvarez et al. |
| 2017/0226137 A1 | 8/2017 | Fujimoto et al. |
| 2017/0233447 A1 | 8/2017 | Qin |
| 2018/0179151 A1 | 6/2018 | Nagase et al. |
| 2018/0289825 A1 | 10/2018 | Alvarez et al. |
| 2019/0031611 A1 | 1/2019 | Fujimoto et al. |
| 2019/0040010 A1 | 2/2019 | Kajita et al. |
| 2020/0017444 A1 | 1/2020 | Kajita et al. |
| 2020/0115399 A1 | 4/2020 | Fujimoto et al. |
| 2020/0207715 A1 | 7/2020 | Kajita et al. |
| 2020/0207734 A1 | 7/2020 | Kajita et al. |
| 2020/0247747 A1 | 8/2020 | Hattori et al. |
| 2020/0255403 A1 | 8/2020 | Bogen et al. |
| 2020/0385345 A1 | 12/2020 | Daini et al. |
| 2020/0385346 A1 | 12/2020 | Fujimoto et al. |
| 2020/0392149 A1 | 12/2020 | Mikami et al. |
| 2021/0078955 A1 | 3/2021 | Nagase et al. |
| 2021/0198240 A1 | 7/2021 | Oda et al. |
| 2021/0269420 A1 | 9/2021 | Fujimoto et al. |
| 2022/0017514 A1 | 1/2022 | Kajita et al. |
| 2022/0017517 A1 | 1/2022 | Yoshida et al. |
| 2022/0081441 A1 | 3/2022 | Ideue et al. |
| 2022/0194926 A1 | 6/2022 | Pennington et al. |
| 2023/0037557 A1 | 2/2023 | Ito et al. |
| 2023/0042358 A1 | 2/2023 | Miyanohana et al. |

FOREIGN PATENT DOCUMENTS

| | | |
|---|---|---|
| EP | 3191468 B1 | 12/2018 |
| EP | 3663281 A1 | 6/2020 |
| EP | 3816154 A1 | 5/2021 |
| EP | 3895707 A1 | 10/2021 |
| EP | 3896060 A1 | 10/2021 |
| JP | 2003508023 A | 3/2003 |
| JP | 2003513656 A | 4/2003 |
| JP | 2003514552 A | 4/2003 |
| JP | 2004528014 A | 9/2004 |
| JP | 2006517191 A | 7/2006 |
| JP | 2008521489 A | 6/2008 |
| JP | 2010536341 A | 12/2010 |
| JP | 2022064180 A | 4/2022 |
| WO | WO1999/046392 A1 | 9/1999 |
| WO | 0103737 A1 | 1/2001 |
| WO | 0158950 A1 | 8/2001 |
| WO | 2002062375 A1 | 8/2002 |
| WO | 2004033651 A2 | 4/2004 |
| WO | 2004044006 A1 | 5/2004 |
| WO | 2004101740 A2 | 11/2004 |
| WO | WO2005/034863 A2 | 4/2005 |
| WO | 2007020889 A1 | 2/2007 |
| WO | 2007062844 A1 | 6/2007 |
| WO | 2007063907 A1 | 6/2007 |
| WO | 2008140595 A2 | 11/2008 |
| WO | 2009153960 A1 | 12/2009 |
| WO | WO2010/127029 A1 | 11/2010 |
| WO | 2010150192 A1 | 12/2010 |
| WO | 2011076781 A1 | 6/2011 |
| WO | 2011090762 A1 | 7/2011 |
| WO | 2011122923 A2 | 10/2011 |
| WO | 2012137982 A2 | 10/2012 |
| WO | 2012146628 A1 | 11/2012 |
| WO | 2012178137 A1 | 12/2012 |
| WO | 2013026833 A1 | 2/2013 |
| WO | 2013139697 A1 | 9/2013 |
| WO | 2013184942 A1 | 12/2013 |
| WO | 2014018572 A2 | 1/2014 |
| WO | 2014023673 A1 | 2/2014 |
| WO | 2014151910 A1 | 9/2014 |
| WO | 2015017548 A2 | 2/2015 |
| WO | 2015117930 A1 | 8/2015 |
| WO | 2016082677 A1 | 6/2016 |
| WO | 2016100788 A1 | 6/2016 |
| WO | 2016133160 A1 | 8/2016 |
| WO | 2017135306 A1 | 8/2017 |
| WO | 2017165464 A1 | 9/2017 |
| WO | 2018005226 A2 | 1/2018 |
| WO | 2019027058 A1 | 2/2019 |
| WO | 2019063605 A1 | 4/2019 |
| WO | 2019191327 A1 | 10/2019 |
| WO | 2020004536 A1 | 1/2020 |
| WO | 2020004537 A1 | 1/2020 |
| WO | 2020122092 A1 | 6/2020 |
| WO | 2020122093 A1 | 6/2020 |
| WO | 2020158958 A1 | 8/2020 |
| WO | 2020167701 A1 | 8/2020 |
| WO | 2020167706 A1 | 8/2020 |
| WO | 2021026047 A1 | 2/2021 |
| WO | 2021048821 A1 | 3/2021 |
| WO | 2021106975 A1 | 6/2021 |
| WO | 2021108628 A1 | 6/2021 |
| WO | 2021142083 A1 | 7/2021 |
| WO | 2022014680 A1 | 1/2022 |
| WO | 2022040058 A1 | 2/2022 |
| WO | 2022040070 A1 | 2/2022 |
| WO | 2022051583 A1 | 3/2022 |
| WO | 2022051596 A1 | 3/2022 |
| WO | 2022094012 A1 | 5/2022 |
| WO | 2022109117 A1 | 5/2022 |
| WO | 2022119888 A1 | 6/2022 |
| WO | 2022132696 A1 | 6/2022 |
| WO | 2022140316 A1 | 6/2022 |
| WO | 2022140317 A1 | 6/2022 |
| WO | 2022187231 A1 | 9/2022 |
| WO | 2022207935 A1 | 10/2022 |
| WO | 2022233872 A1 | 11/2022 |

OTHER PUBLICATIONS

Nagahara, T., et al., "Design and Synthesis of Non-Peptide, Selective Orexin Receptor 2 Agonists", J. Med. Chem., 2015, 58, 7931-7937.

Sabnis, R. W., "Novel 5-Alkyl Pyrrolidine Orexin Receptor Agonists for Treating Sleep Disorders", ACS Med. Chem. Lett., vol. 11, 11 (online at https://dx.doi.org/10.1021/acsmedchemlett.0c00501), Sep. 29, 2020, 2085-2086.

Turku, A., et al., "Orexin receptor agonist Yan 7874 is a weak agonist of orexin/hypocretin receptors and shows orexin receptor-independent cytotoxicity", PLOS ONE, 12(6): e0178526 (online at doi:10.1371/journal.pone.0178526), 2017, 1-15.

Yukitake, H., et al., "TAK-925, an orexin 2 receptor-selective agonist, shows robust wakepromoting effects in mice", Pharmacology, Biochemistry and Behavior, 2019, 187, 172794.

Publications Related to P18510-IL1RA Human, www.uniprot.org 1990.

Uniprot Protein Database, Protein Accession Q8N3074, Human Mucin 20, accessed on Oct. 16, 2016.

"3-(Cycohexylmethoxy)piperidine", PubChem, CID 43196817, create date Jul. 21, 2009.

(56) References Cited

OTHER PUBLICATIONS

"4-[Pyrrolidin-3-yloxy)methyl]piperidine", Pubchem CID 130141993, Create date: Oct. 7, 2017.
Arai, R., et al., "Design of the linkers which effectively separate domains of a bifunctional fusion protein", Protein Engineering, vol. 14, No. 8, Sep. 21, 2001, 529-532.
Cao, W., et al., "Tim-4 inhibition of T-cell activation and T helper type 17 differentiation requires both the immunoglobuln V and mucin domains and occurs via the mitogen-activated protein kinase pathway", Immunology, 133, 2011, 179-189.
Chen, X., et al., "Fusion Protein Linkers: Property, Design and Functionality", Advanced Drug Delivery Reviews, 65, 2012, 1357-1369.
Czajkowsky, D. M., et al., "Fc-fusion proteins: new developments and future perspectives", EMBO Mol Med, vol. 4, No. 10, Jul. 26, 2012, 1015-1028.
Ding, Y., et al., "A Single Amino Acid Determines the Immunostimulatory Activity of Interleukin 10", J. Exp. Med., 191 (2), Jan. 17, 2000, 213-223.
Fontenot, D., et al., "Human Immunodeficiency Virus (HIV) antigens: Structure and Serology of Multivalent Human Mucin MUC1-HIV V3 Chimeric Proteins", Proc. Natl. Acad. Sci. USA, vol. 92, Jan. 1995, 315-319.
Hasanain, S., "Effect of Topical IL-1 RA on Signs and Symptoms of Dry Eye Disease In Patients With Ocular Graftversus-host Disease (GVHD)", ARVO Annual meeting, vol. 53, Abstract 579, Mar. 2012.
Linderholm, A. L, et al., "Immunoglobulin Fc-Fusion Proteins Part 2: Therapeutic Uses and Clinical Development", Bioprocess International, vol. 12(10), Nov. 1, 2014, 1-7.
Nomellini, J. F, et al., "S-Layer-Mediated Display of the Immunoglobulin G-Binding Domain of Streptococcal Protein G on the Surface of Caulobacter crescenius: Development of an Immunoactive Reagent", Appl. Environ. Micro Biol., 73(10), 2007, 3245-3253.
Shen, H., et al., "Deletion of the Linker Connecting the Catalytic and Cellulose-Binding Domains of Endoglucanase A (CenA) of Cellulomonas fimi Alters Its Conformation and Catalytic Activity", The Journal of Biological Chemistry, 266 (17), 1991, 11335-11340.
Shimamoto, G., et al., "Peptibodies: A flexible alternative format to antibodies", MABS, vol. 4, No. 5, Sep. 1, 2012, 586-591.
Vallee, S., et al., "Pulmonary Administration of Interferon Beta-1a-Fc Fusion Protein in Non-Human Primates Using an Immunoglobulin Transport Pathway", Journal of Interferon and Cytokine Research, vol. 32, No. 4, Apr. 1, 2012, 178-184.
Wriggers, W., et al., "Control of Protein Functional Dynamics by Peptide Linkers", Biopolymers (Peptide Science), 80, May 6, 2005, 736-746.
Wu, B., et al., "Pharmacokinetics of Peptide-Fe Fusion Proteins", Journal of Pharmaceutical Sciences, vol. 103, No. 1, Jan. 27, 2014, 53-64.
Yoon, S., et al., "Conformational changes mediate interleukin-10 receptor 2 (IL-10R2) binding to IL-10 and assembly of the signaling complex", J Biol Chem., 281(46), 2006, 35088-96.
Zhang, J., et al., "Design and optimization of a linker for fusion protein construction", Progress in Natural Science, vol. 19, Sep. 17, 2009, 1197-1200.
Zhao, L., et al., "Eradication of non-Hodgkin lymphoma through the induction of tumor-specific T-cell immunity by CD20-Flex BiFP", Blood, 122(26), 2013, 4230-6.
Zheng, X. X, et al., "Administration of noncytolytic IL-10/Fc in murine models of lipopolysaccharide-induced septic shock and allogeneic islet transplantation", J. Immunol., 154(10), May 15, 1995, 5590-5600.
Zheng, X. X, et al., "I L-2 receptor-targeted cytolytic IL-2/Fc fusion protein treatment blocks diabetogenic autoimmunity in nonobese diabetic mice", J. Immunol., 163(7), Oct. 1, 1999, 4041-4048.
Zheng, X. X, et al., "Noncytolytic IL-10/Fc fusion protein prevents diabetes, blocks autoimmunity, and promotes suppressor phenomena in NOD mice", J. Immunol., 158(9), May 1, 1997, 4507-4513.

SUBSTITUTED MACROCYCLIC COMPOUNDS AND RELATED METHODS OF TREATMENT

RELATED APPLICATIONS

This application is a continuation of U.S. application Ser. No. 17/104,993, filed Nov. 25, 2020, which claims the benefit of U.S. Provisional Application No. 62/939,825, filed on Nov. 25, 2019, and U.S. Provisional Application No. 63/030,979, filed on May 28, 2020. The entire contents of the above-identified applications are herein incorporated by reference.

TECHNICAL FIELD

The present invention relates to substituted macrocyclic compounds, particularly, substituted macrocyclic compounds having agonist activity.

BACKGROUND OF THE INVENTION

Orexin is a neuropeptide synthesized and released by a subpopulation of neurons within the lateral hypothalamus and its surrounding regions. It consists of two subtypes: orexin A and orexin B. Orexin A and orexin B bind to orexin receptors. Orexin receptors are G protein-coupled receptors expressed preferentially in the brain. There are two subtypes (type 1 and type 2) of orexin receptors (Cell, Vol. 92, 573-585, 1998). Activation of orexin receptors is known to be important for a variety of central nervous system functions, such as maintenance of wakefulness, energy homeostasis, reward processing and motivation (Saper el al., TRENDS in Neuroscience 2001; Yamanaka et al., Neuron 2003; Sakurai, Nature Reviews Neuroscience 2014).

Narcolepsy is a neurological disease that results in excessive daytime sleepiness, sudden bouts of muscular paralysis (cataplexy), and disrupted sleep patterns (Mahoney et al., Nature Reviews Neuroscience, 2019). It is known that narcolepsy is caused by the degeneration of orexin neurons. Narcoleptic symptoms can be modeled in transgenic mice engineered to degenerate orexin neurons, and their symptoms can be reversed by intraventricular administration of orexin peptides (Proc. Natl. Acad. Sci. USA, Vol. 101, 4649-4654, 2004). Studies of orexin-2 receptor knockout mice have suggested that the orexin-2 receptor plays a preferential role in maintaining wakefulness (Cell, Vol. 98, 437-451, 1999, Neuron, Vol. 38, 715-730, 2003). As such, orexin-2 receptor agonists can be therapeutic agents for narcolepsy or other disorders exhibiting excessive daytime sleepiness, such as Parkinson's disease (CNS Drugs, Vol. 27, 83-90, 2013; Brain, Vol. 130, 2007, 1586-1595).

A compound having agonist activity at the orexin-2 receptor is hypothesized to be useful as a novel therapeutic agent for narcolepsy, idiopathic hypersomnia, hypersomnia, sleep apnea syndrome, disturbance of consciousness such as coma and the like, narcolepsy syndrome, hypersomnolence syndrome characterized by hypersomnia (e.g., in Parkinson's disease, Guillain-Barre syndrome or Kleine Levin syndrome), Alzheimer's disease, obesity, insulin resistance syndrome, cardiac failure, diseases related to bone loss, or sepsis and the like. (Cell Metabolism, Vol. 9, 64-76, 2009; Neuroscience, Vol. 121, 855-863, 2003; Respiration, Vol. 71, 575-579, 2004; Peptides, Vol. 23, 1683-1688, 2002; WO 2015/073707; Journal of the American College of Cardiology, Vol. 66, 2015, pages 2522-2533; WO 2015/048091; WO 2015/147240).

Some compounds having orexin-2 receptor agonist activity have been reported (U.S. Pat. No. 8,258,163; WO 2015/088000; WO 2014/198880; Journal of Medicinal Chemistry, Vol. 58, pages 7931-7937; US 20190040010; US 20190031611; US 20170226137). However, it is considered that these compounds are not satisfactory, for example, in terms of activity, pharmacokinetics, permeability into the brain/central nervous system or safety, and the development of an improved compound having orexin-2 receptor agonist activity is desired.

SUMMARY OF THE INVENTION

The present invention aims to provide substituted macrocyclic compounds having orexin-2 receptor agonist activity.

Accordingly, in an initial aspect, the present invention provides a compound represented by Formula I-A or a pharmaceutically acceptable salt thereof:

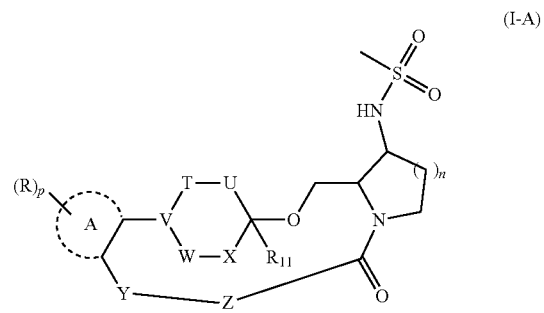

(I-A)

wherein:
  ring A is selected from the group consisting of phenyl, pyridinyl, pyridazinyl, pyrimidinyl, pyrazinyl, and triazinyl;
  n is 1, 2, or 3;
  T is $CR_1R_2$ or O;
  W is $CR_4R_5$ or O;
  U is $CR_6R_7$;
  X is $CR_8R_9$;
  V is $CR_3$ or N;
  Y is $NR_{10}$, O or absent;
  Z is $(CR_{12}R_{13})_m$;
  R is halogen or deuterium; and
  p is 0, 1, 2, 3, or 4;
and further wherein:
  m is 1, 2, 3, or 4;
  $R_1$, $R_2$, $R_4$, and $R_5$ are each, independently, selected from the group consisting of H, halogen, and deuterium;
  or, alternatively, $R_2$ and $R_5$ together with the carbon atoms to which they are attached, form a single bond;
  $R_3$ is selected from the group consisting of H, deuterium, halogen, hydroxyl, and cyano;
  or, alternatively, $R_3$ and $R_1$, together with the carbon atoms to which they are attached, form a $C_3$-$C_5$ cycloalkyl;
  or, alternatively, $R_3$ and $R_4$, together with the carbon atoms to which they are attached, form a $C_3$-$C_5$ cycloalkyl;
  $R_6$, $R_7$, $R_8$, $R_9$, and $R_{11}$ are each, independently, selected from the group consisting of H, halogen, and deuterium;

$R_{10}$ is selected from the group consisting of H, unsubstituted $C_1$-$C_3$alkyl, and $C_1$-$C_3$alkyl substituted with one or more halogen atoms; and each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

In one embodiment, provided herein are compounds of Formula I-A having the structure of Formula I or a pharmaceutically acceptable salt thereof:

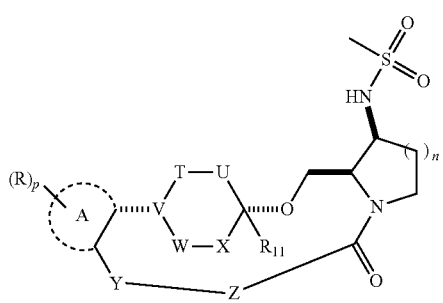

(I)

wherein:
ring A is selected from the group consisting of phenyl, pyridinyl, pyridazinyl, pyrimidinyl, pyrazinyl, and triazinyl;
n is 1, 2, or 3;
T is $CR_1R_2$ or O;
W is $CR_4R_5$ or O;
U is $CR_6R_7$;
X is $CR_8R_9$;
V is $CR_3$ or N;
Y is $NR_{10}$, O or absent;
Z is $(CR_{12}R_{13})_m$;
R is halogen or deuterium; and
p is 0, 1, 2, 3, or 4;
and further wherein:
m is 1, 2, 3, or 4;
$R_1$, $R_2$, $R_4$, and $R_5$ are each, independently, selected from the group consisting of H, halogen, and deuterium;
or, alternatively, $R_2$ and $R_5$ together with the carbon atoms to which they are attached, form a single bond;
$R_3$ is selected from the group consisting of H, deuterium, halogen, hydroxyl, and cyano;
or, alternatively, $R_3$ and $R_1$, together with the carbon atoms to which they are attached, form a $C_3$-$C_5$ cycloalkyl;
or, alternatively, $R_3$ and $R_4$, together with the carbon atoms to which they are attached, form a $C_3$-$C_5$ cycloalkyl;
$R_6$, $R_7$, $R_8$, $R_9$, and $R_{11}$ are each, independently, selected from the group consisting of H, halogen, and deuterium;
$R_{10}$ is selected from the group consisting of H, unsubstituted $C_1$-$C_3$alkyl, and $C_1$-$C_3$alkyl substituted with one or more halogen atoms; and
each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

Also provided herein is a compound having the structure of Formula II-A or a pharmaceutically acceptable salt thereof:

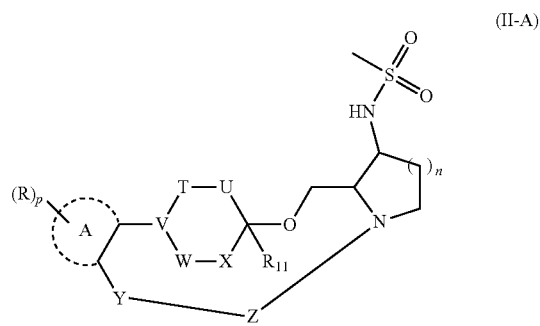

(II-A)

wherein:
ring A is selected from the group consisting of phenyl, pyridinyl, pyridazinyl, pyrimidinyl, pyrazinyl, and triazinyl;
n is 1, 2, or 3;
T is $CR_1R_2$ or O;
W is $CR_4R_5$ or O;
U is $CR_6R_7$;
X is $CR_8R_9$;
V is $CR_3$ or N;
Y is $NR_{10}$, O or absent;
Z is $(CR_{12}R_{13})_m$;
R is halogen or deuterium; and
p is 0, 1, 2, 3, or 4;
and further wherein:
m is 2, 3, 4, or 5 when Y is absent; or
m is 1, 2, 3, or 4 when Y is $NR_{10}$ or O;
$R_1$, $R_2$, $R_4$, and $R_5$ are each, independently, selected from the group consisting of H, halogen, and deuterium;
or, alternatively, $R_2$ and $R_5$ together with the carbon atoms to which they are attached, form a single bond;
$R_3$ is selected from the group consisting of H, deuterium, halogen, hydroxyl, and cyano;
or, alternatively, $R_3$ and $R_1$, together with the carbon atoms to which they are attached, form a $C_3$-$C_5$ cycloalkyl;
or, alternatively, $R_3$ and $R_4$, together with the carbon atoms to which they are attached, form a $C_3$-$C_5$ cycloalkyl;
$R_6$, $R_7$, $R_8$, $R_9$, and $R_{11}$ are each, independently, selected from the group consisting of H, halogen, and deuterium;
$R_{10}$ is selected from the group consisting of H, unsubstituted $C_1$-$C_3$alkyl, and $C_1$-$C_3$alkyl substituted with one or more halogen atoms; and
each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

In one embodiment, provided herein are compounds of Formula II-A having the structure of Formula II or a pharmaceutically acceptable salt thereof:

(II)

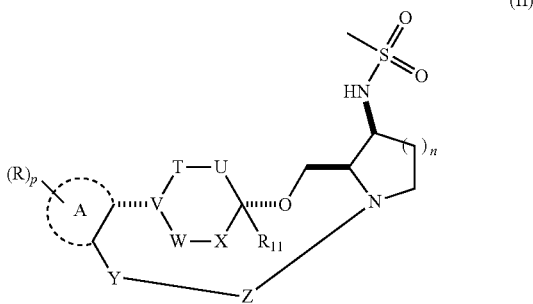

wherein:
ring A is selected from the group consisting of phenyl, pyridinyl, pyridazinyl, pyrimidinyl, pyrazinyl, and triazinyl;
n is 1, 2, or 3;
T is $CR_1R_2$ or O;
W is $CR_4R_5$ or O;
U is $CR_6R_7$;
X is $CR_8R_9$;
V is $CR_3$ or N;
Y is $NR_{10}$, O or absent;
Z is $(CR_{12}R_{13})_m$;
R is halogen or deuterium; and
p is 0, 1, 2, 3, or 4;
and further wherein:
m is 2, 3, 4, or 5 when Y is absent; or
m is 1, 2, 3, or 4 when Y is $NR_{10}$ or O;
$R_1$, $R_2$, $R_4$, and $R_5$ are each, independently, selected from the group consisting of H, halogen, and deuterium;
or, alternatively, $R_2$ and $R_5$ together with the carbon atoms to which they are attached, form a single bond;
$R_3$ is selected from the group consisting of H, deuterium, halogen, hydroxyl, and cyano;
or, alternatively, $R_3$ and $R_1$, together with the carbon atoms to which they are attached, form a $C_3$-$C_5$ cycloalkyl;
or, alternatively, $R_3$ and $R_4$, together with the carbon atoms to which they are attached, form a $C_3$-$C_5$ cycloalkyl;
$R_6$, $R_7$, $R_8$, $R_9$, and $R_{11}$ are each, independently, selected from the group consisting of H, halogen, and deuterium;
$R_{10}$ is selected from the group consisting of H, unsubstituted $C_1$-$C_3$alkyl, and $C_1$-$C_3$alkyl substituted with one or more halogen atoms; and
each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

Also provided herein is a pharmaceutical composition comprising a compound of any of Formula I-A, I, II-A, or II, or a pharmaceutically acceptable salt thereof, and a pharmaceutically acceptable carrier.

In another aspect, provided herein is a method of treating narcolepsy in a subject in need thereof comprising administering to the subject a compound of Formula I-A, I, II-A, or II, or a pharmaceutically acceptable salt thereof.

In another aspect, provided herein is a method of treating cataplexy in a subject in need thereof comprising administering to the subject a compound of Formula I-A, I, II-A, or II, or a pharmaceutically acceptable salt thereof.

DETAILED DESCRIPTION OF THE INVENTION

Provided herein are compounds, e.g., the compounds of Formula I-A, I, II-A, or II, or pharmaceutically acceptable salts thereof, that are useful in the treatment of narcolepsy or cataplexy in a subject.

In a non-limiting aspect, these compounds may modulate the orexin-2 receptor. In a particular embodiment, the compounds provided herein are considered orexin-2 agonists. As such, in one aspect, the compounds provided herein are useful in treatment of narcolepsy in a subject by acting as an agonist of the orexin-2 receptor.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of 20% or ±10%, including ±5%, ±1%, and ±0.1% from the specified value, as such variations are appropriate to perform the disclosed methods.

As used to herein, the term "$EC_{50}$" refers to the concentration of a compound required to achieve an effect that is 50% of the maximal observed effect of a compound.

The term "agonist," as used herein, refers to a compound that, when contacted with a target of interest (e.g., the orexin-2 receptor), causes an increase in the magnitude of a certain activity or function of the target compared to the magnitude of the activity or function observed in the absence of the agonist.

The term "treat," "treated," "treating," or "treatment" includes the diminishment or alleviation of at least one symptom associated or caused by the state, disorder or disease being treated. In certain embodiments, the treatment comprises bringing into contact with the orexin-2 receptor an effective amount of a compound of the invention for conditions related to narcolepsy or cataplexy.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "alkyl," by itself or as part of another substituent means, unless otherwise stated, a straight or branched chain hydrocarbon having the number of carbon atoms designated (i.e., $C_{1-6}$ alkyl means an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "substituted" means that an atom or group of atoms has replaced hydrogen as the substituent attached to another group.

Compounds of the Invention

Accordingly, in an initial aspect, the present invention provides a compound represented by Formula I-A or a pharmaceutically acceptable salt thereof:

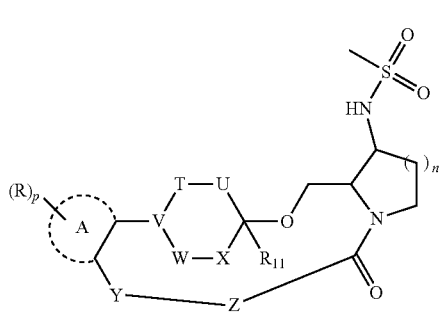 (I-A)

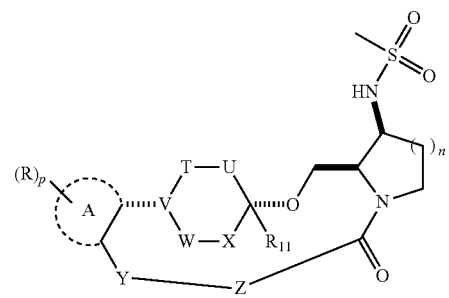 (I)

wherein:
- ring A is selected from the group consisting of phenyl, pyridinyl, pyridazinyl, pyrimidinyl, pyrazinyl, and triazinyl;
- n is 1, 2, or 3;
- T is $CR_1R_2$ or O;
- W is $CR_4R_5$ or O;
- U is $CR_6R_7$;
- X is $CR_8R_9$;
- V is $CR_3$ or N;
- Y is $NR_{10}$, O or absent;
- Z is $(CR_{12}R_{13})_m$;
- R is halogen or deuterium; and
- p is 0, 1, 2, 3, or 4;

and further wherein:
- m is 1, 2, 3, or 4;
- $R_1$, $R_2$, $R_4$, and $R_5$ are each, independently, selected from the group consisting of H, halogen, and deuterium;
- or, alternatively, $R_2$ and $R_5$ together with the carbon atoms to which they are attached, form a single bond;
- $R_3$ is selected from the group consisting of H, deuterium, halogen, hydroxyl, and cyano;
- or, alternatively, $R_3$ and $R_1$, together with the carbon atoms to which they are attached, form a $C_3$-$C_5$ cycloalkyl;
- or, alternatively, $R_3$ and $R_4$, together with the carbon atoms to which they are attached, form a $C_3$-$C_5$ cycloalkyl;
- $R_6$, $R_7$, $R_8$, $R_9$, and $R_{11}$ are each, independently, selected from the group consisting of H, halogen, and deuterium;
- $R_{10}$ is selected from the group consisting of H, unsubstituted $C_1$-$C_3$alkyl, and $C_1$-$C_3$alkyl substituted with one or more halogen atoms; and
- each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

In one embodiment, provided herein is a compound of Formula I-A having the structure of Formula I or a pharmaceutically acceptable salt thereof:

wherein:
- ring A is selected from the group consisting of phenyl, pyridinyl, pyridazinyl, pyrimidinyl, pyrazinyl, and triazinyl;
- n is 1, 2, or 3;
- T is $CR_1R_2$ or O;
- W is $CR_4R_5$ or O;
- U is $CR_6R_7$;
- X is $CR_8R_9$;
- V is $CR_3$ or N;
- Y is $NR_{10}$, O or absent;
- Z is $(CR_{12}R_{13})_m$;
- R is halogen or deuterium; and
- p is 0, 1, 2, 3, or 4;

and further wherein:
- m is 1, 2, 3, or 4;
- $R_1$, $R_2$, $R_4$, and $R_5$ are each, independently, selected from the group consisting of H, halogen, and deuterium;
- or, alternatively, $R_2$ and $R_5$ together with the carbon atoms to which they are attached, form a single bond;
- $R_3$ is selected from the group consisting of H, deuterium, halogen, hydroxyl, and cyano;
- or, alternatively, $R_3$ and $R_1$, together with the carbon atoms to which they are attached, form a $C_3$-$C_5$ cycloalkyl;
- or, alternatively, $R_3$ and $R_4$, together with the carbon atoms to which they are attached, form a $C_3$-$C_5$ cycloalkyl;
- $R_6$, $R_7$, $R_8$, $R_9$, and $R_{11}$ are each, independently, selected from the group consisting of H, halogen, and deuterium;
- $R_{10}$ is selected from the group consisting of H, unsubstituted $C_1$-$C_3$alkyl, and $C_1$-$C_3$alkyl substituted with one or more halogen atoms; and
- each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

In one embodiment of Formula (I), n is 1. In another embodiment of Formula (I), n is 2. In another embodiment of Formula (I), n is 3.

In another embodiment of Formula (I), ring A is phenyl. In another embodiment of Formula (I), ring A is pyridinyl. In another embodiment of Formula (I), ring A is pyridazinyl. In another embodiment of Formula (I), ring A is pyrimidinyl. In another embodiment of Formula (I), ring A is pyrazinyl. In another embodiment of Formula (I), ring A is triazinyl.

In another embodiment of Formula (I), Y is $NR_{10}$. In another embodiment of Formula (I), Y is O. In another embodiment of Formula (I), Y is absent. In another embodiment of Formula (I), ring A is phenyl and Y is $NR_{10}$. In another embodiment of Formula (I), ring A is phenyl and Y is O. In another embodiment of Formula (I), ring A is phenyl and Y is absent. In another embodiment of Formula (I), ring A is pyridinyl and Y is $NR_{10}$. In another embodiment of Formula (I), ring A is pyridinyl and Y is O. In another embodiment of Formula (I), ring A is pyridinyl and Y is absent. In another embodiment of Formula (I), ring A is pyridazinyl and Y is $NR_{10}$. In another embodiment of Formula (I), ring A is pyridazinyl and Y is O. In another embodiment of Formula (I), ring A is pyridazinyl and Y is absent. In another embodiment of Formula (I), ring A is pyrimidinyl and Y is $NR_{10}$. In another embodiment of Formula (I), ring A is pyrimidinyl and Y is O. In another embodiment of Formula (I), ring A is pyrimidinyl and Y is absent. In another embodiment of Formula (I), ring A is pyrazinyl and Y is $NR_{10}$. In another embodiment of Formula (I), ring A is pyrazinyl and Y is O. In another embodiment of Formula (I), ring A is pyrazinyl and Y is absent. In another embodiment of Formula (I), ring A is triazinyl and Y is $NR_{10}$. In another embodiment of Formula (I), ring A is triazinyl and Y is O. In another embodiment of Formula (I), ring A is triazinyl and Y is absent.

In another embodiment of Formula (I), T is $CR_1R_2$. In another embodiment of Formula (I), T is O. In another embodiment of Formula (I), W is $CR_4R_5$. In another embodiment of Formula (I), W is O. In another embodiment of Formula (I), T is $CR_1R_2$ and W is $CR_4R_5$. In another embodiment of Formula (I), T is O and W is $CR_4R_5$. In another embodiment of Formula (I), T is $CR_1R_2$ and W is O.

In another embodiment of Formula (I), V is $CR_3$. In another embodiment of Formula (I), V is N.

In another embodiment of Formula (I), T is $CR_1R_2$ and V is $CR_3$. In another embodiment of Formula (I), T is O and V is $CR_3$. In another embodiment of Formula (I), T is $CR_1R_2$ and V is N. In another embodiment of Formula (I), T is O and V is N.

In another embodiment of Formula (I), W is $CR_4R_5$ and V is $CR_3$. In another embodiment of Formula (I), W is O and V is $CR_3$. In another embodiment of Formula (I), W is $CR_4R_5$ and V is N. In another embodiment of Formula (I), W is O and V is N.

In another embodiment of Formula (I), T is $CR_1R_2$, W is $CR_4R_5$, and V is $CR_3$. In another embodiment of Formula (I), T is $CR_1R_2$, W is O, and V is $CR_3$. In another embodiment of Formula (I), T is $CR_1R_2$, W is $CR_4R_5$, and V is N. In another embodiment of Formula (I), T is $CR_1R_2$, W is O, and V is N. In another embodiment of Formula (I), T is O, W is $CR_4R_5$, and V is $CR_3$.

In another embodiment of Formula (I), m is 1. In another embodiment of Formula (I), m is 2. In another embodiment of Formula (I), m is 3. In another embodiment of Formula (I), m is 4. In another embodiment of Formula (I), m is 1, 2 or 3. In another embodiment of Formula (I), m is 2, 3, or 4. In another embodiment of Formula (I), m is 1 or 2. In another embodiment of Formula (I), m is 3 or 4.

In another embodiment of Formula (I), Y is O and m is 1. In another embodiment of Formula (I), Y is O and m is 2. In another embodiment of Formula (I), Y is O and m is 3. In another embodiment of Formula (I), Y is O and m is 4. In another embodiment of Formula (I), Y is O and m is 1, 2, or 3. In another embodiment of Formula (I), Y is O and m is 2, 3, or 4. In another embodiment of Formula (I), Y is O and m is 1 or 2. In another embodiment of Formula (I), Y is O and m is 3 or 4.

In another embodiment of Formula (I), Y is absent and m is 1. In another embodiment of Formula (I), Y is absent and m is 2. In another embodiment of Formula (I), Y is absent and m is 3. In another embodiment of Formula (I), Y is absent and m is 4. In another embodiment of Formula (I), Y is absent and m is 1, 2, or 3. In another embodiment of Formula (I), Y is absent and m is 2, 3, or 4. In another embodiment of Formula (I), Y is absent and m is 1 or 2. In another embodiment of Formula (I), Y is absent and m is 3 or 4.

In another embodiment of Formula (I), Y is $NR_{10}$ and m is 1. In another embodiment of Formula (I), Y is $NR_{10}$ and m is 2. In another embodiment of Formula (I), Y is $NR_{10}$ and m is 3. In another embodiment of Formula (I), Y is $NR_{10}$ and m is 4. In another embodiment of Formula (I), Y is $NR_{10}$ and m is 1, 2, or 3. In another embodiment of Formula (I), Y is $NR_{10}$ and m is 2, 3, or 4. In another embodiment of Formula (I), Y is $NR_{10}$ and m is 1 or 2. In another embodiment of Formula (I), Y is $NR_{10}$ and m is 3 or 4.

In another embodiment of Formula (I), ring A is phenyl and n is 1. In another embodiment of Formula (I), ring A is phenyl and n is 2. In another embodiment of Formula (I), ring A is phenyl and n is 3. In another embodiment of Formula (I), ring A is pyridinyl and n is 1. In another embodiment of Formula (I), ring A is pyridinyl and n is 2. In another embodiment of Formula (I), ring A is pyridinyl and n is 3. In another embodiment of Formula (I), ring A is pyridazinyl and n is 1. In another embodiment of Formula (I), ring A is pyridazinyl and n is 2. In another embodiment of Formula (I), ring A is pyridazinyl and n is 3. In another embodiment of Formula (I), ring A is pyrimidinyl and n is 1. In another embodiment of Formula (I), ring A is pyrimidinyl and n is 2. In another embodiment of Formula (I), ring A is pyrimidinyl and n is 3. In another embodiment of Formula (I), ring A is pyrazinyl and n is 1. In another embodiment of Formula (I), ring A is pyrazinyl and n is 2. In another embodiment of Formula (I), ring A is pyrazinyl and n is 3. In another embodiment of Formula (I), ring A is triazinyl and n is 1. In another embodiment of Formula (I), ring A is triazinyl and n is 2. In another embodiment of Formula (I), ring A is triazinyl and n is 3.

In another embodiment of Formula (I), ring A is phenyl, n is 1, and Y is $NR_{10}$. In another embodiment of Formula (I), ring A is phenyl, n is 2, and Y is $NR_{10}$. In another embodiment of Formula (I), ring A is phenyl, n is 3, and Y is $NR_{10}$. In another embodiment of Formula (I), ring A is phenyl, n is 1, and Y is O. In another embodiment of Formula (I), ring A is phenyl, n is 2, and Y is O. In another embodiment of Formula (I), ring A is phenyl, n is 3, and Y is O. In another embodiment of Formula (I), ring A is phenyl, n is 1, and Y is absent. In another embodiment of Formula (I), ring A is phenyl, n is 2, and Y is absent. In another embodiment of Formula (I), ring A is phenyl, n is 3, and Y is absent.

In another embodiment of Formula (I), ring A is phenyl, n is 1, Y is $NR_{10}$, and m is 1 or 2. In another embodiment of Formula (I), ring A is phenyl, n is 2, Y is $NR_{10}$, and m is 1 or 2. In another embodiment of Formula (I), ring A is phenyl, n is 3, Y is $NR_{10}$, and m is 1 or 2. In another embodiment of Formula (I), ring A is phenyl, n is 1, Y is O, and m is 1 or 2. In another embodiment of Formula (I), ring A is phenyl, n is 2, Y is O, and m is 1 or 2. In another embodiment of Formula (I), ring A is phenyl, n is 3, Y is O, and m is 1 or 2. In another embodiment of Formula (I), ring A is phenyl, n is 1, Y is absent, and m is 1 or 2. In another embodiment of Formula (I), ring A is phenyl, n is 2, Y is absent, and m is 1 or 2. In another embodiment of Formula (I), ring A is phenyl, n is 3, Y is absent, and m is 1 or 2. In another embodiment of Formula (I), ring A is phenyl, n is 1, Y is $NR_{10}$, and m is 3 or 4. In another embodiment of Formula (I), ring A is phenyl, n is 2, Y is $NR_{10}$, and m is 3 or 4. In another embodiment of Formula (I), ring A is phenyl, n is 3, Y is $NR_{10}$, and m is 3 or 4. In another embodiment of Formula (I), ring A is phenyl, n is 1, Y is O, and m is 3 or 4. In another embodiment of Formula (I), ring A is phenyl, n is 2, Y is O, and m is 3 or 4. In another embodiment of Formula (I), ring A is phenyl, n is 3, Y is O, and m is 3 or 4. In another embodiment of Formula (I), ring A is phenyl, n is 1, Y is absent, and m is 3 or 4. In another embodiment of Formula (I), ring A is phenyl, n is 2, Y is absent, and m is 3 or 4. In another embodiment of Formula (I), ring A is phenyl, n is 3, Y is absent, and m is 3 or 4.

In another embodiment of Formula (I), ring A is pyridinyl, n is 1, and Y is $NR_{10}$. In another embodiment of Formula (I), ring A is pyridinyl, n is 2, and Y is $NR_{10}$. In another embodiment of Formula (I), ring A is pyridinyl, n is 3, and Y is $NR_{10}$. In another embodiment of Formula (I), ring A is pyridinyl, n is 1, and Y is O. In another embodiment of Formula (I), ring A is pyridinyl, n is 2, and Y is O. In another embodiment of Formula (I), ring A is pyridinyl, n is 3, and Y is O. In another embodiment of Formula (I), ring A is pyridinyl, n is 1, and Y is absent. In another embodiment of Formula (I), ring A is pyridinyl, n is 2, and Y is absent. In another embodiment of Formula (I), ring A is pyridinyl, n is 3, and Y is absent.

In another embodiment of Formula (I), ring A is pyridinyl, n is 1, Y is $NR_{10}$, and m is 1 or 2. In another embodiment of Formula (I), ring A is pyridinyl, n is 2, Y is $NR_{10}$, and m is 1 or 2. In another embodiment of Formula (I), ring A is pyridinyl, n is 3, Y is $NR_{10}$, and m is 1 or 2. In another embodiment of Formula (I), ring A is pyridinyl, n is 1, Y is O, and m is 1 or 2. In another embodiment of Formula (I), ring A is pyridinyl, n is 2, Y is O, and m is 1 or 2. In another embodiment of Formula (I), ring A is pyridinyl, n is 3, Y is O, and m is 1 or 2. In another embodiment of Formula (I), ring A is pyridinyl, n is 1, Y is absent, and m is 1 or 2. In another embodiment of Formula (I), ring A is pyridinyl, n is 2, Y is absent, and m is 1 or 2. In another embodiment of Formula (I), ring A is pyridinyl, n is 3, Y is absent, and m is 1 or 2. In another embodiment of Formula (I), ring A is pyridinyl, n is 1, Y is $NR_{10}$, and m is 3 or 4. In another embodiment of Formula (I), ring A is pyridinyl, n is 2, Y is $NR_{10}$, and m is 3 or 4. In another embodiment of Formula (I), ring A is pyridinyl, n is 3, Y is $NR_{10}$, and m is 3 or 4. In another embodiment of Formula (I), ring A is pyridinyl, n is 1, Y is O, and m is 3 or 4. In another embodiment of Formula (I), ring A is pyridinyl, n is 2, Y is O, and m is 3 or 4. In another embodiment of Formula (I), ring A is pyridinyl, n is 3, Y is O, and m is 3 or 4. In another embodiment of Formula (I), ring A is pyridinyl, n is 1, Y is absent, and m is 3 or 4. In another embodiment of Formula (I), ring A is pyridinyl, n is 2, Y is absent, and m is 3 or 4. In another embodiment of Formula (I), ring A is pyridinyl, n is 3, Y is absent, and m is 3 or 4.

In another embodiment of Formula (I), ring A is pyridazinyl, n is 1, and Y is $NR_{10}$. In another embodiment of Formula (I), ring A is pyridazinyl, n is 2, and Y is $NR_{10}$. In another embodiment of Formula (I), ring A is pyridazinyl, n is 3, and Y is $NR_{10}$. In another embodiment of Formula (I), ring A is pyridazinyl, n is 1, and Y is O. In another embodiment of Formula (I), ring A is pyridazinyl, n is 2, and Y is O. In another embodiment of Formula (I), ring A is pyridazinyl, n is 3, and Y is O. In another embodiment of Formula (I), ring A is pyridazinyl, n is 1, and Y is absent. In another embodiment of Formula (I), ring A is pyridazinyl, n is 2, and Y is absent. In another embodiment of Formula (I), ring A is pyridazinyl, n is 3, and Y is absent.

In another embodiment of Formula (I), ring A is pyridazinyl, n is 1, Y is $NR_{10}$, and m is 1 or 2. In another embodiment of Formula (I), ring A is pyridazinyl, n is 2, Y is $NR_{10}$, and m is 1 or 2. In another embodiment of Formula (I), ring A is pyridazinyl, n is 3, Y is $NR_{10}$, and m is 1 or 2. In another embodiment of Formula (I), ring A is pyridazinyl, n is 1, Y is O, and m is 1 or 2. In another embodiment of Formula (I), ring A is pyridazinyl, n is 2, Y is O, and m is 1 or 2. In another embodiment of Formula (I), ring A is pyridazinyl, n is 3, Y is O, and m is 1 or 2. In another embodiment of Formula (I), ring A is pyridazinyl, n is 1, Y is absent, and m is 1 or 2. In another embodiment of Formula (I), ring A is pyridazinyl, n is 2, Y is absent, and m is 1 or 2. In another embodiment of Formula (I), ring A is pyridazinyl, n is 3, Y is absent, and m is 1 or 2. In another embodiment of Formula (I), ring A is pyridazinyl, n is 1, Y is $NR_{10}$, and m is 3 or 4. In another embodiment of Formula (I), ring A is pyridazinyl, n is 2, Y is $NR_{10}$, and m is 3 or 4. In another embodiment of Formula (I), ring A is pyridazinyl, n is 3, Y is $NR_{10}$, and m is 3 or 4. In another embodiment of Formula (I), ring A is pyridazinyl, n is 1, Y is O, and m is 3 or 4. In another embodiment of Formula (I), ring A is pyridazinyl, n is 2, Y is O, and m is 3 or 4. In another embodiment of Formula (I), ring A is pyridazinyl, n is 3, Y is O, and m is 3 or 4. In another embodiment of Formula (I), ring A is pyridazinyl, n is 1, Y is absent, and m is 3 or 4. In another embodiment of Formula (I), ring A is pyridazinyl, n is 2, Y is absent, and m is 3 or 4. In another embodiment of Formula (I), ring A is pyridazinyl, n is 3, Y is absent, and m is 3 or 4.

In another embodiment of Formula (I), ring A is pyrimidinyl, n is 1, and Y is $NR_{10}$. In another embodiment of Formula (I), ring A is pyrimidinyl, n is 2, and Y is $NR_{10}$. In another embodiment of Formula (I), ring A is pyrimidinyl, n is 3, and Y is $NR_{10}$. In another embodiment of Formula (I), ring A is pyrimidinyl, n is 1, and Y is O. In another embodiment of Formula (I), ring A is pyrimidinyl, n is 2, and Y is O. In another embodiment of Formula (I), ring A is pyrimidinyl, n is 3, and Y is O. In another embodiment of Formula (I), ring A is pyrimidinyl, n is 1, and Y is absent. In another embodiment of Formula (I), ring A is pyrimidinyl, n is 2, and Y is absent. In another embodiment of Formula (I), ring A is pyrimidinyl, n is 3, and Y is absent.

In another embodiment of Formula (I), ring A is pyrimidinyl, n is 1, Y is $NR_{10}$, and m is 1 or 2. In another embodiment of Formula (I), ring A is pyrimidinyl, n is 2, Y is $NR_{10}$, and m is 1 or 2. In another embodiment of Formula (I), ring A is pyrimidinyl, n is 3, Y is $NR_{10}$, and m is 1 or 2. In another embodiment of Formula (I), ring A is pyrimidinyl, n is 1, Y is O, and m is 1 or 2. In another embodiment of Formula (I), ring A is pyrimidinyl, n is 2, Y is O, and m is 1 or 2. In another embodiment of Formula (I), ring A is pyrimidinyl, n is 3, Y is O, and m is 1 or 2. In another embodiment of Formula (I), ring A is pyrimidinyl, n is 1, Y is absent, and m is 1 or 2. In another embodiment of Formula (I), ring A is pyrimidinyl, n is 2, Y is absent, and m is 1 or 2. In another embodiment of Formula (I), ring A is pyrimidinyl, n is 3, Y is absent, and m is 1 or 2. In another embodiment of Formula (I), ring A is pyrimidinyl, n is 1, Y is $NR_{10}$, and m is 3 or 4. In another embodiment of Formula (I), ring A is pyrimidinyl, n is 2, Y is $NR_{10}$, and m is 3 or 4. In another embodiment of Formula (I), ring A is pyrimidinyl, n is 3, Y is $NR_{10}$, and m is 3 or 4. In another embodiment of Formula (I), ring A is pyrimidinyl, n is 1, Y is O, and m is 3 or 4. In another embodiment of Formula (I), ring A is pyrimidinyl, n is 2, Y is O, and m is 3 or 4. In another embodiment of Formula (I), ring A is pyrimidinyl, n is 3, Y is O, and m is 3 or 4. In another embodiment of Formula (I), ring A is pyrimidinyl, n is 1, Y is absent, and m is 3 or 4. In another embodiment of Formula (I), ring A is pyrimidinyl, n is 2, Y is absent, and m is 3 or 4. In another embodiment of Formula (I), ring A is pyrimidinyl, n is 3, Y is absent, and m is 3 or 4.

In another embodiment of Formula (I), ring A is pyrazinyl, n is 1, and Y is $NR_{10}$. In another embodiment of Formula (I), ring A is pyrazinyl, n is 2, and Y is $NR_{10}$. In another embodiment of Formula (I), ring A is pyrazinyl, n is 3, and Y is $NR_{10}$. In another embodiment of Formula (I), ring A is pyrazinyl, n is 1, and Y is O. In another embodiment of Formula (I), ring A is pyrazinyl, n is 2, and Y is O. In another embodiment of Formula (I), ring A is pyrazinyl, n is 3, and Y is O. In another embodiment of Formula (I), ring A is pyrazinyl, n is 1, and Y is absent. In another embodiment of Formula (I), ring A is pyrazinyl, n is 2, and Y is absent. In another embodiment of Formula (I), ring A is pyrazinyl, n is 3, and Y is absent.

In another embodiment of Formula (I), ring A is pyrazinyl, n is 1, Y is $NR_{10}$, and m is 1 or 2. In another embodiment of Formula (I), ring A is pyrazinyl, n is 2, Y is $NR_{10}$, and m is 1 or 2. In another embodiment of Formula (I), ring A is pyrazinyl, n is 3, Y is $NR_{10}$, and m is 1 or 2. In another embodiment of Formula (I), ring A is pyrazinyl, n is 1, Y is O, and m is 1 or 2. In another embodiment of Formula (I), ring A is pyrazinyl, n is 2, Y is O, and m is 1 or 2. In another embodiment of Formula (I), ring A is pyrazinyl, n is 3, Y is O, and m is 1 or 2. In another embodiment of Formula (I), ring A is pyrazinyl, n is 1, Y is absent, and m is 1 or 2. In another embodiment of Formula (I), ring A is pyrazinyl, n is 2, Y is absent, and m is 1 or 2. In another embodiment of Formula (I), ring A is pyrazinyl, n is 3, Y is absent, and m is 1 or 2. In another embodiment of Formula (I), ring A is pyrazinyl, n is 1, Y is $NR_{10}$, and m is 3 or 4. In another embodiment of Formula (I), ring A is pyrazinyl, n is 2, Y is $NR_{10}$, and m is 3 or 4. In another embodiment of Formula (I), ring A is pyrazinyl, n is 3, Y is $NR_{10}$, and m is 3 or 4. In another embodiment of Formula (I), ring A is pyrazinyl, n is 1, Y is O, and m is 3 or 4. In another embodiment of Formula (I), ring A is pyrazinyl, n is 2, Y is O, and m is 3 or 4. In another embodiment of Formula (I), ring A is pyrazinyl, n is 3, Y is O, and m is 3 or 4. In another embodiment of Formula (I), ring A is pyrazinyl, n is 1, Y is absent, and m is 3 or 4. In another embodiment of Formula (I), ring A is pyrazinyl, n is 2, Y is absent, and m is 3 or 4. In another embodiment of Formula (I), ring A is pyrazinyl, n is 3, Y is absent, and m is 3 or 4.

In another embodiment of Formula (I), ring A is triazinyl, n is 1, and Y is $NR_{10}$. In another embodiment of Formula (I), ring A is triazinyl, n is 2, and Y is $NR_{10}$. In another embodiment of Formula (I), ring A is triazinyl, n is 3, and Y is $NR_{10}$. In another embodiment of Formula (I), ring A is triazinyl, n is 1, and Y is O. In another embodiment of Formula (I), ring A is triazinyl, n is 2, and Y is O. In another embodiment of Formula (I), ring A is triazinyl, n is 3, and Y is O. In another embodiment of Formula (I), ring A is triazinyl, n is 1, and Y is absent. In another embodiment of Formula (I), ring A is triazinyl, n is 2, and Y is absent. In another embodiment of Formula (I), ring A is triazinyl, n is 3, and Y is absent.

In another embodiment of Formula (I), ring A is triazinyl, n is 1, Y is $NR_{10}$, and m is 1 or 2. In another embodiment of Formula (I), ring A is triazinyl, n is 2, Y is $NR_{10}$, and m is 1 or 2. In another embodiment of Formula (I), ring A is triazinyl, n is 3, Y is $NR_{10}$, and m is 1 or 2. In another embodiment of Formula (I), ring A is triazinyl, n is 1, Y is O, and m is 1 or 2. In another embodiment of Formula (I), ring A is triazinyl, n is 2, Y is O, and m is 1 or 2. In another embodiment of Formula (I), ring A is triazinyl, n is 3, Y is O, and m is 1 or 2. In another embodiment of Formula (I), ring A is triazinyl, n is 1, Y is absent, and m is 1 or 2. In another embodiment of Formula (I), ring A is triazinyl, n is 2, Y is absent, and m is 1 or 2. In another embodiment of Formula (I), ring A is triazinyl, n is 3, Y is absent, and m is 1 or 2. In another embodiment of Formula (I), ring A is triazinyl, n is 1, Y is $NR_{10}$, and m is 3 or 4. In another embodiment of Formula (I), ring A is triazinyl, n is 2, Y is $NR_{10}$, and m is 3 or 4. In another embodiment of Formula (I), ring A is triazinyl, n is 3, Y is $NR_{10}$, and m is 3 or 4. In another embodiment of Formula (I), ring A is triazinyl, n is 1, Y is O, and m is 3 or 4. In another embodiment of Formula (I), ring A is triazinyl, n is 2, Y is O, and m is 3 or 4. In another embodiment of Formula (I), ring A is triazinyl, n is 3, Y is O, and m is 3 or 4. In another embodiment of Formula (I), ring A is triazinyl, n is 1, Y is absent, and m is 3 or 4. In another embodiment of Formula (I), ring A is triazinyl, n is 2, Y is absent, and m is 3 or 4. In another embodiment of Formula (I), ring A is triazinyl, n is 3, Y is absent, and m is 3 or 4.

In another embodiment of Formula (I), ring A is phenyl, T is $CR_1R_2$, W is $CR_4R_5$, and V is $CR_3$. In another embodiment of Formula (I), ring A is phenyl, p is 0, T is $CR_1R_2$, W is $CR_4R_5$, and V is $CR_3$. In another embodiment of Formula (I), ring A is phenyl, T is $CR_1R_2$, W is $CR_4R_5$, V is $CR_3$, and n is 1. In another embodiment of Formula (I), ring A is phenyl, T is $CR_1R_2$, W is $CR_4R_5$, V is $CR_3$, and n is 2. In another embodiment of Formula (I), ring A is phenyl, T is $CR_1R_2$, W is $CR_4R_5$, V is $CR_3$, and n is 3. In another embodiment of Formula (I), ring A is phenyl, p is 0, T is $CR_1R_2$, W is $CR_4R_5$, V is $CR_3$, and n is 1. In another embodiment of Formula (I), ring A is phenyl, p is 0, T is $CR_1R_2$, W is $CR_4R_5$, V is $CR_3$, and n is 2. In another embodiment of Formula (I), ring A is phenyl, p is 0, T is $CR_1R_2$, W is $CR_4R_5$, V is $CR_3$, and n is 3.

In another embodiment of Formula (I), ring A is phenyl, T is $CR_1R_2$, W is $CR_4R_5$, V is $CR_3$, and Y is O. In another embodiment of Formula (I), ring A is phenyl, p is 0, T is $CR_1R_2$, W is $CR_4R_5$, V is $CR_3$, and Y is O. In another embodiment of Formula (I), ring A is phenyl, T is $CR_1R_2$, W is $CR_4R_5$, V is $CR_3$, Y is O, and n is 1. In another embodiment of Formula (I), ring A is phenyl, T is $CR_1R_2$, W is $CR_4R_5$, V is $CR_3$, Y is O, and n is 2. In another embodiment of Formula (I), ring A is phenyl, T is $CR_1R_2$, W is $CR_4R_5$, V is $CR_3$, Y is O, and n is 3. In another embodiment of Formula (I), ring A is phenyl, p is 0, T is $CR_1R_2$, W is $CR_4R_5$, V is $CR_3$, Y is O, and n is 1. In another embodiment of Formula (I), ring A is phenyl, p is 0, T is $CR_1R_2$, W is $CR_4R_5$, V is $CR_3$, Y is O, and n is 2. In another embodiment of Formula (I), ring A is phenyl, p is 0, T is $CR_1R_2$, W is $CR_4R_5$, V is $CR_3$, Y is O, and n is 3.

In another embodiment of Formula (I), ring A is phenyl, T is $CR_1R_2$, W is $CR_4R_5$, V is $CR_3$, Y is O, and m is 1 or 2. In another embodiment of Formula (I), ring A is phenyl, p is 0, T is $CR_1R_2$, W is $CR_4R_5$, V is $CR_3$, Y is O, and m is 1 or 2. In another embodiment of Formula (I), ring A is phenyl, T is $CR_1R_2$, W is $CR_4R_5$, V is $CR_3$, Y is O, n is 1, and m is 1 or 2. In another embodiment of Formula (I), ring A is phenyl, T is $CR_1R_2$, W is $CR_4R_5$, V is $CR_3$, Y is O, n is 2, and m is 1 or 2. In another embodiment of Formula (I), ring A is phenyl, T is $CR_1R_2$, W is $CR_4R_5$, V is $CR_3$, Y is O, n is 3, and m is 1 or 2. In another embodiment of Formula (I), ring A is phenyl, p is 0, T is $CR_1R_2$, W is $CR_4R_5$, V is $CR_3$, Y is O, n is 1, and m is 1 or 2. In another embodiment of Formula (I), ring A is phenyl, p is 0, T is $CR_1R_2$, W is $CR_4R_5$, V is $CR_3$, Y is O, n is 2, and m is 1 or 2. In another embodiment of Formula (I), ring A is phenyl, p is 0, T is $CR_1R_2$, W is $CR_4R_5$, V is $CR_3$, Y is O, n is 3, and m is 1 or 2. In another embodiment of Formula (I), ring A is phenyl, T is $CR_1R_2$, W is $CR_4R_5$, V is $CR_3$, Y is O, and m is 3 or 4. In another embodiment of Formula (I), ring A is phenyl, p is 0, T is $CR_1R_2$, W is $CR_4R_5$, V is $CR_3$, Y is O, and m is 3 or 4. In another embodiment of Formula (I), ring A is phenyl, T is $CR_1R_2$, W is $CR_4R_5$, V is $CR_3$, Y is O, n is 1, and m is 3 or 4. In another embodiment of Formula (I), ring A is phenyl, T is $CR_1R_2$, W is $CR_4R_5$, V is $CR_3$, Y is O, n is 2, and m is 3 or 4. In another embodiment of Formula (I), ring A is phenyl, T is $CR_1R_2$, W is $CR_4R_5$, V is $CR_3$, Y is O, n is 3, and m is 3 or 4. In another embodiment of Formula (I), ring A is phenyl, p is 0, T is $CR_1R_2$, W is $CR_4R_5$, V is $CR_3$, Y is O, n is 1, and m is 3 or 4. In another embodiment of Formula (I), ring A is phenyl, p is 0, T is $CR_1R_2$, W is $CR_4R_5$, V is $CR_3$, Y is O, n is 2, and m is 3 or 4. In another embodiment of Formula (I), ring A is phenyl, p is 0, T is $CR_1R_2$, W is $CR_4R_5$, V is $CR_3$, Y is O, n is 3, and m is 3 or 4.

In another embodiment of Formula (I), p is 0 and $R_1$, $R_2$, $R_4$, and $R_5$ are each H. In another embodiment of Formula (I), p is 0; $R_1$, $R_2$, $R_4$, and $R_5$ are each H; and $R_3$ is H. In another embodiment of Formula (I), p is 0; $R_1$, $R_2$, $R_4$, and $R_5$ are each H; $R_3$ is H; and $R_6$, $R_7$, $R_8$, $R_9$, and $R_{11}$ are each H. In another embodiment of Formula (I), p is 0; $R_1$, $R_2$, $R_4$, and $R_5$ are each H; $R_3$ is H; $R_6$, $R_7$, $R_8$, $R_9$, and Rn are each H; and $R_{12}$ and $R_{13}$ are each H.

In another embodiment of Formula (I), p is 1 and $R_1$, $R_2$, $R_4$, and $R_5$ are each H. In another embodiment of Formula (I), p is 1; $R_1$, $R_2$, $R_4$, and $R_5$ are each H; and $R_3$ is H. In another embodiment of Formula (I), p is 1; $R_1$, $R_2$, $R_4$, and $R_5$ are each H; $R_3$ is H; and $R_6$, $R_7$, $R_8$, $R_9$, and $R_{11}$ are each H. In another embodiment of Formula (I), p is 1; $R_1$, $R_2$, $R_4$, and $R_5$ are each H; $R_3$ is H; $R_6$, $R_7$, $R_8$, $R_9$, and Rn are each H; and $R_{12}$ and $R_{13}$ are each H.

In another embodiment of Formula (I), p is 2 and $R_1$, $R_2$, $R_4$, and $R_5$ are each H. In another embodiment of Formula (I), p is 2; $R_1$, $R_2$, $R_4$, and $R_5$ are each H; and $R_3$ is H. In another embodiment of Formula (I), p is 2; $R_1$, $R_2$, $R_4$, and $R_5$ are each H; $R_3$ is H; and $R_6$, $R_7$, $R_8$, $R_9$, and $R_{11}$ are each H. In another embodiment of Formula (I), p is 2; $R_1$, $R_2$, $R_4$, and $R_5$ are each H; $R_3$ is H; $R_6$, $R_7$, $R_8$, $R_9$, and Rn are each H; and $R_{12}$ and $R_{13}$ are each H.

In another embodiment of Formula (I), p is 1, 2, 3, or 4 and R is fluorine. In another embodiment of Formula (I), p is 1, 2, 3, or 4 and R is deuterium. In another embodiment of Formula (I), one or more of $R_1$, $R_2$, $R_4$, and $R_5$ is fluorine. In another embodiment of Formula (I), one or more of $R_1$, $R_2$, $R_4$, and $R_5$ is deuterium. In another embodiment of Formula (I), one or more of $R_6$, $R_7$, $R_8$, $R_9$, and Rn is fluorine. In another embodiment of Formula (I), one or more of $R_6$, $R_7$, $R_8$, $R_9$, and Rn is deuterium. In another embodiment of Formula (I), one or more of each $R_{12}$ and $R_{13}$ is fluorine. In another embodiment of Formula (I), one or more of each $R_{12}$ and $R_{13}$ is deuterium.

Each of the embodiments described herein with respect to compounds of Formula I also applies to compounds of Formula I-A.

Also provided herein is a compound having the structure of Formula II-A or a pharmaceutically acceptable salt thereof:

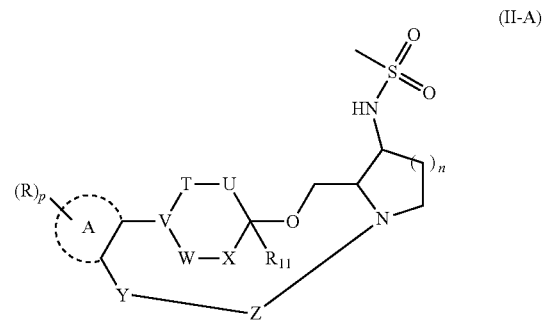

(II-A)

wherein:
ring A is selected from the group consisting of phenyl, pyridinyl, pyridazinyl, pyrimidinyl, pyrazinyl, and triazinyl;

n is 1, 2, or 3;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

R is halogen or deuterium; and p is 0, 1, 2, 3, or 4;

and further wherein:

m is 2, 3, 4, or 5 when Y is absent; or m is 1, 2, 3, or 4 when Y is $NR_{10}$ or O;

$R_1$, $R_2$, $R_4$, and $R_5$ are each, independently, selected from the group consisting of H, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, halogen, and deuterium;

$R_{10}$ is selected from the group consisting of H, unsubstituted $C_1$-$C_3$alkyl, and $C_1$-$C_3$alkyl substituted with one or more halogen atoms; and each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

In one embodiment, provided herein are compounds of Formula II-A having the structure of Formula II or a pharmaceutically acceptable salt thereof:

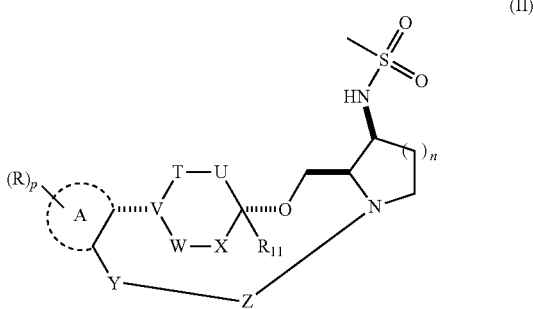

(II)

wherein:
- ring A is selected from the group consisting of phenyl, pyridinyl, pyridazinyl, pyrimidinyl, pyrazinyl, and triazinyl;
- n is 1, 2, or 3;
- T is $CR_1R_2$ or O;
- W is $CR_4R_5$ or O;
- U is $CR_6R_7$;
- X is $CR_8R_9$;
- V is $CR_3$ or N;
- Y is $NR_{10}$, O or absent;
- Z is $(CR_{12}R_{13})_m$;
- R is halogen or deuterium; and
- p is 0, 1, 2, 3, or 4;

and further wherein:
- m is 2, 3, 4, or 5 when Y is absent; or
- m is 1, 2, 3, or 4 when Y is $NR_{10}$ or O;
- $R_1$, $R_2$, $R_4$, and $R_5$ are each, independently, selected from the group consisting of H, halogen, and deuterium;
- or, alternatively, $R_2$ and $R_5$ together with the carbon atoms to which they are attached, form a single bond;
- $R_3$ is selected from the group consisting of H, deuterium, halogen, hydroxyl, and cyano;
- or, alternatively, $R_3$ and $R_1$, together with the carbon atoms to which they are attached, form a $C_3$-$C_5$ cycloalkyl;
- or, alternatively, $R_3$ and $R_4$, together with the carbon atoms to which they are attached, form a $C_3$-$C_5$ cycloalkyl;
- $R_6$, $R_7$, $R_8$, $R_9$, and $R_{11}$ are each, independently, selected from the group consisting of H, halogen, and deuterium;
- $R_{10}$ is selected from the group consisting of H, unsubstituted $C_1$-$C_3$alkyl, and $C_1$-$C_3$alkyl substituted with one or more halogen atoms; and
- each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

In one embodiment of Formula (II), n is 1. In another embodiment of Formula (II), n is 2. In another embodiment of Formula (II), n is 3.

In another embodiment of Formula (II), ring A is phenyl. In another embodiment of Formula (II), ring A is pyridinyl. In another embodiment of Formula (II), ring A is pyridazinyl. In another embodiment of Formula (II), ring A is pyrimidinyl. In another embodiment of Formula (II), ring A is pyrazinyl. In another embodiment of Formula (II), ring A is triazinyl.

In another embodiment of Formula (II), Y is $NR_{10}$. In another embodiment of Formula (II), Y is O. In another embodiment of Formula (II), Y is absent. In another embodiment of Formula (II), ring A is phenyl and Y is $NR_{10}$. In another embodiment of Formula (II), ring A is phenyl and Y is O. In another embodiment of Formula (II), ring A is phenyl and Y is absent. In another embodiment of Formula (II), ring A is pyridinyl and Y is $NR_{10}$. In another embodiment of Formula (II), ring A is pyridinyl and Y is O. In another embodiment of Formula (II), ring A is pyridinyl and Y is absent. In another embodiment of Formula (II), ring A is pyridazinyl and Y is $NR_{10}$. In another embodiment of Formula (II), ring A is pyridazinyl and Y is O. In another embodiment of Formula (II), ring A is pyridazinyl and Y is absent. In another embodiment of Formula (II), ring A is pyrimidinyl and Y is $NR_{10}$. In another embodiment of Formula (II), ring A is pyrimidinyl and Y is O. In another embodiment of Formula (II), ring A is pyrimidinyl and Y is absent. In another embodiment of Formula (II), ring A is pyrazinyl and Y is $NR_{10}$. In another embodiment of Formula (II), ring A is pyrazinyl and Y is O. In another embodiment of Formula (II), ring A is pyrazinyl and Y is absent. In another embodiment of Formula (II), ring A is triazinyl and Y is $NR_{10}$. In another embodiment of Formula (II), ring A is triazinyl and Y is O. In another embodiment of Formula (II), ring A is triazinyl and Y is absent.

In another embodiment of Formula (II), T is $CR_1R_2$. In another embodiment of Formula (II), T is O. In another embodiment of Formula (II), W is $CR_4R_5$. In another embodiment of Formula (II), W is O. In another embodiment of Formula (II), T is $CR_1R_2$ and W is $CR_4R_5$. In another embodiment of Formula (II), T is O and W is $CR_4R_5$. In another embodiment of Formula (II), T is $CR_1R_2$ and W is O.

In another embodiment of Formula (II), V is $CR_3$. In another embodiment of Formula (II), V is N.

In another embodiment of Formula (II), T is $CR_1R_2$ and V is $CR_3$. In another embodiment of Formula (II), T is O and V is $CR_3$. In another embodiment of Formula (II), T is $CR_1R_2$ and V is N. In another embodiment of Formula (II), T is O and V is N.

In another embodiment of Formula (II), W is $CR_4R_5$ and V is $CR_3$. In another embodiment of Formula (II), W is O and V is $CR_3$. In another embodiment of Formula (II), W is $CR_4R_5$ and V is N. In another embodiment of Formula (II), W is O and V is N.

In another embodiment of Formula (II), T is $CR_1R_2$, W is $CR_4R_5$, and V is $CR_3$. In another embodiment of Formula (II), T is $CR_1R_2$, W is O, and V is $CR_3$. In another embodiment of Formula (II), T is $CR_1R_2$, W is $CR_4R_5$, and V is N. In another embodiment of Formula (II), T is $CR_1R_2$, W is O, and V is N. In another embodiment of Formula (II), T is O, W is $CR_4R_5$, and V is $CR_3$.

In another embodiment of Formula (II), m is 1. In another embodiment of Formula (II), m is 2. In another embodiment of Formula (II), m is 3. In another embodiment of Formula (II), m is 4. In another embodiment of Formula (II), m is 5. In another embodiment of Formula (II), m is 1, 2 or 3. In another embodiment of Formula (II), m is 2, 3, or 4. In another embodiment of Formula (II), m is 1 or 2. In another embodiment of Formula (II), m is 3 or 4.

In another embodiment of Formula (II), Y is O and m is 1. In another embodiment of Formula (II), Y is O and m is 2. In another embodiment of Formula (II), Y is O and m is 3. In another embodiment of Formula (II), Y is O and m is 4. In another embodiment of Formula (II), Y is O and m is 1, 2, or 3. In another embodiment of Formula (II), Y is O and m is 2, 3, or 4. In another embodiment of Formula (II), Y is O and m is 1 or 2. In another embodiment of Formula (II), Y is O and m is 3 or 4.

In another embodiment of Formula (II), Y is absent and m is 1. In another embodiment of Formula (II), Y is absent and m is 2. In another embodiment of Formula (II), Y is absent and m is 3. In another embodiment of Formula (II), Y is absent and m is 4. In another embodiment of Formula (II), Y is absent and m is 1, 2, or 3. In another embodiment of Formula (II), Y is absent and m is 2, 3, or 4. In another embodiment of Formula (II), Y is absent and m is 1 or 2. In another embodiment of Formula (II), Y is absent and m is 3 or 4.

In another embodiment of Formula (II), Y is $NR_{10}$ and m is 1. In another embodiment of Formula (II), Y is $NR_{10}$ and m is 2. In another embodiment of Formula (II), Y is $NR_{10}$ and m is 3. In another embodiment of Formula (II), Y is $NR_{10}$ and m is 4. In another embodiment of Formula (II), Y is $NR_{10}$ and m is 1, 2, or 3. In another embodiment of Formula (II), Y is $NR_{10}$ and m is 2, 3, or 4. In another embodiment of Formula (II), Y is $NR_{10}$ and m is 1 or 2. In another embodiment of Formula (II), Y is $NR_{10}$ and m is 3 or 4.

In another embodiment of Formula (II), ring A is phenyl and n is 1. In another embodiment of Formula (II), ring A is phenyl and n is 2. In another embodiment of Formula (II), ring A is phenyl and n is 3. In another embodiment of Formula (II), ring A is pyridinyl and n is 1. In another embodiment of Formula (II), ring A is pyridinyl and n is 2. In another embodiment of Formula (II), ring A is pyridinyl and n is 3. In another embodiment of Formula (II), ring A is pyridazinyl and n is 1. In another embodiment of Formula (II), ring A is pyridazinyl and n is 2. In another embodiment of Formula (II), ring A is pyridazinyl and n is 3. In another embodiment of Formula (II), ring A is pyrimidinyl and n is 1. In another embodiment of Formula (II), ring A is pyrimidinyl and n is 2. In another embodiment of Formula (II), ring A is pyrimidinyl and n is 3. In another embodiment of Formula (II), ring A is pyrazinyl and n is 1. In another embodiment of Formula (II), ring A is pyrazinyl and n is 2. In another embodiment of Formula (II), ring A is pyrazinyl and n is 3. In another embodiment of Formula (II), ring A is triazinyl and n is 1. In another embodiment of Formula (II), ring A is triazinyl and n is 2. In another embodiment of Formula (II), ring A is triazinyl and n is 3.

In another embodiment of Formula (II), ring A is phenyl, n is 1, and Y is $NR_{10}$. In another embodiment of Formula (II), ring A is phenyl, n is 2, and Y is $NR_{10}$. In another embodiment of Formula (II), ring A is phenyl, n is 3, and Y is $NR_{10}$. In another embodiment of Formula (II), ring A is phenyl, n is 1, and Y is O. In another embodiment of Formula (II), ring A is phenyl, n is 2, and Y is O. In another embodiment of Formula (II), ring A is phenyl, n is 3, and Y is O. In another embodiment of Formula (II), ring A is phenyl, n is 1, and Y is absent. In another embodiment of Formula (II), ring A is phenyl, n is 2, and Y is absent. In another embodiment of Formula (II), ring A is phenyl, n is 3, and Y is absent.

In another embodiment of Formula (II), ring A is phenyl, n is 1, Y is $NR_{10}$, and m is 1 or 2. In another embodiment of Formula (II), ring A is phenyl, n is 2, Y is $NR_{10}$, and m is 1 or 2. In another embodiment of Formula (II), ring A is phenyl, n is 3, Y is $NR_{10}$, and m is 1 or 2. In another embodiment of Formula (II), ring A is phenyl, n is 1, Y is O, and m is 1 or 2. In another embodiment of Formula (II), ring A is phenyl, n is 2, Y is O, and m is 1 or 2. In another embodiment of Formula (II), ring A is phenyl, n is 3, Y is O, and m is 1 or 2. In another embodiment of Formula (II), ring A is phenyl, n is 1, Y is absent, and m is 1 or 2. In another embodiment of Formula (II), ring A is phenyl, n is 2, Y is absent, and m is 1 or 2. In another embodiment of Formula (II), ring A is phenyl, n is 3, Y is absent, and m is 1 or 2. In another embodiment of Formula (II), ring A is phenyl, n is 1, Y is $NR_{10}$, and m is 3 or 4. In another embodiment of Formula (II), ring A is phenyl, n is 2, Y is $NR_{10}$, and m is 3 or 4. In another embodiment of Formula (II), ring A is phenyl, n is 3, Y is $NR_{10}$, and m is 3 or 4. In another embodiment of Formula (II), ring A is phenyl, n is 1, Y is O, and m is 3 or 4. In another embodiment of Formula (II), ring A is phenyl, n is 2, Y is O, and m is 3 or 4. In another embodiment of Formula (II), ring A is phenyl, n is 3, Y is O, and m is 3 or 4. In another embodiment of Formula (II), ring A is phenyl, n is 1, Y is absent, and m is 3 or 4. In another embodiment of Formula (II), ring A is phenyl, n is 2, Y is absent, and m is 3 or 4. In another embodiment of Formula (II), ring A is phenyl, n is 3, Y is absent, and m is 3 or 4.

In another embodiment of Formula (II), ring A is pyridinyl, n is 1, and Y is $NR_{10}$. In another embodiment of Formula (II), ring A is pyridinyl, n is 2, and Y is $NR_{10}$. In another embodiment of Formula (II), ring A is pyridinyl, n is 3, and Y is $NR_{10}$. In another embodiment of Formula (II), ring A is pyridinyl, n is 1, and Y is O. In another embodiment of Formula (II), ring A is pyridinyl, n is 2, and Y is O. In another embodiment of Formula (II), ring A is pyridinyl, n is 3, and Y is O. In another embodiment of Formula (II), ring A is pyridinyl, n is 1, and Y is absent. In another embodiment of Formula (II), ring A is pyridinyl, n is 2, and Y is absent. In another embodiment of Formula (II), ring A is pyridinyl, n is 3, and Y is absent.

In another embodiment of Formula (II), ring A is pyridinyl, n is 1, Y is $NR_{10}$, and m is 1 or 2. In another embodiment of Formula (II), ring A is pyridinyl, n is 2, Y is $NR_{10}$, and m is 1 or 2. In another embodiment of Formula (II), ring A is pyridinyl, n is 3, Y is $NR_{10}$, and m is 1 or 2. In another embodiment of Formula (II), ring A is pyridinyl, n is 1, Y is O, and m is 1 or 2. In another embodiment of Formula (II), ring A is pyridinyl, n is 2, Y is O, and m is 1 or 2. In another embodiment of Formula (II), ring A is pyridinyl, n is 3, Y is O, and m is 1 or 2. In another embodiment of Formula (II), ring A is pyridinyl, n is 1, Y is absent, and m is 1 or 2. In another embodiment of Formula (II), ring A is pyridinyl, n is 2, Y is absent, and m is 1 or 2. In another embodiment of Formula (II), ring A is pyridinyl, n is 3, Y is absent, and m is 1 or 2. In another embodiment of Formula (II), ring A is pyridinyl, n is 1, Y is $NR_{10}$, and m is 3 or 4. In another embodiment of Formula (II), ring A is pyridinyl, n is 2, Y is $NR_{10}$, and m is 3 or 4. In another embodiment of Formula (II), ring A is pyridinyl, n is 3, Y is $NR_{10}$, and m is 3 or 4. In another embodiment of Formula (II), ring A is pyridinyl, n is 1, Y is O, and m is 3 or 4. In another embodiment of Formula (II), ring A is pyridinyl, n is 2, Y is O, and m is 3 or 4. In another embodiment of Formula (II), ring A is pyridinyl, n is 3, Y is O, and m is 3 or 4. In another embodiment of Formula (II), ring A is pyridinyl, n is 1, Y is absent, and m is 3 or 4. In another embodiment of Formula (II), ring A is pyridinyl, n is 2, Y is absent, and m is 3 or 4. In another embodiment of Formula (II), ring A is pyridinyl, n is 3, Y is absent, and m is 3 or 4.

In another embodiment of Formula (II), ring A is pyridazinyl, n is 1, and Y is $NR_{10}$. In another embodiment of Formula (II), ring A is pyridazinyl, n is 2, and Y is $NR_{10}$. In another embodiment of Formula (II), ring A is pyridazinyl, n is 3, and Y is $NR_{10}$. In another embodiment of Formula (II), ring A is pyridazinyl, n is 1, and Y is O. In another embodiment of Formula (II), ring A is pyridazinyl, n is 2, and Y is O. In another embodiment of Formula (II), ring A is pyridazinyl, n is 3, and Y is O. In another embodiment of Formula (II), ring A is pyridazinyl, n is 1, and Y is absent. In another embodiment of Formula (II), ring A is pyridazinyl, n is 2, and Y is absent. In another embodiment of Formula (II), ring A is pyridazinyl, n is 3, and Y is absent.

In another embodiment of Formula (II), ring A is pyridazinyl, n is 1, Y is $NR_{10}$, and m is 1 or 2. In another embodiment of Formula (II), ring A is pyridazinyl, n is 2, Y is $NR_{10}$, and m is 1 or 2. In another embodiment of Formula (II), ring A is pyridazinyl, n is 3, Y is $NR_{10}$, and m is 1 or 2. In another embodiment of Formula (II), ring A is pyridazinyl, n is 1, Y is O, and m is 1 or 2. In another embodiment of Formula (II), ring A is pyridazinyl, n is 2, Y is O, and m is 1 or 2. In another embodiment of Formula (II), ring A is pyridazinyl, n is 3, Y is O, and m is 1 or 2. In another embodiment of Formula (II), ring A is pyridazinyl, n is 1, Y is absent, and m is 1 or 2. In another embodiment of Formula (II), ring A is pyridazinyl, n is 2, Y is absent, and m is 1 or 2. In another embodiment of Formula (II), ring A is pyridazinyl, n is 3, Y is absent, and m is 1 or 2. In another embodiment of Formula (II), ring A is pyridazinyl, n is 1, Y is $NR_{10}$, and m is 3 or 4. In another embodiment of Formula (II), ring A is pyridazinyl, n is 2, Y is $NR_{10}$, and m is 3 or 4. In another embodiment of Formula (II), ring A is pyridazinyl, n is 3, Y is $NR_{10}$, and m is 3 or 4. In another embodiment of Formula (II), ring A is pyridazinyl, n is 1, Y is O, and m is 3 or 4. In another embodiment of Formula (II), ring A is pyridazinyl, n is 2, Y is O, and m is 3 or 4. In another embodiment of Formula (II), ring A is pyridazinyl, n is 3, Y is O, and m is 3 or 4. In another embodiment of Formula (II), ring A is pyridazinyl, n is 1, Y is absent, and m is 3 or 4. In another embodiment of Formula (II), ring A is pyridazinyl, n is 2, Y is absent, and m is 3 or 4. In another embodiment of Formula (II), ring A is pyridazinyl, n is 3, Y is absent, and m is 3 or 4.

In another embodiment of Formula (II), ring A is pyrimidinyl, n is 1, and Y is $NR_{10}$. In another embodiment of Formula (II), ring A is pyrimidinyl, n is 2, and Y is $NR_{10}$. In another embodiment of Formula (II), ring A is pyrimidinyl, n is 3, and Y is $NR_{10}$. In another embodiment of Formula (II), ring A is pyrimidinyl, n is 1, and Y is O. In another embodiment of Formula (II), ring A is pyrimidinyl, n is 2, and Y is O. In another embodiment of Formula (II), ring A is pyrimidinyl, n is 3, and Y is O. In another embodiment of Formula (II), ring A is pyrimidinyl, n is 1, and Y is absent. In another embodiment of Formula (II), ring A is pyrimidinyl, n is 2, and Y is absent. In another embodiment of Formula (II), ring A is pyrimidinyl, n is 3, and Y is absent.

In another embodiment of Formula (II), ring A is pyrimidinyl, n is 1, Y is $NR_{10}$, and m is 1 or 2. In another embodiment of Formula (II), ring A is pyrimidinyl, n is 2, Y is $NR_{10}$, and m is 1 or 2. In another embodiment of Formula (II), ring A is pyrimidinyl, n is 3, Y is $NR_{10}$, and m is 1 or 2. In another embodiment of Formula (II), ring A is pyrimidinyl, n is 1, Y is O, and m is 1 or 2. In another embodiment of Formula (II), ring A is pyrimidinyl, n is 2, Y is O, and m is 1 or 2. In another embodiment of Formula (II), ring A is pyrimidinyl, n is 3, Y is O, and m is 1 or 2. In another embodiment of Formula (II), ring A is pyrimidinyl, n is 1, Y is absent, and m is 1 or 2. In another embodiment of Formula (II), ring A is pyrimidinyl, n is 2, Y is absent, and m is 1 or 2. In another embodiment of Formula (II), ring A is pyrimidinyl, n is 3, Y is absent, and m is 1 or 2. In another embodiment of Formula (II), ring A is pyrimidinyl, n is 1, Y is $NR_{10}$, and m is 3 or 4. In another embodiment of Formula (II), ring A is pyrimidinyl, n is 2, Y is $NR_{10}$, and m is 3 or 4. In another embodiment of Formula (II), ring A is pyrimidinyl, n is 3, Y is $NR_{10}$, and m is 3 or 4. In another embodiment of Formula (II), ring A is pyrimidinyl, n is 1, Y is O, and m is 3 or 4. In another embodiment of Formula (II), ring A is pyrimidinyl, n is 2, Y is O, and m is 3 or 4. In another embodiment of Formula (II), ring A is pyrimidinyl, n is 3, Y is O, and m is 3 or 4. In another embodiment of Formula (II), ring A is pyrimidinyl, n is 1, Y is absent, and m is 3 or 4. In another embodiment of Formula (II), ring A is pyrimidinyl, n is 2, Y is absent, and m is 3 or 4. In another embodiment of Formula (II), ring A is pyrimidinyl, n is 3, Y is absent, and m is 3 or 4.

In another embodiment of Formula (II), ring A is pyrazinyl, n is 1, and Y is $NR_{10}$. In another embodiment of Formula (II), ring A is pyrazinyl, n is 2, and Y is $NR_{10}$. In another embodiment of Formula (II), ring A is pyrazinyl, n is 3, and Y is $NR_{10}$. In another embodiment of Formula (II), ring A is pyrazinyl, n is 1, and Y is O. In another embodiment of Formula (II), ring A is pyrazinyl, n is 2, and Y is O. In another embodiment of Formula (II), ring A is pyrazinyl, n is 3, and Y is O. In another embodiment of Formula (II), ring A is pyrazinyl, n is 1, and Y is absent. In another embodiment of Formula (II), ring A is pyrazinyl, n is 2, and Y is absent. In another embodiment of Formula (II), ring A is pyrazinyl, n is 3, and Y is absent.

In another embodiment of Formula (II), ring A is pyrazinyl, n is 1, Y is $NR_{10}$, and m is 1 or 2. In another embodiment of Formula (II), ring A is pyrazinyl, n is 2, Y is $NR_{10}$, and m is 1 or 2. In another embodiment of Formula (II), ring A is pyrazinyl, n is 3, Y is $NR_{10}$, and m is 1 or 2. In another embodiment of Formula (II), ring A is pyrazinyl, n is 1, Y is O, and m is 1 or 2. In another embodiment of Formula (II), ring A is pyrazinyl, n is 2, Y is O, and m is 1 or 2. In another embodiment of Formula (II), ring A is pyrazinyl, n is 3, Y is O, and m is 1 or 2. In another embodiment of Formula (II), ring A is pyrazinyl, n is 1, Y is absent, and m is 1 or 2. In another embodiment of Formula (II), ring A is pyrazinyl, n is 2, Y is absent, and m is 1 or 2. In another embodiment of Formula (II), ring A is pyrazinyl, n is 3, Y is absent, and m is 1 or 2. In another embodiment of Formula (II), ring A is pyrazinyl, n is 1, Y is $NR_{10}$, and m is 3 or 4. In another embodiment of Formula (II), ring A is pyrazinyl, n is 2, Y is $NR_{10}$, and m is 3 or 4. In another embodiment of Formula (II), ring A is pyrazinyl, n is 3, Y is $NR_{10}$, and m is 3 or 4. In another embodiment of Formula (II), ring A is pyrazinyl, n is 1, Y is O, and m is 3 or 4. In another embodiment of Formula (II), ring A is pyrazinyl, n is 2, Y is O, and m is 3 or 4. In another embodiment of Formula (II), ring A is pyrazinyl, n is 3, Y is O, and m is 3 or 4. In another embodiment of Formula (II), ring A is pyrazinyl, n is 1, Y is absent, and m is 3 or 4. In another embodiment of Formula (II), ring A is pyrazinyl, n is 2, Y is absent, and m is 3 or 4. In another embodiment of Formula (II), ring A is pyrazinyl, n is 3, Y is absent, and m is 3 or 4.

In another embodiment of Formula (II), ring A is triazinyl, n is 1, and Y is $NR_{10}$. In another embodiment of Formula (II), ring A is triazinyl, n is 2, and Y is $NR_{10}$. In another embodiment of Formula (II), ring A is triazinyl, n is 3, and Y is $NR_{10}$. In another embodiment of Formula (II), ring A is triazinyl, n is 1, and Y is O. In another embodiment of Formula (II), ring A is triazinyl, n is 2, and Y is O. In another embodiment of Formula (II), ring A is triazinyl, n is 3, and Y is O. In another embodiment of Formula (II), ring A is triazinyl, n is 1, and Y is absent. In another embodiment of Formula (II), ring A is triazinyl, n is 2, and Y is absent. In another embodiment of Formula (II), ring A is triazinyl, n is 3, and Y is absent.

In another embodiment of Formula (II), ring A is triazinyl, n is 1, Y is $NR_{10}$, and m is 1 or 2. In another embodiment of Formula (II), ring A is triazinyl, n is 2, Y is $NR_{10}$, and m is 1 or 2. In another embodiment of Formula (II), ring A is triazinyl, n is 3, Y is $NR_{10}$, and m is 1 or 2. In another embodiment of Formula (II), ring A is triazinyl, n is 1, Y is O, and m is 1 or 2. In another embodiment of Formula (II), ring A is triazinyl, n is 2, Y is O, and m is 1 or 2. In another embodiment of Formula (II), ring A is triazinyl, n is 3, Y is O, and m is 1 or 2. In another embodiment of Formula (II), ring A is triazinyl, n is 1, Y is absent, and m is 1 or 2. In another embodiment of Formula (II), ring A is triazinyl, n is 2, Y is absent, and m is 1 or 2. In another embodiment of Formula (II), ring A is triazinyl, n is 3, Y is absent, and m is 1 or 2. In another embodiment of Formula (II), ring A is triazinyl, n is 1, Y is $NR_{10}$, and m is 3 or 4. In another embodiment of Formula (II), ring A is triazinyl, n is 2, Y is $NR_{10}$, and m is 3 or 4. In another embodiment of Formula (II), ring A is triazinyl, n is 3, Y is $NR_{10}$, and m is 3 or 4. In another embodiment of Formula (II), ring A is triazinyl, n is 1, Y is O, and m is 3 or 4. In another embodiment of Formula (II), ring A is triazinyl, n is 2, Y is O, and m is 3 or 4. In another embodiment of Formula (II), ring A is triazinyl, n is 3, Y is O, and m is 3 or 4. In another embodiment of Formula (II), ring A is triazinyl, n is 1, Y is absent, and m is 3 or 4. In another embodiment of Formula (II), ring A is triazinyl, n is 2, Y is absent, and m is 3 or 4. In another embodiment of Formula (II), ring A is triazinyl, n is 3, Y is absent, and m is 3 or 4.

In another embodiment of Formula (II), ring A is phenyl, T is $CR_1R_2$, W is $CR_4R_5$, and V is $CR_3$. In another embodiment of Formula (II), ring A is phenyl, p is 0, T is $CR_1R_2$, W is $CR_4R_5$, and V is $CR_3$. In another embodiment of Formula (II), ring A is phenyl, T is $CR_1R_2$, W is $CR_4R_5$, V is $CR_3$, and n is 1. In another embodiment of Formula (II), ring A is phenyl, T is $CR_1R_2$, W is $CR_4R_5$, V is $CR_3$, and n is 2. In another embodiment of Formula (II), ring A is phenyl, T is $CR_1R_2$, W is $CR_4R_5$, V is $CR_3$, and n is 3. In another embodiment of Formula (II), ring A is phenyl, p is 0, T is $CR_1R_2$, W is $CR_4R_5$, V is $CR_3$, and n is 1. In another embodiment of Formula (II), ring A is phenyl, p is 0, T is $CR_1R_2$, W is $CR_4R_5$, V is $CR_3$, and n is 2. In another embodiment of Formula (II), ring A is phenyl, p is 0, T is $CR_1R_2$, W is $CR_4R_5$, V is $CR_3$, and n is 3.

In another embodiment of Formula (II), ring A is phenyl, T is $CR_1R_2$, W is $CR_4R_5$, V is $CR_3$, and Y is O. In another embodiment of Formula (II), ring A is phenyl, p is 0, T is $CR_1R_2$, W is $CR_4R_5$, V is $CR_3$, and Y is O. In another embodiment of Formula (II), ring A is phenyl, T is $CR_1R_2$, W is $CR_4R_5$, V is $CR_3$, Y is O, and n is 1. In another embodiment of Formula (II), ring A is phenyl, T is $CR_1R_2$, W is $CR_4R_5$, V is $CR_3$, Y is O, and n is 2. In another embodiment of Formula (II), ring A is phenyl, T is $CR_1R_2$, W is $CR_4R_5$, V is $CR_3$, Y is O, and n is 3. In another embodiment of Formula (II), ring A is phenyl, p is 0, T is $CR_1R_2$, W is $CR_4R_5$, V is $CR_3$, Y is O, and n is 1. In another embodiment of Formula (II), ring A is phenyl, p is 0, T is $CR_1R_2$, W is $CR_4R_5$, V is $CR_3$, Y is O, and n is 2. In another embodiment of Formula (II), ring A is phenyl, p is 0, T is $CR_1R_2$, W is $CR_4R_5$, V is $CR_3$, Y is O, and n is 3.

In another embodiment of Formula (II), ring A is phenyl, T is $CR_1R_2$, W is $CR_4R_5$, V is $CR_3$, Y is O, and m is 1 or 2. In another embodiment of Formula (II), ring A is phenyl, p is 0, T is $CR_1R_2$, W is $CR_4R_5$, V is $CR_3$, Y is O, and m is 1 or 2. In another embodiment of Formula (II), ring A is phenyl, T is $CR_1R_2$, W is $CR_4R_5$, V is $CR_3$, Y is O, n is 1, and m is 1 or 2. In another embodiment of Formula (II), ring A is phenyl, T is $CR_1R_2$, W is $CR_4R_5$, V is $CR_3$, Y is O, n is 2, and m is 1 or 2. In another embodiment of Formula (II), ring A is phenyl, T is $CR_1R_2$, W is $CR_4R_5$, V is $CR_3$, Y is O, n is 3, and m is 1 or 2. In another embodiment of Formula (II), ring A is phenyl, p is 0, T is $CR_1R_2$, W is $CR_4R_5$, V is $CR_3$, Y is O, n is 1, and m is 1 or 2. In another embodiment of Formula (II), ring A is phenyl, p is 0, T is $CR_1R_2$, W is $CR_4R_5$, V is $CR_3$, Y is O, n is 2, and m is 1 or 2. In another embodiment of Formula (II), ring A is phenyl, p is 0, T is $CR_1R_2$, W is $CR_4R_5$, V is $CR_3$, Y is O, n is 3, and m is 1 or 2. In another embodiment of Formula (II), ring A is phenyl, T is $CR_1R_2$, W is $CR_4R_5$, V is $CR_3$, Y is O, and m is 3 or 4. In another embodiment of Formula (II), ring A is phenyl, p is 0, T is $CR_1R_2$, W is $CR_4R_5$, V is $CR_3$, Y is O, and m is 3 or 4. In another embodiment of Formula (II), ring A is phenyl, T is $CR_1R_2$, W is $CR_4R_5$, V is $CR_3$, Y is O, n is 1, and m is 3 or 4. In another embodiment of Formula (II), ring A is phenyl, T is $CR_1R_2$, W is $CR_4R_5$, V is $CR_3$, Y is O, n is 2, and m is 3 or 4. In another embodiment of Formula (II), ring A is phenyl, T is $CR_1R_2$, W is $CR_4R_5$, V is $CR_3$, Y is O, n is 3, and m is 3 or 4. In another embodiment of Formula (II), ring A is phenyl, p is 0, T is $CR_1R_2$, W is $CR_4R_5$, V is $CR_3$, Y is O, n is 1, and m is 3 or 4. In another embodiment of Formula (II), ring A is phenyl, p is 0, T is $CR_1R_2$, W is $CR_4R_5$, V is $CR_3$, Y is O, n is 2, and m is 3 or 4. In another embodiment of Formula (II), ring A is phenyl, p is 0, T is $CR_1R_2$, W is $CR_4R_5$, V is $CR_3$, Y is O, n is 3, and m is 3 or 4.

In another embodiment of Formula (II), p is 0 and $R_1$, $R_2$, $R_4$, and $R_5$ are each H. In another embodiment of Formula (II), p is 0; $R_1$, $R_2$, $R_4$, and $R_5$ are each H; and $R_3$ is H. In another embodiment of Formula (II), p is 0; $R_1$, $R_2$, $R_4$, and $R_5$ are each H; $R_3$ is H; and $R_6$, $R_7$, $R_8$, $R_9$, and $R_{11}$ are each H. In another embodiment of Formula (II), p is 0; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (II), p is 1 and $R_1$, $R_2$, $R_4$, and $R_5$ are each H. In another embodiment of Formula (II), p is 1; $R_1$, $R_2$, $R_4$, and $R_5$ are each H; and $R_3$ is H. In another embodiment of Formula (II), p is 1; $R_1$, $R_2$, $R_4$, and $R_5$ are each H; $R_3$ is H; and $R_6$, $R_7$, $R_8$, $R_9$, and $R_{11}$ are each H. In another embodiment of Formula (II), p is 1; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (II), p is 2 and $R_1$, $R_2$, $R_4$, and $R_5$ are each H. In another embodiment of Formula (II), p is 2; $R_1$, $R_2$, $R_4$, and $R_5$ are each H; and $R_3$ is H. In another embodiment of Formula (II), p is 2; $R_1$, $R_2$, $R_4$, and $R_5$ are each H; $R_3$ is H; and $R_6$, $R_7$, $R_8$, $R_9$, and $R_{11}$ are each H. In another embodiment of Formula (II), p is 2; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (II), p is 1, 2, 3, or 4 and R is fluorine. In another embodiment of Formula (II), p is 1, 2, 3, or 4 and R is deuterium. In another embodiment of Formula (II), one or more of $R_1$, $R_2$, $R_4$, and $R_5$ is fluorine. In another embodiment of Formula (II), one or more of $R_1$, $R_2$, $R_4$, and $R_5$ is deuterium. In another embodiment of Formula (II), one or more of $R_6$, $R_7$, $R_8$, $R_9$, and $R_{11}$ is fluorine. In another embodiment of Formula (II), one or more of $R_6$, $R_7$, $R_8$, $R_9$, and $R_{11}$ is deuterium. In another embodiment of Formula (II), one or more of each $R_{12}$ and $R_{13}$ is fluorine. In another embodiment of Formula (II), one or more of each $R_{12}$ and $R_{13}$ is deuterium.

Each of the embodiments described herein with respect to compounds of Formula II also applies to compounds of Formula II-A.

According to Formula I-A, I, II-A, or II herein, when ring A is pyridinyl, the position of the pyridinyl N atom is specified as shown below:

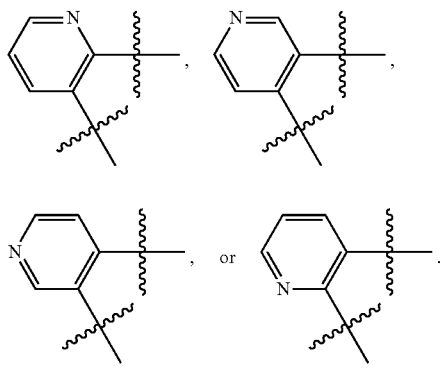

Further, according to Formula I-A, I, II-A, or II herein, when ring A is pyridazinyl, the positions of the pyridazinyl N atoms are specified as shown below:

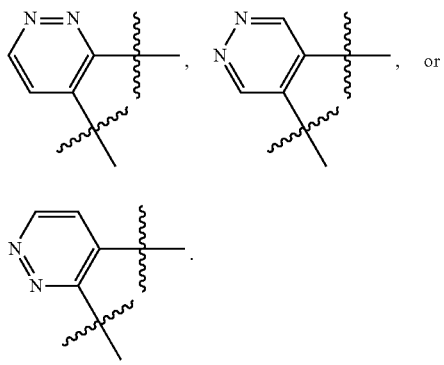

Further, according to Formula I-A, I, II-A, or II herein, when ring A is pyrimidinyl, the positions of the pyrimidinyl N atoms are specified as shown below:

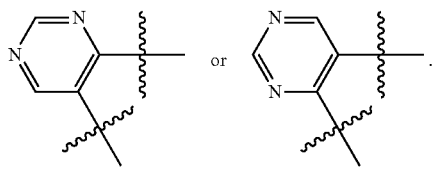 [SMILES: *c1cncnc1* ; *c1cncnc1*]

Further, according to Formula I-A, I, II-A, or II herein, when ring A is pyrazinyl, the positions of the pyrazinyl N atoms are specified as shown below:

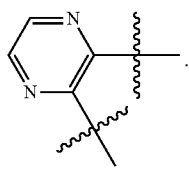 [SMILES: *c1nccnc1*]

Further, according to Formula I-A, I, II-A, or II herein, when ring A is triazinyl, the positions of the triazinyl N atoms are specified as shown below:

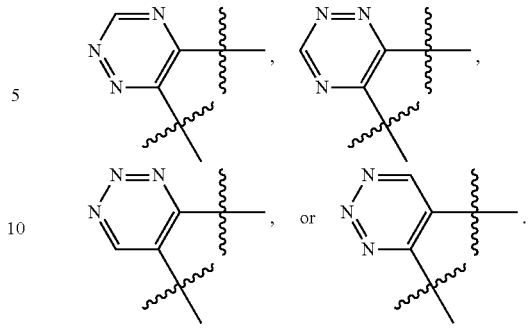

All other variables described in Formula I-A, I, II-A, or II are as defined above.

Certain embodiments of compounds of Formula I-A, I, II-A, II or pharmaceutically acceptable salts thereof, are shown below in Table 1. Compounds of Formula I-A, I, II-A, II or pharmaceutically acceptable salts thereof, and compounds of Table 1, or pharmaceutically acceptable salts thereof, collectively or individually are sometimes referred to herein as "compounds of the invention" or "compounds provided herein".

TABLE 1

| Structure | Compound No. |
|---|---|
| 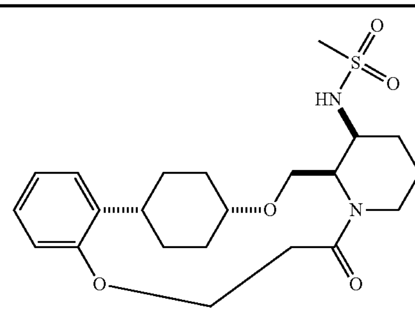 | 1 |
| 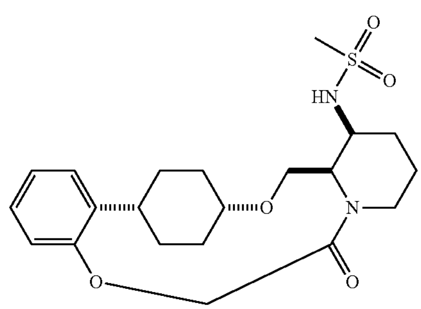 | 2 |
| 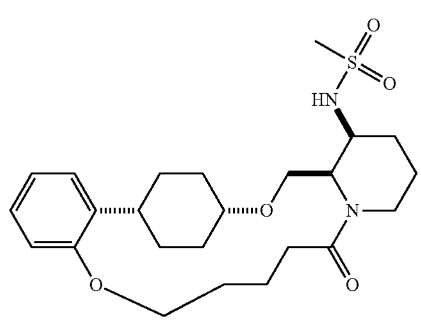 | 3 |

TABLE 1-continued

| Structure | Compound No. |
|---|---|
| 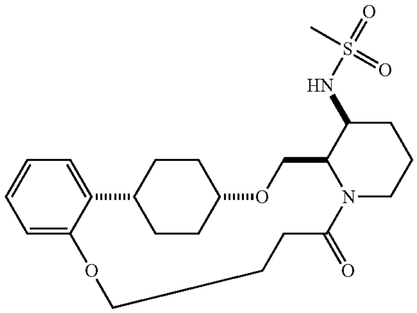 | 4 |
| 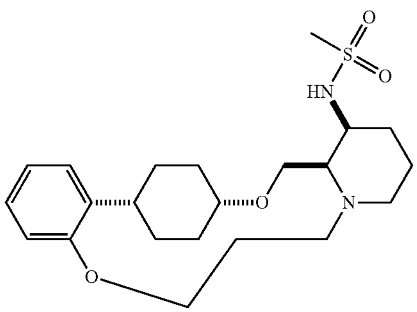 | 5 |
| 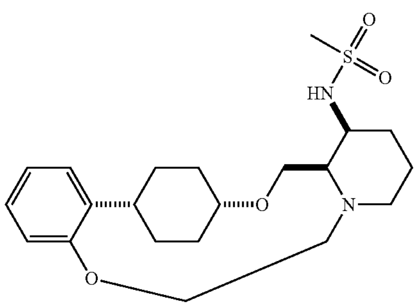 | 6 |
| 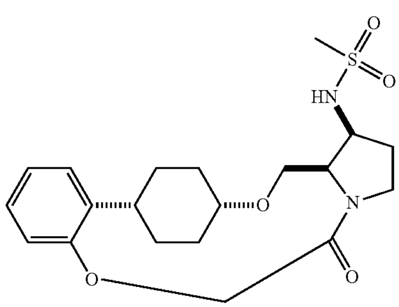 | 7 |
| 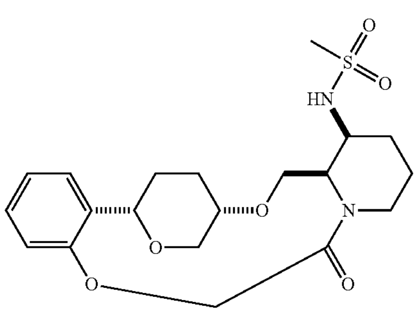 | 8 |

TABLE 1-continued

| Structure | Compound No. |
|---|---|
| 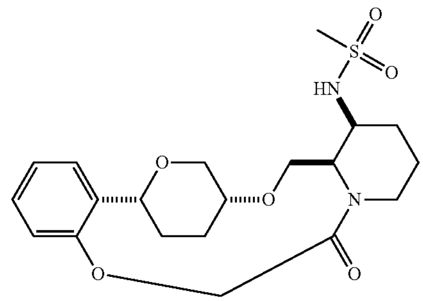 | 9 |
| 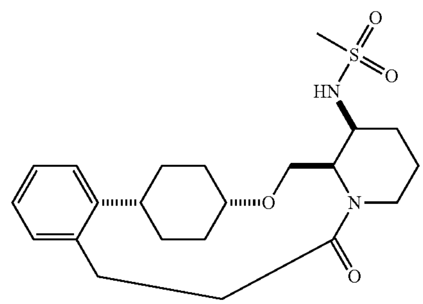 | 10 |
| 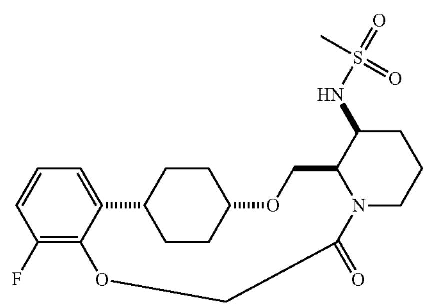 | 11 |
| 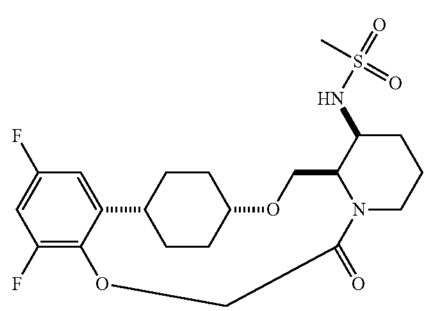 | 12 |
| 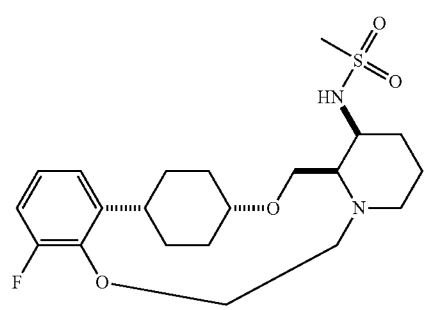 | 13 |

TABLE 1-continued

| Structure | Compound No. |
|---|---|
| (structure) | 14 |
| (structure) | 15 |
| (structure) | 16 |
| (structure) | 17 |
| (structure) | 18 |
| (structure) | 19 |
| (structure) | 20 |
| (structure) | 21 |
| (structure) | 22 |
| (structure) | 23 |

TABLE 1-continued

| Structure | Compound No. |
|---|---|
| 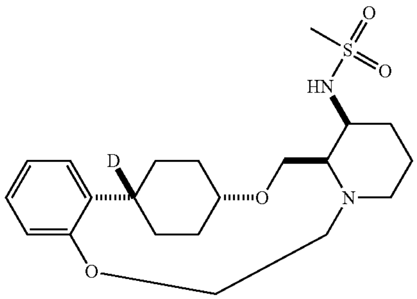 | 24 |
| 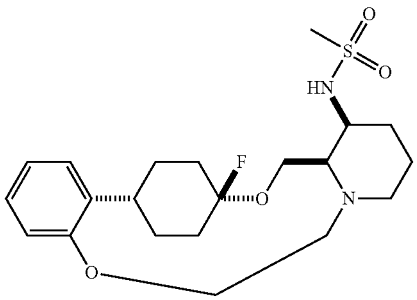 | 25 |
| 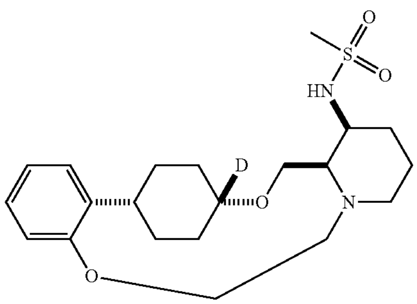 | 26 |
| 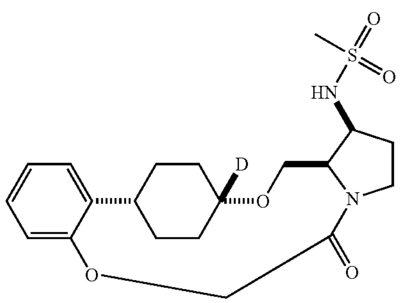 | 27 |
| 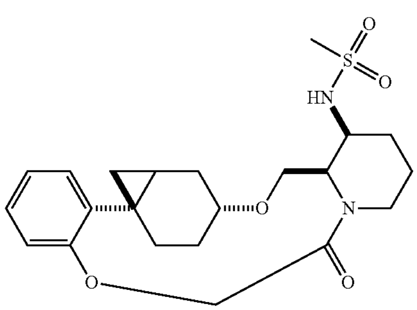 | 28 |
| | 29 |
| | 30 |
| | 31 |
| | 32 |
| | 33 |

TABLE 1-continued
| Structure | Compound No. |
|---|---|
| 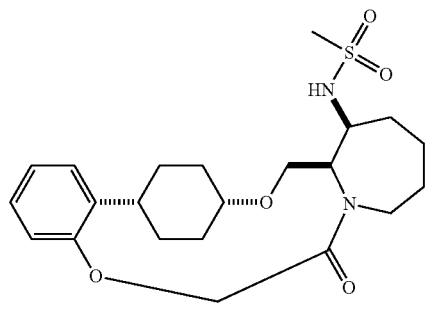 | 34 |
| 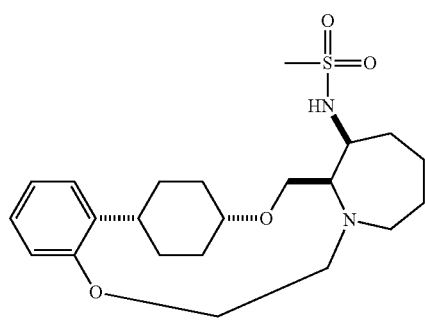 | 35 |
| 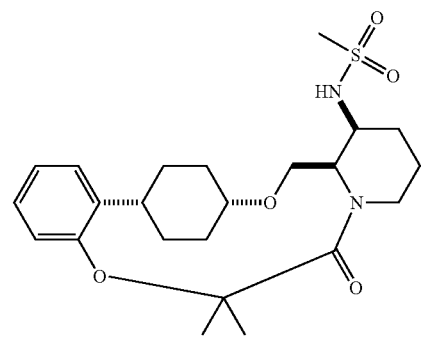 | 36 |
| 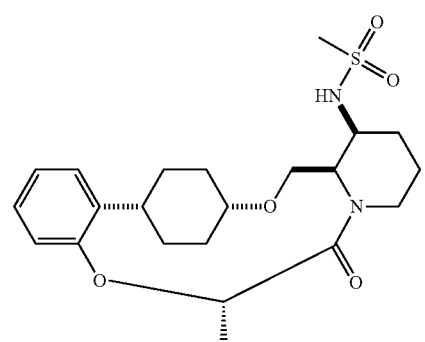 | 37 |
TABLE 1-continued
| Structure | Compound No. |
|---|---|
| 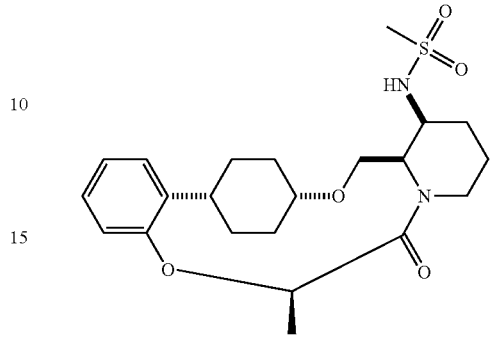 | 38 |
| 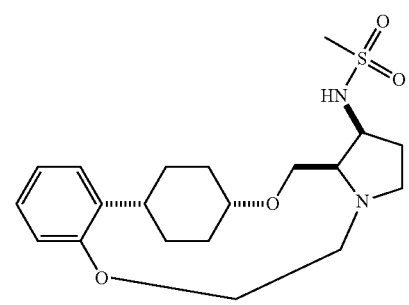 | 39 |
| 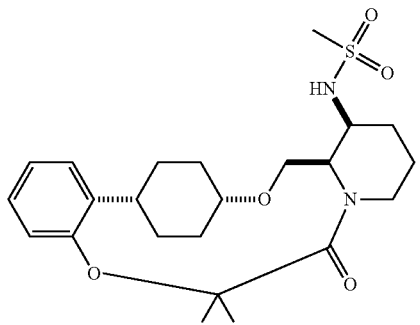 | 40 |
| 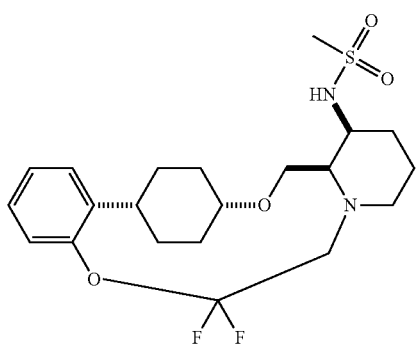 | 41 |

TABLE 1-continued

| Structure | Compound No. |
|---|---|
| 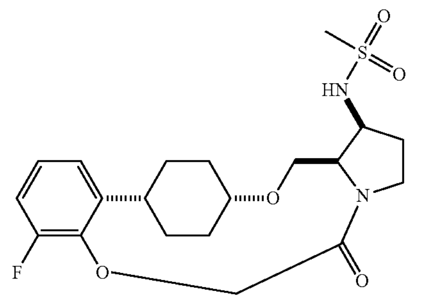 | 42 |
| 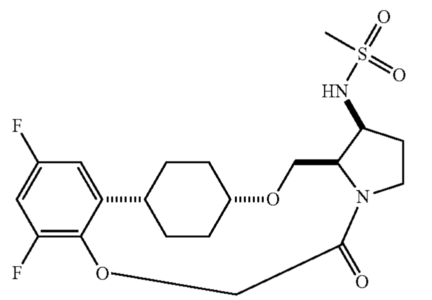 | 43 |
| 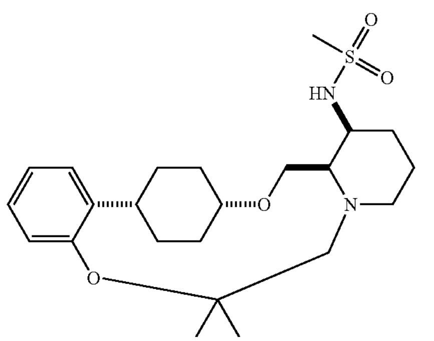 | 44 |
| 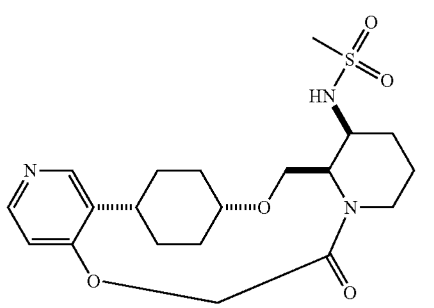 | 45 |
| 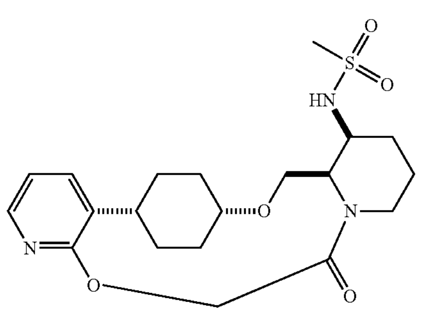 | 46 |
| | 47 |
| | 48 |
| | 49 |
| | 50 |
| | 51 |

TABLE 1-continued
| Structure | Compound No. |
|---|---|
| 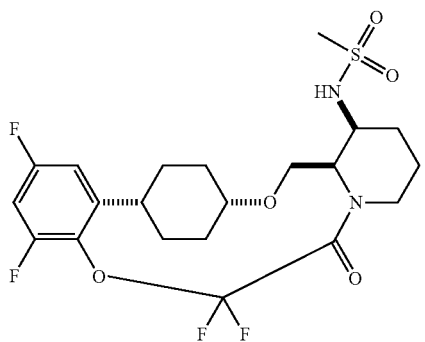 | 52 |
| 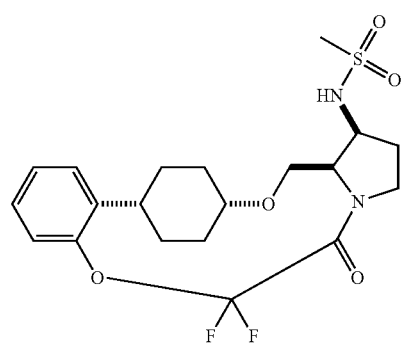 | 53 |
| 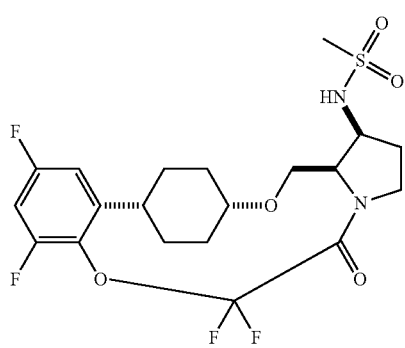 | 54 |
| 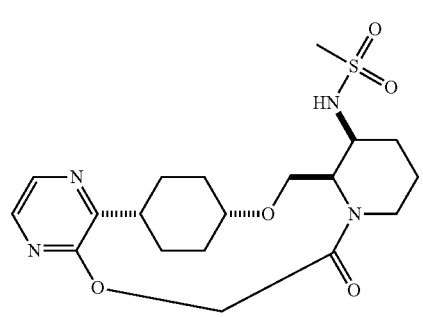 | 55 |
TABLE 1-continued
| Structure | Compound No. |
|---|---|
| 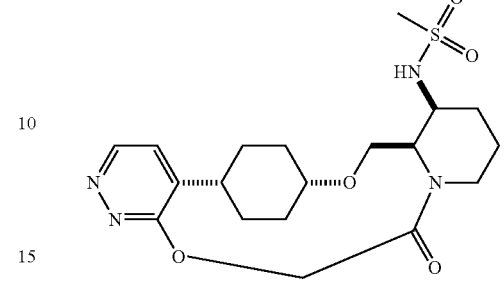 | 56 |
| 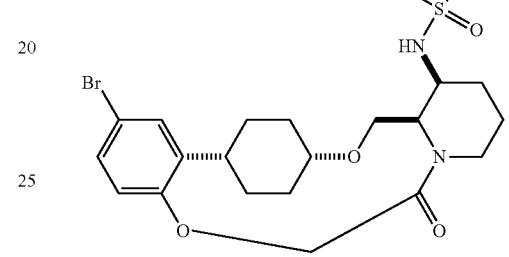 | 57 |
| 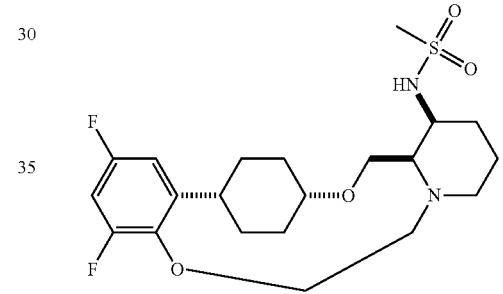 | 58 |
| 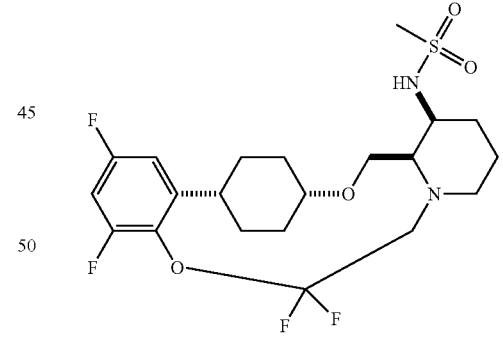 | 59 |
| 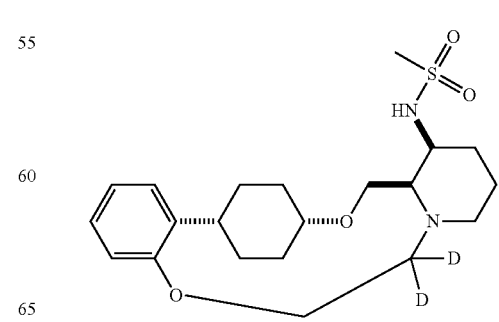 | 60 |

TABLE 1-continued

| Structure | Compound No. |
|---|---|
| 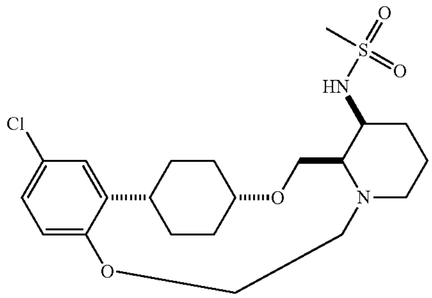 | 61 |
| 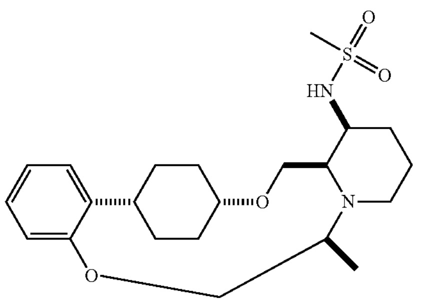 | 62 |
| 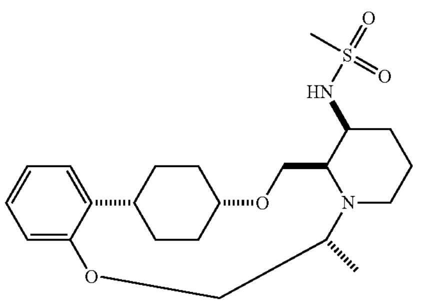 | 63 |
| 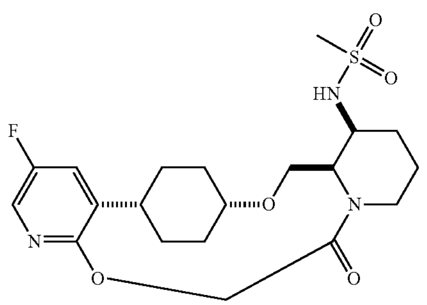 | 64 |
| 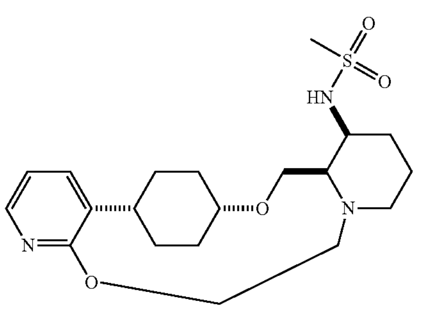 | 65 |
| | 66 |
| | 67 |
| | 68 |
| | 69 |
| | 70 |

TABLE 1-continued
| Structure | Compound No. |
|---|---|
| 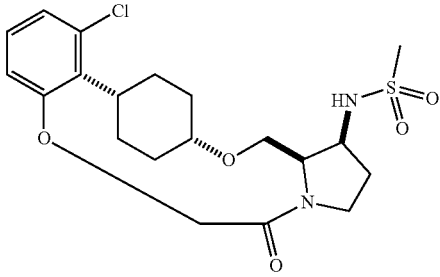 | 71 |
| 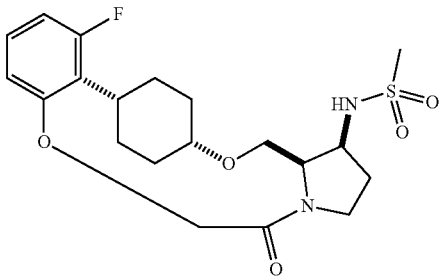 | 72 |
| 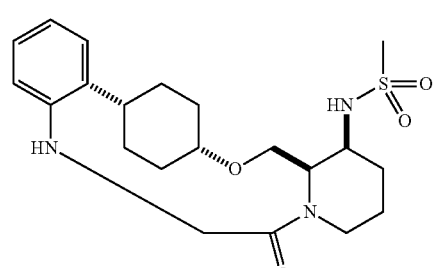 | 73 |
| 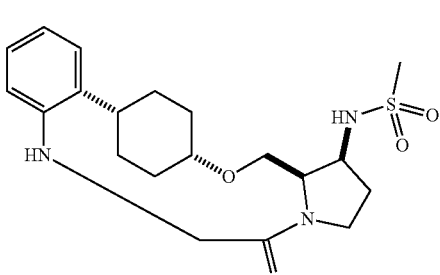 | 74 |
| 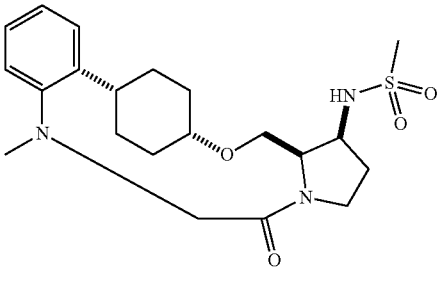 | 75 |
| 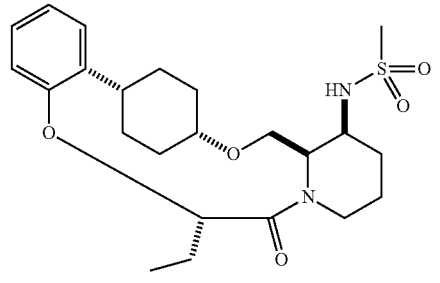 | 76 |
| 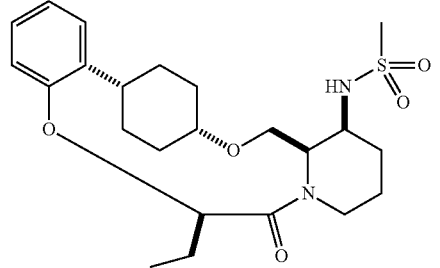 | 77 |
| 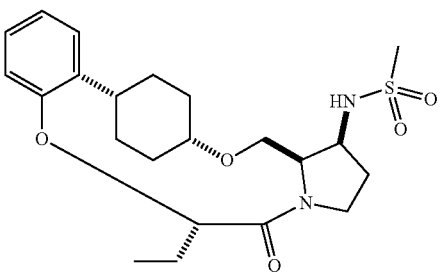 | 78 |
| 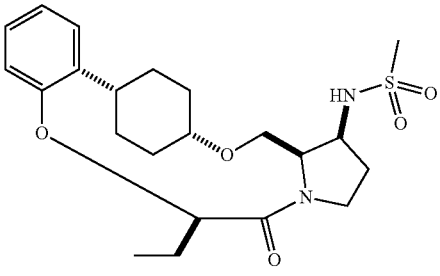 | 79 |
|  | 80 |

TABLE 1-continued

| Structure | Compound No. |
|---|---|
| (structure) | 81 |
| (structure) | 82 |
| (structure) | 83 |
| (structure) | 84 |

The disclosed compounds possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of two or more isomers is utilized as the disclosed compound described herein. In another embodiment, a pure isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In another embodiment, the compounds described herein include a $^2$H (i.e., deuterium) isotope.

In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources or are prepared using procedures described herein.

Methods of Treatment

The compounds of the invention can be used in a method of treating a disease or condition in a subject, said method comprising administering to the subject a compound of the invention, or a pharmaceutical composition comprising a compound of the invention. In one embodiment of the methods described herein, the subject is human. In one aspect, the compounds provided herein are useful in treatment of a disease or condition by acting as an agonist of the orexin-2 receptor.

The compounds of the invention can be used to treat a disease or condition selected from the group consisting of narcolepsy, cataplexy, or hypersomnia in a subject in need thereof.

In one embodiment, the compounds of the invention can be used to treat narcolepsy in a subject. In one embodiment, the compounds of the invention can be used to treat cataplexy in a subject. In one embodiment, the compounds of the invention can be used to treat hypersomnia in a subject.

Orexin-2 receptors are important in a wide range of biological functions. This suggests that orexin-2 receptors play a role in diverse disease processes in humans or other species. The compound of the present invention is useful for treating, preventing, or ameliorating the risk of one or more of the following symptoms or diseases of various neurological and psychiatric diseases associated with alterations in sleep/wake function. That is, narcolepsy, narcolepsy with cataplexy, idiopathic hypersomnia, hypersomnia, sleep apnea syndrome, narcolepsy syndrome, hypersomnolence syndrome characterized by hypersomnia (e.g., in subjects with Kleine Levin syndrome, major depression with hypersomnia, Lewy body dementia, Parkinson's disease, progressive supranuclear paralysis, Prader-Willi syndrome, Mobius syndrome, hypoventilation syndrome, Niemann-Pick disease type C, brain contusion, cerebral infarction, brain tumor, muscular dystrophy, multiple sclerosis, multiple systems atrophy, acute disseminated encephalomyelitis, Guillain-Barre syndrome, Rasmussen's encephalitis, Wernicke's encephalitis, limbic encephalitis, or Hashimoto's encephalopathy), coma, loss of consciousness, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, or central obesity), insulin resistance syndrome, Alzheimer's disease, disturbance of consciousness such as coma and the like, side effects and complications due to anesthesia, sleep disturbance, excessive daytime sleepiness, sleep problem, insomnia, intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, sundowning, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, polycysticovarian disease, craniopharingioma, Prader-Willi syndrome, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity, such as lowering the risk of left ventricular hypertrophy, migraine pain, headache, neuropathic pain, Parkinson's disease, psychosis, autoimmune encephalitis, cancer related fatigue (such as excessive daytime sleepiness or fatigue associated with cancer and/or chemotherapy), cancer related nausea and vomiting, corticobasal degeneration, Huntington's disease, neuromyelitis optica, nociception, progressive supranuclear palsy, schizophrenia, systemic lupus erythematosus, traumatic brain injury, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, post-traumatic stress disorder (PTSD), separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's chorea, amyotrophic lateral sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury (TBI).

Particularly, the compound of the present invention is useful as a therapeutic or prophylactic drug for narcolepsy, idiopathic hypersomnia, hypersomnia, sleep apnea syndrome, narcolepsy syndrome, hypersomnolence syndrome characterized by hypersomnia (e.g., in Parkinson's disease, Guillain-Barre syndrome or Kleine Levin syndrome), Alzheimer's disease, obesity, insulin resistance syndrome, cardiac failure, diseases related to bone loss, sepsis, disturbance of consciousness such as coma and the like, side effects and complications due to anesthesia, and the like, or anesthetic antagonist.

In one embodiment, the compound of the present invention has orexin-2 receptor agonist activity and is useful as a prophylactic or therapeutic agent for narcolepsy.

In another embodiment, the compound of the present invention is useful as a prophylactic or therapeutic agent for narcolepsy type-1. In another embodiment, the compound of the present invention is useful as a prophylactic or therapeutic agent for narcolepsy type-2. In another embodiment, the compound of the present invention is useful as a prophylactic or therapeutic agent for narcolepsy and excessive daytime sleepiness. In another embodiment, the compound of the present invention is useful as a prophylactic or therapeutic agent for narcolepsy, cataplexy, and excessive daytime sleepiness. In another embodiment, the compound of the present invention is useful as a prophylactic or therapeutic agent for narcolepsy and cataplexy. In another embodiment, the compound of the present invention is useful as a prophylactic or therapeutic agent for excessive daytime sleepiness. In another embodiment, the compound of the present invention is useful as a prophylactic or therapeutic agent for idiopathic hypersomnia. In another embodiment, the compound of the present invention is useful as a prophylactic or therapeutic agent for obstructive sleep apnea.

In another embodiment, the compound of the present invention has orexin-2 receptor agonist activity and is useful as a prophylactic or therapeutic agent for hypersomnia in Parkinson's disease.

In another embodiment, the compound of the present invention has orexin-2 receptor agonist activity and is useful as a prophylactic or therapeutic agent for hypersomnia. In another embodiment, the compound of the present invention has orexin-2 receptor agonist activity and is useful as a prophylactic or therapeutic agent for excessive daytime sleepiness associated with Parkinson's disease.

In another embodiment, the compound of the present invention has orexin-2 receptor agonist activity and is useful as a prophylactic or therapeutic agent for excessive daytime sleepiness or fatigue associated with cancer and/or chemotherapy.

In another embodiment, the present invention provides a method of treating narcolepsy in a subject in need thereof comprising administering to the subject a compound of Formula I-A, I, II-A, or II, or a pharmaceutically acceptable salt thereof.

In another embodiment, the present invention provides a method of treating narcolepsy type-1 in a subject in need thereof comprising administering to the subject a compound of Formula I-A, I, II-A, or II, or a pharmaceutically acceptable salt thereof.

In another embodiment, the present invention provides a method of treating narcolepsy type-2 in a subject in need thereof comprising administering to the subject a compound of Formula I-A, I, II-A, or II, or a pharmaceutically acceptable salt thereof.

In another embodiment, the present invention provides a method of treating narcolepsy and excessive daytime sleepiness in a subject in need thereof comprising administering to the subject a compound of Formula I-A, I, II-A, or II, or a pharmaceutically acceptable salt thereof.

In another embodiment, the present invention provides a method of treating narcolepsy, cataplexy, and excessive daytime sleepiness in a subject in need thereof comprising administering to the subject a compound of Formula I-A, I, II-A, or II, or a pharmaceutically acceptable salt thereof.

In another embodiment, the present invention provides a method of treating narcolepsy and cataplexy in a subject in need thereof comprising administering to the subject a compound of Formula I-A, I, II-A, or II, or a pharmaceutically acceptable salt thereof.

In another embodiment, the present invention provides a method of treating excessive daytime sleepiness in a subject in need thereof comprising administering to the subject a compound of Formula I-A, I, II-A, or II, or a pharmaceutically acceptable salt thereof.

In another embodiment, the present invention provides a method of treating idiopathic hypersomnia in a subject in need thereof comprising administering to the subject a compound of Formula I-A, I, II-A, or II, or a pharmaceutically acceptable salt thereof.

In another embodiment, the present invention provides a method of treating excessive daytime sleepiness and idiopathic hypersomnia in a subject in need thereof comprising administering to the subject a compound of Formula I-A, I, II-A, or II, or a pharmaceutically acceptable salt thereof.

In another embodiment, the present invention provides a method of treating obstructive sleep apnea in a subject in need thereof comprising administering to the subject a compound of Formula I-A, I, II-A, or II, or a pharmaceutically acceptable salt thereof.

In another embodiment, the present invention provides a method of treating excessive daytime sleepiness and obstructive sleep apnea in a subject in need thereof comprising administering to the subject a compound of Formula I-A, I, II-A, or II, or a pharmaceutically acceptable salt thereof.

In any of the methods as described herein, the subject is administered a compound of Formula I. In any of the methods as described herein, the subject is administered a compound of Formula II.

Each of the embodiments described herein with respect to the use of compounds of Formula I also applies to compounds of Formula I-A. Each of the embodiments described herein with respect to the use of compounds of Formula II also applies to compounds of Formula II-A.

In any of the compositions or methods as described herein, the compound of Formula I-A, I, II-A, II, or a pharmaceutically acceptable salt thereof, is present and/or administered in a therapeutically effective amount.

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of narcolepsy or cataplexy in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 1,000 mg. In some embodiments, a dose of a disclosed compound used in compositions described herein is less than about 1,000 mg, or less than about 800 mg, or less than about 600 mg, or less than about 500 mg, or less than about 300 mg, or less than about 200 mg, or less than about 100 mg, or less than about 50 mg, or less than about 20 mg, or less than about 10 mg. For example, a dose is about 10 mg, 20 mg, 25 mg, 30 mg, 40 mg, 50 mg, 60 mg, 70 mg, 80 mg, 90 mg, 100 mg, 120 mg, 140 mg, 160 mg, 180 mg, 200 mg, 220 mg, 240, 260 mg, 280 mg, 300 mg, 350 mg, 400 mg, 450 mg, 500 mg, 550 mg, or about 600 mg.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application. The following examples further illustrate aspects of the present invention. However, they are in no way a limitation of the teachings or disclosure of the present invention as set forth herein.

EXAMPLES

The invention is further illustrated by the following examples, which should not be construed as further limiting. The practice of the present invention will employ, unless otherwise indicated, conventional techniques of organic synthesis, cell biology, cell culture, molecular biology, transgenic biology, microbiology and immunology, which are within the skill of the art.

General Procedures

Example 1: Synthesis Procedures

Synthesis procedures for preparation of the compounds of the invention are readily available to the ordinary skilled artisan. Unless otherwise indicated, starting materials were generally obtained from commercial sources.

The following abbreviations are used in the synthetic examples below:
AcOH=acetic acid
DCM=dichloromethane
MsCl=methanesulfonyl chloride
SFC=supercritical fluid chromatography
MeOH=methanol
DABCO=1,4-diazabicyclo[2.2.2]octane
THF=tetrahydrofuran
EtOH=ethanol
$PtO_2$=platinum dioxide
HATU=1-[bis(dimethylamino)methylene]-1H-1,2,3-triazolo[4,5-b]pyridinium 3-oxide hexafluorophosphate
DIPEA=N,N-diisopropylethylamine
ACN or MeCN=acetonitrile
$NEt_3$ or TEA=triethylamine
PE=petroleum ether
EtOAc=ethyl acetate
DMF=dimethyl formamide
TFA=trifluoroacetic acid
EA=ethyl acetate
$LiOH \cdot H_2O$=lithium hydroxide monohydrate
NMO=N-methylmorpholine-N-oxide
min=minutes
hr=hours NaH=sodium hydride
Pd₂(dba)₃=tris(dibenzylideneacetone)dipalladium(0)
MeI=methyl iodide
DMSO=dimethyl sulfoxide
TMSOTf=trimethylsilyl trifluoromethanesulfonate
i-PrOH=isopropanol
PPh₃=triphenylphosphine
DIAD=diisopropyl azodicarboxylate
Pd/C=palladium on carbon
XantPhos=4,5-bis(diphenylphosphino)-9,9-dimethylxanthene
Boc=tert-butyloxycarbonyl
Ms=methanesulfonyl
Bn=benzyl
Cbz=carboxybenzyl
TBS=tert-butyldimethylsilyl
TfO=trifluoromethanesulfonate
KHMDS=Potassium bis(trimethylsilyl)amide solution
BH₃Me₂S=borane dimethyl sulfide complex
TMSCl=chlorotrimethylsilane
DMPU=1,3-dimethyl-3,4,5,6-tetrahydro-2(1H)-pyrimidinone
LDA=lithium diisopropylamide
DBU=1,8-diazabicyclo[5.4.0]undec-7-ene
PMB=para-methoxybenzy
Et=ethyl
Me=methyl
CMPI=2-chloro-1-methylpyridinium iodide
IrCl(CO)(PPh₃)₂=bis(triphenylphosphine)iridium(I) carbonyl chloride Scheme 1

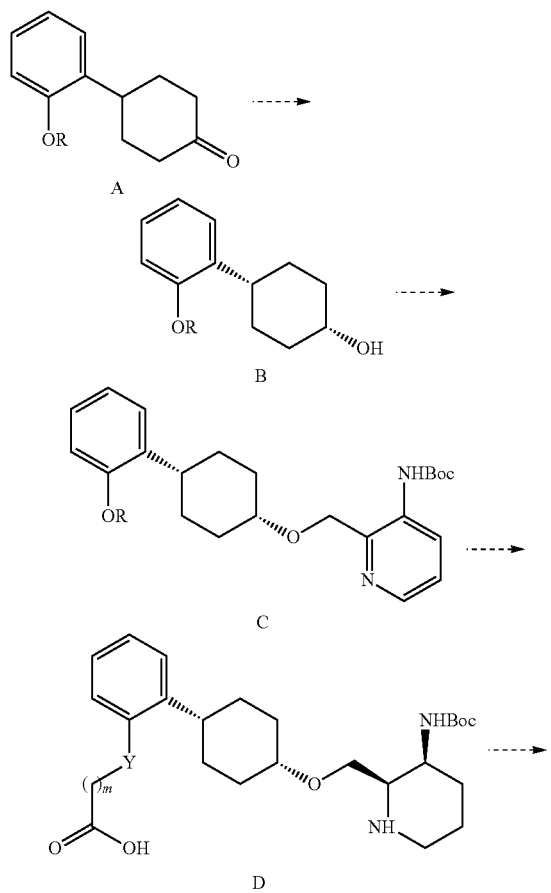

A

B

C

D

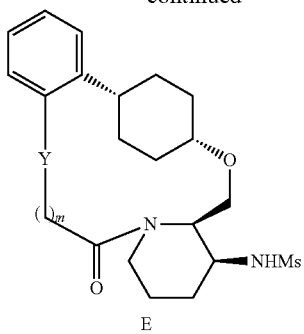

E

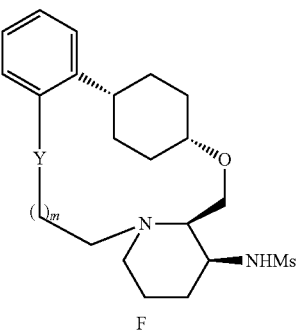

F

Example 1.1

Into a 5-L 4-necked round-bottom flask purged and maintained with an inert atmosphere of nitrogen, was placed 4-[2-(benzyloxy)phenyl]cyclohexan-1-one (210 g, 749 mmol, 1.00 equiv.) in tetrahydrofuran (2.1 L). This was followed by the addition of L-selectride (1 mol/L in THF) (1123 mL, 5257 mmol, 1.50 equiv.) dropwise with stirring at 0 degrees C. The resulting solution was stirred for 4 hr at room temperature. The reaction was then quenched by the addition of water/ice. The resulting solution was extracted with ethyl acetate, and the organic phase was washed with brine. The mixture was dried over anhydrous sodium sulfate, filtered, concentrated under vacuum. The residue was purified by silica gel column chromatography with ethyl acetate/petroleum ether (1:100-1:5) to give 137 g (64%) of (1s,4s)-4-[2-(benzyloxy)phenyl] cyclohexan-1-ol as a solid. ¹H NMR (400 MHz, CDCl₃): δ 7.45-7.26 (6H, m), 7.16 (1H, dd), 6.98-6.90 (2H, m), 5.09 (2H, s), 4.13 (1H, s), 3.12-3.02 (1H, m), 1.93-1.82 (4H, m), 1.73-1.41 (4H, m).

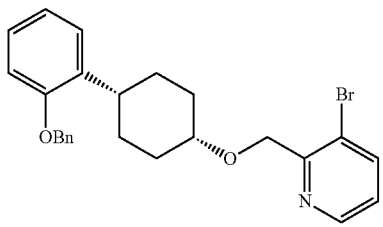 [SMILES: Brc1cccnc1CO[C@H]1CC[C@@H](c2ccccc2OCc2ccccc2)CC1]

Into a 2-L 4-necked round-bottom flask purged and maintained with an inert atmosphere of nitrogen, was placed NaH (60% wt, 26.9 g, 2.00 equiv.) in tetrahydrofuran (200 mL). This was followed by the addition of a solution of (is, 4s)-4-[2-(benzyloxy)phenyl]cyclohexan-1-ol (95 g, 336 mmol, 1.00 equiv.) in THF (200 mL) dropwise with stirring at 50-55 degrees C. After stirring for 2 hr, to this was added a solution of 3-bromo-2-(bromomethyl)pyridine (143.5 g, 571 mmol, 1.70 equiv.) in THF (550 mL) dropwise with stirring at 50-55 degrees C. The resulting solution was stirred for 14 hr at 50-55 degrees C. The reaction mixture was cooled. The reaction was then quenched by the addition of water. The resulting solution was extracted with ethyl acetate and the organic layers combined and dried over anhydrous sodium sulfate. The solids were filtered out. The resulting mixture was concentrated under vacuum. The residue was purified by silica gel column chromatography with ethyl acetate/petroleum ether (1:100-1:2) to give 94 g (62%) of 3-bromo-2-([[(1s,4s)-4-[2-(benzyloxy) phenyl]cyclohexyl]oxy]methyl)pyridine as a solid. $^1$H NMR (400 MHz, CDCl$_3$): δ 8.57 (1H, d), 7.90 (1H, dd), 7.48-7.26 (6H, m), 7.18-7.14 (2H, m), 6.98-6.91 (2H, m), 5.12 (2H, s), 4.77 (2H, s), 3.86 (1H, s), 3.17-3.10 (1H, m), 2.20-2.15 (2H, m), 1.98-1.88 (2H, m), 1.69-1.57 (4H, m).

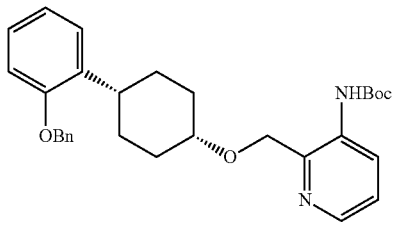 [SMILES: CC(C)(C)OC(=O)Nc1cccnc1CO[C@H]1CC[C@@H](c2ccccc2OCc2ccccc2)CC1]

Into a 2-L 4-necked round-bottom flask purged and maintained with an inert atmosphere of nitrogen, was placed Xantphos (10.7 g, 18 mmol, 0.10 equiv.), Cs$_2$CO$_3$ (84 g, 258 mmol, 1.39 equiv.), 3-bromo-2-([[(1s,4s)-4-[2-(benzyloxy) phenyl]cyclohexyl]oxy]methyl)pyridine (84 g, 185 mmol, 1.00 equiv.), Pd$_2$(dba)$_3$ (8.5 g, 9 mmol, 0.05 equiv.) and tert-butyl carbamate (26 g, 222 mmol, 1.20 equiv.) in dioxane (840 mL). The resulting solution was stirred for 5 hr at 100 degrees C. The solids were filtered out. The filtrate was concentrated under vacuum. The residue was purified by silica gel column chromatography with ethyl acetate/petroleum ether (1:100-1:4) to provide 74 g (82%) of tert-butyl N-[2-([[(1s,4s)-4-[2-(benzyloxy)phenyl]cyclohexyl]oxy]methyl)pyridin-3-yl]carbamate as a solid.

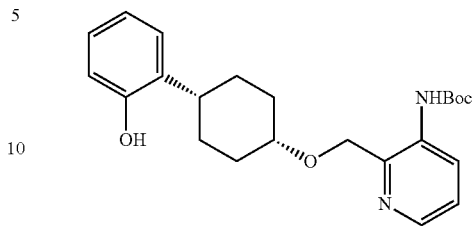

Into a 2-L 3-necked round-bottom flask, was placed tert-butyl N-[2-([[(1s,4s)-4-[2-(benzyloxy)phenyl]cyclohexyl]oxy]methyl)pyridin-3-yl]carbamate (74 g, 151 mmol, 1.00 equiv.) and Pd/C (7.4 g, 10% wt) in ethyl alcohol (740 mL), then, hydrogen gas was through in. The resulting solution was stirred for 14 hr at room temperature. The solids were filtered out. The filtrate was concentrated under vacuum. The residue was purified by silica gel column chromatography with ethyl acetate/petroleum ether (1:100-1:2) to provide 51.36 g (85%) of tert-butyl N-[2-([[(1s,4s)-4-(2-hydroxyphenyl)cyclohexyl]oxy]methyl)pyridin-3-yl] carbamate as a solid. LCMS (ESI): m/z [M+H]$^+$=399.1; $^1$H NMR (300 MHz, CDCl$_3$): δ 8.65 (1H, s), 8.47 (1H, d), 8.19 (1H, q), 7.26-7.21 (1H, m), 7.09-7.03 (1H, m), 6.92-6.86 (1H, m), 6.75 (1H, q), 5.77 (1H, s), 4.84 (1H, s), 3.80 (1H, s), 2.94-2.93 (1H, m), 2.15-2.06 (2H, m), 1.88-1.47 (7H, m), 1.45 (9H, s), 1.26 (1H, d).

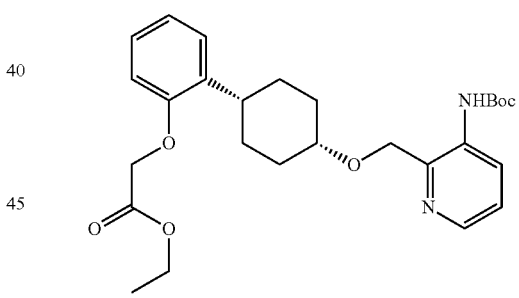

Into a 250-mL round-bottom flask purged and maintained with an inert atmosphere of nitrogen, was placed tert-butyl N-[2-([[(1s,4s)-4-(2-hydroxyphenyl)cyclohexyl]oxy] methyl)pyridin-3-yl]carbamate (8 g, 20.075 mmol, 1 equiv.), K$_2$CO$_3$ (13.97 g, 100.35 mmol, 5 equiv.), acetone (120 mL) and ethyl bromoacetate (5.03 g, 30.119 mmol, 1.5 equiv.). The resulting solution was stirred for 24 hr at 50 degrees C. The solids were filtered out. The filtrate was concentrated under vacuum. The residue was purified by silica gel column chromatography with ethyl acetate/petroleum ether (1:2) to provide ethyl 2-[2-[(1s,4s)-4-([3-[(tert-butoxycarbonyl) amino]pyridin-2-yl]methoxy)cyclohexyl]phenoxy]acetate (8.7 g, 89.43%) as a yellow oil. LCMS (ESI): m/z [M+H]$^+$= 485.

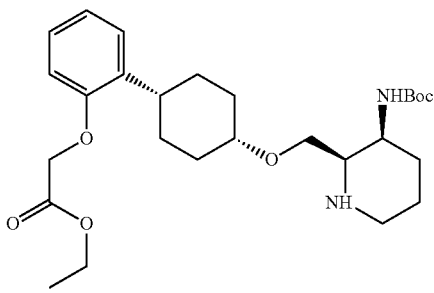 [SMILES: CCOC(=O)COc1ccccc1[C@H]1CC[C@@H](OC[C@@H]2NCCC[C@@H]2NC(=O)OC(C)(C)C)CC1]

To a stirred mixture of ethyl 2-[2-[(1s,4s)-4-([3-[(tert-butoxycarbonyl)amino]pyridin-2-yl]methoxy)cyclohexyl]phenoxy]acetate (7.89 g, 16.268 mmol, 1 equiv.) in MeOH (142 mL) and AcOH (15.8 mL) were added PtO$_2$ (1.85 g, 8.142 mmol, 0.50 equiv.) at room temperature under hydrogen atmosphere. The resulting mixture was stirred for 2 hr at room temperature under hydrogen atmosphere. The resulting mixture was filtered, the filter cake was concentrated under reduced pressure. The reaction was quenched with sat. NaHCO$_3$ (aq.) at 0 degrees C. The resulting mixture was extracted with CH$_2$Cl$_2$ (3×500 mL). The combined organic layers were washed with brine (3×200 mL), dried over anhydrous Na$_2$SO$_4$. After filtration, the filtrate was concentrated under reduced pressure to afford diastereomeric cis and trans mixture (7 g, 88.7%) as a solid. The crude product was purified by Prep-TLC (DCM/MeOH=20:1) to afford cis-racemic mixture of ethyl 2-(2-((1S,4s)-4-((3-((tert-butoxycarbonyl)amino)piperidin-2-yl)methoxy)cyclohexyl)phenoxy)acetate (4.1 g) and trans-racemic mixture (1.7 g). LCMS (ESI): m/z [M+H]$^+$=491.

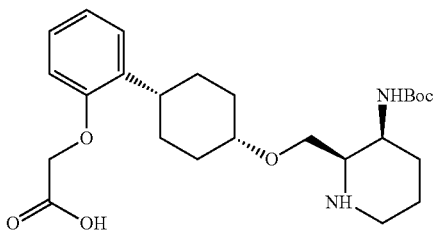 [SMILES: CC(C)(C)OC(=O)N[C@H]1CCCN[C@H]1CO[C@H]1CC[C@@H](c2ccccc2OCC(=O)O)CC1]

Into a 500 mL round-bottom flask purged and maintained with an atmosphere of nitrogen, was placed cis-racemic mixture of ethyl 2-(2-((1S,4s)-4-((3-((tert-butoxycarbonyl)amino)piperidin-2-yl)methoxy)cyclohexyl)phenoxy)acetate (4.1 g, 8.356 mmol, 1 equiv.), MeOH (30 mL), THF (60 mL), H$_2$O (30 mL) and lithium hydroxide (83 mg, 3.465 mmol, 5 equiv.). The reaction was stirred for 2 hr at room temperature. The reaction was concentrated and the residue was purified by reverse phase flash with the following conditions, then freezing-drying to afford 2-(2-((1s,4s)-4-((3-((tert-butoxycarbonyl)amino)piperidin-2-yl)methoxy)cyclohexyl)phenoxy)acetic acid (2.35 g, 60.8%) as a solid. LCMS (ESI): m/z [M+H]$^+$=463.

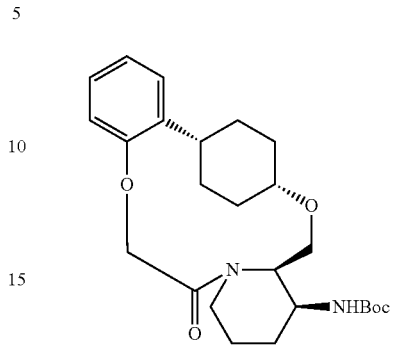

Into a 2000-mL round-bottom flask was added 2-(2-((1s,4s)-4-((3-((tert-butoxycarbonyl)amino)piperidin-2-yl)methoxy)cyclohexyl)phenoxy)acetic acid (100 mg, 0.216 mmol, 1 equiv.), MeCN (36 mL), DMF (9 mL), HATU (124 mg, 0.326 mmol, 1.51 equiv.) and DIPEA (56 mg, 0.436 mmol, 2.02 equiv.) under nitrogen atmosphere. The resulting solution was stirred for 3 hr at room temperature. LCMS showed full conversation. The resulting mixture was concentrated. The crude product tert-butyl ((2$^1$S,2$^4$S,5$^2$R,5$^3$S)-6-oxo-3,8-dioxa-5(2,1)-piperidina-1(1,2)-benzena-2(1,4)-cyclohexanacyclooctaphane-5$^3$-yl)carbamate was used directly for the next step without purification. LCMS (ESI): m/z [M+H]$^+$=445.

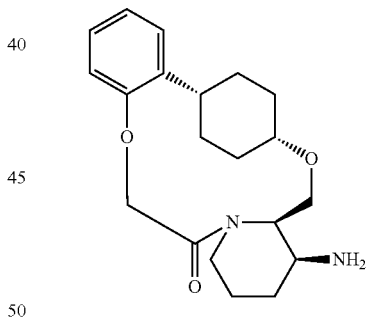

Into a 500-mL round-bottom flask purged and maintained with an inert atmosphere of nitrogen, was placed crude mixture tert-butyl ((2$^1$S,2$^4$S,5$^2$R,5$^3$S)-6-oxo-3,8-dioxa-5(2,1)-piperidina-1(1,2)-benzena-2(1,4)-cyclohexanacyclooctaphane-5$^3$-yl)carbamate (2 g, 4.499 mmol, 1 equiv.), DCM (120 mL), TFA (40 mL). The resulting solution was stirred for 1 hr at 25 degrees C. LCMS showed full conversation. The resulting mixture was concentrated under vacuum. The crude product was purified by Prep-HPLC to afford (2$^1$S,2$^4$S,5$^2$R,5$^3$S)-5$^3$-amino-3,8-dioxa-5(2,1)-piperidina-1(1,2)-benzena-2(1,4)-cyclohexanacyclooctaphan-6-one 32.1 g (800 mg, 51.6%) as a solid. LCMS (ESI): m/z [M+H]$^+$=345.

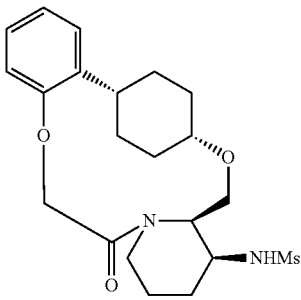

(Compound 2)

To (2¹S,2⁴S,5²R,5³S)-5³-amino-3,8-dioxa-5(2,1)-piperidina-1(1,2)-benzena-2(1,4)-cyclohexanacyclooctaphan-6-one 32.1 g (900 mg, 2.613 mmol, 1 equiv.) and DIPEA (1.69 g, 13.064 mmol, 5 equiv.) in DCM (148 mL) was added MsCl (900 mg, 7.858 mmol, 3 equiv.) dropwise at room temperature under nitrogen atmosphere. The resulting solution was stirred for 2 hr at room temperature. The reaction was then quenched by the addition of 50 mL of water. The resulting solution was extracted with 3×200 mL of dichloromethane, dried over anhydrous sodium sulfate and concentrated under vacuum. The crude product was purified by Prep-HPLC to afford racemic crude product (800 mg, 72.46%) as a solid. The crude product was purified by prep-SFC to afford N-((2¹S,2⁴S,5²R,5³S)-6-oxo-3,8-dioxa-5(2,1)-piperidina-1(1,2)-benzena-2(1,4)-cyclohexanacyclooctaphane-5³-yl)methanesulfonamide (270.6 mg, 27.1%) as a solid and its enantiomer, N-((2¹R,2⁴R,5²S,5³R)-6-oxo-3,8-dioxa-5(2,1)-piperidina-1(1,2)-benzena-2(1,4)-cyclohexanacyclooctaphane-5³-yl)methanesulfonamide (361.4 mg, 36.1%) as a solid. LCMS (ESI): m/z calculated for $C_{21}H_{30}N_2O_5S$ [M+H]⁺=423.19, found [M+H]⁺=423.15; ¹H NMR (400 MHz, CDCl₃): δ 7.19 (td, J=7.7, 1.8 Hz, 1H), 7.11 (dd, J=7.5, 1.7 Hz, 1H), 6.96-6.86 (m, 1H), 6.77 (dd, J=8.0, 1.1 Hz, 1H), 5.24 (dd, J=9.8, 4.9 Hz, 1H), 5.14 (d, J=10.5 Hz, 1H), 4.34 (dd, J=14.1, 9.4 Hz, 2H), 3.84 (t, J=9.2 Hz, 1H), 3.73 (d, J=14.9 Hz, 3H), 3.60-3.46 (m, 2H), 3.09 (s, 3H), 2.77-2.49 (m, 2H), 2.33-2.16 (m, 1H), 2.06 (d, J=12.8 Hz, 2H), 2.00-1.82 (m, 2H), 1.68 (d, J=11.5 Hz, 2H), 1.10-1.45 (m, 4H).

Example 1.2

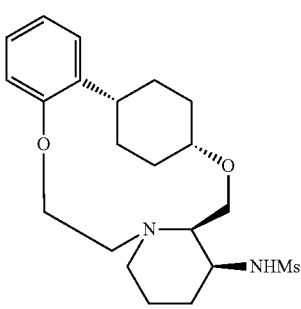

(Compound 6)

To a stirred solution of N-((2¹S,2⁴S,5²R,5³S)-6-oxo-3,8-dioxa-5(2,1)-piperidina-1(1,2)-benzena-2(1,4)-cyclohexanacyclooctaphane-5³-yl)methanesulfonamide (185 mg, 0.438 mmol, 1 equiv.) in THF (3.56 mL) was added borane-methyl sulfide complex (1.095 mL, 2.189 mmol, 5 equiv.) dropwise at room temperature. The resulting solution was stirred for 90 min. After 90 min, MeOH (3.60 mL) was added dropwise and the mixture was allowed to stir another 30 min at room temperature. After 30 min, the solvent was removed under reduced pressure. The residue was purified by silica gel column chromatography with ethyl acetate/hexane (0:1-1:0) to provide 123 mg (69%) of N-((2¹S,2⁴S, 5²R,5³S)-3,8-dioxa-5(2,1)-piperidina-1(1,2)-benzena-2(1,4)-cyclohexanacyclooctaphane-5³-yl)methanesulfonamide as a solid. LCMS (ESI): m/z [M+H]⁺=409; ¹H NMR (400 MHz, DMSO-d₆): δ 7.11 (td, J=7.7, 1.8 Hz, 1H), 7.04 (dd, J=7.5, 1.7 Hz, 1H), 6.93 (dd, J=8.1, 1.0 Hz 1H), 6.89 (d, J=6.3 Hz, 1H), 6.78 (dt, J=7.4, 1.1 Hz, 1H), 4.04 (d, J=10.1 Hz, 1H), 3.80 (td, J=10.2, 2.3 Hz, 1H), 3.67 (s, 1H), 3.60-3.53 (m, 2H), 3.48-3.41 (m, 1H), 3.14-2.94 (m, 3H), 2.93 (m, 3H), 2.89-2.83 (m, 1H), 2.80-2.70 (m, 1H), 2.63 (qd, J=12.7, 4.2 Hz, 1H) 2.48-2.37 (m, 1H), 2.00 (d, J=13.2 Hz, 1H), 1.81 (d, J=13.4 Hz, 1H), 1.68-1.20 (m, 8H), 1.10 (m, 1H).

Example 1.3

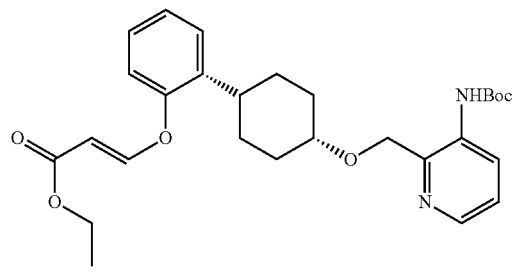

Into a 100-mL round-bottom flask purged and maintained with an inert atmosphere of nitrogen, was placed a solution of ethyl propiolate (295.41 mg, 3.011 mmol, 1.20 equiv.) and DABCO (28.15 mg, 0.251 mmol, 0.10 equiv.) in THF (11 mL) at 0 degrees C. To this was added a solution of tert-butyl N-[2-([[(1s,4s)-4-(2-hydroxyphenyl)cyclohexyl]oxy]methyl)pyridin-3-yl]carbamate (1.00 g, 2.509 mmol, 1.00 equiv.) in THF (1 mL) at 0 degrees C. The resulting solution was stirred for 5 hr at room temperature. Reaction mixture was diluted with 20 mL of water. The resulting solution was extracted with 3×15 mL of ethyl acetate, washed with 1×20 mL of brine, dried with anhydrous Na₂SO₄, then concentrated. The resulting residue was applied onto a silica gel column with ethyl acetate/petroleum ether (4:1). This resulted in 1.1 g (80.25%) of ethyl (E)-3-(2-(((1s,4s)-4-((3-((tert-butoxycarbonyl)amino)pyridin-2-yl)methoxy)cyclohexyl)phenoxy)acrylate as light yellow oil. LCMS (ESI): m/z [M+H]⁺=497.

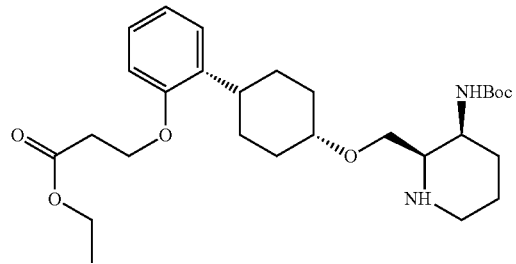

Under an H$_2$ atmosphere, into a 100-mL round-bottom flask, was placed ethyl (E)-3-(2-((1s,4s)-4-((3-((tert-butoxycarbonyl)amino)pyridin-2-yl)methoxy)cyclohexyl)phenoxy)acrylate (1.05 g, 2.114 mmol, 1.00 equiv.), EtOH (9.00 mL, 195.358 mmol, 1.00 equiv.), AcOH (1.00 mL, 17.452 mmol, 1.00 equiv.) and PtO$_2$ (240.07 mg, 1.057 mmol, 0.50 equiv.). The resulting solution was stirred for 4 hr at room temperature. Reaction mixture was filtered, filtrate was collected and concentrated. The pH value of resulting residue was adjusted to 8 with saturation NaHCO$_3$ solution (100%). The resulting solution was extracted with 3×30 mL of dichloromethane dried over Na$_2$SO$_4$, then concentrated. The residue was purified by Flash-Prep-HPLC. This resulted in 280 mg (18.10%) of ethyl 3-(2-((1S,4s)-4-(((2R,3S)-3-((tert-butoxycarbonyl)amino)piperidin-2-yl)methoxy)cyclohexyl)phenoxy)propanoate as light yellow oil. LCMS (ESI): m/z [M+H]$^+$=505.

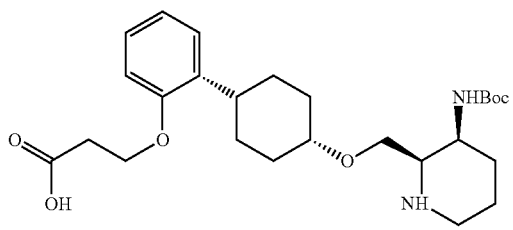

Into a 10-mL round-bottom flask purged and maintained with an inert atmosphere of nitrogen, was placed ethyl 3-(2-((1S,4s)-4-(((2R,3S)-3-((tert-butoxycarbonyl)amino)piperidin-2-yl)methoxy)cyclohexyl)phenoxy)propanoate (200.00 mg, 0.396 mmol, 1.00 equiv.), THF (1.00 mL), H$_2$O (1.00 mL) and lithium hydroxide (47.46 mg, 1.982 mmol, 5.00 equiv.). The resulting solution was stirred for 5 hr at room temperature. The resulting mixture was concentrated. The obtained residue was purified by Flash-Prep-HPLC to provide 80 mg (42.35%) of 3-(2-((1S,4s)-4-(((2R,3S)-3-((tert-butoxycarbonyl)amino)piperidin-2-yl)methoxy)cyclohexyl)phenoxy)propanoic acid as a solid. LCMS (ESI): m/z [M+H]$^+$=477.

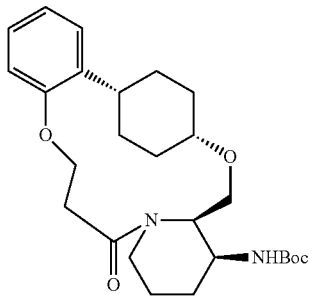 [SMILES: CC(C)(C)OC(=O)N[C@H]1CCCN2C(=O)CCOc3ccccc3[C@H]3CC[C@H](CC3)OC[C@@H]12]

Into a 40-mL round-bottom flask purged and maintained with an inert atmosphere of nitrogen, was placed 3-(2-((1S,4s)-4-(((2R,3S)-3-((tert-butoxycarbonyl)amino)piperidin-2-yl)methoxy)cyclohexyl)phenoxy)propanoic acid (25.00 mg, 0.052 mmol, 1.00 equiv.), HATU (29.92 mg, 0.079 mmol, 1.50 equiv.), DIPEA (13.56 mg, 0.105 mmol, 2.00 equiv.) and ACN (7.00 mL). The resulting solution was stirred for 18 hr at room temperature. The solids were filtered out. The resulting mixture was concentrated. The resulting residue was purified by Flash-Prep-HPLC to provide 100 mg (80.31%) of tert-butyl ((2$^1$S,2$^4$S,5$^2$R,5$^3$S)-6-oxo-3,9-dioxa-5(2,1)-piperidina-1(1,2)-benzena-2(1,4)-cyclohexanacyclononaphane-5$^3$-yl)carbamate as a solid. LCMS (ESI): m/z [M+H]$^+$=459.

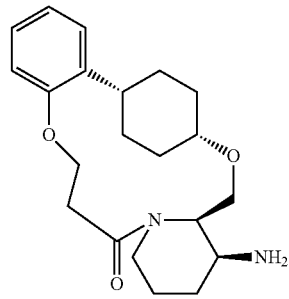 [SMILES: N[C@H]1CCCN2C(=O)CCOc3ccccc3[C@H]3CC[C@H](CC3)OC[C@@H]12]

Into a 25-mL round-bottom flask, was placed tert-butyl ((2$^1$S,2$^4$S,5$^2$R,5$^3$S)-6-oxo-3,9-dioxa-5(2,1)-piperidina-1(1,2)-benzena-2(1,4)-cyclohexanacyclononaphane-5$^3$-yl)carbamate (100.00 mg, 0.218 mmol, 1.00 equiv.), DCM (7.50 mL) and CF$_3$COOH (2.50 mL, 33.658 mmol, 154.35 equiv.). The resulting solution was stirred for 5 hr at room temperature. The resulting mixture was concentrated. The crude product was purified by Flash-Prep-HPLC to provide 20 mg (25.59%) of racemate of (2$^1$S,2$^4$S,5$^2$R,5$^3$S)-5$^3$-amino-3,9-dioxa-5(2,1)-piperidina-1(1,2)-benzena-2(1,4)-cyclohexanacyclononaphan-6-one as a solid. LCMS (ESI): m/z [M+H]$^+$=359.

(Compound 1)

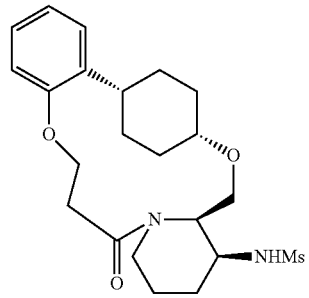

Into a 10-mL round-bottom flask, was placed (2$^1$S,2$^4$S, 5$^2$R,5$^3$S)-5$^3$-amino-3,9-dioxa-5(2,1)-piperidina-1(1,2)-benzena-2(1,4)-cyclohexanacyclononaphan-6-one (20.00 mg, 0.056 mmol, 1.00 equiv.), DCM (2.00 mL), NEt$_3$ (11.29 mg, 0.112 mmol, 2.00 equiv.) and MsCl (7.67 mg, 0.067 mmol, 1.20 equiv.) at 0 degrees C. The resulting solution was stirred for 4 hr at room temperature. The resulting mixture was concentrated. The crude product was purified by Flash-Prep-HPLC to provide 5 mg (19.67%) of N-((2$^1$S,2$^4$S,5$^2$R, 5$^3$S)-6-oxo-3,9-dioxa-5(2,1)-piperidina-1(1,2)-benzena-2(1, 4)-cyclohexanacyclononaphane-5$^3$-yl)methanesulfonamide. LCMS (ESI): m/z [M+H]$^+$=437; $^1$H NMR (400 MHz, DMSO-d$_6$): δ 7.40 (d, J=6.4 Hz, 1H), 7.11 (m, 2H), 7.02 (d, J=6.9 Hz, 1H), 6.87-6.70 (m, 2H), 4.57-4.11 (m, 3H), 3.96 (d, J=7.9 Hz, 1H), 3.71 (dd, J=28.1, 9.6 Hz, 3H), 3.54 (d, J=16.8 Hz, 1H), 3.27 (d, J=12.6 Hz, 2H), 2.97 (d, J=18.2 Hz, 2H), 2.70-2.54 (m, 1H), 2.45-2.17 (m, 3H), 1.92-1.64 (m, 4H), 1.58-0.94 (m, 6H).

Example 1.4

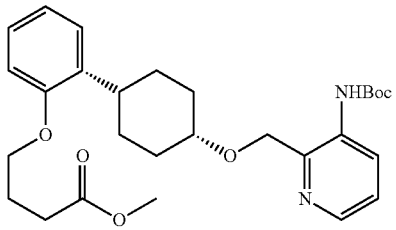

To a stirred solution of tert-butyl N-[2-([[(1s,4s)-4-(2-hydroxyphenyl)cyclohexyl]oxy]methyl)pyridin-3-yl]carbamate (2.00 g, 5.019 mmol, 1.00 equiv.) and $K_2CO_3$ (3.47 g, 25.094 mmol, 5.00 equiv.) in acetone (40.00 mL) was added methyl-4-bromobutanoate (1.82 g, 10.038 mmol, 2.00 equiv.) in portions at room temperature. The resulting mixture was stirred for overnight at 50 degrees C. under nitrogen atmosphere. The resulting mixture was concentrated under reduced pressure. The residue was purified by silica gel column chromatography, eluted with PE/EtOAc (5:1) to afford methyl 4-[2-[(1s,4s)-4-([3-[(tert-butoxycarbonyl)amino]pyridin-2-yl]methoxy)cyclohexyl]phenoxy]butanoate (1.65 g, 65.93%) as a yellow oil. LCMS (ESI) m/z $[M+H]^+$=499.

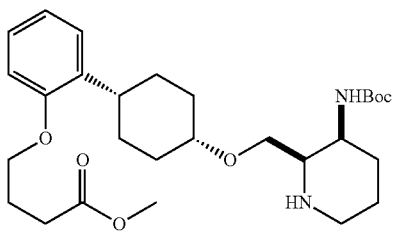 [SMILES: COC(=O)CCCOc1ccccc1[C@H]1CC[C@@H](OC[C@@H]2NCCC[C@@H]2NC(=O)OC(C)(C)C)CC1]

To a stirred solution of methyl 4-[2-[(1s,4s)-4-([3-[(tert-butoxycarbonyl)amino]pyridin-2-yl]methoxy)cyclohexyl]phenoxy]butanoate (1.65 g, 3.309 mmol, 1.00 equiv.) in AcOH/MeOH (20.00 mL/180.00 mL) was added $PtO_2$ (375.72 mg, 1.655 mmol, 0.50 equiv.) in portions at room temperature. The resulting mixture was stirred for 5 hr at room temperature under hydrogen atmosphere. The resulting mixture was filtered, the filter cake was washed with MeOH (3×100 mL). The filtrate was concentrated under reduced pressure. The mixture was neutralized to pH 7 with saturated $NaHCO_3$ (aq.). The resulting mixture was extracted with $CH_2C_2$ (3×100 mL). The combined organic layers were washed with brine (1×100 mL), dried over anhydrous $Na_2SO_4$. After filtration, the filtrate was concentrated under reduced pressure. The crude product was used in the next step directly without further purification. LCMS (ESI): m/z $[M+H]^+$=505.3.

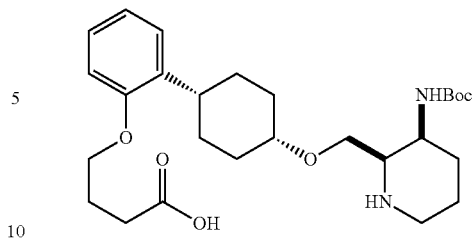

To a stirred solution of methyl 4-(2-((1S,4s)-4-((cis-3-((tert-butoxycarbonyl)amino)piperidin-2-yl)methoxy)cyclohexyl)phenoxy)butanoate (1.65 g, 3.269 mmol, 1.00 equiv.) in $THF/H_2O$ (30.00 mL/30.00 mL) was added lithium hydroxide (391.52 mg, 16.347 mmol, 5.00 equiv.) in portions at room temperature under nitrogen atmosphere. The resulting mixture was stirred for 4 hr at room temperature under nitrogen atmosphere. The mixture was neutralized to pH 7 with HCl (1N). The resulting mixture was concentrated under reduced pressure. The residue was purified by reverse flash chromatography to provide 4-(2-((1S,4s)-4-((cis-3-((tert-butoxycarbonyl)amino)piperidin-2-yl)methoxy)cyclohexyl)phenoxy)butanoic acid (800 mg, 49.87%) as a solid. LCMS (ESI): m/z $[M+H]^+$=491.3.

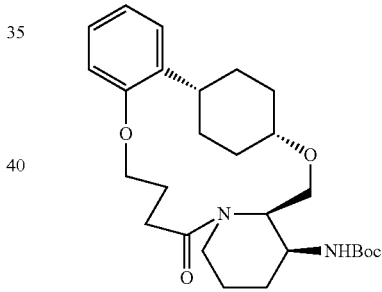

To a stirred solution of 4-(2-((1S,4s)-4-((cis-3-((tert-butoxycarbonyl)amino)piperidin-2-yl)methoxy)cyclohexyl)phenoxy)butanoic acid (800.00 mg, 1.631 mmol, 1.00 equiv.) and HATU (1239.94 mg, 3.261 mmol, 2.00 equiv.) in acetonitrile/DMF (80.00 mL/10.00 mL) was added DIPEA (632.20 mg, 4.892 mmol, 3.00 equiv.) in portions at room temperature under nitrogen atmosphere. The resulting mixture was stirred for 2 hr at room temperature under nitrogen atmosphere. The resulting mixture was concentrated under reduced pressure. The residue was purified by reverse flash chromatography to provide racemate of tert-butyl (($2^1$S,$2^4$S,$5^2$R,$5^3$S)-6-oxo-3,10-dioxa-5(2,1)-piperidina-1(1,2)-benzena-2(1,4)-cyclohexanacyclodecaphane-$5^3$-yl)carbamate (600 mg, 77.86%) as a solid. LCMS (ESI): m/z $[M+H]^+$=473.4.

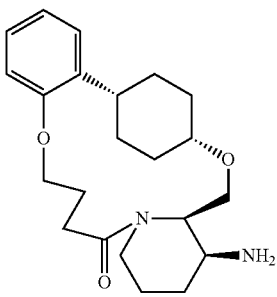 [SMILES: N[C@H]1CCCN2C(=O)CCCOc3ccccc3[C@H]3CC[C@H](CC3)OC[C@@H]12]

To a stirred solution of tert-butyl ((2¹S,2⁴S,5²R,5³S)-6-oxo-3,10-dioxa-5(2,1)-piperidina-1(1,2)-benzena-2(1,4)-cyclohexanacyclodecaphane-5³-yl)carbamate (200.00 mg, 0.423 mmol, 1.00 equiv.) in DCM (6.00 mL) was added TFA (2.00 mL) in portions at room temperature. The resulting mixture was stirred for 1 hr at room temperature under nitrogen atmosphere. The mixture was neutralized to pH 7 with saturated NaHCO$_3$ (aq.). The resulting mixture was extracted with CH$_2$Cl$_2$ (3×50 mL). The combined organic layers were washed with brine (3×30 mL), dried over anhydrous Na$_2$SO$_4$. After filtration, the filtrate was concentrated under reduced pressure. The crude product was used in the next step directly without further purification. LCMS (ESI): m/z [M+H]$^+$=373.2.

(Compound 4)

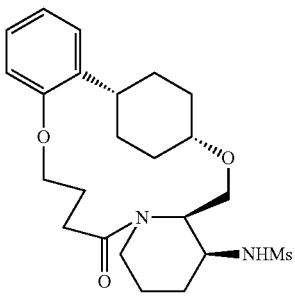

To a stirred solution of (2¹S,2⁴S,5²R,5³S)-5³-amino-3,10-dioxa-5(2,1)-piperidina-1(1,2)-benzena-2(1,4)-cyclohexanacyclodecaphan-6-one (150.00 mg, 0.403 mmol, 1.00 equiv.) and TEA (81.49 mg, 0.805 mmol, 2.00 equiv.) in DCM (6.00 mL) was added MsCl (50.74 mg, 0.443 mmol, 1.10 equiv.) in portions at 0 degrees C. The resulting mixture was stirred for 1 hr at room temperature under nitrogen atmosphere. The resulting mixture was concentrated under reduced pressure. The residue was purified by reverse flash chromatography to provide racemate of the product (60 mg, 33.07%) as a solid. LCMS (ESI): m/z [M+H]$^+$=451.2. The racemate (60 mg) was purified by a chiral HPLC to provide 10.8 mg N-((2¹S,2⁴S,5²R,5³S)-6-oxo-3,10-dioxa-5(2,1)-piperidina-1(1,2)-benzena-2(1,4)cyclohexanacyclodecaphane-5³-yl)methanesulfonamide. LCMS (ESI): m/z [M+H]$^+$=451.15; $^1$H NMR (300 MHz, methanol-d$_4$): δ 7.20-6.99 (m, 2H), 6.92-6.88 (m, 1H), 6.85-6.78 (m, 1H), 4.68-4.47 (m, 2H), 4.26-4.13 (m, 1H), 4.07-3.62 (m, 4H), 3.58-3.43 (m, 2H), 3.01 (s, 3H), 2.84-2.69 (m, 1H), 2.61-2.42 (m, 4H), 2.21-1.97 (m, 3H), 1.94-1.79 (m, 3H), 1.69-1.29 (m, 6H).

Example 1.5

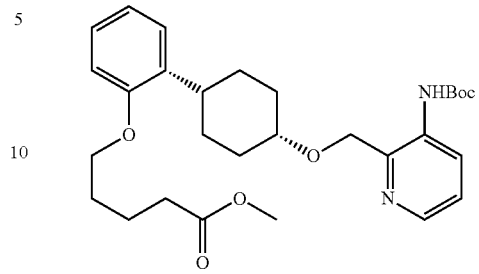

Into a 40-mL round-bottom flask purged and maintained with an inert atmosphere of nitrogen, was placed tert-butyl N-[2-([[(1s,4s)-4-(2-hydroxyphenyl)cyclohexyl]oxy]methyl)pyridin-3-yl]carbamate (200.00 mg, 0.502 mmol, 1.00 equiv.), methyl 5-bromopentanoate (587.37 mg, 3.011 mmol, 6 equiv.), K$_2$CO$_3$ (416.17 mg, 3.011 mmol, 6 equiv.), acetone (50.00 mL). The resulting solution was stirred for 1 (one) overnight at 50 degrees C. The resulting mixture was concentrated under vacuum. The residue was applied onto a silica gel column with (EtOAc:PE=4:1) to provide 240 mg (93.28%) of methyl 5-[2-[(1s,4s)-4-([3-[(tert-butoxycarbonyl)amino]pyridin-2-yl]methoxy)cyclohexyl]phenoxy]pentanoate as colorless oil. LCMS (ESI): m/z calculated for C$_{29}$H$_{40}$N$_2$O$_6$ [M+H]$^+$=513.3, found [M+H]$^+$=513.4.

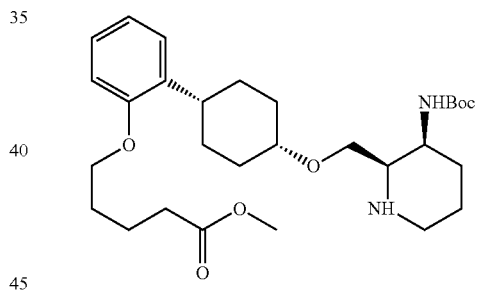

Into a 100-mL round-bottom flask purged and maintained with an inert atmosphere of nitrogen, was placed methyl 5-[2-[(1s,4s)-4-([3-[(tert-butoxycarbonyl)amino]pyridin-2-yl]methoxy)cyclohexyl]phenoxy]pentanoate (1.10 g, 2.146 mmol, 1.00 equiv.), MeOH (50.00 mL), AcOH (5.00 mL), PtO$_2$ (818.59 mg, 3.605 mmol, 1.68 equiv.). The resulting solution was stirred for 4 hr at 25 degrees C. The solids were filtered out. The resulting mixture was concentrated under vacuum. The pH value of the solution was adjusted to 8 with aqueous NaHCO$_3$ solution. The resulting solution was extracted with 4×50 mL of dichloromethane, dried over anhydrous sodium sulfate. Removal of solvent gave 400 mg methyl 5-[2-[(1s,4s)-4-[[cis-3-[(tert-butoxycarbonyl)amino]piperidin-2-yl]methoxy]cyclohexyl]phenoxy]pentanoate. This crude product was used for the next step without further purification. LCMS (ESI): m/z calculated for C$_{29}$H$_{46}$N$_2$O$_6$ [M+H]$^+$=519.3, found [M+H]$^+$=519.4.

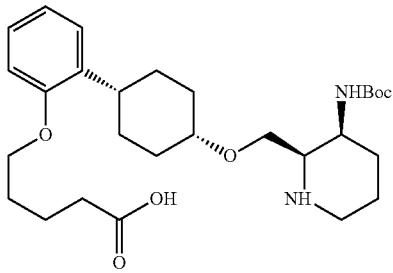 [SMILES: CC(C)(C)OC(=O)N[C@H]1CCCN[C@H]1CO[C@H]1CC[C@@H](c2ccccc2OCCCCC(=O)O)CC1]

Into a 100-mL round-bottom flask purged and maintained with an inert atmosphere of nitrogen, was placed methyl 5-[2-[(1s,4s)-4-[[cis-3-[(tert-butoxycarbonyl)amino]piperidin-2-yl]methoxy]cyclohexyl]phenoxy]pentanoate (265.00 mg, 0.511 mmol, 1.00 equiv.), LiOH·H$_2$O (107.20 mg, 2.554 mmol, 5.00 equiv.), H$_2$O (10.00 mL), THF (25.00 mL). The resulting solution was stirred overnight at 25 degrees C. The resulting mixture was concentrated under vacuum. The crude product was purified by reversed phase HPLC to provide 260 mg (99.67%) of lithio 5-[2-[(1s,4s)-4-[[cis-3-[(tert-butoxycarbonyl)amino]piperidin-2-yl]methoxy]cyclohexyl]phenoxy]pentanoate as a solid. LCMS (ESI): m/z calculated for C$_{28}$H$_{44}$N$_2$O$_6$, [M+H]$^+$=505.3, found [M+H]$^+$= 505.4.

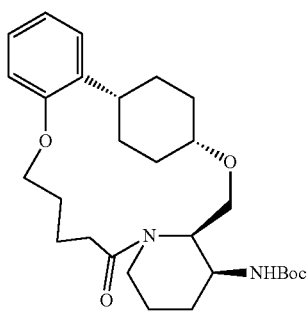 [SMILES: CC(C)(C)OC(=O)N[C@H]1CCCN2C(=O)CCCCOc3ccccc3[C@H]3CC[C@H](CC3)OC[C@@H]12]

Into a 100-mL round-bottom flask purged and maintained with an inert atmosphere of nitrogen, was placed lithio 5-[2-[(1s,4s)-4-[cis-3-[(tert-butoxycarbonyl)amino]piperidin-2-yl]methoxy]cyclohexyl]phenoxy]pentanoate (250.00 mg, 0.490 mmol, 1.00 equiv.), HATU (279.25 mg, 0.734 mmol, 1.50 equiv.), DIPEA (148.63 mg, 1.469 mmol, 3.00 equiv.), DMF (10 mL), MeCN (20 mL). The resulting solution was stirred overnight at 25 degrees C. The resulting mixture was concentrated under vacuum. Resulting residue was purified by reversed phase HPLC to provide 210 mg (88.13%) of tert-butyl ((2$^1$S,2$^4$S,5$^2$R,5$^3$S)-6-oxo-3,11-dioxa-5(2,1)-piperidina-1(1,2)-benzena-2(1,4)-cyclohexanacycloundecaphane-5$^3$-yl)carbamate as a solid. LCMS (ESI): m/z calculated for C$_{28}$H$_{42}$N$_2$O$_5$ [M+H]$^+$=487.3, found [M+H]$^+$=487.3.

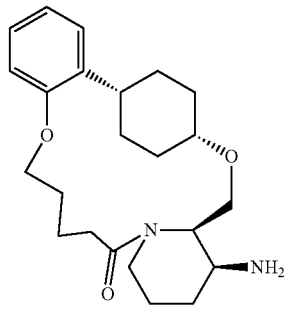 [SMILES: N[C@H]1CCCN2C(=O)CCCCOc3ccccc3[C@H]3CC[C@H](CC3)OC[C@@H]12]

Into a 100-mL round-bottom flask purged and maintained with an inert atmosphere of nitrogen, was placed tert-butyl ((2$^1$S,2$^4$S,5$^2$R,5$^3$S)-6-oxo-3,11-dioxa-5(2,1)-piperidina-1(1,2)-benzena-2(1,4)-cyclohexanacycloundecaphane-5$^3$-yl) carbamate (racemate, 210.00 mg, 0.432 mmol, 1.00 equiv.), TFA (10.00 mL), DCM (30 mL). The resulting solution was stirred for 1 hr at 25 degrees C. The resulting mixture was concentrated under vacuum. The pH value of the solution was adjusted to 8 with NaHCO$_3$(1 mol/L). The resulting solution was extracted with 3×50 mL of dichloromethane This resulted in 165 mg (98.92%) of (2$^1$S,2$^4$S,5$^2$R,5$^3$S)-5$^3$-amino-3,11-dioxa-5(2,1)-piperidina-1(1,2)-benzena-2(1,4)-cyclohexanacycloundecaphan-6-one as a solid. LCMS (ESI): m/z calculated for C$_{23}$H$_{34}$N$_2$O$_3$ [M+H]$^+$=387.3, found [M+H]$^+$=387.4.

(Compound 3)

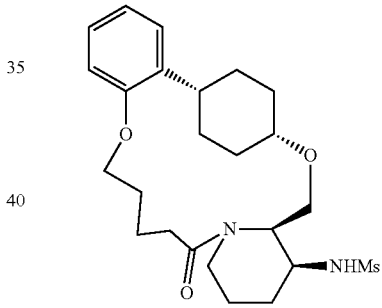

Into a 50-mL round-bottom flask purged and maintained with an inert atmosphere of nitrogen, was placed (2$^1$S,2$^4$S,5$^2$R,5$^3$S)-5$^3$-amino-3,11-dioxa-5(2,1)-piperidina-1(1,2)-benzena-2(1,4)-cyclohexanacycloundecaphan-6-one (racemate, 100.00 mg, 0.259 mmol, 1.00 equiv.), DIPEA (78.54 mg, 0.776 mmol, 3 equiv.), MsCl (59.27 mg, 0.517 mmol, 2 equiv.), DCM (20.00 mL). The resulting solution was stirred for 2 hr at 25 degrees C. The reaction was then quenched by the addition of 50 mL of water. The resulting solution was extracted with 3×50 mL of dichloromethane, then concentrated under vacuum. Resulting residue was purified by reverse phase column (MeCN/H$_2$O=1:1, 0.05% NH$_3$·H$_2$O). Then racemic product was purified by Chiral-HPLC to provide 50 mg (41.60%) of N-((2$^1$S,2$^4$S,5$^2$R,5$^3$S)-6-oxo-3,11-dioxa-5(2,1)-piperidina-1(1,2)-benzena-2(1,4)-cyclohexanacycloundecaphane-5$^3$-yl)methanesulfonamide as a solid. LCMS (ESI): m/z calculated for C$_{24}$H$_{36}$N$_2$O$_5$S [M+H]$^+$=465.2, found [M+H]$^+$=465.2; $^1$H NMR (300 MHz, CDCl$_3$): δ 7.17 (t, J=7.7 Hz, 1H), 7.09 (dd, J=7.6, 1.8 Hz, 1H), 6.91-6.77 (m, 2H), 4.87 (d, J=5.6 Hz, 1H), 4.57 (d, J=13.8 Hz, 1H), 4.34 (d, J=5.3 Hz, 1H), 4.23-4.11 (m, 1H), 3.89-3.75 (m, 2H), 3.74-3.57 (m, 3H), 3.07 (s, 3H), 2.80-

2.67 (m, 1H), 2.64-2.20 (m, 6H), 2.13-1.91 (m, 4H), 1.90-1.72 (m, 3H), 1.57-1.36 (m, 5H).

Example 1.6

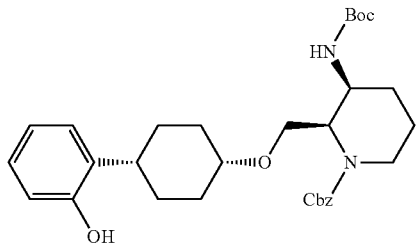 [SMILES: CC(C)(C)OC(=O)N[C@H]1CCCN(C(=O)OCc2ccccc2)[C@H]1CO[C@H]1CC[C@@H](c2ccccc2O)CC1]

To a stirring suspension of tert-butyl ((2R,3S)-2-((((1s,4S)-4-(2-hydroxyphenyl)cyclohexyl)oxy)methyl)piperidin-3-yl)carbamate (8.03 g, 19.85 mmol) and potassium carbonate (8.23 g, 59.5 mmol) in THF (130 mL) at 0 degrees C. was added benzyl chloroformate (3.40 mL, 23.82 mmol) and the reaction mixture was allowed to slowly warm to room temperature and stirred for 16 hr. An additional 1 equiv. of benzyl chloroformate was added and the reaction was heated at 50 degrees C. for 4 hr at which point LC-MS indicated completion of the reaction. The mixture was diluted with EtOAc (300 mL), washed with water (300 mL) and brine (300 mL) and the organic layer was dried MgSO$_4$, filtered and concentrated to afford the crude product which was purified by silica gel column chromatography (0-60% EtOAc in heptane) to yield benzyl (2R,3S)-3-((tert-butoxycarbonyl)amino)-2-((((1s,4S)-4-(2-hydroxyphenyl)cyclohexyl)oxy)methyl)piperidine-1-carboxylate (9.00 g, 16.71 mmol, 84% yield) as a solid. (ESI): m/z [M−H]$^−$ for C$_{31}$H$_{42}$N$_2$O$_6$=537.4.

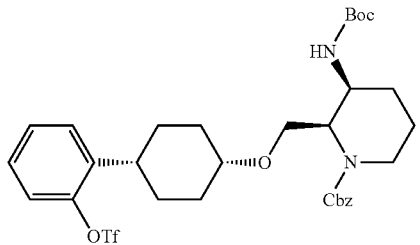 [SMILES: CC(C)(C)OC(=O)N[C@H]1CCCN(C(=O)OCc2ccccc2)[C@H]1CO[C@H]1CC[C@@H](c2ccccc2OS(=O)(=O)C(F)(F)F)CC1]

Benzyl (2R,3S)-3-((tert-butoxycarbonyl)amino)-2-((((1s,4S)-4-(2-hydroxyphenyl)cyclohexyl)oxy)methyl)piperidine-1-carboxylate (8.96 g, 16.63 mmol) was dissolved in DMF (95 mL), and then 1,1,1-trifluoro-N-phenyl-N-((trifluoromethyl)sulfonyl)methanesulfonamide (8.02 g, 22.45 mmol) and potassium carbonate (3.10 g, 22.45 mmol) were added. The reaction was stirred at room temperature for 2 hr at which point LC-MS indicated completion of the reaction. Water (400 mL) was added to the reaction mixture and the aqueous layer was extracted with EtOAc (3×1200 mL). The combined organics were dried (MgSO$_4$), filtered and concentrated to afford the crude product which was purified by silica gel column chromatography (0-60% EtOAc in heptane) to yield benzyl (2R,3S)-3-((tert-butoxycarbonyl)amino)-2-((((1s,4S)-4-(2-(((trifluoromethyl)sulfonyl)oxy)phenyl)cyclohexyl)oxy)methyl)piperidine-1-carboxylate (8.40 g, 12.52 mmol, 75% yield) as a solid. LCMS (ESI): m/z [M−H]$^−$ for C$_{32}$H$_{41}$F3N$_2$O$_8$S=669.4.

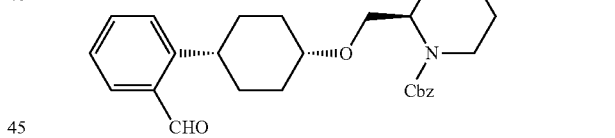

To a mixture of benzyl (2R,3S)-3-((tert-butoxycarbonyl)amino)-2-((((1s,4S)-4-(2-(((trifluoromethyl)sulfonyl)oxy)phenyl)cyclohexyl)oxy)methyl)piperidine-1-carboxylate (1.90 g, 2.83 mmol), potassium vinyltrifluoroborate (0.46 g, 3.40 mmol) and 1,1'-bis(diphenylphosphino)ferrocenedichloro palladium (II) dichloromethane complex (1.85 g, 2.27 mmol) in dry n-propanol (35 mL) was added triethylamine (0.40 mL, 2.83 mmol) and the system evacuated and purged with nitrogen three times. The reaction mixture was stirred and heated at 90 degrees C. for 2 hr, after which point LC-MS indicated completion of the reaction. The reaction mixture was filtered through Celite® and concentrated in vacuum. The crude product was purified by silica gel column chromatography (0-60% EtOAc in heptane) to yield benzyl (2R,3S)-3-((tert-butoxycarbonyl)amino)-2-((((1s,4S)-4-(2-vinylphenyl)cyclohexyl)oxy)methyl)piperidine-1-carboxylate (1.08 g, 1.97 mmol, 70% yield) as a solid. LCMS (ESI): m/z [M−H]$^−$ for C$_{33}$H$_{44}$N$_2$O$_5$=547.4.

To a solution of benzyl (2R,3S)-3-((tert-butoxycarbonyl)amino)-2-((((1s,4S)-4-(2-vinylphenyl)cyclohexyl)oxy)methyl)piperidine-1-carboxylate (0.82 g, 1.50 mmol) in THF (8 mL), acetone (8 mL), and water (1.5 mL) was added NMO (0.21 g, 1.80 mmol) and osmium tetroxide (0.12 mL, 0.015 mmol). After 3 hr, LC-MS showed complete conversion to the diol. The reaction was quenched with solid NaHSO$_3$ and diluted with EtOAc (8 mL), dried with MgSO$_4$, filtered and concentrated under reduced pressure. The resulting diol was dissolved in THF (8 mL) and water (4 mL) and then directly treated with sodium periodate (0.37 g, 1.71 mmol) and the reaction allowed to stir for 1 hr, at which point the LC-MS confirmed full conversion to the desired aldehyde. The reaction was diluted with H$_2$O (4 mL), extracted with EtOAc (3×25 mL), dried over MgSO$_4$, filtered, and concentrated under reduced pressure to afford benzyl (2R,3S)-3-((tert-butoxycarbonyl)amino)-2-((((1s,4S)-4-(2-formylphenyl)cyclohexyl)oxy)methyl)piperidine-1-carboxylate (0.69 g, 1.25 mmol, 83% yield) as a solid. LCMS (ESI): m/z [M−H]$^−$ for C$_{32}$H$_{42}$N$_2$O$_6$=549.4.

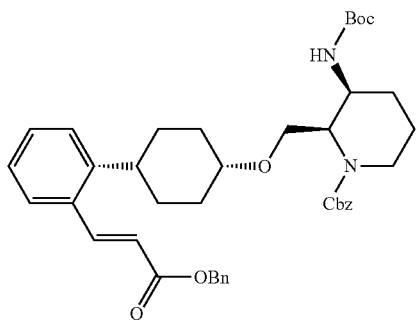

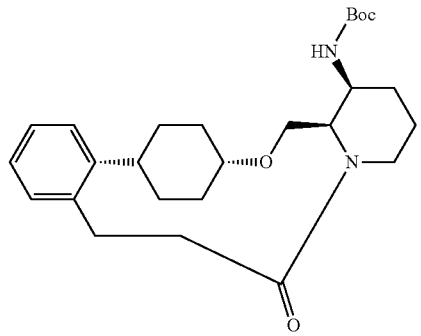

Benzyl (2R,3S)-3-((tert-butoxycarbonyl)amino)-2-(((((1s,4S)-4-(2-formylphenyl)cyclohexyl)oxy)methyl)piperidine-1-carboxylate (1.40 g, 2.54 mmol) and (2-(benzyloxy)-2-oxoethyl)triphenylphosphonium bromide (2.50 g, 5.08 mmol) were dissolved in DCM (15 mL). 1,1,3,3-Tetramethylguanidine (0.96 mL, 7.63 mmol) was then added and the reaction was left to stir for 5 hr at room temperature. LC-MS indicated completion of the reaction. The reaction was quenched with aqueous saturated $NH_4Cl$ (35 mL) and the phases were separated. The aqueous layer was extracted with DCM (3×45 mL) and the combined organics were dried over $MgSO_4$, filtered, and concentrated. Purification by silica gel flash column chromatography (0-60% EtOAc in heptane) afforded benzyl (2R,3S)-2-((((1s,4S)-4-(2-((E)-3-(benzyloxy)-3-oxoprop-1-en-1-yl)phenyl)cyclohexyl)oxy)methyl)-3-((tert-butoxycarbonyl)amino)piperidine-1-carboxylate (1.27 g, 1.86 mmol, 73% yield) as a solid. LC-MS indicated a 98:2 ratio of E to Z isomers. LCMS (ESI): m/z $[M-Boc+2H]^+$ for $C_{41}H_{50}N_2O_7$=583.4.

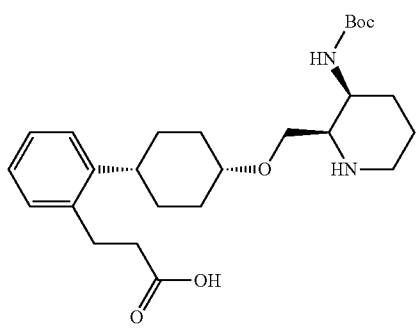 [SMILES: CC(C)(C)OC(=O)N[C@H]1CCCN[C@H]1CO[C@H]1CC[C@@H](c2ccccc2CCC(=O)O)CC1]

Benzyl (2R,3S)-2-((((1s,4S)-4-(2-((E)-3-(benzyloxy)-3-oxoprop-1-en-1-yl)phenyl)cyclohexyl)oxy)methyl)-3-((tert-butoxycarbonyl)amino)piperidine-1-carboxylate (1.26 g, 1.85 mmol) was dissolved in ethanol (22 mL). Palladium hydroxide on carbon (20 wt. %, 0.19 g, 0.28 mmol) was then added followed by ammonium formate (0.58 g, 9.23 mmol). The reaction was heated at 70 degrees C. for 30 min at which point LC-MS indicated completion of the reaction. The reaction mixture was filtered through Celite® and concentrated in vacuum to afford the crude product which was purified by silica gel flash column chromatography (0-40% MeOH in DCM) affording 3-(2-((1S,4s)-4-(((2R,3S)-3-((tert-butoxycarbonyl)amino)piperidin-2-yl)methoxy)cyclohexyl)phenyl)propanoic acid (0.58 g, 1.26 mmol, 68% yield) as a solid. LCMS (ESI): m/z $[M+H]^+$ for $C_{26}H_{40}N_2O_5$=461.4.

To a stirred mixture of 3-(2-((1S,4s)-4-(((2R,3S)-3-((tert-butoxycarbonyl)amino)piperidin-2-yl)methoxy)cyclohexyl)phenyl)propanoic acid (0.037 g, 0.08 mmol) in MeCN (220 mL) was added HATU (0.046 g, 0.12 mmol) and DIPEA (0.028 mL, 0.16 mmol). The reaction was left to stir for 2 hr at which point LC-MS indicated ~40% formation of the desired monomer with the remainder being dimeric product and a few trace impurities. The excess DIPEA was quenched with a few drops of 1M HCl. The reaction mixture was concentrated under reduced pressure and the crude material was purified on the Gilson prep HPLC (10-95% acetonitrile in (0.2% $NH_4OH$ in $H_2O$)) to afford tert-butyl (($2^1S,2^4S,5^2R,5^3S$)-6-oxo-3-oxa-5(2,1)-piperidina-1(1,2)-benzena-2(1,4)-cyclohexanacyclooctaphane-$5^3$-yl)carbamate (0.0068 g, 0.015 mmol, 19% yield) as a solid after lyophilization. $^1$H NMR (400 MHz, DMSO-$d_6$): δ 7.31 (br d, 1H), 7.27 (d, 1H), 7.16 (td, 1H), 7.11-7.02 (m, 2H), 4.52-4.42 (m, 1H), 4.41-4.31 (m, 1H), 4.16 (apparent dd, 1H), 3.92-3.76 (m, 2H), 3.54 (d, 1H), 3.30-3.22 (m, 1H), 2.86-2.68 (m, 3H), 2.66-2.54 (m, 1H), 2.49-2.40 (m, 1H), 2.15-2.00 (m, 1H), 1.96-1.71 (m, 3H), 1.69-1.60 (m, 1H), 1.60-1.44 (m, 4H), 1.43-1.24 (m, 12H); LCMS (ESI): m/z $[M+H]^+$ for $C_{26}H_{38}N_2O_4$=443.4.

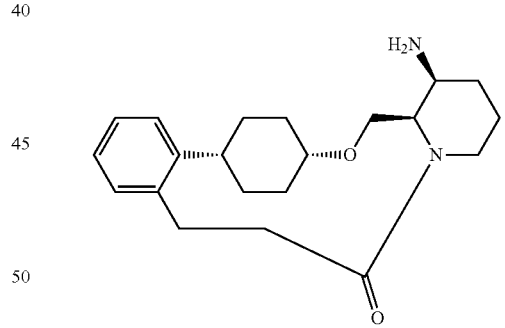

To a stirred mixture of tert-butyl (($2^1S,2^4S,5^2R,5^3S$)-6-oxo-3-oxa-5(2,1)-piperidina-1(1,2)-benzena-2(1,4)-cyclohexanacyclooctaphane-$5^3$-yl)carbamate (0.028 g, 0.063 mmol) in DCM (1.60 mL) was added TFA (0.32 mL). The reaction was left to stir for 45 min at which point LC-MS indicated completion of the reaction. The reaction was quenched with saturated $NaHCO_3$ until neutral pH was attained. The aqueous layer was extracted with DCM (3×20 mL) and the combined organics were dried over $MgSO_4$, filtered, and concentrated under reduced pressure to afford ($2^1S,2^4S,5^2R,5^3S$)-$5^3$-amino-3-oxa-5(2,1)-piperidina-1(1,2)-benzena-2(1,4)-cyclohexanacyclooctaphan-6-one (0.019 g, 0.055 mmol, 88% yield) as a solid. LCMS (ESI): m/z $[M+H]^+$ for $C_{21}H_{30}N_2O_2$=343.3.

(Compound 10)

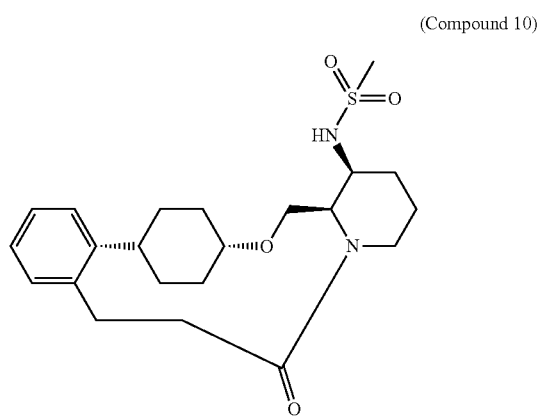

To a stirred mixture of (2¹S,2⁴S,5²R,5³S)-5³-amino-3-oxa-5(2,1)-piperidina-1(1,2)-benzena-2(1,4)-cyclohexana-cyclooctaphan-6-one (0.016 g, 0.047 mmol) in DCM (2.6 ml) was added DIPEA (0.041 mL, 0.23 mmol) and methanesulfonyl chloride (10.92 μL, 0.14 mmol). The resulting solution was stirred at room temperature for 2 hr at which point LC-MS indicated completion of the reaction. The reaction was quenched with water (1 mL) and the aqueous layer was extracted with DCM (3×5 mL). The combined organics were dried over MgSO₄, filtered, and concentrated under reduced pressure to afford the crude product which was purified on the Gilson prep HPLC (10-95% acetonitrile in (0.2% NH₄OH in H₂O)) to afford N-((2¹S,2⁴S,5²R,5³S)-6-oxo-3-oxa-5(2,1)-piperidina-1(1,2)-benzena-2(1,4)-cyclohexanacyclooctaphane-5³-yl)methanesulfonamide (0.0123 g, 0.029 mmol, 63% yield) as a solid after lyophilization. ¹H NMR (400 MHz, DMSO-d₆): δ 7.45 (br d, 1H), 7.26 (d, 1H), 7.18-7.11 (m, 1H), 7.11-7.01 (m, 2H), 4.41-4.28 (m, 2H), 4.20-4.08 (m, 1H), 3.86-3.80 (m, 1H), 3.80-3.70 (m, 2H), 2.93 (s, 3H), 2.87-2.65 (m, 4H), 2.49-2.38 (m, 2H), 2.24-2.13 (m, 1H), 2.12-1.97 (m, 1H), 1.92-1.77 (m, 2H), 1.71-1.60 (m, 2H), 1.59-1.50 (m, 2H), 1.50-1.30 (m, 4H); LCMS (ESI): m/z [M+H]⁺ for $C_{22}H_{32}N_2O_4S$=421.3. Both enantiomers of the racemate were obtained in >99% ee by chiral SFC separation.

Scheme 2

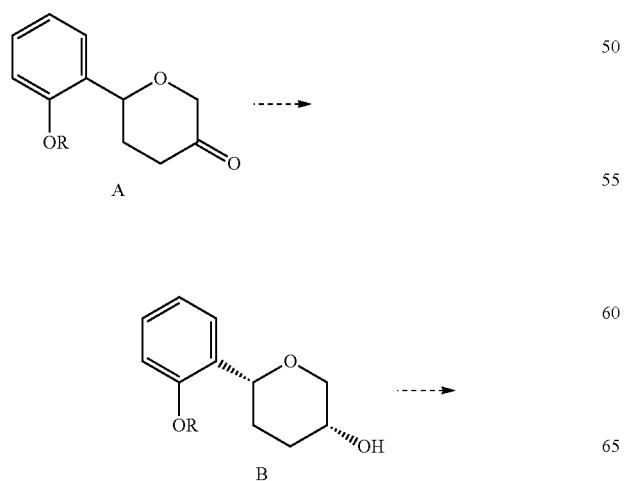

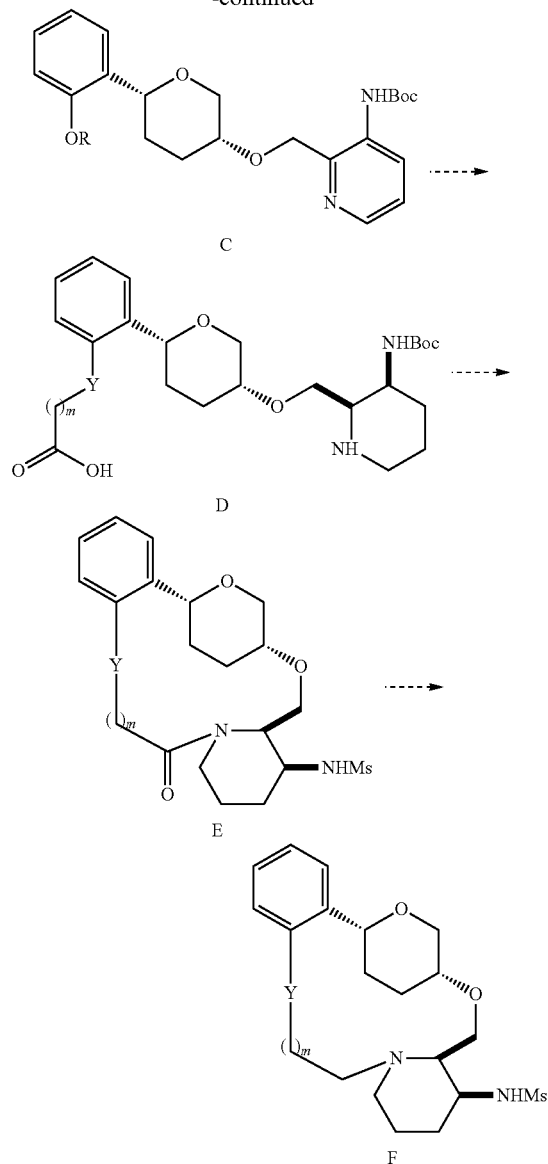

Example 1.7

Into a 100 mL 3-necked round-bottom flask were added 6-[2-(benzyloxy)phenyl]oxan-3-one (1.478 g, 5.235 mmol, 1 equiv.) and THF (15 mL) and L-selectride (15.7 mL, 15.700 mmol, 3 equiv.) at room temperature. The resulting mixture was stirred for 2 hr at room temperature under nitrogen atmosphere. H₂O (9.43 mg, 0.523 mmol, 0.1 equiv.) and EtOH (4.82 mg, 0.105 mmol, 0.02 equiv.) were added. The resulting mixture was stirred for 30 min at room temperature under nitrogen atmosphere, then was added H$_2$O$_2$ (30%) (2 mL, 85.845 mmol, 16.4 equiv.). The resulting mixture was stirred for 1 hr at 0 degrees C. under nitrogen atmosphere. The resulting mixture was washed with 2×100 mL of water. The residue was purified by silica gel column chromatography, eluted with PE/EtOAc (4:1) to afford 6-[2-(benzyloxy)phenyl]oxan-3-ol (960 mg, 64.5%) as a light yellow oil. LCMS (ESI): m/z [M+H]$^+$=285.25; $^1$H NMR (400 MHz, DMSO-d$_6$): δ 7.49-7.28 (m, 6H), 7.27-7.17 (m, 1H), 7.03 (dd, J=1.1, 8.4 Hz, 1H), 6.99-6.90 (m, 1H), 5.14 (s, 2H), 4.70-4.53 (m, 2H), 3.93-3.85 (m, 1H), 3.67-3.59 (m, 2H), 1.80-1.59 (m, 4H).

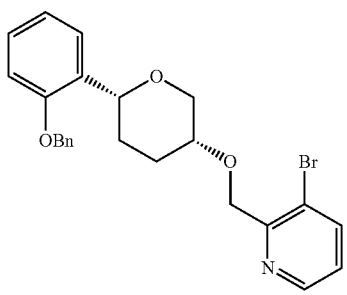 [SMILES: Brc1cccnc1CO[C@@H]1CC[C@H](c2ccccc2OCc2ccccc2)OC1]

A mixture of 6-[2-(benzyloxy)phenyl]oxan-3-ol (0.96 g, 3.376 mmol, 1 equiv.) and NaH (0.68 g, 17.002 mmol, 5.04 equiv., 60%) in THF (15 mL) was stirred for 1 hr at 0 degrees C. under nitrogen atmosphere. To the above mixture was added 3-bromo-2-(bromomethyl)pyridine (1.03 g, 4.085 mmol, 1.21 equiv.) at 0 degrees C. The resulting mixture was stirred for additional 5 hr at room temperature under nitrogen atmosphere. The reaction was quenched by the addition of water (10 mL) at 0 degrees C. The resulting mixture was diluted with water (20 mL). The resulting mixture was extracted with EtOAc (2×10 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc (3:1). The resulting mixture was concentrated under vacuum. The product was purified by Prep-Chiral HPLC to afford 2-([[(3S,6S)-6-[2-(benzyloxy)phenyl]oxan-3-yl]oxy]methyl)-3-bromopyridine (460 mg, 30%) as a light yellow oil, and 2-([[(3R,6R)-6-[2-(benzyloxy)phenyl]oxan-3-yl]oxy]methyl)-3-bromopyridine (464 mg, 30.3%) as light yellow oil. LCMS (ESI): m/z [M+H]$^+$=475.3.

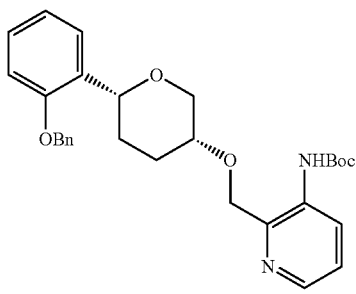

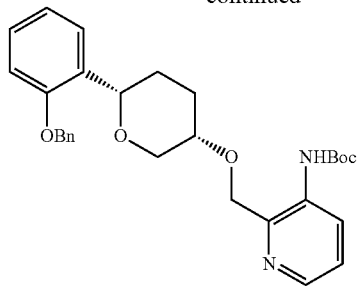

To a solution of 2-([[[(3R,6R)-6-[2-(benzyloxy)phenyl]oxan-3-yl]oxy]methyl)-3-bromopyridine (520 mg, 1.144 mmol, 1.00 equiv.) and tert-butyl carbamate (268 mg, 2.289 mmol, 2 equiv.) in dioxane (5 mL) were added Cs$_2$CO$_3$ (1.12 g, 3.433 mmol, 3 equiv.), Pd$_2$(dba)$_3$·CHCl$_3$ (118 mg, 0.114 mmol, 0.1 equiv.), and XantPhos (132 mg, 0.229 mmol, 0.2 equiv.). After stirring for 1 hr at 100 degrees C. under a nitrogen atmosphere, the resulting mixture was concentrated under reduced pressure. The residue was purified by Prep-TLC, eluted with PE/EtOAc (10:1) to afford tert-butyl N-[2-([[(3R,6R)-6-[2-(benzyloxy)phenyl]oxan-3-yl]oxy]methyl)pyridin-3-yl]carbamate (500 mg, 89.1%) as a light yellow oil. LCMS (ESI): m/z [M+H]$^+$=491.3. The corresponding enantiomer was prepared using the same method to afford tert-butyl N-[2-([[(3S,6S)-6-[2-(benzyloxy)phenyl]oxan-3-yl]oxy]methyl)pyridin-3-yl]carbamate (500 mg, 84.2%) as a solid.

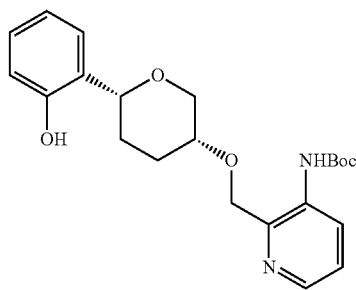

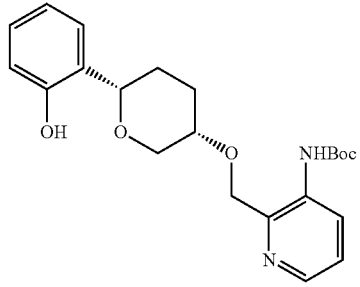

To a stirred mixture of tert-butyl N-[2-([[(3R,6R)-6-[2-(benzyloxy)phenyl]oxan-3-yl]oxy]methyl)pyridin-3-yl]carbamate (706 mg, 1.439 mmol, 1 equiv.) and Pd/C (153 mg) in MeOH (10 mL) at room temperature under hydrogen atmosphere. The resulting mixture was stirred for 3 hr at room temperature under hydrogen atmosphere. The precipitated solids were collected by filtration and washed with MeOH (3×3 mL). The resulting mixture was concentrated under reduced pressure to afford tert-butyl N-[2-([[(3R,6R)-6-(2-hydroxyphenyl)oxan-3-yl]oxy]methyl)pyridine-3-yl]carbamate (467 mg, 66.2%) as a solid. $^1$H NMR (400 MHz, DMSO-d$_6$): δ 9.36 (s, 1H), 8.63 (s, 1H), 8.21 (dd, J=1.5, 4.7

Hz, 1H), 8.16 (d, J=8.2 Hz, 1H), 7.34 (dd, J=4.7, 8.3 Hz, 1H), 7.29-7.23 (m, 1H), 7.08-7.00 (m, 1H), 6.75 (t, J=7.6, 7.6 Hz, 2H), 4.86-4.74 (m, 2H), 4.60 (dd, J=2.8, 10.2 Hz, 1H), 4.12-4.05 (m, 1H), 3.65-3.58 (m, 1H), 3.56 (s, 1H), 2.02 (d, J=13.9 Hz, 1H), 1.81 (t, J=14.3, 14.3 Hz, 1H), 1.72-1.60 (m, 2H), 1.37 (d, J=1.0 Hz, 9H). The corresponding enantiomer was prepared using the same method to afford tert-butyl N-[2-([[(3S,6S)-6-(2-hydroxyphenyl)oxan-3-yl]oxy]methyl)pyridin-3-yl]carbamate (446 mg, 64.1%) as a light yellow oil.

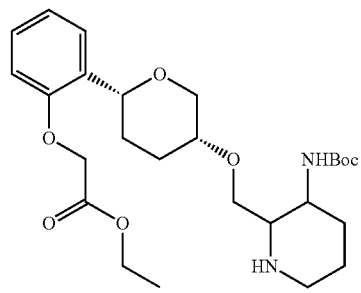

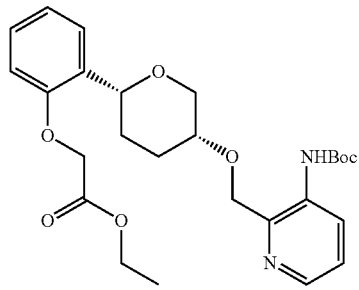

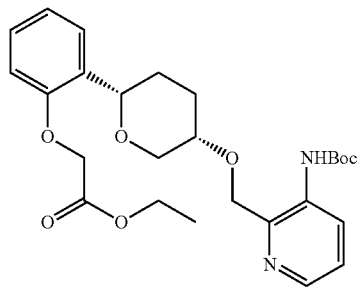

Ethyl bromoacetate (279 mg, 1.671 mmol, 1.5 equiv.) was added dropwise into a mixture of tert-butyl N-[2-([[(3R,6R)-6-(2-hydroxyphenyl)oxan-3-yl]oxy]methyl)pyridine-3-yl]carbamate (446 mg, 1.114 mmol, 1 equiv.) and $K_2CO_3$ (770 mg, 5.568 mmol, 5 equiv.) in acetone (8 mL) at 0 degrees C. The resulting solution was stirred for 12 hr at 50 degrees C. The solids were filtered out. The filtrate was concentrated under vacuum. The residue was purified by Prep-TLC (PE/EtOAc=3:1) to afford ethyl 2-[2-[(2R,5R)-5-([3-[(tert-butoxycarbonyl)amino]pyridin-2-yl]methoxy)oxan-2-yl]phenoxy]acetate (461 mg, 85.1%) as a light yellow oil. $^1$H NMR (400 MHz, DMSO-$d_6$): δ 8.63 (s, 1H), 8.21 (dd, J=1.5, 4.7 Hz, 1H), 8.15 (d, J=8.3 Hz, 1H), 7.36 (ddd, J=3.2, 7.9, 12.9 Hz, 2H), 7.23-7.14 (m, 1H), 6.98-6.90 (m, 1H), 6.85 (d, J=8.2 Hz, 1H), 4.88-4.74 (m, 4H), 4.69 (d, J=10.7 Hz, 1H), 4.15 (q, J=7.1 Hz, 3H), 3.63 (d, J=12.5 Hz, 1H), 3.57 (s, 1H), 2.03 (d, J=13.5 Hz, 1H), 1.81 (d, J=7.5 Hz, 2H), 1.61 (d, J=14.7 Hz, 1H), 1.37 (s, 9H), 1.20 (t, J=7.1 Hz, 3H); LCMS (ESI): m/z [M+H]$^+$=487.3. The corresponding enantiomer was prepared using the same method to afford ethyl 2-[2-[(2S,5S)-5-([3-[(tert-butoxycarbonyl)amino]pyridin-2-yl]methoxy)oxan-2-yl]phenoxy]acetate (490 mg, 86.4%) as a light yellow oil.

Into a 50-mL round-bottom flask, was placed ethyl 2-[2-[(2R,5R)-5-([3-[(tert-butoxycarbonyl)amino]pyridin-2-yl]methoxy)oxan-2-yl]phenoxy]acetate (461 mg, 0.947 mmol, 1 equiv.), AcOH (1 mL), MeOH (9 mL) and $PtO_2$ (108 mg, 0.474 mmol, 0.5 equiv.) under $H_2$ atmosphere. The resulting solution was stirred for 30 min at room temperature. The solids were filtered out. The filtrate was concentrated under vacuum. The residue was diluted with 20 mL of saturation $NaHCO_3$. The resulting solution was extracted with 3×30 mL DCM. The combined organic phase was washed with 30 mL of brine. Dried over anhydrous $Na_2SO_4$ and concentrated. This resulted in ethyl 2-[2-[(2R,5R)-5-([3-[(tert-butoxycarbonyl)amino]piperidin-2-yl]methoxy)oxan-2-yl]phenoxy]acetate (390 mg, 83.6%) as a yellow green oil. LCMS (ESI): m/z [M+H]$^+$=493.4, The corresponding enantiomer was prepared using the same method to afford ethyl 2-[2-[(2S,5S)-5-([3-[(tert-butoxycarbonyl)amino] piperidin-2-yl]methoxy)oxan-2-yl]phenoxy]acetate (407 mg, 81.9%) as a yellow green oil.

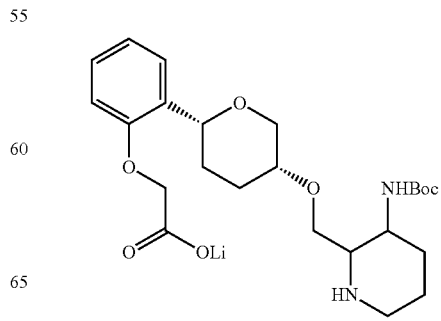

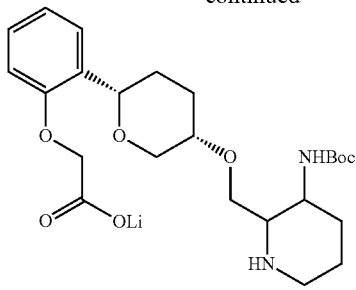

The mixture of ethyl 2-[2-[(2R,5R)-5-([3-[(tert-butoxycarbonyl)amino] piperidin-2-yl]methoxy)oxan-2-yl]phenoxy]acetate (390 mg, 0.792 mmol, 1 equiv.) and LiOH·H$_2$O (95 mg, 3.959 mmol, 5 equiv.) in MeOH (1 mL)/THF (2 mL)/H$_2$O (1 mL) was stirred at room temperature under air atmosphere for 3 hr. The resulting mixture was concentrated under reduced pressure. The crude product was purified by Prep-HPLC to afford lithium 2-(2-((2R,5R)-5-((3-((tert-butoxycarbonyl)amino)piperidin-2-yl)methoxy)tetrahydro-2H-pyran-2-yl)phenoxy)acetate (167 mg, 45.4%) as a solid. LCMS (ESI): m/z [M+H]$^+$=465.1. The corresponding enantiomer was prepared using the same method to afford lithium 2-(2-((2S,5S)-5-((3-((tert-butoxycarbonyl)amino)piperidin-2-yl)methoxy)tetrahydro-2H-pyran-2-yl)phenoxy)acetate (160 mg, 42.4%) as a solid. LCMS (ESI): m/z [M+H]$^+$=465.2.

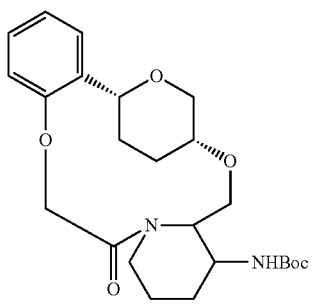

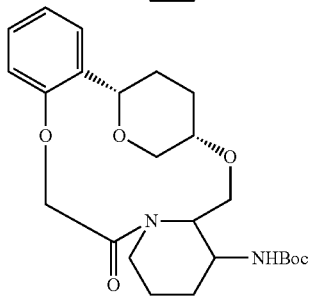

To the mixture of lithium 2-(2-((2R,5R)-5-((3-((tert-butoxycarbonyl)amino)piperidin-2-yl)methoxy)tetrahydro-2H-pyran-2-yl)phenoxy)acetate (31 mg, 0.0668 mmol, 1 equiv.) and HATU (39 mg, 0.100 mmol, 1.5 equiv.) at room temperature in DMF (3 mL), MeCN (15 mL) was added DIEA (17 mg, 0.133 mmol, 2 equiv.) at room temperature under nitrogen atmosphere. The resulting mixture was stirred for 2 hr at room temperature under nitrogen atmosphere. The resulting mixture was concentrated under reduced pressure to afford the crude product which was used in the next step directly without further purification.

The corresponding enantiomer was prepared using the same method to afford the crude product which was used in the next step directly without further purification.

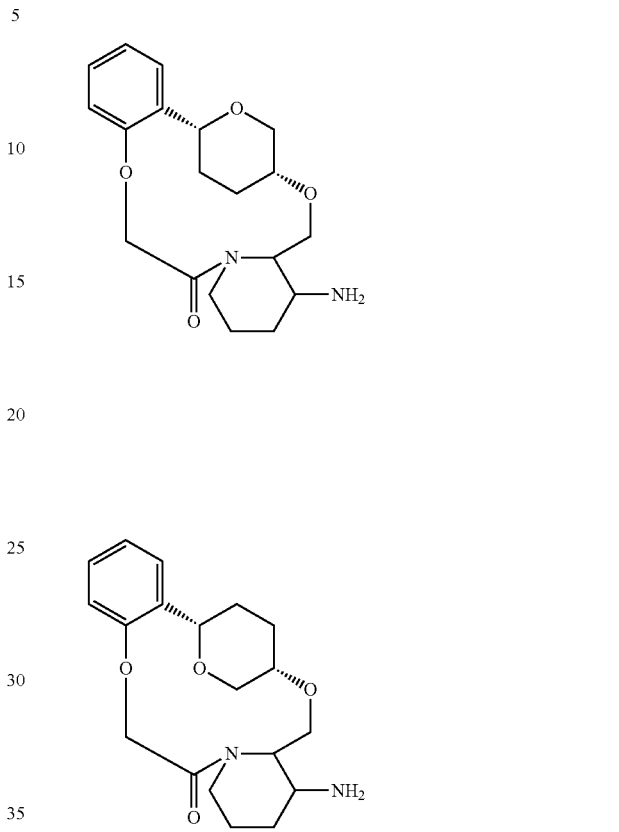

To a stirred solution of tert-butyl N-[(1R,19R)-10-oxo-8,18,21-trioxa-11-azatetracyclo[17.2.2.0ˆ[2,7]ˆ[11,16]]tricosa-2,4,6-trien-15-yl]carbamate in DCM (1 mL) was added TFA (0.30 mL) at 0 degrees C. The resulting mixture was stirred for 2 hr at room temperature. The resulting mixture was concentrated under reduced pressure. The crude product (mg) was purified by Prep-HPLC to afford (1R,19R)-15-amino-8,18,21-trioxa-11-azatetracyclo[17.2.2.0ˆ[2,7]ˆ[11,16]]tricosa-2,4,6-trien-10-one (60 mg, 44.2%) as a solid. LCMS (ESI): m/z [M+H]$^+$=347.1 The corresponding enantiomer was prepared using the same method to afford (1S,19S)-15-amino-8,18,21-trioxa-11-azatetracyclo[17.2.2.0ˆ[2,7]ˆ[11,16]]tricosa-2,4,6-trien-10-one (54.5 mg, 43.9%) as a solid. LCMS (ESI): m/z [M+H]$^+$=347.1.

(Compound 9)

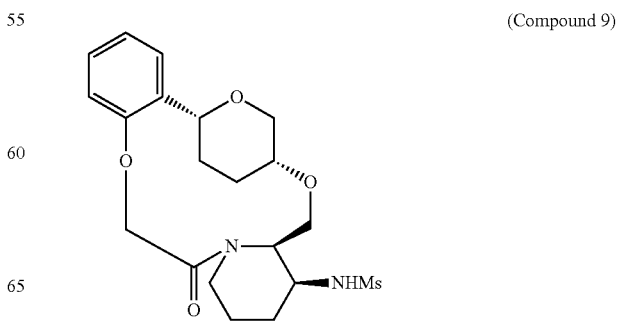

(Compound 8)

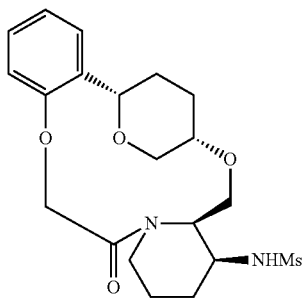

MsCl (60 mg, 0.520 mmol, 3 equiv.) was added into a solution of (1R,19R)-15-amino-8,18,21-trioxa-11-azatetracyclo[17.2.2.0^[2,7]^[11,16]]tricosa-2,4,6-trien-10-one (60 mg, 0.173 mmol, 1 equiv.) and DIPEA (112 mg, 0.866 mmol, 5 equiv.) in DCM (10 mL) at 0 degrees C. The resulting solution was stirred for 2 hr at room temperature. The reaction was concentrated into a residue to give 65 mg of crude product which was purified by a chiral prep-HPLC to provide 10.2 mg of N-(($2^2$R,$2^5$R,$5^2$R,$5^3$S)-6-oxo-$2^3$,$2^4$,$2^5$,$2^6$-tetrahydro-$2^2$H-3,8-dioxa-5(2,1)-piperidina-2(2,5)-pyrana-1(1,2)-benzenacyclooctaphane-$5^3$-yl)methanesulfonamide as a solid. LCMS (ESI): m/z [M+H]$^+$=425.1 The corresponding enantiomer was prepared using the same method to afford 6.8 mg of N-(($2^2$S,$2^5$S,$5^2$R,$5^3$S)-6-oxo-$2^3$,$2^4$,$2^5$,$2^6$-tetrahydro-$2^2$H-3,8-dioxa-5(2,1)-piperidina-2(2,5)-pyrana-1(1,2) benzenacyclooctaphane-$5^3$-yl)methanesulfonamide as a solid.

Example 1.8

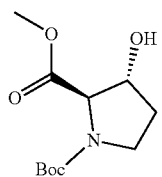

To a stirred mixture of (2R,3R)-1-(tert-butoxycarbonyl)-3-hydroxypyrrolidine-2-carboxylic acid (20.0 g, 86.487 mmol, 1.00 equiv.) and K$_2$CO$_3$ (19.12 g, 138.380 mmol, 1.6 equiv.) in DMF (300 mL) was added MeI (14.85 g, 104.65 mmol, 1.21 equiv.). The resulting mixture was stirred for 2 hr at 90 degrees C. under nitrogen atmosphere. The resulting mixture was concentrated under reduced pressure. The resulting mixture was diluted with water and then extracted with EtOAc. The combined organic layers were washed with brine and dried over anhydrous MgSO$_4$. After filtration, the filtrate was concentrated under reduced pressure. This resulted in 1-(tert-butyl) 2-methyl (2R,3R)-3-hydroxypyrrolidine-1,2-dicarboxylate (21 g, 99.00%) as a colorless oil. LCMS (ESI): m/z [M+H]$^+$=246; $^1$H NMR (400 MHz, CDCl$_3$): δ 4.45 (d, J=4.6 Hz, 1H), 4.25 (d, J=47.6 Hz, 1H), 3.76 (s, 3H), 3.71-3.46 (m, 2H), 2.14 (ddd, J=13.7, 9.0, 4.9 Hz, 1H), 1.92 (d, J=14.1 Hz, 1H), 1.46 (d, J=22.4 Hz, 9H).

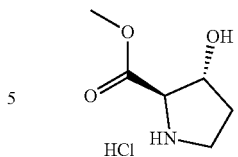

A mixture of 1-(tert-butyl) 2-methyl (2R,3R)-3-hydroxypyrrolidine-1,2-dicarboxylate (21 g, 85.618 mmol, 1.00 equiv.) and HCl (gas) (4N) in 1,4-dioxane (300.0 mL) was stirred for 4 hr at room temperature under nitrogen atmosphere. The precipitated solids were collected by filtration and washed with ethyl ether. This resulted in methyl (2R,3R)-3-hydroxypyrrolidine-2-carboxylate hydrochloride (14.4 g, 92.60%) as a solid. LCMS (ESI): m/z [M+H]$^+$=146.

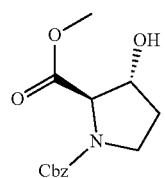 [SMILES: COC(=O)[C@H]1[C@H](O)CCN1C(=O)OCc1ccccc1]

To a stirred solution of methyl (2R,3R)-3-hydroxypyrrolidine-2-carboxylate hydrochloride (14.40 g, 79.286 mmol, 1.00 equiv.) and DIEA (25.62 g, 198.216 mmol, 2.50 eq.) in DCM (300.00 mL) were added benzyl 2,5-dioxopyrrolidin-1-yl carbonate (19.76 g, 79.286 mmol, 1.00 equiv.) in portions at 0 degrees C. under nitrogen atmosphere. The resulting mixture was stirred for 4 hr at room temperature under nitrogen atmosphere. The resulting mixture was diluted with dichloromethane (300 mL). The resulting mixture was washed with 2N HCl (aqueous) (500 mL×3). The resulting organic layers were washed with brine and dried over anhydrous MgSO$_4$. After filtration, the filtrate was concentrated under reduced pressure. The residue was purified by silica gel column chromatography, eluted with PE/EtOAc (2:3) to afford 1-benzyl 2-methyl (2R,3R)-3-hydroxypyrrolidine-1,2-dicarboxylate (18 g, 81.29%) as a solid. LCMS (ESI): m/z [M+H]$^+$=280; $^1$H NMR (400 MHz, CDCl$_3$): δ 7.45-7.21 (m, 5H), 5.31-4.96 (m, 2H), 4.54-4.24 (m, 2H), 3.88-3.53 (m, 5H), 2.66 (s, 1H), 2.11 (dd, J=13.8, 4.6 Hz, 1H), 1.95 (dtt, J=13.7, 6.7, 3.6 Hz, 1H).

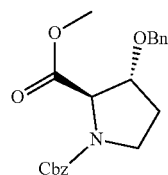 [SMILES: COC(=O)[C@H]1[C@H](OCc2ccccc2)CCN1C(=O)OCc1ccccc1]

To a stirred solution of 1-benzyl 2-methyl (2R,3R)-3-hydroxypyrrolidine-1,2-dicarboxylate (18.00 g, 64.449 mmol, 1.00 equiv.) and benzyl bromide (16.53 g, 96.673 mmol, 1.5 equiv.) in DCM (360.00 mL) was added Ag$_2$O (44.81 g, 193.346 mmol, 3 equiv.) under nitrogen atmosphere. The mixture was stirred at room temperature for 2 days with tin foil to cover the light. The resulting mixture was filtered, the filter cake was washed with DCM. The filtrate was concentrated under reduced pressure. The residue was purified by silica gel column chromatography, eluted with PE/EtOAc (5:1) to afford 1-benzyl 2-methyl (2R,3R)-3-(benzyloxy)pyrrolidine-1,2-dicarboxylate (17.2 g, 72.24%) as a colorless oil. LCMS (ESI): m/z [M+H]+= 370; ¹H NMR (400 MHz, CDCl₃): δ 7.36 (dq, J=16.0, 8.4, 7.1 Hz, 10H), 5.36-4.95 (m, 2H), 4.83-4.42 (m, 3H), 4.18 (q, J=3.9 Hz, 1H), 3.89-3.56 (m, 5H), 2.10 (dq, J=8.1, 4.1 Hz, 2H).

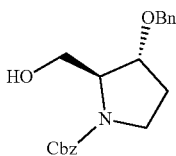

To a stirred solution of 1-benzyl 2-methyl (2R,3R)-3-(benzyloxy)pyrrolidine-1,2-dicarboxylate (17.20 g, 46.560 mmol, 1.00 equiv.) in THF (400.00 mL) were added NaBH₄ (17.61 g, 465.598 mmol, 10.00 equiv.) and LiCl (19.74 g, 465.598 mmol, 10.00 equiv.) in portions at 0 degrees C. under nitrogen atmosphere. The resulting mixture was stirred for 2 days at room temperature under nitrogen atmosphere. The mixture was allowed to cool down to 0 degrees C. The reaction was quenched by the addition of saturated NH₄C₁ (aq.) at 0 degrees C. The resulting mixture was extracted with EtOAc. The combined organic layers were washed with brine and dried over anhydrous MgSO₄. After filtration, the filtrate was concentrated under reduced pressure. The residue was purified by silica gel column chromatography, eluted with PE/EtOAc (1:2) to afford benzyl (2S,3R)-3-(benzyloxy)-2-(hydroxymethyl)pyrrolidine-1-carboxylate (15 g, 94.36%) as a colorless oil. LCMS (ESI): m/z [M+H]+=342; ¹H NMR (400 MHz, CDCl₃): δ 7.36 (dd, J=13.7, 6.5 Hz, 10H), 5.28-5.04 (m, 2H), 4.71-4.41 (m, 2H), 4.13 (q, J=6.4, 5.8 Hz, 1H), 3.95 (d, J=27.1 Hz, 1H), 3.80-3.43 (m, 5H), 2.04 (ddd, J=11.3, 7.1, 3.5 Hz, 2H).

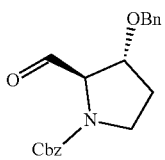

To a stirred solution of (COCl)₂ (6.69 g, 52.723 mmol, 1.20 equiv.) in DCM (300.00 mL) was added a solution of DMSO (8.24 g, 105.446 mmol, 2.40 equiv.) in DCM (50.00 mL) dropwise at −78 degrees C. under nitrogen atmosphere. The mixture was stirred at this temperature for 1.5 hr. A solution of benzyl (2S,3R)-3-(benzyloxy)-2-(hydroxymethyl)pyrrolidine-1-carboxylate (15.00 g, 43.936 mmol, 1.00 equiv.) in DCM (50.00 mL) was added dropwise. The mixture was stirred at −78 degrees C. for 1 hr, then TEA (22.23 g, 219.679 mmol, 5.00 equiv.) was added dropwise. The mixture was stirred at −78 degrees C. for 1 hr and the reaction mixture was allowed to warm to room temperature. The reaction was quenched by the addition of water. The resulting mixture was extracted with CH₂C₂. The combined organic layers were washed with brine, dried over anhydrous MgSO₄. After filtration, the filtrate was concentrated under reduced pressure. The residue was purified by silica gel column chromatography, eluted with hexane/EtOAc (3:1) to afford benzyl (2R,3R)-3-(benzyloxy)-2-formylpyrrolidine-1-carboxylate (13.8 g, 80.71%) as a colorless oil. LCMS (ESI): m/z [M+H]+=340; ¹H NMR (400 MHz, CDCl₃): δ 9.60 (d, J=41.5 Hz, 1H), 7.45-7.29 (m, 10H), 5.26-5.06 (m, 2H), 4.71-4.33 (m, 3H), 4.23 (d, J=4.6 Hz, 1H), 3.71 (ddt, J=14.9, 10.1, 5.4 Hz, 2H), 2.14 (dt, J=12.7, 4.4 Hz, 1H), 1.91 (dqd, J=13.6, 8.8, 4.7 Hz, 1H).

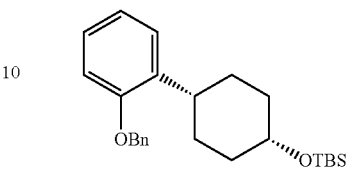

To the stirred solution of (1s,4s)-4-[2-(benzyloxy)phenyl]cyclohexan-1-ol (8.00 g, 28.330 mmol, 1.00 equiv.) in DCM (150.00 mL) were added tert-butyldimethylchlorosilane (4.70 g, 31.163 mmol, 1.1 equiv.) and imidazole (3.86 g, 56.661 mmol, 2.00 equiv.). The mixture was stirred overnight at room temperature. The reaction was monitored by TLC. The resulting mixture was diluted with water (100 mL). The resulting mixture was extracted with EtOAc (3×100 mL). The combined organic layers were washed with brine (2×100 mL) and dried over anhydrous Na₂SO₄. After filtration, the filtrate was concentrated under reduced pressure. The residue was purified by silica gel column chromatography, eluted with PE to (((1s,4s)-4-(2-(benzyloxy)phenyl)cyclohexyl)oxy)(tert-butyl)dimethylsilane (10 g, 88.99%) as a solid. ¹H NMR (400 MHz, CDCl₃): δ 7.51-7.39 (m, 4H), 7.39-7.29 (m, 2H), 7.22-7.13 (m, 1H), 7.00 (tq, J=7.5, 1.2 Hz, 1H), 6.94 (dq, J=8.1, 1.2 Hz, 1H), 5.13 (d, J=2.1 Hz, 2H), 4.10 (q, J=3.0 Hz, 1H), 3.11 (tt, J=12.1, 3.3 Hz, 1H), 1.95 (qd, J=12.8, 6.0 Hz, 2H), 1.86-1.76 (m, 2H), 1.69-1.57 (m, 4H), 1.00-0.93 (m, 9H), 0.11-0.08 (m, 6H).

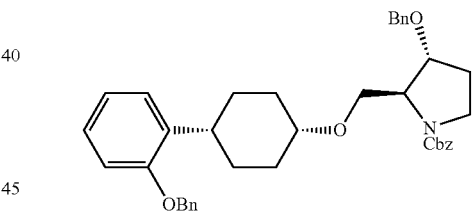

To benzyl (2R,3R)-3-(benzyloxy)-2-formylpyrrolidine-1-carboxylate (14.00 g, 41.236 mmol, 1.20 equiv.) dried under high vacuum for an hour was then added a solution of (((1s,4s)-4-(2-(benzyloxy)phenyl)cyclohexyl)oxy)(tert-butyl)dimethylsilane (13.63 g, 34.363 mmol, 1.00 equiv.) in dried DCM (200.00 mL) under nitrogen atmosphere. The mixture was then cooled down to −78 degrees C. with stirring under nitrogen atmosphere. A solution of TMSOTf (7.64 g, 34.363 mmol, 1.00 equiv.) in dried DCM (20.00 mL) was added dropwise at −78 degrees C., and following a solution of Et₃SiH (7.19 g, 61.854 mmol, 1.80 equiv.) in DCM (1.00 mL) was added dropwise. The reaction was then stirred for 0.5 hr at −78 degrees C. and additional 0.5 hr at room temperature. The reaction was quenched with saturated NaHCO₃ (aq.), the resulting mixture was extracted with CH₂C₂. The combined organic layers were washed with brine, dried over anhydrous MgSO₄. After filtration, the filtrate was concentrated under reduced pressure. The residue was purified by silica gel column chromatography, eluted with PE/EtOAc (8:1) to afford benzyl (2S,3R)-3-

(benzyloxy)-2-((((1s,4R)-4-(2-(benzyloxy)phenyl)cyclohexyl)oxy)methyl)pyrrolidine-1-carboxylate (15 g, 72.06%) as a colorless oil. LCMS (ESI): m/z [M+H]$^+$=606; $^1$H NMR (400 MHz, CDCl$_3$): δ 7.53-7.27 (m, 15H), 7.25-7.15 (m, 2H), 7.05-6.92 (m, 2H), 5.35-5.06 (m, 4H), 4.74-4.50 (m, 2H), 4.26-4.11 (m, 2H), 3.81-3.23 (m, 5H), 3.12 (tdt, J=11.3, 7.6, 4.1 Hz, 1H), 2.32-2.14 (m, 1H), 2.08-1.89 (m, 2H), 1.87-1.35 (m, 7H).

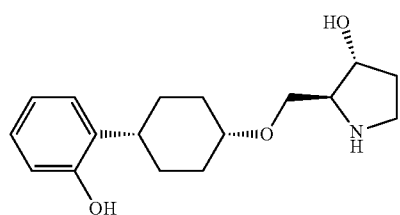 [SMILES: Oc1ccccc1[C@H]1CC[C@@H](OC[C@@H]2NCC[C@H]2O)CC1]

To a stirred solution of benzyl (2S,3R)-3-(benzyloxy)-2-((((1s,4R)-4-(2-(benzyloxy)phenyl)cyclohexyl)oxy)methyl) pyrrolidine-1-carboxylate (15.00 g, 24.762 mmol, 1.00 equiv.) in i-PrOH (400.00 mL) was added HCl (12.38 mL, 49.524 mmol, 2.00 equiv., 4N in i-PrOH) and Pd(OH)$_2$/C (3.48 g, 4.952 mmol, 0.20 equiv., 20%). The resulting mixture was stirred for 4 hr at room temperature under hydrogen atmosphere. The resulting mixture was filtered, the filter cake was washed with i-PrOH. The filtrate was concentrated under reduced pressure. Water (200 mL) was added and the product was lyophilized to afford (2S,3R)-2-((((1s,4R)-4-(2-hydroxyphenyl)cyclohexyl)oxy)methyl)pyrrolidin-3-ol (8 g, 98.55%) as a solid. LCMS (ESI): m/z calculated for C$_{17}$H$_{25}$NO$_3$ [M+H]$^+$=292.19, found 292.2.

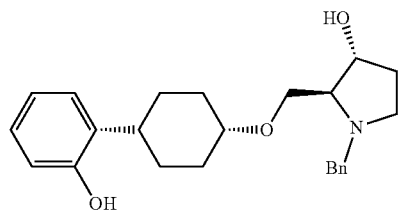

NaBH(OAc)$_3$ (4.80 g, 22.650 mmol, 3.00 equiv.) was added to the mixture of (2S,3R)-2-((((1s,4R)-4-(2-hydroxyphenyl)cyclohexyl)oxy)methyl)pyrrolidin-3-ol (2.20 g, 7.550 mmol, 1.00 equiv.) and benzaldehyde (1.60 g, 15.100 mmol, 2.00 equiv.) in DCM (30.00 mL), the resulting mixture was stirred for 1 hr at room temperature. The reaction was quenched with MeOH at room temperature. The resulting mixture was concentrated under reduced pressure. The residue was purified by silica gel column chromatography, eluted with PE/EtOAc (1:2) to afford (2S,3R)-1-benzyl-2-((((1s,4R)-4-(2-hydroxyphenyl)cyclohexyl)oxy)methyl)pyrrolidin-3-ol (2.4 g, 83.32%) as a yellow oil. LCMS (ESI): m/z calculated [M+H]$^+$=382.24, found=382.2; $^1$H NMR (400 MHz, DMSO-d$_6$): δ 9.16 (s, 1H), 7.42-7.16 (m, 5H), 7.01-6.83 (m, 2H), 6.74 (dd, J=8.0, 1.3 Hz, 1H), 6.61 (td, J=7.4, 1.3 Hz, 1H), 4.76 (d, J=4.3 Hz, 1H), 4.26 (d, J=13.2 Hz, 1H), 3.90 (ddd, J=6.9, 4.0, 2.1 Hz, 1H), 3.57 (s, 1H), 3.47 (d, J=13.2 Hz, 1H), 3.39 (d, J=5.7 Hz, 2H), 2.88 (t, J=11.9 Hz, 1H), 2.71 (ddd, J=9.0, 7.6, 1.8 Hz, 1H), 2.59 (td, J=5.6, 3.5 Hz, 1H), 2.40 (ddd, J=10.5, 8.7, 6.8 Hz, 1H), 2.00-1.89 (m, 2H), 1.89-1.78 (m, 1H), 1.72-1.37 (m, 7H).

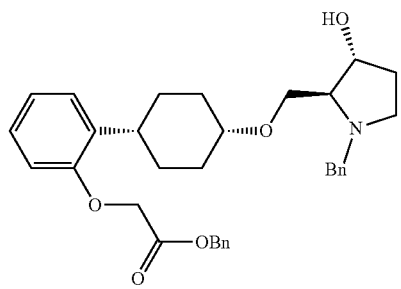 [SMILES: O=C(COc1ccccc1[C@H]1CC[C@@H](OC[C@H]2[C@H](O)CCN2Cc2ccccc2)CC1)OCc1ccccc1]

To a stirred mixture of (2S,3R)-1-benzyl-2-((((1s,4R)-4-(2-hydroxyphenyl)cyclohexyl)oxy)methyl)pyrrolidin-3-ol (8 g, 20.969 mmol, 1.00 equiv.) and K$_3$PO$_4$ (8.90 g, 41.938 mmol, 2.00 equiv.) in ACN (200.00 mL) was added benzyl 2-bromoacetate (7.21 g, 31.453 mmol, 1.50 equiv.). The resulting mixture was stirred for 3 hr at 50 degrees C. LCMS showed more than 90% conversion. The solid was filtered out. The filtrate was concentrated under reduced pressure. The residue was purified by silica gel column chromatography, eluted with PE/EtOAc (from 4:1 to 3:2) to afford benzyl 2-(2-((1R,4s)-4-(((2S,3R)-1-benzyl-3-hydroxypyrrolidin-2-yl)methoxy)cyclohexyl)phenoxy)acetate (7.8 g, 70.23%) as a yellow oil. LCMS (ESI): m/z [M+H]$^+$=530.

To a stirred solution of benzyl 2-(2-((1R,4s)-4-(((2S,3R)-1-benzyl-3-hydroxypyrrolidin-2-yl)methoxy)cyclohexyl)phenoxy)acetate (7.80 g, 14.726 mmol, 1.00 equiv.) and tert-butyl N-methanesulfonylcarbamate (5.75 g, 29.452 mmol, 2.00 equiv.) and PPh$_3$ (7.72 g, 29.452 mmol, 2.00 equiv.) in THF (40.00 mL) were added DIAD (5.96 g, 29.452 mmol, 2.00 equiv.) dropwise at room temperature under nitrogen atmosphere. The resulting mixture was stirred for 4 hr at room temperature under nitrogen atmosphere. The resulting mixture was concentrated under vacuum. The residue was purified by silica gel column chromatography, eluted with PE/EtOAc (2:1) to afford benzyl 2-(2-((1S,4s)-4-(((2R,3S)-1-benzyl-3-(N-(tert-butoxycarbonyl)methanesulfonamido)pyrrolidin-2-yl)methoxy)cyclohexyl)phenoxy)acetate (4.8 g, 46.11%) as a yellow oil. LCMS (ESI): m/z [M+H]$^+$=707.4; $^1$H NMR (400 MHz, CDCl$_3$): δ 7.43-7.21 (m, 10H), 7.14-7.05 (m, 2H), 6.87 (td, J=7.5, 1.1 Hz, 1H), 6.69 (dd, J=8.1, 1.2 Hz, 1H), 5.24 (s, 2H), 5.06-4.88 (m, 2H), 4.68 (s, 2H), 4.40-4.29 (m, 1H), 3.75-3.65 (m, 1H), 3.61 (s, 1H), 3.59-3.53 (m, 2H), 3.33 (s, 3H), 3.13-2.97 (m, 4H), 2.55 (dt, J=18.1, 9.6 Hz, 1H), 2.27-2.10 (m, 1H), 2.10-1.91 (m, 3H), 1.81-1.66 (m, 2H), 1.50 (s, 9H), 1.45-1.49 (m, 2H).

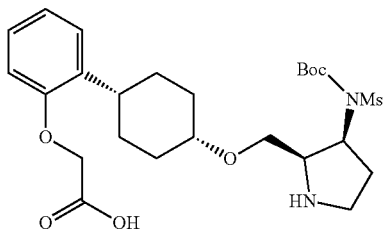

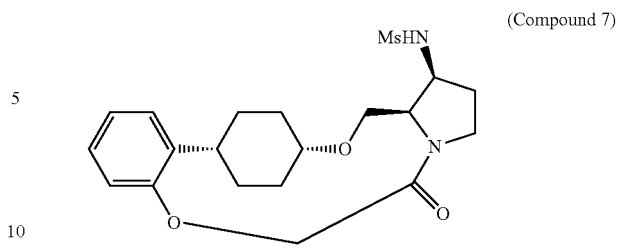

(Compound 7)

To a stirred solution of benzyl 2-(2-((1S,4s)-4-(((2R,3S)-1-benzyl-3-(N-(tert-butoxycarbonyl)methanesulfonamido)pyrrolidin-2-yl)methoxy)cyclohexyl)phenoxy)acetate (1.13 g, 1.599 mmol, 1.00 equiv.) in i-PrOH (150.00 mL) at room temperature was added Pd(OH)$_2$/C (594.88 mg, 0.847 mmol, 0.53 equiv., 20%). The resulting mixture was stirred for 6 hr at room temperature under hydrogen atmosphere. The resulting mixture was filtered, the filter cake was washed with MeOH (3×50 mL). The filtrate was concentrated under reduced pressure and via lyophilization to afford 2-(2-((1S,4s)-4-(((2R,3S)-3-(N-(tert-butoxycarbonyl)methanesulfonamido)pyrrolidin-2-yl)methoxy)cyclohexyl)phenoxy)acetic acid (607 mg, 72.10%) as a solid. LCMS (ESI): m/z [M+H]$^+$=527.

To a stirred solution of tert-butyl (methylsulfonyl)((2$^1$S, 2$^4$S,5$^2$R,5$^3$S)-6-oxo-3,8-dioxa-5(2,1)-pyrrolidina-1(1,2)-benzena-2(1,4)-cyclohexanacyclooctaphane-5$^3$-yl)carbamate (217.00 mg, 0.427 mmol, 1.00 equiv.) and TFA (2.00 mL, 26.926 mmol, 63.11 equiv.) in DCM (4 mL) was stirred for 1 hr at room temperature under nitrogen atmosphere. The resulting mixture was concentrated under reduced pressure. The crude product (150 mg) was purified by Prep-HPLC to afford N-((2$^1$S,2$^4$S,5$^2$R,5$^3$S)-6-oxo-3,8-dioxa-5(2,1)-pyrrolidina-1(1,2)-benzena-2(1,4)-cyclohexanacyclooctaphane-5$^3$-yl)methanesulfonamide (90 mg, 51.64%) as a solid. LCMS (ESI): m/z [M+H]$^+$=409; $^1$H NMR (400 MHz, methanol-d$_4$): δ 7.18 (dt, 1H), 7.09 (dd, 1H), 6.93-6.84 (m, 2H), 5.16 (d, 1H), 4.37 (dd, 1H), 4.29 (dt, 1H), 4.23-4.09 (m, 3H), 3.80 (s, 1H), 3.70 (dt, 1H), 3.55-3.48 (m, 1H), 3.04 (s, 3H), 2.74-2.51 (m, 2H), 2.49-2.34 (m, 1H), 2.34-2.19 (m, 1H), 2.23-2.09 (m, 2H), 1.90 (d, 1H), 1.58-1.42 (m, 2H), 1.42-1.24 (m, 2H).

Example 1.9

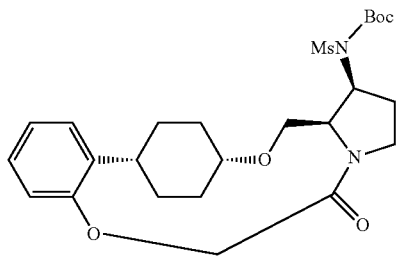

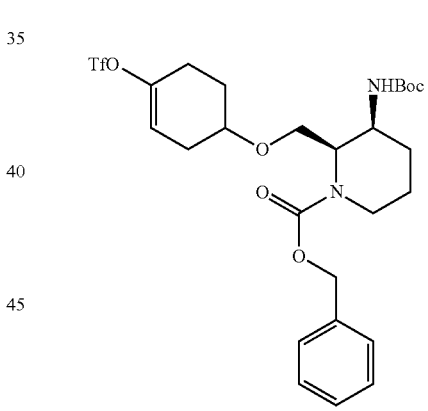

To a stirred solution of 2-(2-((1S,4s)-4-(((2R,3S)-3-(N-(tert-butoxycarbonyl) methanesulfonamido)pyrrolidin-2-yl)methoxy)cyclohexyl)phenoxy)acetic acid (100.00 mg, 0.190 mmol, 1.00 equiv.) and DIPEA (73.62 mg, 0.570 mmol, 3 equiv.) in MeCN (80 mL) was added HATU (108.30 mg, 0.285 mmol, 1.5 equiv.) at room temperature under nitrogen atmosphere. The resulting mixture was stirred for 2 hr at room temperature under nitrogen atmosphere. The residue was purified by reverse flash chromatography to afford tert-butyl (methylsulfonyl)((2$^1$S,2$^4$S, 5$^2$R,5$^3$S)-6-oxo-3,8-dioxa-5(2,1)-pyrrolidina-1(1,2)-benzena-2(1,4)-cyclohexanacyclooctaphane-5$^3$-yl)carbamate (29.9 mg, 31.00%) as a solid. LCMS (ESI): m/z [M+H]$^+$=509; $^1$H NMR (400 MHz, CDCl$_3$): δ 7.19 (dt, 1H), 7.09 (dd, 1H), 6.91 (dt, 1H), 6.79 (dd, 1H), 5.01 (d, 1H), 4.73-4.59 (m, 2H), 4.40-4.24 (m, 2H), 4.14 (dd, 1H), 3.70 (s, 1H), 3.58 (dt, 1H), 3.51 (s, 2H), 3.42-3.28 (m, 4H), 3.21 (dd, 1H), 2.69-2.49 (m, 2H), 2.32 (dt, 1H), 2.21-2.07 (m, 2H), 1.89 (d, 1H), 1.50 (s, 9H) 1.25-1.49 (m, 2H).

To a stirred solution of benzyl (2R,3S)-3-[(tert-butoxycarbonyl)amino]-2-[[(4-oxocyclohexyl)oxy]methyl]piperidine-1-carboxylate (30.0 g, 1.0 equiv., 65.1 mmol) in THF (300 mL) was added KHMDS (78.2 mL, 1.2 equiv., 78.2 mmol) at −78 degrees C. under nitrogen atmosphere. The resulting mixture was stirred for 3 hr at −78 degrees C. Followed by 1,1,1-trifluoro-N-phenyl-N-trifluoromethanesulfonylmethanesulfonamide (27.9 g, 1.2 equiv., 78.2 mmol) in THF (100 mL) dropwise at −78 degrees C. The resulting mixture was stirred for 2 hr at −78 degrees C. The mixture was added dropwise to 200 mL of sat. NH$_4$C$_1$ (aq.) at 0 degrees C. The resulting mixture was extracted with ethyl acetate (2×50 mL). The combined organic layers were dried over anhydrous Na$_2$SO$_4$. After filtration, the filtrate was concentrated under reduced pressure. The residue was purified by silica gel column chromatography to afford benzyl (2R,3S)-3-[(tert-butoxycarbonyl)amino]-2-([[4-(trifluoromethanesulfonyloxy)cyclohex-3-en-1-yl]oxy]methyl)piperidine-1-carboxylate (41.0 g, crude) as an oil.

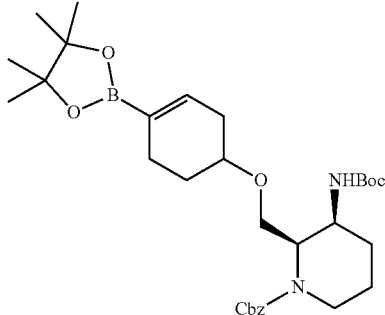 [SMILES: CC(C)(C)OC(=O)N[C@H]1CCCN(C(=O)OCc2ccccc2)[C@H]1COC1CC=C(B2OC(C)(C)C(C)(C)O2)CC1]

To a solution of benzyl (2R,3S)-3-[(tert-butoxycarbonyl)amino]-2-([[4-(trifluoromethanesulfonyloxy)cyclohex-3-en-1-yl]oxy]methyl)piperidine-1-carboxylate (350 g, 1.0 equiv., 0.59 mol) and bis(pinacolato)diboron (180 g, 1.2 equiv., 0.71 mol) in 1,4-dioxane (3.5 L) were added Pd(dppf)Cl$_2$·CH$_2$Cl$_2$ (24.1 g, 0.05 equiv., 29.5 mmol) and potassium acetate (116 g, 2.0 equiv., 1.18 mol) under nitrogen atmosphere. The resulting mixture was stirred for 16 hr at 100 degrees C. under nitrogen atmosphere. The resulting mixture was concentrated under reduced pressure. The residue was purified by silica gel column chromatography to afford crude product. The crude product was purified by reverse flash chromatography to afford benzyl (2R,3S)-3-[(tert-butoxycarbonyl)amino]-2-([[4-(4,4,5,5-tetramethyl-1,3,2-dioxaborolan-2-yl)cyclohex-3-en-1-yl]oxy]methyl)piperidine-1-carboxylate (90.8 g, 26.2%) as a solid. LCMS (ESI): m/z [M+H]$^+$=571; $^1$H-NMR (300 MHz, DMSO-d$_6$): δ 7.41-7.24 (m, 5H), 6.91 (brs, 1H), 6.30 (brs, 1H), 5.08 (brs, 2H), 4.54 (brs, 1H), 3.85 (d, J=13.3 Hz, 1H), 3.75-3.40 (m, 4H), 2.91-2.70 (s, 1H), 2.40-2.24 (m, 1H), 2.21-2.05 (m, 1H), 2.02-1.85 (m, 2H), 1.80-1.70 (m, 1H), 1.70-1.61 (m, 1H), 1.60-1.50 (m, 2H), 1.39 (s, 11H), 1.18 (s, 12H).

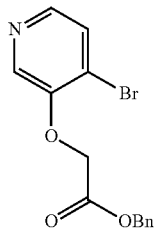

To a stirred solution/mixture of 4-bromopyridin-3-ol (500 mg, 1.0 equiv., 2.87 mmol) and benzyl 2-bromoacetate (658 mg, 1.0 equiv., 2.87 mmol) in acetonitrile (10.0 mL) was added K$_3$PO$_4$ (915 mg, 1.5 equiv., 4.31 mmol) dropwise at room temperature under air atmosphere. The resulting mixture was stirred for 2 hr at room temperature and concentrated under reduced pressure. The residue was purified by Prep-TLC to afford benzyl 2-[(4-bromopyridin-3-yl)oxy]acetate (60.0 mg, 16.2%) as a solid. LCMS (ESI): m/z [M+H]$^+$=322.0; $^1$H-NMR (300 MHz, DMSO-d$_6$): δ 8.36 (s, 1H), 8.09 (d, 1H), 7.71 (d, 1H), 7.32-7.43 (m, 5H), 7.32 (d, 1H), 5.22 (s, 2H), 5.16 (s, 2H), 4.50 (s, 1H).

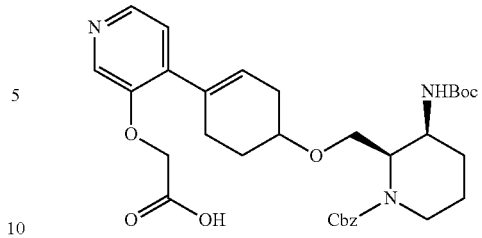

To a solution of benzyl 3-[(tert-butoxycarbonyl)amino]-2-([[4-(4,4,5,5-tetramethyl-1,3,2-dioxaborolan-2-yl)cyclohex-3-en-1-yl]oxy]methyl)piperidine-1-carboxylate (400.0 mg, 1.0 equiv., 0.701 mmol) and benzyl 2-[(4-bromopyridin-3-yl)oxy]acetate (271.0 mg, 1.0 equiv., 0.841 mmol) in 1,4-dioxane (4.0 mL) and H$_2$O (1.0 mL) were added Pd(dppf)Cl$_2$—CH$_2$Cl$_2$ (114.5 mg, 0.20 equiv., 0.140 mmol) and Na$_2$CO$_3$ (148.6 mg, 2.0 equiv., 1.40 mmol). After stirring for 5 hr at 85 degrees C. under a nitrogen atmosphere, the resulting mixture was concentrated under reduced pressure. The residue was purified by reverse flash chromatography to afford ([4-[4-([1-[(benzyloxy)carbonyl]-3-[(tert-butoxycarbonyl)amino]piperidin-2-yl]methoxy)cyclohex-1-en-1-yl]pyridin-3-yl]oxy)acetic acid (300.0 mg, 64.7%) as an oil. LCMS (ESI): m/z [M+H]$^+$=596.3.

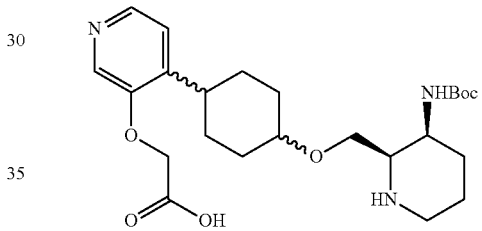

To a stirred solution of benzyl 3-[(tert-butoxycarbonyl)amino]-2-[([4-[3-(2-oxo-2-phenoxyethoxy)pyridin-4-yl]cyclohex-3-en-1-yl]oxy)methyl]piperidine-1-carboxylate (200.0 mg, 1.0 equiv., 0.298 mmol) and Pd(OH)$_2$/C (125.4 mg, 3.0 equiv., 0.893 mmol) in isobutanol (10.0 mL) was added HCOONH$_4$ (375.5 mg, 20.0 equiv., 5.95 mmol) dropwise at room temperature under air atmosphere. The resulting mixture was stirred for 2 hr at room temperature under hydrogen atmosphere. The resulting mixture was filtered, the filter cake was washed with acetonitrile (3×10 mL). The filtrate was concentrated under reduced pressure to give ([4-[4-([3-[(tert-butoxycarbonyl)amino]piperidin-2-yl]methoxy)cyclohexyl]pyridin-3-yl]oxy)acetic acid (80 mg, 52.2%) as a solid. LCMS (ESI): m/z [M+H]$^+$=464.3.

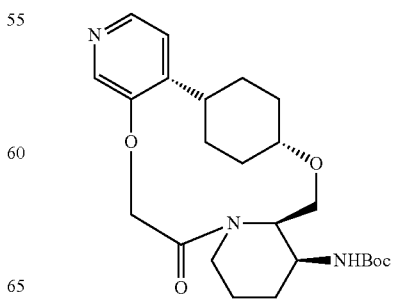

To a stirred solution of ([4-[4-([3-[(tert-butoxycarbonyl)amino]piperidin-2-yl]methoxy)cyclohexyl]pyridin-3-yl]oxy)acetic acid (80.0 mg, 1.0 equiv., 0.173 mmol) and HATU (98.4 mg, 1.5 equiv., 0.259 mmol) in acetonitrile (800.0 mL) was added diisopropylethylamine (66.9 mg, 3.0 equiv., 0.518 mmol) dropwise at room temperature under air atmosphere. The resulting mixture was stirred for 2 hr at room temperature under air atmosphere. The resulting mixture was concentrated under reduced pressure. The residue was purified by reverse flash chromatography to give tert-butyl ((2$^1$S,2$^4$S,5$^2$R,5$^3$S)-6-oxo-3,8-dioxa-1(4,3)-pyridina-5(2,1)-piperidina-2(1,4)-cyclohexanacyclooctaphane-5$^3$-yl)carbamate (25.0 mg, 23.4%) as a solid. LCMS (ESI): m/z [M+H]$^+$=445.3.

(Compound 47)

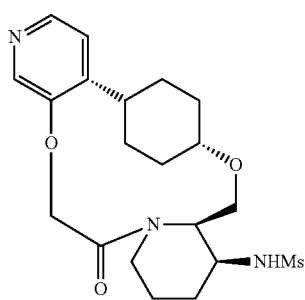

To a stirred solution of tert-butyl ((2$^1$S,2$^4$S,5$^2$R,5$^3$S)-6-oxo-3,8-dioxa-1(4,3)-pyridina-5(2,1)-piperidina-2(1,4)-cyclohexanacyclooctaphane-5$^3$-yl)carbamate (15.0 mg, 1.0 equiv., 0.034 mmol) in HCl (gas) in 1,4-dioxane (5.0 mL) at room temperature under air atmosphere. The resulting mixture was stirred for 1 hr at room temperature under air atmosphere. The resulting mixture was concentrated under reduced pressure. The crude product was used in next step without further purification. LCMS (ESI): m/z [M+H]$^+$= 303.2.

To a stirred solution of crude amine (15.0 mg, 1.0 equiv., 0.043 mmol) and triethylamine (22.0 mg, 5.0 equiv., 0.217 mmol) in dichloromethane (5.0 mL) was added MsCl (24.9 mg, 5.0 equiv., 0.217 mmol) dropwise at room temperature under air atmosphere and the resulting mixture was stirred for 1 hr at room temperature. The resulting mixture was concentrated under reduced pressure. The residue was purified by Prep-HPLC to afford N-((2$^1$S,2$^4$S,5$^2$R,5$^3$S)-6-oxo-3,8-dioxa-1(4,3)-pyridina-5(2,1)-piperidina-2(1,4)-cyclohexanacyclooctaphane-5$^3$-yl) methanesulfonamide (1.0 mg, 5.0%) as a solid. LCMS (ESI): m/z [M+H]$^+$=423.2; $^1$H NMR (400 MHz, Methanol-d$_4$) δ 8.17-8.07 (m, 2H), 7.20 (d, 1H), 5.49 (d, 1H), 5.27-5.20 (m, 1H), 4.24 (d, 1H), 4.00-3.91 (m, 1H), 3.85 (d, 1H), 3.75 (s, 1H), 3.64 (d, 1H), 3.58-3.56 (m, 1H), 3.04 (s, 3H), 2.70 (s, 2H), 2.28 (s, 1H), 2.20 (d, 2H), 1.90 (s, 4H), 1.74 (d, 2H), 1.50 (s, 2H), 1.31 (s, 1H).

Example 1.10

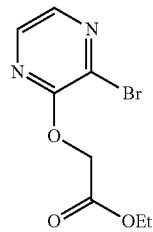 [SMILES: CCOC(=O)COc1nccnc1Br]

To a stirred solution of 2-bromo-3-fluoropyrazine 0.00 g, 1.0 equiv., 11.3 mmol), K$_2$CO$_3$ (3.12 g, 2.0 equiv., 22.6 mmol) in DMF (80 mL) was added ethyl 2-hydroxyacetate (0.94 g, 0.8 equiv., 9.04 mmol) at room temperature under air atmosphere. The resulting mixture was stirred for 1 hr at 60 degrees C. The resulting mixture was diluted with water (500 mL) and extracted with EtOAc (3×200 mL). The combined organic layers were washed with brine, dried over anhydrous Na$_2$SO$_4$. After filtration, the filtrate was concentrated under reduced pressure. The residue was purified by silica gel column chromatography to afford ethyl 2-[(3-bromopyrazin-2-yl)oxy]acetate (1.70 g, 57.6%) as an oil. LCMS (ESI): m/z [M+H]$^+$=262; $^1$H NMR (400 MHz, CDCl$_3$) δ 8.00 (d, 2H), 4.98 (s, 2H), 4.25 (m, 2H), 1.28 (t, 3H).

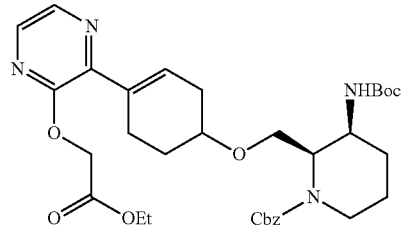 [SMILES: CCOC(=O)COc1nccnc1C1=CCC(OC[C@H]2[C@@H](NC(=O)OC(C)(C)C)CCCN2C(=O)OCc2ccccc2)CC1]

To a stirred solution of ethyl 2-[(3-bromopyrazin-2-yl)oxy]acetate (1.60 g, 1.2 equiv., 6.31 mmol) and benzyl 3-[(tert-butoxycarbonyl)amino]-2-([[4-(4,4,5,5-tetramethyl-1,3,2-dioxaborolan-2-yl)cyclohex-3-en-1-yl]oxy]methyl)piperidine-1-carboxylate (3.00 g, 1.0 equiv., 5.26 mmol) in dioxane (48 mL) and water (12 mL) were added Na$_2$CO$_3$ (1.67 g, 3.0 equiv., 15.8 mmol) and Pd(dppf)Cl$_2$ (384 mg, 0.1 equiv., 0.526 mmol) at room temperature under nitrogen. The resulting mixture was stirred for 2 hr at 80 degrees C. under nitrogen atmosphere. The residue was purified by silica gel column chromatography to afford benzyl 3-[(tert-butoxycarbonyl)amino]-2-[([4-[3-(2-ethoxy-2-oxoethoxy)pyrazin-2-yl]cyclohex-3-en-1-yl]oxy) methyl]piperidine-1-carboxylate (2.70 g, 82.2%) as an oil. LCMS (ESI): m/z [M+H]$^+$=626; $^1$H NMR (400 MHz, CDCl$_3$) δ 8.16 (d, 1H), 7.90 (d, 1H), 7.40-7.30 (m, 5H), 6.77 (s, 1H), 5.62 (s, 1H), 5.26-5.05 (m, 2H), 4.94 (t, 2H), 4.61 (s, 1H), 4.26 (m, 2H), 4.06 (d, 1H), 3.92 (s, 1H), 3.80 (s, 1H), 3.69 (s, 2H), 2.96-2.71 (m, 2H), 2.60 (d, 2H), 2.31 (d, 1H), 2.03 (s, 1H), 1.95 (s, 1H), 1.83 (s, 2H), 1.72 (d, 1H), 1.63 (d, 2H), 1.42 (d, 9H), 1.32-1.27 (m, 4H).

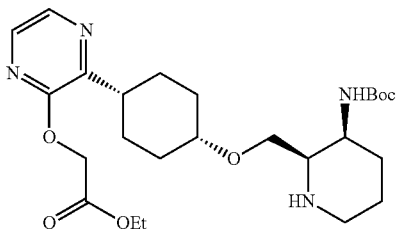 [SMILES: CC(C)(C)OC(=O)N[C@H]1CCCN[C@H]1CO[C@H]1CC[C@@H](c2nccnc2OCC(=O)O)CC1]

A mixture of benzyl 3-[(tert-butoxycarbonyl)amino]-2-[([4-[3-(2-ethoxy-2-oxoethoxy) pyrazin-2-yl]cyclohex-3-en-1-yl]oxy)methyl]piperidine-1-carboxylate (4.00 g, 1.0 equiv., 6.40 mmol) and Pd/C (1.36 g, 2.0 equiv., 12.8 mmol) in i-PrOH (300 mL) was stirred for 6 hr at room temperature under hydrogen atmosphere. The resulting mixture was filtered, the filter cake was washed with i-PrOH and concentrated to afford a residue which was purified by reverse flash chromatography to afford ethyl 2-((3-((1S,4s)-4-(((2R,3S)-3-((tert-butoxycarbonyl) amino)piperidin-2-yl)methoxy)cyclohexyl)pyrazin-2-yl)oxy)acetate (1.20 g, 38.1%) as a solid. LCMS (ESI): m/z [M+H]⁺=494; ¹H NMR (400 MHz, Methanol-d₄) δ 8.09 (d, 1H), 7.94 (d, 1H), 4.99 (s, 2H), 4.21 (q, 2H), 3.81 (q, 1H), 3.67-3.61 (m, 1H), 3.47 (dd, 1H), 3.40 (dd, 1H), 3.19 (m, 1H), 3.10-2.94 (m, 2H), 2.70 (td, 1H), 2.08 (dd, 2H), 1.97 (td, 2H), 1.85 (dd, 1H), 1.74-1.59 (m, 6H), 1.58-1.50 (m, 1H), 1.44 (s, 9H), 1.26 (m, 3H).

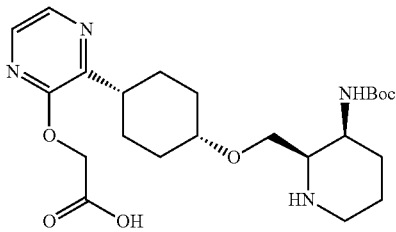

To a stirred solution of ethyl 2-([3-[4-([3-[(tert-butoxycarbonyl)amino]piperidin-2-yl]methoxy)cyclohexyl]pyrazin-2-yl]oxy)acetate (900 mg, 1.0 equiv., 1.83 mmol) in water (3 mL) and i-PrOH (20 mL) was added lithium hydroxide (87.5 mg, 2.0 equiv., 3.65 mmol) at room temperature. The resulting mixture was stirred for 2 hr at room temperature. HCl (3.7 mL, 1M) was added thereto and then concentrated. The residue was purified by reverse flash chromatography to afford 2-((3-((1S,4s)-4-(((2R,3S)-3-((tert-butoxycarbonyl)amino)piperidin-2-yl)methoxy)cyclohexyl)pyrazin-2-yl)oxy)acetic acid (600 mg, 70.7%) as a solid. LCMS (ESI):

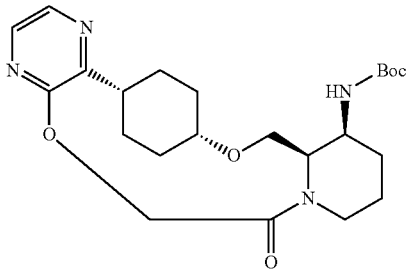

To a stirred solution of 2-((3-((1S,4s)-4-(((2R,3S)-3-((tert-butoxycarbonyl)amino) piperidin-2-yl)methoxy)cyclohexyl)pyrazin-2-yl)oxy)acetic acid (500 mg, 1.0 equiv., 1.08 mmol) and HATU (614 mg, 1.5 equiv., 1.61 mmol) in MeCN (500 mL) was added diisopropylethylamine (417 mg, 3.0 equiv., 3.23 mmol) dropwise at room temperature under nitrogen atmosphere. The resulting mixture was stirred for 1 hr at room temperature under nitrogen atmosphere. After filtration, the filtrate was concentrated under reduced pressure. The residue was purified by reverse flash chromatography to afford tert-butyl ((2¹S,2⁴S,5²R,5³S)-6-oxo-3,8-dioxa-1(2,3)-pyrazina-5(2,1)-piperidina-2(1,4)-cyclohexanacyclooctaphane-5³-yl)carbamate (200 mg, 42.1%) as a solid. LCMS (ESI): m/z [M+H]⁺=448; ¹H NMR (400 MHz, CDCl₃) δ 8.06-7.93 (m, 2H), 5.56-5.18 (m, 2H), 5.03-4.59 (m, 2H), 4.43 (s, 1H), 3.87 (d, 2H), 3.78-3.61 (m, 2H), 3.50 (td, 1H), 2.97 (dd, 1H), 2.62 (d, 1H), 2.38-2.05 (m, 3H), 2.03-1.78 (m, 4H), 1.76-1.55 (m 5H), 1.40 (s, 13H).

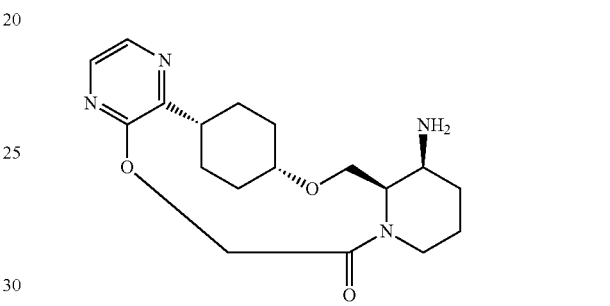

To a stirred solution of tert-butyl ((2¹S,2⁴S,5²R,5³S)-6-oxo-3,8-dioxa-1(2,3)-pyrazina-5(2,1)-piperidina-2(1,4)-cyclohexanacyclooctaphane-5³-yl)carbamate (300 mg) in dichloromethane (10 mL) was added TFA (2.00 mL) at room temperature. The resulting mixture was stirred for 1 hr at room temperature. Removed the solvent to give a residue which was purified by reverse flash chromatography to afford (2¹S,2⁴S,5²R,5³S)-5³-amino-3,8-dioxa-1(2,3)-pyrazina-5(2,1)-piperidina-2(1,4)-cyclohexanacyclooctaphan-6-one (220 mg, 94.5%) as a solid. LCMS (ESI): m/z [M+H]⁺=347.

(Compound 55)

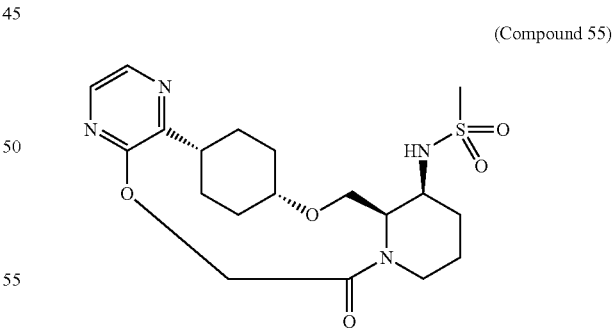

To a stirred solution of (2¹S,2⁴S,5²R,5³S)-5³-amino-3,8-dioxa-1(2,3)-pyrazina-5(2,1)-piperidina-2(1,4)-cyclohexanacyclooctaphan-6-one (260 mg, 1.0 equiv., 0.751 mmol) and diisopropylethylamine (484 mg, 5.0 equiv., 3.75 mmol) in dichloromethane (8 mL) were added MsCl (257.9 mg, 3.0 equiv., 2.25 mmol) dropwise at 0 degrees C. under nitrogen atmosphere. The resulting mixture was stirred for 1 hr at room temperature under nitrogen atmosphere. The reaction mixture was concentrated to give a residue which was purified by reverse flash chromatography to give N-(($2^1$S,$2^4$S,$5^2$R,$5^3$S)-6-oxo-3,8-dioxa-1(2,3)-pyrazina-5(2,1)-piperidina-2(1,4)-cyclohexanacyclooctaphane-$5^3$-yl)methanesulfonamide (260 mg, 81.6%) as an oil. The racemic product was separated by Chiral-Prep-HPLC to afford pure enantiomer (97.6 mg, 37.5%) as a solid. LCMS (ESI): m/z [M+H]$^+$=426; $^1$H NMR (400 MHz, Methanol-d$_4$) δ 8.08-7.96 (m, 2H), 5.37 (d, 1H), 5.25 (dt, 1H), 4.82 (d, 1H), 4.50 (d, 1H), 4.12-3.87 (m, 2H), 3.85-3.73 (m, 1H), 3.71-3.56 (m, 2H), 3.48 (d, 1H), 3.04 (s, 2H), 3.02-2.88 (m, 3H), 2.66 (d, 1H), 2.44-2.17 (m, 2H), 2.01-1.82 (m, 3H), 1.82-1.63 (m, 2H), 1.64-1.48 (m, 2H), 1.48-1.27 (m, 2H).

Example 1.11

(Compound 67)

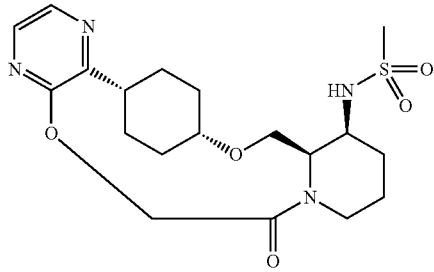

To a stirred solution of N-(($2^1$S,$2^4$S,$5^2$R,$5^3$S)-6-oxo-3,8-dioxa-1(2,3)-pyrazina-5(2,1)-piperidina-2(1,4)-cyclohexanacyclooctaphane-$5^3$-yl)methanesulfonamide (10.00 mg, 1.0 equiv., 0.024 mmol) in THF (2 mL) was added BH$_3$Me$_2$S (8.95 mg, 5.0 equiv., 0.118 mmol) dropwise at 0 degrees C. under nitrogen atmosphere. The resulting mixture was stirred for 1 hr at room temperature under nitrogen atmosphere. The resulting mixture was purified by Prep-HPLC to afford N-(($2^1$S,$2^4$S,$5^2$R,$5^3$S)-3,8-dioxa-1(2,3)-pyrazina-5(2,1)-piperidina-2(1,4)-cyclohexanacyclooctaphane-$5^3$-yl)methanesulfonamide (7.4 mg, 76.5%) as a solid. LCMS (ESI): m/z [M+H]$^+$=411.5; $^1$H NMR (400 MHz, Methanol-d$_4$) δ 8.01 (d, J=2.9 Hz, 1H), 7.93 (d, 1H), 4.48-4.37 (m, 1H), 4.27 (t, 1H), 3.87 (d, 2H), 3.77-3.63 (m, 2H), 3.28 (d, 1H), 3.00 (s, 7H), 2.96-2.81 (m, 2H), 2.76-2.62 (m, 1H), 2.49 (s, 1H), 2.20-2.05 (m, 2H), 2.04 (d, 1H), 1.90-1.79 (m, 1H), 1.74 (d, 2H), 1.67 (s, 1H), 1.50 (dd, 3H), 1.40-1.30 (m, 1H).

Example 1.12

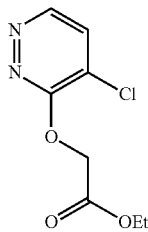 [SMILES: CCOC(=O)COc1nnccc1Cl]

To a solution of 4-chloropyridazin-3(2H)-one (5.00 g, 1.0 equiv., 38.3 mmol) and diacetoxyrhodium (1.69 g, 0.1 equiv., 3.83 mmol) in CH$_2$Cl$_2$ (25 mL) was added ethyl 2-diazoacetate (4.37 g, 1.0 equiv., 38.3 mmol) in CH$_2$Cl$_2$ (40 mL) dropwise over 5 hr at 45 degrees C. The resulting mixture was stirred for an additional 6 hr at 45 degrees C. The resulting mixture was concentrated under reduced pressure. The residue was purified by Prep-TLC to afford ethyl 2-((4-chloropyridazin-3-yl)oxy)acetate (1 g) as an oil. LCMS (ESI): m/z [M+H]$^+$=217; 1H NMR (400 MHz, Chloroform-d) δ 8.78 (d, J=5.0 Hz, 1H), 7.54 (d, J=5.0 Hz, 1H), 5.19 (s, 2H), 4.29-4.25 (m, 2H), 1.31 (t, J=7.1 Hz, 4H).

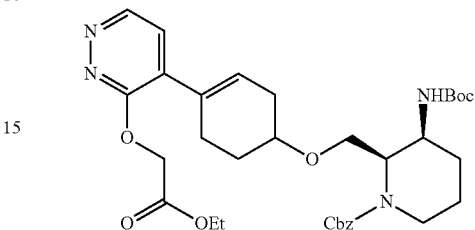

To a solution of ethyl 2-((4-chloropyridazin-3-yl)oxy)acetate (1.00 g, 1.0 equiv., 4.62 mmol) and benzyl (2R,3S)-3-((tert-butoxycarbonyl)amino)-2-(((4-(4,4,5,5-tetramethyl-1,3,2-dioxaborolan-2-yl)cyclohex-3-en-1-yl)oxy)methyl)piperidine-1-carboxylate (2.64 g, 1.0 equiv., 4.62 mmol) in 1,4-dioxane (50 mL) and water (10 mL) were added cesium carbonate (3.10 g, 1.0 equiv., 9.23 mmol) and Pd(Ph$_3$P)$_4$ (1.10 g, 0.2 equiv., 923.3 μmol). After stirring for 3 hr at 80 degrees C. under a nitrogen atmosphere, the resulting mixture was diluted with H$_2$O (50 mL) and extracted with EtOAc (3×300 mL). The combined organic layers were washed with brine (300 mL), dried over anhydrous Na$_2$SO$_4$. After filtration, the filtrate was concentrated under reduced pressure. The residue was purified by reverse flash chromatography to afford benzyl (2R,3S)-3-((tert-butoxycarbonyl)amino)-2-(((4-(3-(2-ethoxy-2-oxoethoxy)pyridazin-4-yl)cyclohex-3-en-1-yl)oxy)methyl)piperidine-1-carboxylate (1.21 g, 38.0%) as a solid. LCMS (ESI): m/z [M+H]$^+$=625; $^1$H NMR (400 MHz, Chloroform-d) δ 8.79 (d, J=4.8 Hz, 1H), 7.37 (t, J=2.8 Hz, 5H), 7.23 (s, 1H), 6.24 (s, 1H), 5.54 (s, 1H), 5.29-4.97 (m, 4H), 4.61 (s, 1H), 4.26 (q, J=7.1 Hz, 2H), 4.06 (d, J=13.2 Hz, 1H), 3.85-3.87 (m, 2H), 3.69 (d, J=12.6 Hz, 2H), 2.86 (s, 1H), 2.51 (s, 3H), 2.30 (s, 1H), 1.67-2.05 (m, 6H), 1.40-1.42 (m, 10H), 1.29-1.31 (m, 4H).

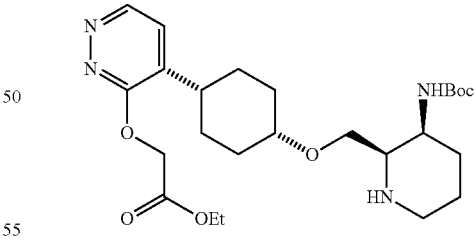

To a solution of benzyl (2R,3S)-3-tert-butoxycarbonyl)amino-2-(4-(3-(2-ethoxy-2-oxoethoxy)pyridazin-4-yl)cyclohex-3-en-1-yl)oxy)methyl)piperidine-1-carboxylate (1.21 g, 1.0 equiv., 1.94 mmol) in i-propanol (100 mL) was added Pd/C (1.10 g, 10% Wt, 0.5 equiv., 968.4 μmol) at nitrogen atmosphere. The resulting mixture was hydrogenated at room temperature for 4 hr under hydrogen atmosphere using a hydrogen balloon. The reaction mixture was concentrated under reduced pressure. The residue was purified by reverse flash chromatography to afford ethyl 2-((4-((1R,4r)-4-(((2R,3S)-3-((tert-butoxycarbonyl)amino)piperidin-2-yl)methoxy) cyclohexyl)pyridazin-3-yl)oxy)acetate (270.0 mg) as a solid and ethyl 2-((4-((1S,4s)-4-(((2R,3S)-3-((tert-butoxycarbonyl)amino)piperidin-2-yl)methoxy)cyclohexyl)pyridazin-3-yl)oxy)acetate (410.0 mg) as a solid. LCMS (ESI): m/z [M+H]$^+$=493; $^1$H NMR (400 MHz, Chloroform-d) δ 8.78 (d, J=4.8 Hz, 1H), 7.35 (s, 1H), 5.14 (s, 2H), 4.25 (q, J=7.1 Hz, 2H), 3.65 (s, 1H), 3.53 (d, 1H), 2.90 (s, 1H), 2.74 (s, 1H), 2.13-2.01 (m, 2H), 1.92 (d, J=13.6 Hz, 1H), 1.73 (s, 5H), 1.59-1.61 (m, 10H), 1.45 (s, 9H), 1.29-1.31 (m, 4H).

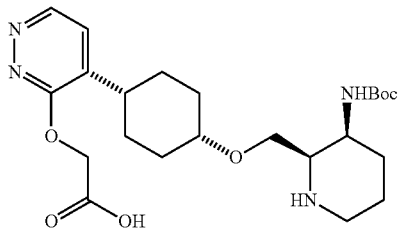

To a solution of ethyl 2-((4-((1S,4s)-4-(((2R,3S)-3-((tert-butoxycarbonyl)amino) piperidin-2-yl)methoxy)cyclohexyl)pyridazin-3-yl)oxy)acetate (400.0 mg, 1.0 equiv., 812.0 μmol) in MeOH (10 mL) was added lithium hydroxide (59.0 mg, 3.0 equiv., 2.44 mmol) in water (3 mL). The resulting mixture was stirred for 1 hr at 25 degrees C. The reaction was concentrated under reduced pressure. The crude product was purified by reverse flash chromatography to afford 2-((4-((1S,4s)-4-(((2R,3S)-3-((tert-butoxycarbonyl)amino)piperidin-2-yl)methoxy) cyclohexyl)pyridazin-3-yl)oxy)acetic acid (355.0 mg, 85%) as a solid. LCMS (ESI): m/z [M+H]$^+$=465; $^1$H NMR (400 MHz, Chloroform-d) δ 8.54 (d, J=4.5 Hz, 1H), 7.16 (s, 1H), 5.84 (s, 1H), 4.72 (s, 2H), 3.79 (s, 1H), 3.55 (s, 1H), 3.47 (d, J=8.1 Hz, 1H), 3.15-3.17 (m, 6H), 2.88 (s, 2H), 2.65 (s, 1H), 1.97-1.99 (m, 2H, 1.86-1.88 (m, 1H), 1.61-1.63 (m, 4H), 1.43 (s, 9H).

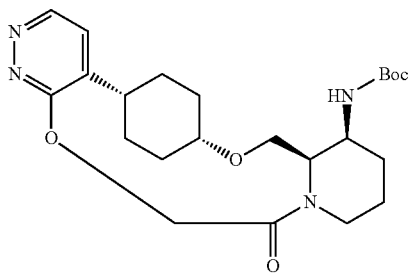 [SMILES: CC(C)(C)OC(=O)N[C@H]1CCCN2C(=O)COc3nnccc3[C@H]3CC[C@H](CC3)OC[C@@H]12]

To a solution of 2-((4-((1S,4s)-4-(((2R,3S)-3-((tert-butoxycarbonyl)amino)piperidin-2-yl) methoxy)cyclohexyl) pyridazin-3-yl)oxy)acetic acid (350.0 mg, 1.0 equiv., 0.753 mmol) and HATU (344.0 mg, 1.2 equiv., 0.904 mmol) in MeCN (800 mL) was added diisopropylethylamine (146 mg, 1.5 equiv., 1.13 mmol). The resulting mixture was stirred for 2 hr at 25 degrees C. The reaction mixture was concentrated under reduced pressure. The crude product was purified by reverse flash chromatography to afford tert-butyl ((2$^1$S,2$^4$S,5$^2$R,5$^3$S)-6-oxo-3,8-dioxa-1(4,3)-pyridazina-5(2,1)-piperidina-2(1,4)-cyclohexanacyclooctaphane-5$^3$-yl) carbamate (283.0 mg, 76%) as a solid. LCMS (ESI): m/z [M+H]$^+$=447.

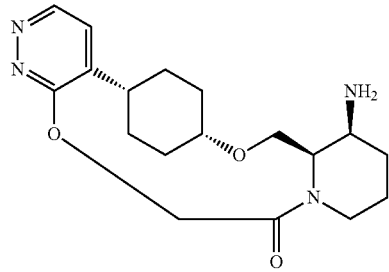 [SMILES: N[C@H]1CCCN2C(=O)COc3nnccc3[C@H]3CC[C@H](CC3)OC[C@@H]12]

To a solution of tert-butyl ((2$^1$S,2$^4$S,5$^2$R,5$^3$S)-6-oxo-3,8-dioxa-1(4,3)-pyridazina-5(2,1)-piperidina-2(1,4)-cyclohexanacyclooctaphane-5$^3$-yl)carbamate (270.0 mg, 1.0 equiv., 0.605 mmol) in dichloromethane (5 mL) was added TFA (1 mL). The resulting mixture was stirred for 1 hr at room temperature. The reaction mixture was basified to pH 8 with saturated Na$_2$CO$_3$ (aq. 10 mL). The resulting mixture was extracted with CH$_2$C$_2$ (3×20 mL). The combined organic layers were washed with brine (20 mL), dried over anhydrous Na$_2$SO$_4$. After filtration, the filtrate was concentrated under reduced pressure. The crude products was purified by reverse flash chromatography to afford (2$^1$S,2$^4$S, 5$^2$R,5$^3$S)-5$^3$-amino-3,8-dioxa-1(4,3)-pyridazina-5(2,1)-piperidina-2(1,4)-cyclohexanacyclooctaphan-6-one (140.0 mg, 60%) as a solid. LCMS (ESI): m/z [M+H]$^+$=347.

(Compound 56)

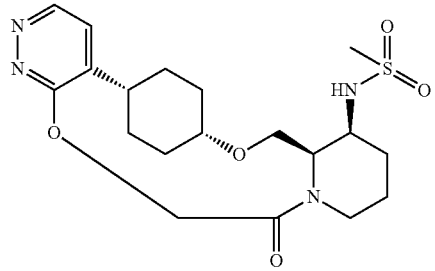

To a solution of (2$^1$S,2$^4$S,5$^2$R,5$^3$S)-5$^3$-amino-3,8-dioxa-1(4,3)-pyridazina-5(2,1)-piperidina-2(1,4)-cyclohexanacyclooctaphan-6-one (50.0 mg, 1.0 equiv., 0.14 mmol) in dichloromethane (2 mL) was added MsCl (25.0 mg, 1.5 equiv., 0.22 mmol) dropwise. The resulting mixture was stirred for 3 hr at room temperature. The reaction mixture was concentrated under reduced pressure. The crude mixture was purified by reverse flash chromatography to afford N-((2$^1$S,2$^4$S,5$^2$R,5$^3$S)-6-oxo-3,8-dioxa-1(4,3)-pyridazina-5 (2,1)-piperidina-2(1,4)-cyclohexanacyclooctaphane-5$^3$-yl) methanesulfonamide (44.0 mg, 0.10 mmol, 72%) as a solid. LCMS (ESI): m/z [M+H]$^+$=425; The racemic mixture (44.0 mg) was separated by Prep-Chiral HPLC to afford pure enantiomers as a solid. LCMS (ESI): m/z [M+H]$^+$=425: $^1$H NMR (400 MHz, Methanol-d$_4$) δ 8.70 (td, 1H), 7.44 (td, J=5.0, 1.6 Hz, 1H), 5.52 (dt, J=12.2, 2.6 Hz, 1H), 5.26 (dt, J=10.5, 4.7 Hz, 1H), 4.99-4.90 (m, 1H), 4.67-4.39 (m, 1H), 4.09-3.92 (m, 1H), 3.90-3.78 (m, 1H), 3.75 (s, 1H), 3.66 (dt, J=6.6, 3.9 Hz, 1H), 3.58 (ddd, J=9.3, 4.1, 1.5 Hz, 1H), 3.47 (t, J=12.2 Hz, 1H), 3.00-3.02 (m, 3H), 2.88-2.72 (m, 1H), 2.71-2.53 (m, 1H), 2.42-2.27 (m, 1H), 2.22 (d, 1H), 1.88 (d, J=12.6 Hz, 3H), 1.80-1.54 (m, 2H), 1.52-1.35 (m, 3H), 1.34-1.25 (m, 1H).

Example 1.13

(Compound 46)

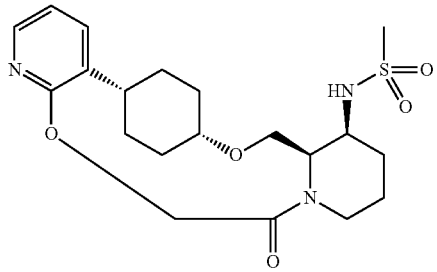

To a solution of $(2^1S,2^4S,5^2R,5^3S)$-$5^3$-amino-3,8-dioxa-1(3,2)-pyridina-5(2,1)-piperidina-2(1,4)-cyclohexanacyclooctaphan-6-one (338 mg, 1.0 equiv., 0.98 mmol) in dichloromethane (20 mL) were added TEA (297 mg, 1.0 equiv., 2.94 mmol) and MsCl (561 mg, 5.0 equiv., 4.90 mmol) at room temperature. The mixture was stirred for 1.5 hr at 25 degrees C. The resulting mixture was concentrated under reduced pressure. The residue was purified by reverse flash chromatography to afford N-$((2^1S,2^4S,5^2R,5^3S)$-6-oxo-3,8-dioxa-1(3,2)-pyridina-5(2,1)-piperidina-2(1,4)-cyclohexanacyclooctaphane-$5^3$-yl)methanesulfonamide (300 mg, 72.3%) as a solid. LCMS (ESI): m/z [M+H]$^+$=424: $^1$H NMR (400 MHz, Methanol-d$_4$) δ 7.97 (dd, J=5.0, 2.0 Hz, 1H), 7.49 (ddd, J=12.6, 7.1, 1.9 Hz, 1H), 6.91 (ddd, J=13.8, 7.1, 5.1 Hz, 1H), 5.33-5.35 (m, 1H), 5.24 (dt, J=10.3, 4.7 Hz, 1H), 4.45 (t, J=10.9 Hz, 1H), 3.97 (t, J=9.9 Hz, 1H), 3.71-3.91 (m, 2H), 3.65 (dt, J=11.0, 5.0 Hz, 1H), 3.57 (dd, J=9.1, 4.0 Hz, 1H), 3.44-3.54 (m, 1H), 3.04 (s, 2H), 2.98 (s, 1H), 2.66 (d, J=7.1 Hz, 2H), 2.14-2.42 (m, 2H), 1.80-1.99 (m, 3H), 1.62-1.80 (m, 2H), 1.36-1.60 (m, 3H), 1.22-1.36 (m, 1H).

Example 1.14

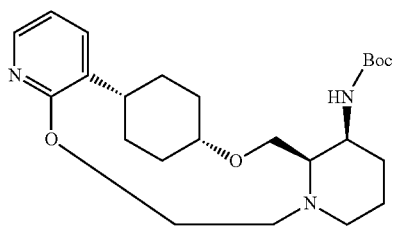 [SMILES: CC(C)(C)OC(=O)N[C@H]1CCCN2CCOc3ncccc3[C@H]3CC[C@H](CC3)OC[C@@H]12]

To a solution of tert-butyl $((2^1S,2^4S,5^2R,5^3S)$-6-oxo-3,8-dioxa-1(3,2)-pyridina-5(2,1)-piperidina-2(1,4)-cyclohexanacyclooctaphane-$5^3$-yl)carbamate (250 mg, 1.0 equiv., 0.561 mmol) in THF (10 mL) was added BH$_3$Me$_2$S (213 mg, 5.0 equiv., 2.81 mmol) at room temperature. The solution was stirred for 2 hr at 25 degrees C. The reaction was quenched with MeOH. The resulting solution was concentrated under reduced pressure. The residue was purified by reverse flash chromatography to afford tert-butyl $((2^1S,2^4S,5^2R,5^3S)$-3,8-dioxa-1(3,2)-pyridina-5(2,1)-piperidina-2(1,4)-cyclohexanacyclooctaphane-$5^3$-yl)carbamate (160 mg, 66.1%) as a solid. LCMS (ESI): m/z [M+H]$^+$=432.

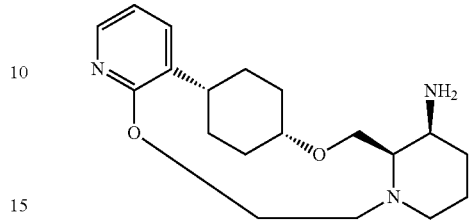

To the solution of tert-butyl $((2^1S,2^4S,5^2R,5^3S)$-3,8-dioxa-1(3,2)-pyridina-5(2,1)-piperidina-2(1,4)-cyclohexanacyclooctaphane-$5^3$-yl)carbamate (160 mg, 1.0 equiv., 0.371 mmol) in dichloromethane (5 mL) was added TFA (1 mL) at room temperature. The resulting mixture was stirred for 2 hr at 25 degrees C. The resulting solution was concentrated under reduced pressure. The residue was purified by reverse flash chromatography to afford $(2^1S,2^4S,5^2R,5^3S)$-3,8-dioxa-1(3,2)-pyridina-5(2,1)-piperidina-2(1,4)-cyclohexanacyclooctaphan-53-amine (120 mg, 72.7%) as a solid. LCMS (ESI): m/z [M+H]$^+$=332.

(Compound 65)

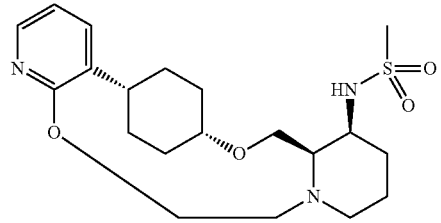

To the solution of $(2^1S,2^4S,5^2R,5^3S)$-3,8-dioxa-1(3,2)-pyridina-5(2,1)-piperidina-2(1,4)-cyclohexanacyclooctaphan-53-amine (60 mg, 1.0 equiv., 0.18 mmol) in 1,2-dichloroethane (4 mL) were added methanesulfonyl chloride (62 mg, 1.0 equiv., 0.54 mmol) and triethylamine (92 mg, 5.0 equiv., 0.91 mmol) dropwise. The resulting mixture was stirred for 3 hr at room temperature. The resulting solution was concentrated under reduced pressure. The residue was purified by reverse flash chromatography to afford N-$((2^1S,2^4S,5^2R,5^3S)$-3,8-dioxa-1(3,2)-pyridina-5(2,1)-piperidina-2(1,4)-cyclohexanacyclooctaphane-$5^3$-yl)methanesulfonamide (50 mg, 67%) as a solid. LCMS (ESI): m/z [M+H]$^+$=410. $^1$H NMR (400 MHz, Methanol-d$_4$) δ 7.94 (dd, J=5.1, 1.9 Hz, 1H), 7.47 (dd, J=7.2, 1.9 Hz, 1H), 6.86 (dd, J=7.2, 5.1 Hz, 1H), 4.20-4.37 (m, 2H), 3.89 (s, 1H), 3.79 (s, 1H), 3.67 (s, 2H), 3.05 (d, J=7.1 Hz, 1H), 2.99 (s, 3H), 2.94 (s, 1H), 2.84 (d, J=13.0 Hz, 1H), 2.65 (d, J=7.3 Hz, 2H), 2.44 (s, 1H), 1.98-2.12 (m, 2H), 1.89 (s, 1H), 1.79 (d, J=6.7 Hz, 1H), 1.58-1.73 (m, 2H), 1.43-1.53 (m, 2H), 1.40 (d, J=6.3 Hz, 1H), 1.32 (d, J=7.6 Hz, 1H).

Example 1.15

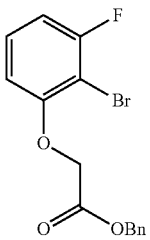 [SMILES: O=C(COc1cccc(F)c1Br)OCc1ccccc1]

A mixture of 2-bromo-3-fluorophenol (3.00 g, 1.0 equiv., 15.7 mmol), benzyl 2-bromoacetate (4.32 g, 1.2 equiv., 18.9 mmol) and K$_3$PO$_4$ (6.67 g, 2.0 equiv., 31.4 mmol) in acetonitrile (45.0 mL) was stirred for 16 hr at room temperature under nitrogen atmosphere. The reaction was quenched with water at room temperature. The resulting mixture was extracted with EtOAc (3×50 mL), dried over anhydrous Na$_2$SO$_4$. After filtration, the filtrate was concentrated under reduced pressure to afford benzyl 2-(2-bromo-3-fluorophenoxy)acetate (5.3 g, 99.5%) as a solid. LCMS (ESI): m/z [M+H]$^+$=340; $^1$H-NMR (300 MHz, DMSO-d$_6$): δ 7.35-7.40 (5H, m), 7.31-7.35 (1H, m), 7.00 (1H, td), 6.91 (1H, dt), 5.21 (2H, s), 5.06 (2H, s).

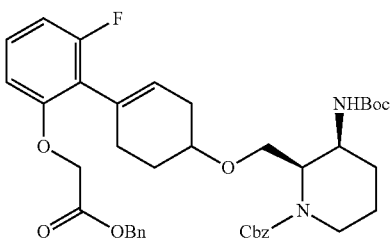 [SMILES: CC(C)(C)OC(=O)N[C@H]1CCCN(C(=O)OCc2ccccc2)[C@H]1COC1CC=C(c2c(F)cccc2OCC(=O)OCc2ccccc2)CC1]

A mixture of benzyl (2R,3S)-3-[(tert-butoxycarbonyl)amino]-2-([[4-(4,4,5,5-tetramethyl-1,3,2-dioxaborolan-2-yl)cyclohex-3-en-1-yl]oxy]methyl)piperidine-1-carboxylate (500.0 mg, 1.0 equiv., 0.876 mmol), benzyl 2-(2-bromo-3-fluorophenoxy)acetate (386.4 mg, 1.3 equiv., 1.14 mmol), Pd(dppf)Cl$_2$·CH$_2$Cl$_2$ (142.8 mg, 0.2 equiv., 0.175 mmol) and K$_2$CO$_3$ (302.8 mg, 2.5 equiv., 2.19 mmol) in 1,4-dioxane (8.0 mL) and H$_2$O (2.0 mL) was stirred overnight at 80 degrees C. under nitrogen atmosphere. The reaction was quenched with water at room temperature. The resulting mixture was extracted with EtOAc (3×20 mL), dried over anhydrous Na$_2$SO$_4$. After filtration, the filtrate was concentrated under reduced pressure. The residue was purified by Prep-TLC to afford benzyl 2-[[(4-[2-[2-(benzyloxy)-2-oxoethoxy]-6-fluorophenyl]cyclohex-3-en-1-yl)oxy]methyl]-3-[(tert-butoxycarbonyl)amino]piperidine-1-carboxylate (470 mg, 76.3%) as an oil. LCMS (ESI): m/z [M+H]$^+$=704.

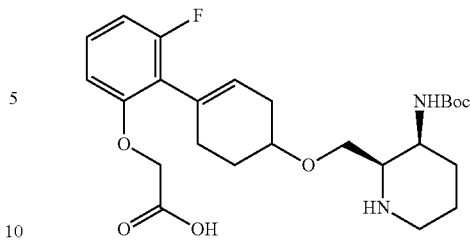

A mixture of benzyl 2-[[(4-[2-[2-(benzyloxy)-2-oxoethoxy]-6-fluorophenyl]cyclohex-3-en-1-yl)oxy]methyl]-3-[(tert-butoxycarbonyl)amino]piperidine-1-carboxylate (100.0 mg, 1.0 equiv., 0.142 mmol) and Pd/C (30.3 mg, 2.0 equiv., 0.285 mmol) in i-PrOH (6.0 mL) was stirred for 1 hr at room temperature under hydrogen atmosphere. The resulting mixture was filtered, the filter cake was washed with i-PrOH (3×3 mL). The filtrate was concentrated under reduced pressure to afford 2-[4-([3-[(tert-butoxycarbonyl)amino]piperidin-2-yl]methoxy)cyclohex-1-en-1-yl]-3-fluorophenoxyacetic acid (58.0 mg, 85.2%) as a solid. LCMS (ESI): m/z [M+H]$^+$=480.

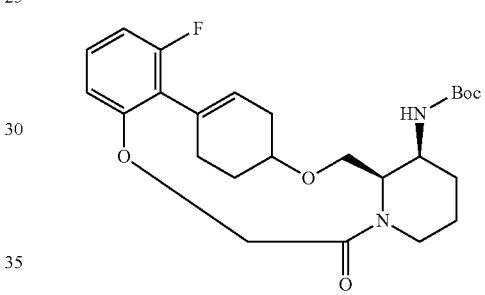

To a solution of 2-((4'-(((2R,3S)-3-((tert-butoxycarbonyl)amino)piperidin-2-yl)methoxy)-6-fluoro-2',3',4',5'-tetrahydro-[1,1'-biphenyl]-2-yl)oxy)acetic acid (53.0 mg, 1.0 equiv., 0.11 mmol) and diisopropylethylamine (43 mg, 3.0 equiv., 0.33 mmol) in acetonitrile (53 mL) were added HATU (63.0 mg, 1.5 equiv., 0.17 mmol). After stirring for 2 hr at room temperature under nitrogen atmosphere, the resulting mixture was concentrated under reduced pressure. The crude was purified by reverse flash chromatography to afford tert-butyl ((5$^2$R,5$^3$S,E)-1$^6$-fluoro-6-oxo-3,8-dioxa-5(2,1)-piperidina-1(1,2)-benzena-2(1,4)-cyclohexanacyclooctaphan-2$^1$-en-5$^3$-yl)carbamate (36.0 mg, 71%) as a solid. LCMS (ESI): m/z [M+H]$^+$=462.

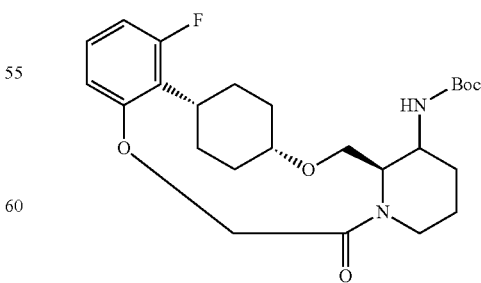

To a solution of tert-butyl ((5$^2$R,5$^3$S,E)-1$^6$-fluoro-6-oxo-3,8-dioxa-5(2,1)-piperidina-1(1,2)-benzena-2(1,4)-cyclohexanacyclooctaphan-2$^1$-en-5$^3$-yl)carbamate (30.0 mg, 1.0 equiv., 65 µmol) and Pd/C (6.9 mg, 1 Eq, 65 µmol) in MeOH (6 mL). After stirring for 3 hr at room temperature under a hydrogen atmosphere, the resulting mixture was filtered, the filter cake was washed with MeOH (3×3 mL). The filtrate was concentrated under reduced pressure to afford tert-butyl (($2^1$S,$2^4$S,$5^2$R,$5^3$S)-$1^6$-fluoro-6-oxo-3,8-dioxa-5(2,1)-piperidina-1(1,2)-benzena-2(1,4)-cyclohexanacyclooctaphane-$5^3$-yl)carbamate (28.0 mg, 93%) as a solid. LCMS (ESI): m/z [M+H]$^+$=463.6.

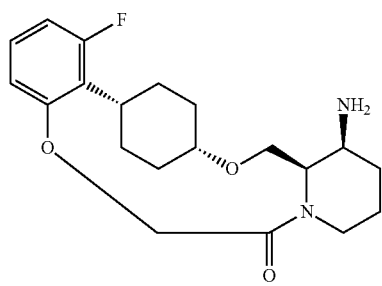 [SMILES: N[C@H]1CCCN2C(=O)COc3cccc(F)c3[C@H]3CC[C@H](CC3)OC[C@@H]12]

To a solution of tert-butyl (($2^1$S,$2^4$S,$5^2$R,$5^3$S)-$1^6$-fluoro-6-oxo-3,8-dioxa-5(2,1)-piperidina-1(1,2)-benzena-2(1,4)-cyclohexanacyclooctaphane-$5^3$-yl)carbamate (28.0 mg, 1.0 equiv., 61 µmol) in TFA (1.25 mL) and dichloromethane (5 mL) to stir for 1 hr at room temperature. The resulting mixture was concentrated under reduced pressure to afford ($2^1$S,$2^4$S,$5^2$R,$5^3$S)-$5^3$-amino-$1^6$-fluoro-3,8-dioxa-5(2,1)-piperidina-1(1,2)-benzena-2(1,4)-cyclohexanacyclooctaphan-6-one (20.0 mg, 91%) as a solid. LCMS (ESI): m/z [M+H]$^+$=363.5.

(Compound 49)

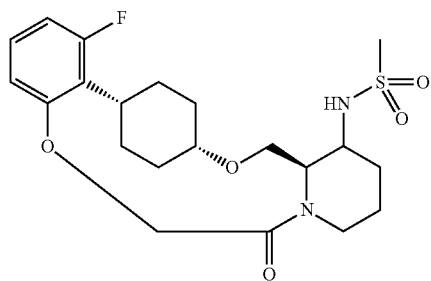

To a solution of ($2^1$S,$2^4$S,$5^2$R,$5^3$S)-$5^3$-amino-$1^6$-fluoro-3,8-dioxa-5(2,1)-piperidina-1(1,2)-benzena-2(1,4)-cyclohexanacyclooctaphan-6-one (15.0 mg, 1.0 equiv., 41 µmol) and diisopropylethylamine (11.0 mg, 2.0 equiv., 83 µmol) in dichloromethane (3 mL) were added MsCl (5.7 mg, 1.2 equiv., 50 µmol). After stirring for 2 h at room temperature under a nitrogen atmosphere, the resulting mixture was concentrated under reduced pressure. The residue was purified by reverse flash chromatography to afford N-(($2^1$S,$2^4$S,$5^2$R,$5^3$S)-$1^6$-fluoro-6-oxo-3,8-dioxa-5(2,1)-piperidina-1(1,2)-benzena-2(1,4)-cyclohexanacyclooctaphane-$5^3$-yl)methanesulfonamide (18.0 mg, 99%) as a solid. LCMS (ESI): m/z [M+H]$^+$=441.4; $^1$H NMR (400 MHz, DMSO-$d_6$) δ 7.15 (td, J=8.2, 6.4 Hz, 1H), 6.71 (t, J=8.8 Hz, 2H), 5.33 (d, J=10.5 Hz, 1H), 5.23 (dt, J=10.5, 4.7 Hz, 1H), 4.66-4.89 (m, 1H), 4.14 (d, J=10.5 Hz, 1H), 3.95 (dd, J=11.0, 9.1 Hz, 1H), 3.69-3.84 (m, 2H), 3.64 (dt, J=11.4, 5.4 Hz, 1H), 3.43-3.59 (m, 2H), 3.16 (tt, J=12.2, 5.6 Hz, 1H), 3.00-3.03 (m, 3H), 2.61-2.77 (m, 1H), 2.24-2.36 (m, 1H), 2.19-2.21 (m, 1H), 2.05 (s, 1H), 1.81-1.96 (m, 3H), 1.71 (q, J=9.7, 8.1 Hz, 2H), 1.50 (ddd, J=14.7, 12.9, 5.2 Hz, 1H), 1.41 (dq, J=11.4, 6.4, 4.6 Hz, 2H), 1.31 (d, J=2.9 Hz, 1H), 1.24 (d, J=13.4 Hz, 1H).

Example 1.16

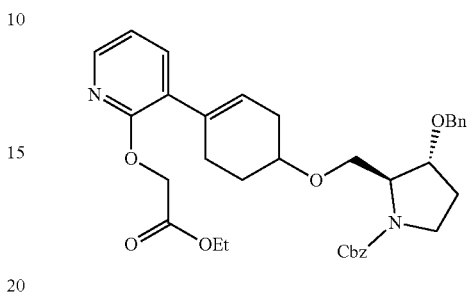

To a stirred solution of benzyl (2S,3R)-3-(benzyloxy)-2-([[4-(4,4,5,5-tetramethyl-1,3,2-dioxaborolan-2-yl)cyclohex-3-en-1-yl]oxy]methyl)pyrrolidine-1-carboxylate (11.2 g, 1.0 equiv., 20.5 mmol) and Na$_2$CO$_3$ (4.34 g, 2.0 equiv., 0.041 mmol) in 1,4-dioxane (200 mL) and H$_2$O (20.0 mL) were added Pd(dppf)Cl$_2$ (2.99 g, 0.2 equiv., 0.004 mmol) at room temperature under nitrogen atmosphere. The resulting mixture was stirred for 1 hr at 100 degrees C. The reaction was quenched with water at room temperature and the resulting mixture was extracted with EtOAc (3×300 mL). The combined organic mixture was dried over anhydrous Na$_2$SO$_4$. After filtration, the filtrate was concentrated under reduced pressure. The residue was purified by Prep-TLC to afford benzyl (2S,3R)-3-(benzyloxy)-2-[([4-[2-(2-ethoxy-2-oxoethoxy)pyridin-3-yl]cyclohex-3-en-1-yl]oxy)methyl]pyrrolidine-1-carboxylate (8.3 g, 67.5%) as a solid. LCMS (ESI): m/z [M+H]$^+$=601.5; H NMR (400 MHz, Chloroform-d) δ 7.99 (dd, J=4.9, 2.2 Hz, 1H), 7.44 (dt, J=7.2, 1.8 Hz, 1H), 7.29-7.41 (m, 10H), 6.88 (dd, J=7.3, 5.0 Hz, 1H), 5.83 (d, J=13.8 Hz, 1H), 5.06-5.35 (m, 2H), 4.93 (d, J=2.2 Hz, 2H), 4.48-4.66 (m, 2H), 4.24 (q, J=7.1 Hz, 2H), 4.08-4.11 (m, 2H), 3.61-3.83 (m, 2H), 3.28-3.60 (m, 3H), 2.43-2.48 (m, 3H), 1.86-2.25 (m, 4H), 1.62-1.83 (m, 1H), 1.28 (t, J=7.2 Hz, 3H).

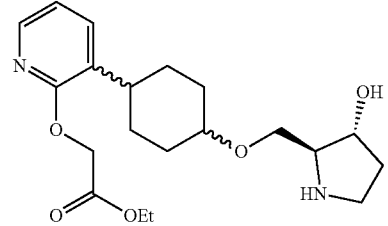 [SMILES: CCOC(=O)COc1ncccc1C1CCC(OC[C@@H]2NCC[C@H]2O)CC1]

To a stirred solution of benzyl (2S,3R)-3-(benzyloxy)-2-[([4-[2-(2-ethoxy-2-oxoethoxy) pyridin-3-yl]cyclohex-3-en-1-yl]oxy)methyl]pyrrolidine-1-carboxylate (8.30 g, 1.0 equiv., 13.8 mmol) and HCOONH$_4$ (8.71 g, 10.0 equiv., 138 mmol) in i-PrOH (200 mL) were added Pd(OH)$_2$/C (1.94 g, 0.014 mmol) at room temperature under nitrogen atmosphere. The resulting mixture was stirred for an additional 5 hr at 80 degrees C. The resulting mixture was filtered, the filter cake was washed with i-PrOH (2×100 mL). The filtrate was concentrated under reduced pressure to afford ethyl 2-[[3-(4-[[(2S,3R)-3-hydroxypyrrolidin-2-yl]methoxy]cyclohexyl)pyridin-2-yl]oxy]acetate (4.2 g, 80.3%) as a solid. LCMS (ESI): m/z [M+H]$^+$=379.3; $^1$H NMR (400 MHz, DMSO-d$_6$) δ 7.87-8.00 (m, 1H), 7.58 (ddd, J=9.7, 7.4, 1.9 Hz, 1H), 6.97 (dt, J=7.3, 5.1 Hz, 1H), 4.93 (s, 2H), 4.67 (s, 1H), 4.11 (q, J=7.1 Hz, 2H), 3.88-3.92 (m, 1H), 3.58 (s, 1H), 3.32-3.42 (m, 2H), 3.26 (d, J=9.0 Hz, 1H), 2.74-3.00 (m, 4H), 2.04-2.18 (m, 1H), 1.96 (d, J=13.2 Hz, 1H), 1.76-1.91 (m, 2H), 1.69 (t, J=11.6 Hz, 1H), 1.44-1.63 (m, 4H), 1.26 (d, J=13.2 Hz, 1H), 1.17 (t, J=7.1 Hz, 3H).

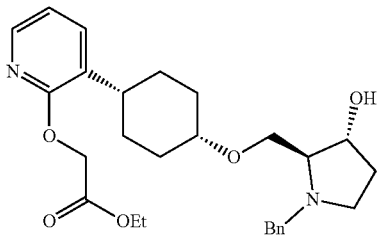 [SMILES: CCOC(=O)COc1ncccc1[C@H]1CC[C@@H](OC[C@H]2[C@H](O)CCN2Cc2ccccc2)CC1]

To a stirred solution of ethyl 2-[[3-(4-[[(2S,3R)-3-hydroxypyrrolidin-2-yl]methoxy]cyclohexyl)pyridin-2-yl]oxy]acetate (7.50 g, 1.0 equiv., 19.8 mmol) and MgSO$_4$ (2.39 g, 1.0 equiv., 0.020 mmol) in dichloromethane (500 mL) were added benzaldehyde (3.15 g, 1.5 equiv., 0.030 mmol) and sodium triacetoxyborohydride (8.40 g, 2.0 equiv., 0.040 mmol) at room temperature under nitrogen atmosphere. The resulting mixture was stirred for an additional 8 hr at room temperature. The crude product was purified by Prep-Chiral HPLC to afford ethyl 2-((3-((1R,4s)-4-(((2S,3R)-1-benzyl-3-hydroxypyrrolidin-2-yl)methoxy)cyclohexyl)pyridin-2-yl)oxy) acetate (3.0 g, 32.3%) as a solid. LCMS (ESI): m/z [M+H]$^+$=469.5; $^1$H NMR (400 MHz, Chloroform-d) δ 7.94 (dd, J=4.9, 1.8 Hz, 1H), 7.45 (dd, J=7.3, 2.0 Hz, 1H), 7.30-7.40 (m, 4H), 7.29 (d, J=1.8 Hz, 1H), 6.86 (dd, J=7.3, 5.0 Hz, 1H), 4.94 (s, 2H), 4.23 (q, J=7.1 Hz, 2H), 4.05 (d, J=13.0 Hz, 1H), 3.72-3.84 (m, 2H), 3.65 (dt, J=11.6, 4.2 Hz, 2H), 3.45 (t, J=8.4 Hz, 1H), 2.92-2.97 (m, 1H), 2.77 (d, J=4.9 Hz, 1H), 2.62 (q, J=8.8 Hz, 1H), 1.98-2.12 (m, 2H), 1.84-1.94 (m, 2H), 1.74 (ddd, J=10.4, 9.9, 3.1 Hz, 4H), 1.53-1.66 (m, 2H), 1.27 (t, J=7.1 Hz, 3H).

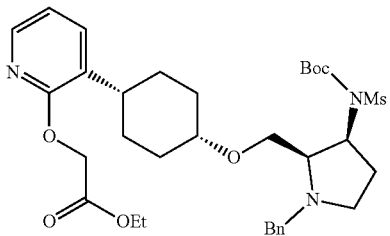

To a stirred solution of ethyl 2-[[3-(4-[[(2S,3R)-1-benzyl-3-hydroxypyrrolidin-2-yl]methoxy]cyclohexyl)pyridin-2-yl]oxy]acetate (620.0 mg, 1.0 equiv., 1.32 mmol) and tert-butyl N-methanesulfonylcarbamate (516.6 mg, 2.0 equiv., 2.65 mmol) in THF (50.0 mL) were added PPh$_3$ (694.1 mg, 2.0 equiv., 2.65 mmol) and diisopropyl azodicarboxylate (535.1 mg, 2.0 equiv., 2.65 mmol) in portions at 0 degrees C. under nitrogen atmosphere for 1 hr. The resulting mixture was stirred for 5 hr at room temperature. The resulting mixture was extracted with EtOAc (2×100 mL). The combined organic layers were dried over anhydrous Na$_2$SO$_4$. After filtration, the filtrate was concentrated under reduced pressure. The residue was purified by Prep-TLC to afford ethyl 2-([3-[(1s,4s)-4-[[(2R,3S)-1-benzyl-3-[N-(tert-butoxycarbonyl) methanesulfonamido]pyrrolidin-2-yl]methoxy] cyclohexyl]pyridin-2-yl]oxy)acetate (420.0 mg, 49.2%) as a solid. LCMS (ESI): m/z [M+H]$^+$=646.25; $^1$H NMR (400 MHz, Chloroform-d) δ 7.94 (dd, J=5.0, 1.8 Hz, 1H), 7.44 (dd, J=7.5, 1.8 Hz, 1H), 7.30-7.39 (m, 4H), 7.27 (d, J=7.1 Hz, 1H), 6.87 (dd, J=7.4, 5.0 Hz, 1H), 4.93 (s, 3H), 4.09-4.30 (m, 3H), 3.71 (q, J=8.7 Hz, 1H), 3.58 (dd, J=9.9, 5.2 Hz, 1H), 3.47 (d, J=13.1 Hz, 1H), 3.36 (s, 3H), 2.99 (t, J=8.3 Hz, 2H), 2.80-2.90 (m, 1H), 2.52-2.66 (m, 1H), 2.15 (d, J=11.9 Hz, 3H), 2.00 (d, J=12.5 Hz, 3H), 1.28 (d, J=6.9 Hz, 3H).

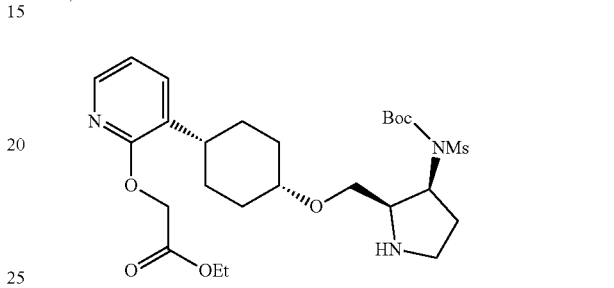

To a solution of ethyl 2-([3-[(1s,4s)-4-[[(2R,3S)-1-benzyl-3-[N-(tert-butoxycarbonyl) methanesulfonamido]pyrrolidin-2-yl]methoxy]cyclohexyl]pyridin-2-yl]oxy)acetate) (360.8 mg, 1.0 equiv., 0.650 mmol) in i-PrOH (20.0 mL) was added Pd(OH)$_2$/C (18.3 mg, 0.2 equiv., 0.130 mmol) under nitrogen atmosphere. The mixture was hydrogenated at room temperature for 24 hr under hydrogen atmosphere using a hydrogen balloon, filtered through a Celite pad and concentrated under reduced pressure. The resulting mixture was filtered, the filter cake was washed with i-PrOH (2×20 mL). The filtrate was concentrated under reduced pressure to afford ethyl 2-([3-[(1s,4s)-4-[[(2R,3S)-3-[N-(tert-butoxycarbonyl)methanesulfonamido]pyrrolidin-2-yl]methoxy]cyclohexyl]pyridin-2-yl]oxy)acetate (200.0 mg, 55.3%) as a solid. LCMS (ESI): m/z [M+H]$^+$=556.5.

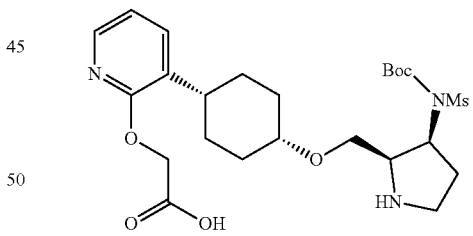

To a stirred solution of ethyl 2-([3-[(1s,4s)-4-[[(2R,3S)-3-[N-(tert-butoxycarbonyl)methanesulfonamido] pyrrolidin-2-yl]methoxy]cyclohexyl]pyridin-2-yl]oxy)acetate (200.0 mg, 1.0 equiv., 0.360 mmol) in i-PrOH (5.0 mL) were added LiOH (10.3 mg, 1.2 equiv., 0.432 mmol) at room temperature under nitrogen atmosphere. The resulting mixture was stirred for 2 hr at room temperature. The residue was purified by reverse flash chromatography to afford ([3-[(1s,4s)-4-[[(2R,3S)-3-[N-(tert-butoxycarbonyl)methanesulfonamido]pyrrolidin-2-yl]methoxy]cyclohexyl]pyridin-2-yl]oxy)acetic acid (100.0 mg, 52.7%) as a solid. LCMS (ESI): m/z [M+H]$^+$=528.5; $^1$H NMR (400 MHz, DMSO-d$_6$) δ 7.89 (dd, J=4.9, 1.8 Hz, 1H), 7.49 (dd, J=7.4, 1.9 Hz, 1H), 6.86 (dd, J=7.3, 5.0 Hz, 2H), 3.86-3.93 (m, 1H), 3.67-3.75 (m, 3H), 3.60 (d, J=9.7 Hz, 2H), 3.18 (s, 3H), 2.98 (s, 3H), 2.77 (t, J=12.1 Hz, 1H), 1.80-2.20 (m, 6H), 1.41 (s, 9H), 1.27 (q, J=11.1, 10.5 Hz, 2H).

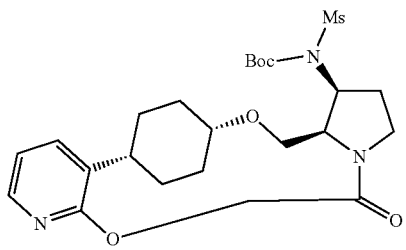 [SMILES: CC(C)(C)OC(=O)N([C@H]1CCN2C(=O)COc3ncccc3[C@H]3CC[C@H](CC3)OC[C@@H]12)S(C)(=O)=O]

To a stirred solution of ([3-[(1s,4s)-4-[[(2R,3S)-3-[N-(tert-butoxycarbonyl)methanesulfonamido]pyrrolidin-2-yl]methoxy]cyclohexyl]pyridin-2-yl]oxy)acetic acid (50.0 mg, 1.0 equiv., 0.095 mmol) and HATU (72.1 mg, 2.0 equiv., 0.190 mmol) in acetonitrile (10.0 mL) were added diisopropylethylamine (24.5 mg, 2.0 equiv., 0.190 mmol) at room temperature under nitrogen atmosphere. The resulting mixture was stirred for 2 hr at room temperature. The resulting mixture was concentrated under reduced pressure. The residue was purified by reverse flash chromatography to afford tert-butyl (methylsulfonyl)(($2^1$S,$2^4$S,$5^2$R,$5^3$S)-6-oxo-3,8-dioxa-1(3,2)-pyridina-5(2,1)-pyrrolidina-2(1,4)-cyclohexanacyclooctaphane-$5^3$-yl)carbamate (20.0 mg, 41.4%) as a solid. LCMS (ESI): m/z [M+H]$^+$=510.5.

(Compound 18)

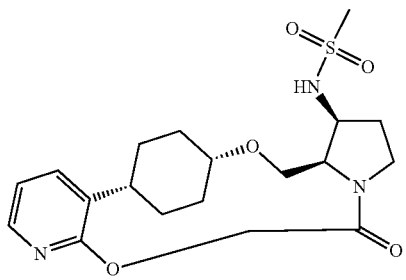

To a stirred solution of tert-butyl (methylsulfonyl)(($2^1$S, $2^4$S,$5^2$R,$5^3$S)-6-oxo-3,8-dioxa-1(3,2)-pyridina-5(2,1)-pyrrolidina-2(1,4)-cyclohexanacyclooctaphane-$5^3$-yl)carbamate (3.40 mg, 1.0 equiv., 0.007 mmol) in dichloromethane (1.0 mL) were added TFA (0.10 mL) in portions at room temperature under nitrogen atmosphere. The resulting mixture was stirred for an additional 1 hr at room temperature. The resulting mixture was concentrated under vacuum. The mixture was neutralized to pH 7 with 7N NH$_3$ in MeOH. The residue was purified by reverse flash chromatography to afford N-(($2^1$S,$2^4$S,$5^2$R,53S)-6-oxo-3,8-dioxa-1(3,2)-pyridina-5(2,1)-pyrrolidina-2(1,4)-cyclohexanacyclooctaphane-$5^3$-yl)methanesulfonamide (2.1 mg, 76.1%) as a solid. LCMS (ESI): m/z [M+H]$^+$=410.3; $^1$H NMR (400 MHz, Methanol-d$_4$) δ 8.00 (dd, J=5.0, 1.9 Hz, 1H), 7.53 (dd, J=7.2, 1.9 Hz, 1H), 6.95 (dd, J=7.2, 5.0 Hz, 1H), 5.01 (d, J=10.8 Hz, 1H), 4.66 (d, J=10.8 Hz, 1H), 4.38 (dd, J=7.8, 3.4 Hz, 1H), 4.06-4.27 (m, 3H), 3.82 (d, J=4.2 Hz, 1H), 3.74 (td, J=9.9, 7.9 Hz, 1H), 3.52 (d, J=9.2 Hz, 1H), 3.05 (s, 3H), 2.58-2.71 (m, 2H), 2.37-2.50 (m, 1H), 2.31 (ddt, J=11.6, 7.8, 2.0 Hz, 1H), 2.09-2.21 (m, 2H), 1.91 (d, J=13.2 Hz, 1H), 1.44-1.60 (m, 2H), 1.38 (td, J=14.5, 3.5 Hz, 1H), 1.24-1.29 (m, 1H).

Example 1.17

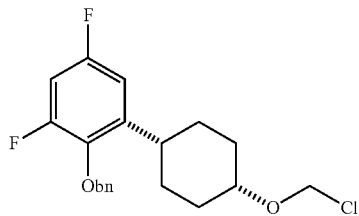

Into a 100 mL round-bottom flask were added 4-[2-(benzyloxy)-3,5-difluorophenyl]cyclohexan-1-ol (5.0 g, 1.0 equiv., 15.7 mmol) and paraformaldehyde (0.71 g, 0.5 equiv., 7.85 mmol) in TMSCl (15.0 mL) at room temperature. The resulting mixture was stirred overnight at room temperature under nitrogen atmosphere. The resulting mixture was concentrated under reduced pressure to afford 2-(benzyloxy)-1-[4-(chloromethoxy)cyclohexyl]-3,5-difluorobenzene (5.5 g, 95.5%) as an oil.

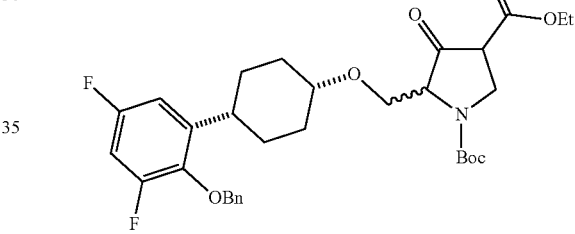

To a stirred solution of 1-tert-butyl 3-ethyl 4-oxopyrrolidine-1,3-dicarboxylate (6.90 g, 1.0 equiv., 7.66 mmol) and DMPU (11.8 g, 3.3 equiv., 18.4 mmol) in THF (140 mL) were added LDA (32.0 mL, 2.2 equiv., 47.2 mmol) dropwise over 5 minutes at −78 degrees C. under nitrogen atmosphere. The resulting mixture was stirred for additional 1.5 hr at −78 degrees C. Dissolved the 2-(benzyloxy)-1-[4-(chloromethoxy)cyclohexyl]-3,5-difluorobenzene (9.84 g, 1.0 equiv., 3.7 62 mmol) in THF (20 mL) and the solution was filtered. To the above mixture was added the filtrate dropwise over 8 minutes at −78 degrees C. The final mixture was stirred for an additional 30 minutes at −78 degrees C., then the resulting mixture was stirred for an additional 3 hr at room temperature. The resulting mixture was diluted with water (250 mL). The resulting mixture was extracted with EtOAc (3×200 mL). The combined organic layers were washed with brine (1×250 mL), dried over anhydrous Na$_2$SO$_4$. After filtration, the filtrate was concentrated under reduced pressure. The residue was purified by reverse flash chromatography to afford 1-tert-butyl 3-ethyl 5-[([4-[2-(benzyloxy)-3,5-difluorophenyl]cyclohexyl]oxy)methyl]-4-oxopyrrolidine-1,3-dicarboxylate (10.2 g, 63.5%) as an oil. LCMS (ESI): m/z [M-100]$^+$=488.40; $^1$H NMR (400 MHz, Chloroform-d) δ 7.31-7.48 (m, 5H), 6.65-6.75 (m, J=2H), 5.01 (d, J=5.5 Hz, 2H), 4.27 (dtd, J=9.6, 7.1, 6.3, 3.7 Hz, 2H), 4.13 (d, J=13.0 Hz, 1H), 4.04 (d, J=13.9 Hz, 1H), 3.86-3.98 (m, 1H), 3.80 (t, J=10.3 Hz, 1H), 3.64-3.76 (m, 1H), 3.60-3.65 (m, 1H), 3.50-3.55 (m, 1H), 2.87 (s, 1H), 1.89-1.91 (m, 2H), 1.57-1.78 (m, 2H), 1.49 (d, J=8.2 Hz, 9H), 1.40 (d, J=10.3 Hz, 1H), 1.32 (dt, J=10.2, 7.1 Hz, 6H).

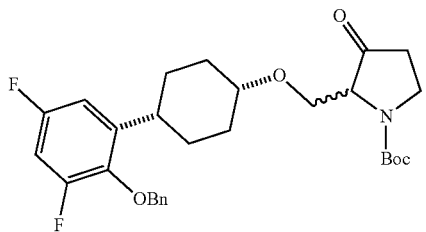

The solution of 1-tert-butyl 3-ethyl 5-[([4-[2-(benzyloxy)-3,5-difluorophenyl]cyclohexyl]oxy)methyl]-4-oxopyrrolidine-1,3-dicarboxylate (2.00 g, 1.0 equiv., 3.40 mmol) in DMSO (20.0 mL) and H$_2$O (2.0 mL) was stirred for 3 hr at 125 degrees C. under nitrogen atmosphere. The reaction was quenched with water (10 mL). The resulting mixture was extracted with EtOAc (3×20 mL), the filtrate was concentrated under reduced pressure. The residue was purified by reverse flash chromatography to afford tert-butyl 3-oxo-2-([[(1s,4s)-4-[2-(benzyloxy)-3,5-difluorophenyl]cyclohexyl]oxy]methyl)pyrrolidine-1-carboxylate (1.40 g, 80.0%) as an oil. LCMS (ESI): m/z [M-100]$^+$=416.3; $^1$H NMR (400 MHz, Chloroform-d) δ 7.38 (q, J=7.7, 7.0 Hz, 5H), 6.72 (ddd, J=11.1, 8.2, 2.9 Hz, 1H), 6.60-6.68 (m, 1H), 5.01 (s, 2H), 3.84-4.15 (m, 3H), 3.71-3.76 (m, 2H), 3.51 (s, 1H), 2.79-2.94 (m, 1H), 2.53-2.60 (m, 2H), 1.90-1.96 (m, 2H), 1.11-1.41 (m, 6H).

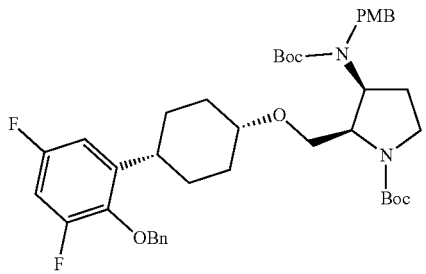

To a stirred solution of tert-butyl 2-((((1s,4s)-4-(2-(benzyloxy)-3,5-difluorophenyl) cyclohexyl)oxy)methyl)-3-oxopyrrolidine-1-carboxylate (2.50 g, 1.0 equiv., 4.8 mmol) and MgSO$_4$ (1.8 g, 3.0 equiv., 15 mmol) in dichloromethane (50 mL) then added sodium triacetoxyborohydride (2.6 g, 2.5 equiv., 12 mmol) and (4-methoxyphenyl)methanamine (2.60 g, 2.5 equiv., 12 mmol) at 25 degrees C. The resulting mixture was stirred for 2 hr at 25 degrees C. The resulting mixture was filtered, the filter cake was washed with dichloromethane (50 mL). The filtrate was washed with water and brine then concentrated under reduced pressure. The crude product was used for the next step directly without further purification.

To a stirred solution of tert-butyl (2R,3S)-2-((((1s,4S)-4-(2-(benzyloxy)-3,5-difluorophenyl)cyclohexyl)oxy) methyl)-3-((4-methoxybenzyl)amino)pyrrolidine-1-carboxylate (3.0 g, 1.0 equiv., 5.0 mmol) and triethylamine (0.91 g, 2.0 equiv., 9.00 mmol) in dichloromethane (50 mL) was added Boc$_2$O (1.31 g, 1.0 equiv., 6.00 mmol) at 25 degrees C. The resulting mixture was stirred for 2 hr at 25 degrees C. and concentrated. The crude product was purified by silica gel column chromatography to afford tert-butyl (2R,3S)-2-((((1s,4S)-4-(2-(benzyloxy)-3,5-difluorophenyl) cyclohexyl)oxy)methyl)-3-((tert-butoxycarbonyl)(4-methoxybenzyl)amino)pyrrolidine-1-carboxylate (1.92 g, 55.3%) as an oil. LCMS (ESI): m/z [M+H]$^+$=637.60.

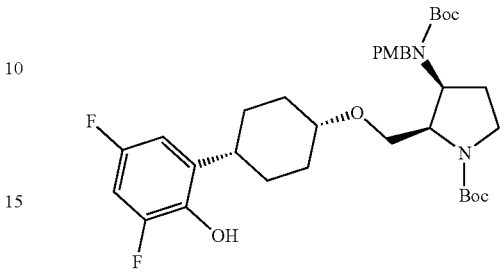

To a mixture of tert-butyl 2-[([4-[2-(benzyloxy)-3,5-difluorophenyl]cyclohexyl]oxy) methyl]-3-[(tert-butoxycarbonyl)[(4-methoxyphenyl)methyl]amino]pyrrolidine-1-carboxylate (1.40 g, 1.0 equiv., 1.90 mmol) in ethanol (30 mL) was added Pd/C (101.1 mg, 0.5 equiv., 0.950 mmol) and was stirred for 2 hr at room temperature under hydrogen atmosphere. The resulting mixture was filtered, the filter cake was washed with ethanol (3×20 mL). The filtrate was concentrated under reduced pressure. The residue was purified by reverse flash chromatography to afford tert-butyl 3-[(tert-butoxycarbonyl)[(4-methoxyphenyl)methyl]amino]-2-([[4-(3,5-difluoro-2-hydroxyphenyl)cyclohexyl]oxy]methyl)pyrrolidine-1-carboxylate (1.37 g, 84.1%) as a solid. LCMS (ESI): m/z [M+H]$^+$=647.5; 1H NMR (400 MHz, DMSO-d$_6$) δ 9.21-9.37 (m, 1H), 7.08 (dd, J=8.3, 5.5 Hz, 2H), 7.00 (t, J=9.5 Hz, 1H), 6.83-6.92 (m, 2H), 6.66 (d, J=9.7 Hz, 1H), 4.76 (s, 1H), 4.43 (s, 2H), 3.93 (s, 1H), 3.81 (d, J=9.8 Hz, 1H), 3.72 (s, 3H), 3.67 (t, J=7.3 Hz, 1H), 3.58 (s, 1H), 3.31 (s, 1H), 3.16-3.22 (m, 1H), 2.98 (s, 1H), 2.22 (d, J=11.4 Hz, 1H), 1.82-2.05 (m, 2H), 1.26-1.78 (m, 25H).

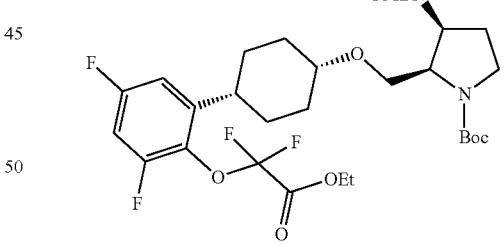

A solution of tert-butyl 3-[(tert-butoxycarbonyl)[(4-methoxyphenyl)methyl]amino]-2-([[4-(3,5-difluoro-2-hydroxyphenyl)cyclohexyl]oxy]methyl)pyrrolidine-1-carboxylate (900.0 mg, 1.0 equiv., 1.39 mmol) and DBU (529.6 mg, 2.5 equiv., 3.48 mmol) in DMF (10 mL) was stirred for 15 minutes at 70 degrees C. To the above mixture was added ethyl 2-bromo-2,2-difluoroacetate (706.1 mg, 2.5 equiv., 3.48 mmol) dropwise over 1 minute at 70 degrees C. The resulting mixture was stirred for additional 6 hr at 70 degrees C. and concentrated. The residue was purified by reverse flash chromatography to afford tert-butyl 3-[(tert-butoxycarbonyl)[(4-methoxyphenyl)methyl]amino]-2-[[[4-[2-(2-ethoxy-1,1-difluoro-2-oxoethoxy)-3,5-difluorophenyl]cyclohexyl]oxy)methyl]pyrrolidine-1-carboxylate (900.0 mg, 84.1%) as a semi-solid. LCMS (ESI): m/z [M+H]$^+$=769.7; $^1$H NMR (400 MHz, DMSO-d$_6$) δ 7.38 (d, J=8.5 Hz, 1H), 7.10 (dd, J=8.4, 4.7 Hz, 2H), 6.75-6.99 (m, 3H), 4.43 (q, J=7.1 Hz, 4H), 3.95 (s, 1H), 3.81 (s, 1H), 3.72 (s, 3H), 3.60 (s, 1H), 3.21-3.28 (m, 2H), 2.95 (t, J=12.1 Hz, 1H), 2.23 (q, J=11.7 Hz, 1H), 1.94-1.98 (m, 2H), 1.25-1.77 (m, 28H).

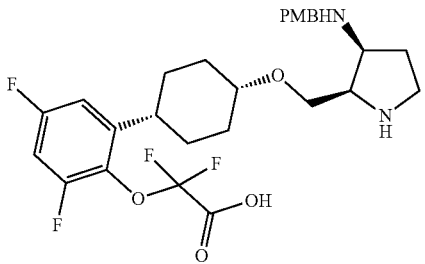

To a stirred solution of tert-butyl 3-[(tert-butoxycarbonyl)[(4-methoxyphenyl)methyl]amino]-2-[([4-[2-(2-ethoxy-1,1-difluoro-2-oxoethoxy)-3,5-difluorophenyl]cyclohexyl]oxy)methyl]pyrrolidine-1-carboxylate (900.0 mg, 1.0 equiv., 1.17 mmol) in dichloromethane (15 mL) were added TFA (3.00 mL, 34.5 equiv., 40.4 mmol) dropwise at room temperature. The resulting mixture was stirred for 1 hr at room temperature. The crude product was used in the next step directly without further purification. Then to a stirred solution of ethyl 2-(2,4-difluoro-6-[4-[(3-[[(4-methoxyphenyl)methyl]amino]pyrrolidin-2-yl)methoxy]cyclohexyl]phenoxy)-2,2-difluoroacetate (650.0 mg, 1.0 equiv., 1.14 mmol) in i-PrOH (15 mL) and water (3 mL) were added LiOH H$_2$O (239.9 mg, 5.0 equiv., 5.72 mmol) at room temperature. The resulting mixture was stirred overnight at room temperature. The mixture was neutralized to pH 7 with HCl (5.7 mL, 1M) and dried. The residue was purified by reverse flash chromatography to afford 2,4-difluoro-6-[4-[(3-[[(4-methoxyphenyl)methyl]amino]pyrrolidin-2-yl)methoxy]cyclohexyl] phenoxydifluoroacetic acid (300.0 mg, 48.6%) as a solid. LCMS (ESI): m/z [M+H]$^+$=541.4; $^1$H NMR (400 MHz, DMSO-d$_6$) δ 7.20-7.26 (m, 2H), 7.14 (ddd, J=11.2, 8.7, 3.0 Hz, 1H), 6.80-6.83 (m, 3H), 3.56-3.64 (m, 2H), 3.54 (dd, J=9.5, 4.8 Hz, 1H), 3.43 (dd, J=9.5, 6.0 Hz, 2H), 3.17 (h, J=6.1 Hz, 2H), 3.01 (ddd, J=10.2, 8.4, 5.1 Hz, 1H), 2.77 (dt, J=10.1, 7.8 Hz, 1H), 1.80-2.00 (m, 3H), 1.52-1.71 (m, 3H), 1.42 (d, J=11.2 Hz, 4H).

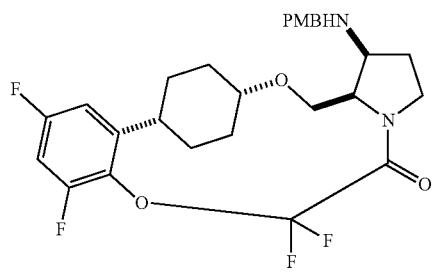

The mixture solution of 2,4-difluoro-6-[4-[(3-[[(4-methoxyphenyl)methyl]amino]pyrrolidin-2-yl)methoxy]cyclohexyl]phenoxydifluoroacetic acid (100.0 mg, 1.0 equiv., 0.185 mmol) and diisopropylamine (47.8 mg, 2.0 equiv., 0.370 mmol) in dichloromethane (5 mL) was stirred at room temperature for 30 minutes. To the above mixture was added the solution of HATU (105.5 mg, 1.5 equiv., 0.277 mmol) in acetonitrile (5 ml) dropwise at room temperature. The resulting mixture was stirred for an additional 3 hr at room temperature and concentrated under reduced pressure. The residue was purified by reverse flash chromatography to afford (2$^1$S,2$^4$S,5$^2$R,5$^3$S)-1$^3$,1$^5$,7,7-tetrafluoro-5$^3$-((4-methoxybenzyl)amino)-3,8-dioxa-5(2,1)-pyrrolidina-1(1,2)-benzena-2(1,4)-cyclohexanacyclooctaphan-6-one (38.0 mg, 39.3%) as an oil. LCMS (ESI): m/z [M+H]$^+$=523.4; $^1$H NMR (400 MHz, Chloroform-d) δ 7.31 (d, J=8.5 Hz, 2H), 6.87-6.94 (m, 2H), 6.82 (ddd, J=10.7, 8.0, 3.1 Hz, 1H), 6.70 (dt, J=9.2, 2.3 Hz, 1H), 4.47 (d, J=6.8 Hz, 1H), 4.26 (t, J=9.5 Hz, 1H), 4.19 (dd, J=9.5, 3.8 Hz, 1H), 3.84 (d, J=1.9 Hz, 4H), 3.78 (d, J=4.4 Hz, 2H), 3.60-3.65 (m, 1H), 3.45-3.50 (m, 2H), 2.49-2.63 (m, 1H), 2.31-2.43 (m, 1H), 2.30 (s, 1H), 2.15-2.20 (m, 3H), 1.72-1.77 (m, 2H), 1.25-1.30 (m, 7H), 0.90 (t, J=6.4 Hz, 1H).

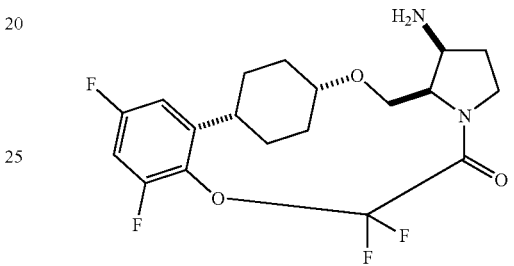

The mixture solution of (2$^1$S,2$^4$S,5$^2$R,5$^3$S)-1$^3$,1$^5$,7,7-tetrafluoro-5$^3$-((4-methoxybenzyl) amino)-3,8-dioxa-5(2,1)-pyrrolidina-1(1,2)-benzena-2(1,4)-cyclohexanacyclooctaphan-6-one (10.0 mg, 1.0 equiv., 0.019 mmol) and Pd/C (50.0 mg, 25 equiv., 0.470 mmol), HCOONH$_4$ (75.0 mg, 62 equiv., 1.19 mmol) and i-PrOH (3.0 mL) at room temperature. The resulting mixture was stirred for 3 hr at 80 degrees C. under nitrogen atmosphere. The resulting mixture was filtered, the filtrate was concentrated under reduced pressure to afford (2$^1$S,2$^4$S,5$^2$R,5$^3$S)-5$^3$-amino-13, 15,7,7-tetrafluoro-3,8-dioxa-5(2,1)-pyrrolidina-1(1,2)-benzena-2(1,4)-cyclohexanacyclooctaphan-6-one (6.5 mg, 84.4%) as an oil. LCMS (ESI): m/z [M+H]$^+$=403.2.

(Compound 54)

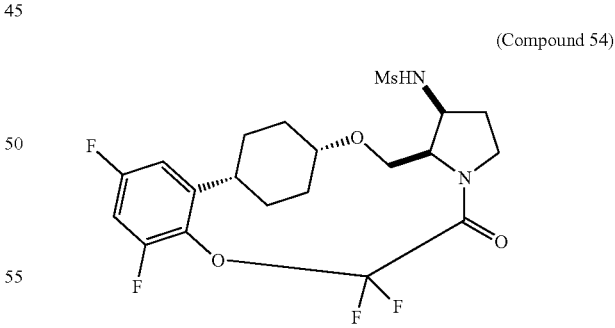

To a solution of (2$^1$S,2$^4$S,5$^2$R,5$^3$S)-5$^3$-amino-13,15,7,7-tetrafluoro-3,8-dioxa-5(2,1)-pyrrolidina-1(1,2)-benzena-2(1,4)-cyclohexanacyclooctaphan-6-one (20.0 mg, 1.0 equiv., 0.050 mmol) in dichloromethane (5.0 mL) was added a solution of MsCl (113.9 mg, 20 equiv., 0.994 mmol) and diisopropylethylamine (160.6 mg, 25 equiv., 1.243 mmol) dropwise at room temperature under nitrogen atmosphere. The resulting mixture was stirred overnight at room temperature and the mixture was concentrated under reduced pressure. The residue was purified by reverse flash chromatography to afford N-((2¹S,2⁴S,5²R,5³S)-1315,7,7-tetrafluoro-6-oxo-3,8-dioxa-5(2,1)-pyrrolidina-1(1,2)-benzena-2(1,4)-cyclohexanacyclooctaphane-5³-yl) methanesulfonamide (16.0 mg, 67.0%) as a solid. LCMS (ESI): m/z [M+H]⁺=481.2; ¹H NMR (400 MHz, Methanol-d₄) δ 7.02 (t, J=9.7 Hz, 1H), 6.89 (d, J=8.9 Hz, 1H), 4.41 (s, 1H), 4.25 (d, J=7.4 Hz, 1H), 4.16 (d, J=8.0 Hz, 1H), 3.68-3.82 (m, 2H), 3.57 (d, J=9.3 Hz, 1H), 3.05 (s, 2H), 2.71 (s, 1H), 2.36-2.42 (m, 2H), 2.29 (s, 1H), 2.15-2.19 (m, 1H), 1.90-1.95 (m, 1H), 1.74-1.78 (m, 1H), 1.50-1.54 (m, 2H), 1.29-1.43 (m, 3H).

Example 1.18

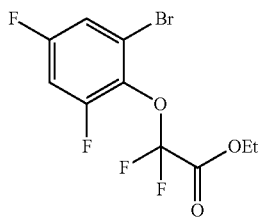 [SMILES: CCOC(=O)C(F)(F)Oc1c(F)cc(F)cc1Br]

To a stirred solution of 2-bromo-4,6-difluorophenol (5.70 g, 1.0 equiv., 27.3 mmol) and ethyl 2-bromo-2,2-difluoroacetate (11.1 g, 2.0 equiv., 54.5 mmol) in DMF (120.0 mL) was added K₂CO₃ (7.54 g, 2.0 equiv., 54.5 mmol) in portions at room temperature under nitrogen atmosphere. The resulting mixture was stirred overnight at room temperature under nitrogen atmosphere. The mixture was diluted with water (100 mL). The resulting mixture was extracted with EtOAc (3×120 mL). The combined organic layers were washed with brine (2×100 mL), dried over anhydrous Na₂SO₄. After filtration, the filtrate was concentrated under reduced pressure. The residue was purified by silica gel column chromatography to afford ethyl 2-(2-bromo-4,6-difluorophenoxy)-2,2-difluoroacetate (4.56 g, 50.5%) as an oil. LCMS (ESI): m/z [M+H]⁺=331.0; ¹H NMR (400 MHz, Chloroform-d) δ 7.20-7.24 (m, 1H), 6.93-6.96 (m, 1H), 4.47 (q, J=7.1 Hz, 2H), 1.44 (t, J=7.2 Hz, 3H).

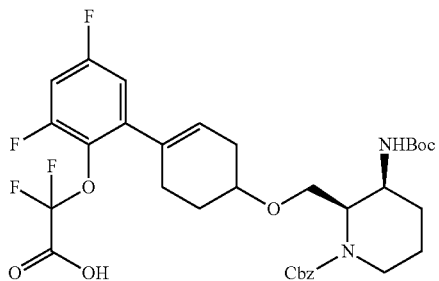 [SMILES: CC(C)(C)OC(=O)N[C@H]1CCCN(C(=O)OCc2ccccc2)[C@H]1COC1CC=C(c2cc(F)cc(F)c2OC(F)(F)C(=O)O)CC1]

To a stirred solution of benzyl 3-[(tert-butoxycarbonyl)amino]-2-([[4-(4,4,5,5-tetramethyl-1,3,2-dioxaborolan-2-yl)cyclohex-3-en-1-yl]oxy]methyl)piperidine-1-carboxylate (2.00 g, 1.0 equiv., 3.501 mmol), ethyl 2-(2-bromo-4,6-difluorophenoxy)-2,2-difluoroacetate (1.50 g, 1.3 equiv., 4.53 mmol), Pd(dppf)C₁₂ (0.26 g, 0.1 equiv., 0.351 mmol) and Na₂CO₃ (0.74 g, 1.3 equiv., 7.01 mmol) in 1,4-dioxane (40.0 mL) was added H₂O (4 mL) at room temperature under nitrogen atmosphere. The resulting mixture was stirred for 2 hr at 80 degrees C. under nitrogen atmosphere. The mixture was diluted with water (50 mL). The resulting mixture was extracted with EtOAc (3×60 mL). The combined organic layers were washed with brine (100 mL), dried over anhydrous Na₂SO₄. After filtration, the filtrate was concentrated under reduced pressure. The residue was purified by reverse flash chromatography to afford benzyl 3-[(tert-butoxycarbonyl)amino]-2-[([4-[2-(2-ethoxy-1,1-difluoro-2-oxoethoxy)-3,5-difluorophenyl]cyclohex-3-en-1-yl]oxy)methyl]piperidine-1-carboxylate (2.25 g, 92.4%) as a solid. LCMS (ESI): m/z [M+H]⁺=667.3.

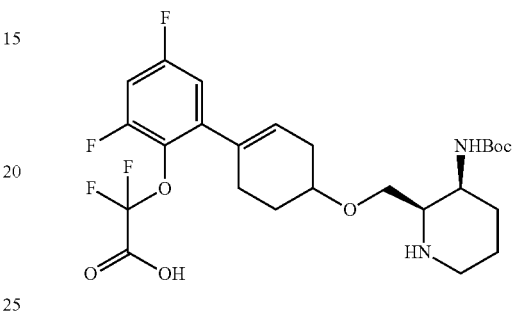

To a stirred solution of 2-[4-([1-[(benzyloxy)carbonyl]-3-[(tert-butoxycarbonyl)amino]piperidin-2-yl]methoxy)cyclohex-1-en-1-yl]-4,6-difluorophenoxydifluoroacetic acid (1.60 g, 1.0 equiv., 2.40 mmol) in i-PrOH (300.0 mL) was added Pd/C (0.54 g, 2.1 equiv., 5.04 mmol) at room temperature under nitrogen atmosphere. The resulting mixture was stirred overnight at room temperature under hydrogen atmosphere. The mixture was filtered and washed with i-PrOH (3×60 mL). Then the resulting mixture was concentrated under reduced pressure. The residue was purified by reverse flash chromatography to afford 2-[4-([3-[(tert-butoxycarbonyl) amino]piperidin-2-yl]methoxy)cyclohex-1-en-1-yl]-4,6-difluorophenoxydifluoroacetic acid (750.0 mg, 58.7%) as a solid. LCMS (ESI): m/z [M+H]⁺=533.2; ¹H NMR (400 MHz, Methanol-d₄) δ 6.96-6.99 (m, 1H), 6.87-6.90 (m, 1H), 5.79 (d, J=10.5 Hz, 1H), 4.08 (s, 1H), 3.81-3.88 (m, 1H), 3.74 (d, J=6.4 Hz, 1H), 3.55-3.71 (m, 1H), 3.03-3.07 (m, 1H), 2.67-2.71 (m, 1H), 2.36-2.42 (m, 2H), 2.18-2.34 (m, 1H), 1.94-2.10 (m, 2H), 1.77-1.93 (m, 4H), 1.48 (d, J=2.4 Hz, 9H).

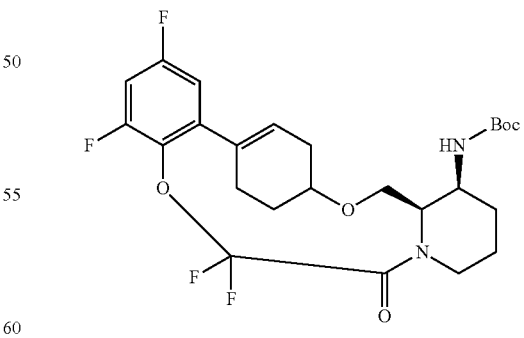

To a stirred solution of 2-[4-([3-[(tert-butoxycarbonyl)amino]piperidin-2-yl]methoxy)cyclohex-1-en-1-yl]-4,6-difluorophenoxydifluoroacetic acid (680.0 mg, 1.0 equiv., 1.28 mmol) and CMPI (489.3 mg, 1.5 equiv., 1.92 mmol) in acetonitrile were added diisopropylethylamine (330.1 mg, 2.0 equiv., 2.55 mmol) dropwise at room temperature under nitrogen atmosphere. The resulting mixture was stirred overnight at room temperature under nitrogen atmosphere. The resulting mixture was concentrated under reduced pressure. The residue was purified by reverse flash chromatography to afford tert-butyl ((2⁴R,5²R,5³S,E)-1³,1⁵,7,7-tetrafluoro-6-oxo-3,8-dioxa-5(2,1)-piperidina-1(1,2)-benzena-2(1,4)-cyclohexanacyclooctaphan-2¹-en-5³-yl)carbamate (208.0 mg, 31.7%) as a solid. LCMS (ESI): m/z, [M-tBu+H]+=459.

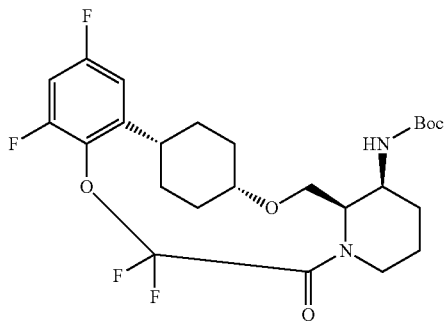 [SMILES: CC(C)(C)OC(=O)N[C@H]1CCCN2C(=O)C(F)(F)Oc3c(F)cc(F)cc3[C@H]3CC[C@H](CC3)OC[C@@H]12]

To a solution of tert-butyl ((2⁴R,5²R,5³S,E)-1³,1⁵,7,7-tetrafluoro-6-oxo-3,8-dioxa-5(2,1)-piperidina-1(1,2)-benzena-2(1,4)-cyclohexanacyclooctaphan-2¹-en-5³-yl)carbamate (208.0 mg, 1.0 equiv., 0.404 mmol) in EtOH (200 mL) was added Pd/C (430.2 mg, 10 equiv., 4.043 mmol) at room temperature under nitrogen atmosphere. The resulting mixture was stirred overnight at room temperature under hydrogen atmosphere. The resulting mixture was filtered, the filter cake was washed with EtOH (3×50 mL). The filtrate was concentrated under reduced pressure. The residue was purified by reverse flash chromatography to afford tert-butyl ((2¹S,2⁴S,5²R,5³S)-1³,1⁵,7,7-tetrafluoro-6-oxo-3,8-dioxa-5(2,1)-piperidina-1(1,2)-benzena-2(1,4)-cyclohexanacyclooctaphane-5³-yl)carbamate (105.0 mg, 50.3%) as a solid. LCMS (ESI): m/z [M-tBu+H]+=461; ¹H NMR (400 MHz, Methanol-d₄) δ 7.00-7.05 (m, 1H), 6.88 (dt, J=9.3, 2.4 Hz, 1H), 5.23-5.28 (m, 1H), 4.07-4.12 (m, 1H), 3.87-3.93 (m, 1H), 3.82 (s, 1H), 3.73 (s, 1H), 3.38-3.52 (m, 2H), 2.65-2.80 (m, 1H), 2.46-2.40 (m, 1H), 2.17-2.28 (m, 1H), 1.93 (dd, J=9.5, 2.6 Hz, 1H), 1.76-1.89 (m, 3H), 1.60-1.74 (m, 3H), 1.45-1.50 (m, 11H), 1.29-1.44 (m, 4H).

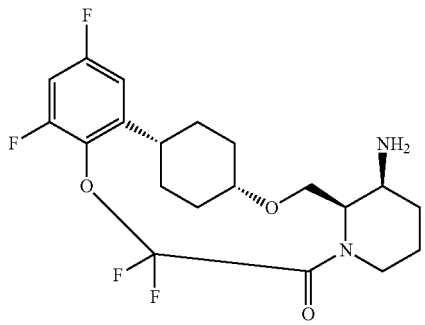 [SMILES: N[C@H]1CCCN2C(=O)C(F)(F)Oc3c(F)cc(F)cc3[C@H]3CC[C@H](CC3)OC[C@@H]12]

To a stirred solution of tert-butyl ((2¹S,2⁴S,5²R,5³S)-1³,1⁵,7,7-tetrafluoro-6-oxo-3,8-dioxa-5(2,1)-piperidina-1(1,2)-benzena-2(1,4)-cyclohexanacyclooctaphane-5³-yl)carbamate (105.0 mg, 1.0 equiv., 0.203 mmol) in dichloromethane (7.5 mL) was added TFA (1.50 mL) at room temperature. The resulting mixture was stirred for 1 hr at room temperature. The resulting mixture was concentrated under reduced pressure. The residue was purified by reverse flash chromatography to afford (2¹S,2⁴S,5²R,5³S)-5³-amino-1³,1⁵,7,7-tetrafluoro-3,8-dioxa-5(2,1)-piperidina-1(1,2)-benzena-2(1,4)-cyclohexanacyclooctaphan-6-one (82.0 mg, 96.9%) as a solid. LCMS (ESI): m/z [M+H]+=417.2.

(Compound 52)

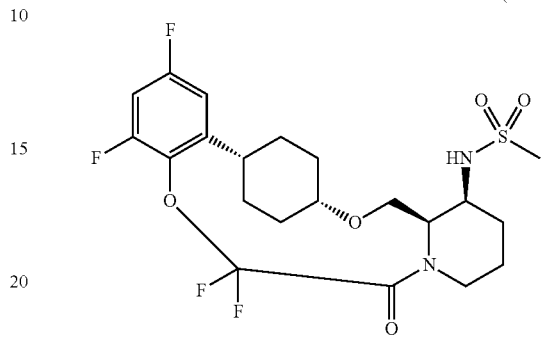

To a stirred solution of (2¹S,2⁴S,5²R,5³S)-5³-amino-1³,1⁵,7,7-tetrafluoro-3,8-dioxa-5(2,1)-piperidina-1(1,2)-benzena-2(1,4)-cyclohexanacyclooctaphan-6-one (85.0 mg, 1.0 equiv., 0.204 mmol) and triethylamine (103.3 mg, 5.0 equiv., 1.021 mmol) in dichloromethane (5.0 mL) was added MsCl (70.2 mg, 3.0 equiv., 0.612 mmol) dropwise at room temperature under nitrogen atmosphere. The resulting mixture was stirred for 2.5 hr at room temperature under nitrogen atmosphere. The resulting mixture was concentrated under reduced pressure. The residue was purified by reverse flash chromatography to afford N-((2¹S,2⁴S,5²R,5³S)-1³,1⁵,7,7-tetrafluoro-6-oxo-3,8-dioxa-5(2,1)-piperidina-1(1,2)-benzena-2(1,4)-cyclohexanacyclooctaphane-5³-yl) methanesulfonamide (52.0 mg, 51.5%) as a solid. LCMS (ESI): m/z [M+H]+=495.2; ¹H NMR (400 MHz, Methanol-d₄) δ 7.00-7.05 (m, 1H), 6.85-6.90 (m, 1H), 5.20-5.35 (m, 1H), 4.07-4.12 (m, 1H), 3.90-3.95 (m, 1H), 3.75 (s, 1H), 3.67-3.73 (m, 1H), 3.60-3.62 (m, 1H), 3.41-3.44 (m, 1H), 3.04 (s, 3H), 2.70-2.73 (m, 1H), 2.46-2.52 (m, 1H), 2.20-2.25 (m, 1H), 1.90-2.01 (m, 2H), 1.79-1. (m, 2H), 1.63-1.78 (m, 2H), 1.46-1.59 (m, 2H), 1.35-1.45 (m, 2H).

Example 1.19

(Compound 59)

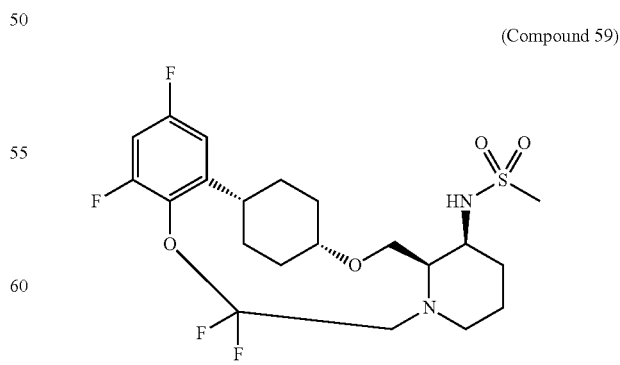

To a stirred solution of N-((2¹S,2⁴S,5²R,5³S)-1³,1⁵,7,7-tetrafluoro-6-oxo-3,8-dioxa-5(2,1)-piperidina-1(1,2)-benzena-2(1,4)-cyclohexanacyclooctaphane-5³-yl) methanesulfonamide (12.0 mg, 1.0 equiv., 0.024 mmol) in THF (2.0 mL) was added BH₃Me₂S (18.4 mg, 10.0 equiv., 0.24 mmol) dropwise at 0 degrees C. under nitrogen atmosphere. The resulting mixture was stirred for 3 hr at room temperature under nitrogen atmosphere. The reaction was quenched by the addition of MeOH (3 mL) at 0 degrees C. The resulting mixture was concentrated under reduced pressure. The crude product was purified by Prep-HPLC to afford N-((2¹S,2⁴S, 5²R,5³S)-1³,1⁵,7,7-tetrafluoro-3,8-dioxa-5(2,1)-piperidina-1(1,2)-benzena-2(1,4)-cyclohexanacyclooctaphane-5³-yl) methanesulfonamide (2.8 mg, 24.0%) as a solid. LCMS (ESI): m/z [M+H]⁺=481.2; ¹H NMR (400 MHz, Methanol-d₄) δ 6.79-6.97 (m, 2H), 4.62 (s, 2H), 3.69-3.85 (m, 4H), 3.61 (d, J=5.0 Hz, 1H), 3.15-3.19 (m, 3H), 3.00 (s, 3H), 2.95 (s, 1H), 2.68-2.79 (m, 1H), 2.52-2.62 (m, 1H), 2.25-2.30 (m, 1H), 2.14-2.18 (m, 1H), 1.90-1.96 (m, 1H), 1.61-1.83 (m, 4H), 1.35-1.40 (m, 4H).

Example 1.20

(Compound 51)

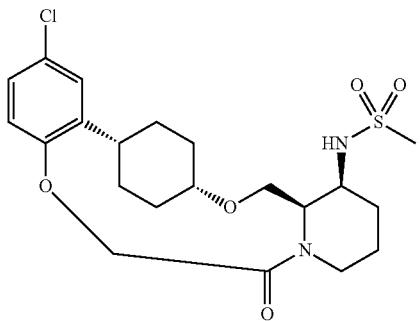

To a stirred mixture of N-((2¹S,2⁴S,5²R,5³S)-6-oxo-3,8-dioxa-5(2,1)-piperidina-1(1,2)-benzena-2(1,4)-cyclohexanacyclooctaphane-5³-yl)methanesulfonamide (300.0 mg, 1.0 equiv., 0.710 mmol) in THF (2.5 mL) and MeCN (2.5 mL) was added N-chlorosuccinimide (104.3 mg, 1.1 equiv., 0.781 mmol) in portions at room temperature under nitrogen atmosphere. The resulting mixture was stirred overnight at room temperature under nitrogen atmosphere. The crude product was purified by reverse phase flash with the following conditions to afford N-((2¹S,2⁴S,5²R,5³S)-1⁵-chloro-6-oxo-3,8-dioxa-5(2,1)-piperidina-1(1,2)-benzena-2 (1,4)-cyclohexanacyclooctaphane-5³-yl)methanesulfonamide (100.0 mg, 30.8%) as a solid. LCMS (ESI): m/z [M+H]+=457.1; ¹H NMR (400 MHz, CDCl₃): δ 7.26-7.45 (6H, m), 7.16 (1H, dd), 6.90-6.98 (2H, m), 5.09 (2H, s), 4.13 (1H, s), 3.02-3.12 (1H, m), 1.82-1.93 (4H, m), 1.41-1.73 (4H, m).

Example 1.21

(Compounds 62 and 63)

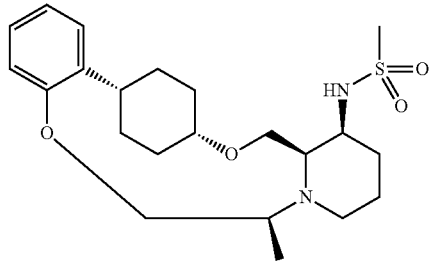

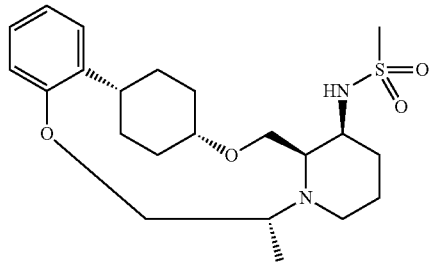

To a stirred mixture of N-((2¹S,2⁴S,5²R,5³S)-6-oxo-3,8-dioxa-5(2,1)-piperidina-1(1,2)-benzena-2(1,4)-cyclohexanacyclooctaphane-5³-yl)methanesulfonamide (100.0 mg, 1.0 equiv., 0.237 mmol) and tetramethyldisilane (63.0 mg, 2.0 equiv., 0.474 mmol) in dichloromethane (1 mL) was added IrCl(CO)(PPh₃)₂ (2.0 mg, 0.01 equiv., 0.002 mmol) in portions at room temperature under nitrogen atmosphere. After stirring for 20 minutes, MeMgBr (85.0 mg, 3.0 equiv., 0.711 mmol) was added into the mixture at −78 degrees C. under nitrogen atmosphere. The resulting mixture was stirred for 4 hr at room temperature under nitrogen atmosphere. The resulting mixture was concentrated under reduced pressure. The crude product was purified by reverse phase flash with the following conditions to afford N-((2¹S, 2⁴R,5²R,5³S,6S)-6-methyl-3,8-dioxa-5(2,1)-piperidina-1(1, 2)-benzena-2(1,4)-cyclohexanacyclooctaphane-5³-yl)methanesulfonamide (28 mg, 28%) and N-((2¹S,2⁴R,5²R,5³S, 6R)-6-methyl-3,8-dioxa-5(2,1)-piperidina-1(1,2)-benzena-2 (1,4)-cyclohexanacyclooctaphane-5³-yl)methanesulfonamide (8.0 mg, 8.0%) as a solid. For major diastereomer: LCMS (ESI): m/z [M+H]+=423.3; ¹H NMR (400 MHz, DMSO-d₆) δ 7.07-7.14 (m, 1H), 7.05 (dd, J=7.5, 1.8 Hz, 1H), 6.94-7.00 (m, 1H), 6.88 (d, J=8.3 Hz, 1H), 6.75-6.81 (m, 1H), 4.10 (d, J=9.0 Hz, 1H), 3.62-3.67 (m, 3H), 3.51 (s, 1H), 3.37 (d, J=9.9 Hz, 1H), 3.21-3.30 (m, 2H), 2.93 (s, 3H), 2.60-2.87 (m, 3H), 2.57 (s, 1H), 2.47 (s, 1H), 1.96-2.09 (m, 1H), 1.75-1.79 (m, 1H), 1.60 (s, 2H), 1.35-1.51 (m, 3H), 1.26-1.35 (m, 2H), 1.24 (d, J=6.6 Hz, 3H), 1.08 (d, J=6.9 Hz, 1H). For minor diastereomer: LCMS (ESI): m/z [M+H]+= 423.3; ¹H NMR (400 MHz, DMSO-d₆) δ 6.99-7.17 (m, 3H), 6.88 (d, J=8.0 Hz, 1H), 6.71-6.81 (m, 1H), 3.81 (dd, J=9.9, 3.6 Hz, 1H), 3.58-3.73 (m, 3H), 3.41 (dd, J=11.5, 5.9 Hz, 1H), 3.30 (s, 1H), 3.00-3.13 (m, 1H), 2.94 (s, 3H), 2.66-2.91 (m, 3H), 2.55-2.67 (m, 1H), 2.41-2.50 (m, 1H), 2.07-2.11 (m, 1H), 1.66-1.79 (m, 2H), 1.17-1.59 (m, 7H), 1.05-1.09 (m, 4H).

Example 1.22

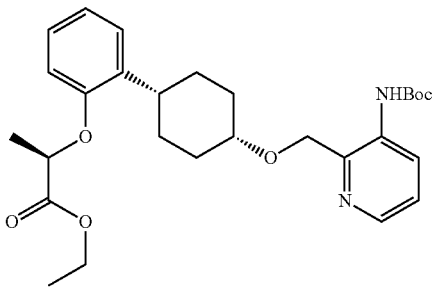 [SMILES: CCOC(=O)[C@@H](C)Oc1ccccc1[C@H]1CC[C@@H](OCc2ncccc2NC(=O)OC(C)(C)C)CC1]

To a stirred mixture of tert-butyl N-[2-([[4-(2-hydroxyphenyl)cyclohexyl]oxy]methyl) pyridin-3-yl]carbamate (2.50 g, 1.0 equiv., 6.27 mmol), ethyl lactate (1.48 g, 2.0 equiv., 12.5 mmol) and PPh$_3$ (4.11 g, 2.5 equiv., 15.7 mmol) in THF (60 mL) at room temperature was added diisopropyl azodicarboxylate (3.17 g, 2.5 equiv., 15.7 mmol) at 0 degrees C. under nitrogen. The reaction was stirred at 35 degrees C. for 2 days. The crude product was purified by Prep-HPLC and Prep-TLC to afford ethyl (2R)-2-[2-[4-([3-[(tert-butoxycarbonyl)amino]pyridin-2-yl]methoxy)cyclohexyl]phenoxy]propanoate (1.20 g, 38.4%) as an oil. LCMS (ESI): m/z [M+H]+=499.4.

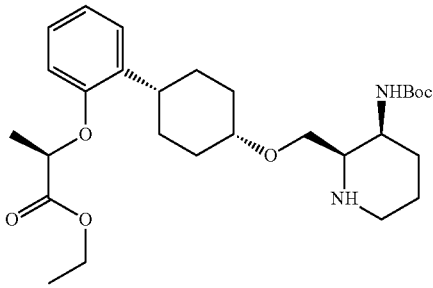

Into a 100 mL 3-necked round-bottom flask were added ethyl (2R)-2-[2-[(1s,4s)-4-([3-[(tert-butoxycarbonyl)amino]pyridin-2-yl]methoxy)cyclohexyl]phenoxy]propanoate (2.90 g, 1.0 equiv., 5.82 mmol) and PtO$_2$ (1.24 g, 0.8 equiv, 85%, 4.65 mmol) in AcOH (5.8 mL) and MeOH (50 mL) at room temperature. The reaction was stirred at room temperature for 16 hr under hydrogen atmosphere. The solvent was removed under reduced pressure. The residue was dissolved in dichloromethane (100 mL). The mixture was basified with saturated Na$_2$CO$_3$ (aq.). The resulting mixture was extracted with CH$_2$Cl$_2$ (3×50 mL). The combined organic layers were dried over anhydrous Na$_2$SO$_4$. After filtration, the filtrate was concentrated under reduced pressure. The residue was purified by Prep-TLC to afford cis-mixture (1.80 g) and trans-mixture (0.90 g). cis: $^1$H NMR (400 MHz, DMSO-d$^6$) δ 7.19 (t, J=9.6 Hz, 1H), 7.05-7.13 (m, 1H), 6.90 (t, J=7.4 Hz, 1H), 6.76 (d, J=8.1 Hz, 1H), 6.23 (d, J=8.8 Hz, 1H), 4.91 (q, J=6.6 Hz, 1H), 4.13 (q, J=7.1 Hz, 2H), 3.68 (d, J=8.7 Hz, 1H), 3.52 (s, 1H), 3.09-3.30 (m, 3H), 2.71-3.02 (m, 3H), 1.92 (s, 2H), 1.57-1.79 (m, 4H), 1.41-1.56 (m, 8H), 1.37 (s, 10H), 1.24 (s, 1H), 1.16 (t, J=7.1 Hz, 3H). trans: $^1$H NMR (400 MHz, DMSO-d$^6$) δ 7.21 (d, J=7.6 Hz, 1H), 7.12-7.08 (m, 1H), 6.91 (t, J=7.4 Hz, 1H), 6.70-6.76 (m, 2H), 4.91 (q, J=6.7 Hz, 1H), 4.13 (q, J=7.1 Hz, 2H), 3.53 (s, 1H), 3.44 (d, J=9.0 Hz, 1H), 3.04-3.26 (m, 3H), 2.85-3.00 (m, 2H), 2.31-2.50 (m, 2H), 1.85-2.04 (m, 2H), 1.62-1.85 (m, 3H), 1.44-1.58 (m, 7H), 1.37 (s, 10H), 1.24 (s, 2H), 1.16 (t, J=7.1 Hz, 3H).

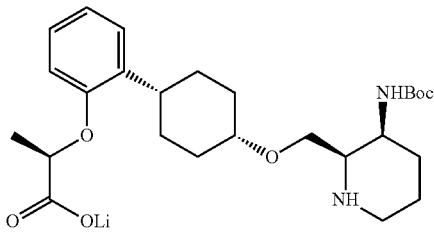

To a solution of ethyl (2R)-2-[2-[(1s,4s)-4-([3-[(tert-butoxycarbonyl)amino]piperidin-2-yl]methoxy)cyclohexyl]phenoxy] propanoate (2.00 g, 1.0 equiv., 3.96 mmol) in MeOH (40 mL), THF (80 mL), H$_2$O (40 mL) was added LiOH (831.0 mg, 5.0 equiv., 19.8 mmol). The reaction was stirred for 2 hr at room temperature. The reaction mixture was concentrated and the residue was purified by Prep-HPLC to afford (2R)-2-[2-[(1s,4s)-4-([3-[(tert-butoxycarbonyl)amino]piperidin-2-yl]methoxy)cyclohexyl]phenoxy] propanoic acid (1.50 g, 79.4%) as a solid. LCMS (ESI): m/z [M+H]+=477.5.

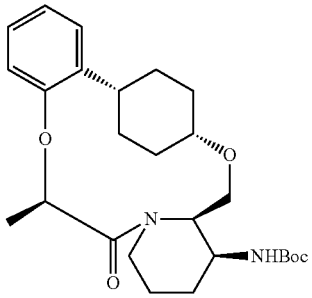 [SMILES: C[C@H]1Oc2ccccc2[C@H]2CC[C@H](CC2)OC[C@H]2[C@@H](NC(=O)OC(C)(C)C)CCCN2C1=O]

To a solution of (2R)-2-[2-[(1s,4s)-4-([3-[(tert-butoxycarbonyl)amino]piperidin-2-yl]methoxy)cyclohexyl]phenoxy] propanoic acid (200.0 mg, 1.0 equiv., 0.420 mmol) in DMF (20 mL) and MeCN (180 mL) at room temperature was added HATU (241.0 mg, 1.5 equiv., 0.634 mmol) and DIPEA (110.0 mg, 1.0 equiv., 0.848 mmol). The reaction was stirred at room temperature for 2 hr under nitrogen. The resulting mixture was concentrated under reduced pressure and used in the next step directly without further purification. LCMS (ESI): m/z [M+H]+=459.3.

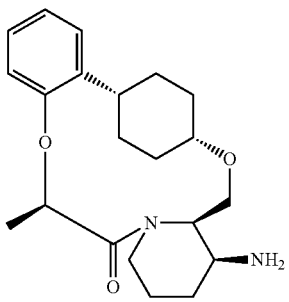 [SMILES: C[C@H]1Oc2ccccc2[C@H]2CC[C@H](CC2)OC[C@H]2[C@@H](N)CCCN2C1=O]

To a solution of tert-butyl ((2¹S,2⁴S,5²R,5³S,7R)-7-methyl-6-oxo-3,8-dioxa-5(2,1)-piperidina-1(1,2)-benzena-2(1,4)-cyclohexanacyclooctaphane-5³-yl)carbamate (1.00 g, 1.0 equiv., 2.18 mmol) in dichloromethane (60 mL) at room temperature was added TFA (20.0 mL, 123.0 equiv., 269.3 mmol) at room temperature and the reaction was stirred at room temperature for 1 hr. The resulting mixture was concentrated under vacuum. The resulting mixture was diluted with $CH_2C_2$ (100 mL). The mixture was basified with saturated $Na_2CO_3$ (aq.). The resulting mixture was extracted with $CH_2C_2$ (3×50 mL). The combined organic layers were dried over anhydrous $Na_2SO_4$. After filtration, the filtrate was concentrated under reduced pressure. The crude product was purified by Prep-HPLC to afford (2¹S,2⁴S,5²R,5³S,7R)-5³-amino-7-methyl-3,8-dioxa-5(2,1)-piperidina-1(1,2)-benzena-2(1,4)-cyclohexanacyclooctaphan-6-one (150.0 mg, 19.2%) as a solid. LCMS (ESI): m/z [M+H]+=359.2.

(Compound 38)

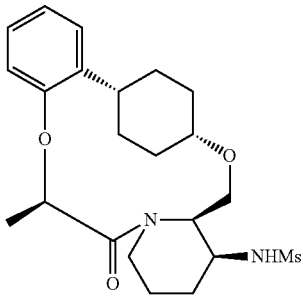

To a solution of (2¹S,2⁴S,5²R,5³S,7R)-5³-amino-7-methyl-3,8-dioxa-5(2,1)-piperidina-1(1,2)-benzena-2(1,4)-cyclohexanacyclooctaphan-6-one (200.0 mg, 1.0 equiv., 0.558 mmol) and diisopropylethylamine (361.0 mg, 5.0 equiv., 2.79 mmol) in dichloromethane (30 mL) at room temperature was added methanesulfonyl chloride (192 mg, 3.0 equiv., 1.674 mmol) at 0 degrees C. The reaction was stirred at room temperature for 1.5 hr. The reaction was then quenched by the addition of 50 mL of water. The resulting solution was extracted with dichloromethane (3×200 mL), dried over anhydrous sodium sulfate and concentrated under vacuum. The crude product was purified by Prep-HPLC to afford N-((2¹S,2⁴S,5²R,5³S,7R)-7-methyl-6-oxo-3,8-dioxa-5(2,1)-piperidina-1(1,2)-benzena-2(1,4)-cyclohexanacyclooctaphane-5³-yl)methanesulfonamide (140.0 mg, 57.5%) as a solid. LCMS (ESI): m/z [M+H]+=437.2. ¹H NMR (400 MHz, DMSO-d⁶) δ 7.23 (d, J=6.8 Hz, 1H), 7.00-7.19 (m, 2H), 6.93 (d, J=8.0 Hz, 1H), 6.79 (t, J=7.3 Hz, 1H), 5.42-5.47 (m, 1H), 5.0-5.18 (m, 1H), 3.70-3.83 (m, 1H), 3.62-3.66 (m, 2H), 3.42 (d, J=3.8 Hz, 1H), 3.15-3.19 (m, 1H), 2.96 (s, 3H), 2.54-2.59 (m, 1H), 2.35-2.49 (m, 1H), 2.20-2.25 (m, 1H), 2.05-2.09 (m, 1H), 1.11-1.86 (m, 13H).

Example 1.23

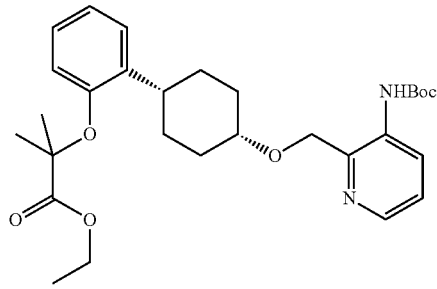 [SMILES: CCOC(=O)C(C)(C)Oc1ccccc1[C@H]1CC[C@@H](OCc2ncccc2NC(=O)OC(C)(C)C)CC1]

To a stirred mixture of tert-butyl N-[2-([[(1s,4s)-4-(2-hydroxyphenyl) cyclohexyl]oxy]methyl)pyridin-3-yl]carbamate (2.00 g, 1.0 equiv., 5.02 mmol) and $K_2CO_3$ (3.50 g, 5.0 equiv., 25.1 mmol) in acetonitrile (5 mL) was added ethyl-bromoisobutyrate (1.47 g, 1.5 equiv., 7.53 mmol) in portions at room temperature under nitrogen atmosphere. The resulting mixture was stirred overnight at 80 degrees C. under nitrogen atmosphere. The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by Prep-TLC to afford ethyl 2-methyl-2-[2-[(1s,4s)-4-([3-[(tert-butoxycarbonyl)amino]pyridin-2-yl]methoxy)cyclohexyl]phenoxy]propanoate (1.20 g, 46.6%) as an oil. LCMS (ESI): m/z [M+H]+=513.3; ¹H NMR (400 MHz, DMSO-d₆) δ 8.69 (s, 1H), 8.10-8.28 (m, 2H), 7.32 (dd, J=8.3, 4.7 Hz, 1H), 7.12-7.21 (m, 1H), 7.07 (dd, J=8.5, 6.8 Hz, 1H), 6.91 (d, J=7.4 Hz, 1H), 6.59 (d, J=8.2 Hz, 1H), 4.76 (s, 2H), 3.76 (s, 1H), 3.18 (d, J=3.3 Hz, 2H), 2.90-2.96 (m, 1H), 1.95-2.04 (m, 2H), 1.63-1.79 (m, 2H), 1.46-1.63 (m, 10H), 1.41 (s, 9H), 1.14 (t, J=7.1 Hz, 3H).

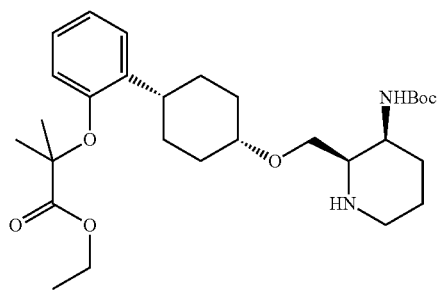

To a stirred mixture of ethyl 2-methyl-2-[2-[(1s,4s)-4-([3-[(tert-butoxycarbonyl) amino]pyridin-2-yl]methoxy)cyclohexyl]phenoxy]propanoate (1.23 g, 1.0 equiv., 2.40 mmol) and AcOH (2.46 mL) in i-PrOH (22.0 mL) was added $PtO_2$ (0.44 g, 1.0 equiv., 1.919 mmol) in portions at room temperature under nitrogen atmosphere. The resulting mixture was stirred overnight at room temperature under hydrogen atmosphere. The resulting mixture was filtered, the filter cake was washed with MeOH (3×30 mL). The filtrate was concentrated under reduced pressure. The residue was purified by Prep-TLC to afford ethyl 2-methyl-2-[2-[(1s,4s)-4-([3-[(tert-butoxycarbonyl)amino]piperidin-2-yl]methoxy)cyclohexyl]phenoxy]propanoate (550.0 mg, 44.2%) as a solid. LCMS (ESI): m/z [M+H]+=519.4; ¹H NMR (400

MHz, DMSO-d$_6$) δ 7.21 (dd, J=7.7, 1.7 Hz, 1H), 7.06 (t, J=1.7 Hz, 1H), 6.91 (td, J=7.5, 1.2 Hz, 1H), 6.58 (dd, J=8.2, 1.2 Hz, 1H), 6.26 (d, J=8.9 Hz, 1H), 4.16 (q, J=7.1 Hz, 2H), 3.69 (dd, J=8.9, 3.1 Hz, 1H), 3.52 (s, 1H), 3.23-3.43 (m, 2H), 3.07-3.24 (m, 2H), 2.84-2.90 (m, 2H), 2.67-2.83 (m, 1H), 1.93 (t, J=10.7 Hz, 2H), 1.57-1.77 (m, 3H), 1.39-1.57 (m, 12H), 1.32-1.37 (m, 10H), 1.15 (t, J=7.1 Hz, 3H).

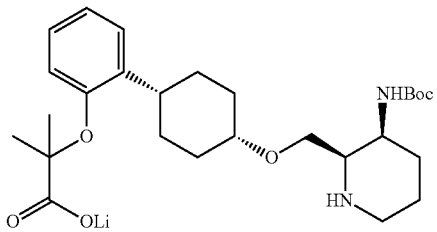

To a stirred mixture of ethyl 2-methyl-2-[2-[(1s,4s)-4-([3-[(tert-butoxycarbonyl) amino]piperidin-2-yl]methoxy)cyclohexyl]phenoxy]propanoate (660.0 mg, 1.0 equiv., 1.27 mmol) in MeOH (10 mL), THF (20 mL) and H$_2$O (10 mL) was added LiOH (267.0 mg, 5.0 equiv., 6.36 mmol) in portions at room temperature under nitrogen atmosphere. The resulting mixture was stirred for 2 hr at room temperature under nitrogen atmosphere. The resulting mixture was concentrated under reduced pressure to remove MeOH and THF. The residue/crude product was purified by reverse phase flash to afford lithio 2-methyl-2-[2-[(1s,4s)-4-([3-[(tert-butoxycarbonyl)amino]piperidin-2-yl]methoxy)cyclohexyl]phenoxy]propanoate (300.0 mg, 47.5%) as a solid. LCMS (ESI): m/z [M+H]+=491.4.

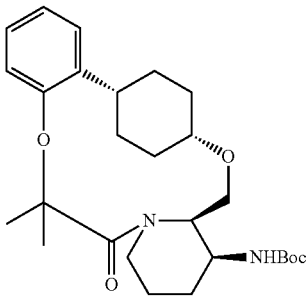 [SMILES: CC(C)(C)OC(=O)N[C@H]1CCCN2C(=O)C(C)(C)Oc3ccccc3[C@H]3CC[C@H](CC3)OC[C@@H]12]

To a stirred mixture of lithio 2-methyl-2-[2-[(1s,4s)-4-([3-[(tert-butoxycarbonyl) amino]piperidin-2-yl]methoxy)cyclohexyl]phenoxy]propanoate (50.0 mg, 1.0 equiv., 0.101 mmol) and CMPI (39.0 mg, 1.5 equiv., 0.151 mmol) in acetonitrile (750 mL) was added diisopropylethylamine (26.0 mg, 2.0 equiv., 0.201 mmol) in portions at room temperature under nitrogen atmosphere. The resulting mixture was stirred overnight at 50 degrees C. under nitrogen atmosphere. The resulting mixture was concentrated under reduced pressure. The residue was purified by reverse phase flash to afford tert-butyl ((2$^1$S,2$^4$S,5$^2$R,5$^3$S)-7,7-dimethyl-6-oxo-3,8-dioxa-5(2,1)-piperidina-1(1,2)-benzena-2(1,4)-cyclohexanacyclooctaphane-5$^3$-yl)carbamate (440.0 mg, 68.0%) as a solid. LCMS (ESI): m/z [M+H]+=473.4; $^1$H NMR (400 MHz, DMSO-d$_6$) δ 7.04-7.14 (m, 3H), 6.96 (d, J=7.9 Hz, 1H), 6.87 (dd, J=7.8, 2.4 Hz, 1H), 5.03-5.23 (m, 1H), 4.21-4.27 (m, 1H), 3.70-3.75 (m, 1H), 3.57-3.63 (m, 2H), 3.11-3.31 (m, 2H), 2.53-2.69 (m, 1H), 1.99-2.19 (m, 2H), 1.87 (s, 3H), 1.61 (s, 6H), 1.36-1.44 (m, 10H), 1.33 (s, 3H), 1.11-1.29 (m, 3H).

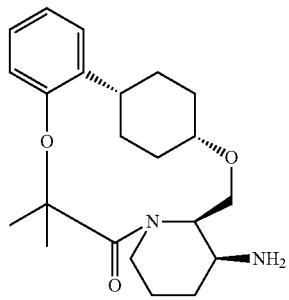 [SMILES: CC1(C)Oc2ccccc2[C@H]2CC[C@H](CC2)OC[C@H]2[C@@H](N)CCCN2C1=O]

To a stirred solution of tert-butyl ((2$^1$S,2$^4$S,5$^2$R,5$^3$S)-7,7-dimethyl-6-oxo-3,8-dioxa-5(2,1)-piperidina-1(1,2)-benzena-2(1,4)-cyclohexanacyclooctaphane-5$^3$-yl)carbamate (430.0 mg, 1.0 equiv., 0.91 mmol) in dichloromethane (25 mL) was added TFA (8.4 mL) in portions at room temperature under nitrogen atmosphere. The resulting mixture was stirred for 1 hr at room temperature under nitrogen atmosphere. The resulting mixture was concentrated under reduced pressure to afford crude product (2$^1$S,2$^4$S,5$^2$R,5$^3$S)-5$^3$-amino-7,7-dimethyl-3,8-dioxa-5(2,1)-piperidina-1(1,2)-benzena-2(1,4)-cyclohexanacyclooctaphan-6-one (230.0 mg, 67.9%) as a solid. LCMS (ESI): m/z [M+H]+=373.3; 1H NMR (400 MHz, DMSO-d$_6$) δ 7.02-7.18 (m, 3H), 6.80-6.90 (m, 1H), 4.95-5.05 (m, 1H), 4.14-4.24 (m, 1H), 3.74 (dd, J=11.3, 8.9 Hz, 1H), 3.61 (s, 1H), 3.45 (dd, J=8.9, 3.8 Hz, 1H), 3.23 (t, J=12.7 Hz, 1H), 2.93-2.83 (m, 1H), 2.72-2.53 (m, 1H), 2.49 (s, 2H), 2.05-2.20 (m, 2H), 1.86 (s, 3H), 1.57-1.74 (m, 2H), 1.35 (d, J=10.5 Hz, 7H), 1.11-1.30 (m, 4H).

(Compound 36)

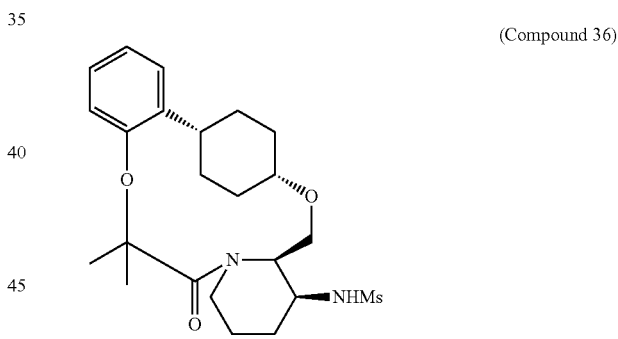

To a stirred mixture of (2$^1$S,2$^4$S,5$^2$R,5$^3$S)-5$^3$-amino-7,7-dimethyl-3,8-dioxa-5(2,1)-piperidina-1(1,2)-benzena-2(1,4)-cyclohexanacyclooctaphan-6-one (220.0 mg, 1.0 equiv., 0.591 mmol) and diisopropylethylamine (382.0 mg, 5.0 equiv., 2.95 mmol) in dichloromethane (35 mL) was added MsCl (203.0 mg, 3.0 equiv., 1.77 mmol) dropwise at 0 degrees C. under nitrogen atmosphere. The resulting mixture was stirred for 1 hr at room temperature under nitrogen atmosphere. The reaction was quenched with water at room temperature. The resulting mixture was concentrated under reduced pressure. The crude product was purified by Chiral-HPLC to afford N-((2$^1$S,2$^4$S,5$^2$R,5$^3$S)-7,7-dimethyl-6-oxo-3,8-dioxa-5(2,1)-piperidina-1(1,2)-benzena-2(1,4) cyclohexanacyclooctaphane-5$^3$-yl)methanesulfonamide (72.0 mg, 27.0%) as a solid. LCMS (ESI): m/z [M+H]+=451.3; 1H NMR (400 MHz, DMSO-d$_6$) δ 7.22 (d, J=6.9 Hz, 1H), 7.09 (d, J=1.5 Hz, 3H), 6.88 (dd, J=6.2, 2.2 Hz, 1H), 5.13 (t, J=4.7 Hz, 1H), 4.21-4.27 (m, 1H), 3.67-3.76 (m, 1H), 3.65 (s, 1H), 3.35-3.53 (m, 2H), 3.15-3.33 (m, 1H), 2.95 (s, 3H), 2.52-2.65 (m, 1H), 2.37-2.50 (m, 1H), 1.97-2.22 (m, 2H), 1.87 (s, 3H), 1.68-1.82 (m, 2H), 1.41-1.69 (m, 3H), 1.34 (s, 4H), 1.19-1.30 (m, 2H), 1.12-1.20 (m, 1H).

Example 2: Human OX$_2$R IP1 Assay

T-Rex CHO cells stably overexpressing the human orexin-2 receptor (OX$_2$R) were induced overnight with 1 μg/mL of doxycycline in a T225 flask. 24 hours post induction, cells were lifted with accutase and plated into a 384-well proxy plate at 30,000 cells/well. Cells were then treated with different test compounds in 1× stimulation buffer containing 10 mM Hepes, 1 mM CaCl$_2$, 0.5 mM MgCl$_2$, 4.2 mM KCl, 146 mM NaCl, 5.5 mM glucose, and 50 mM LiCl, pH 7.4, for 1 hr at 37 degrees C. Following incubation, the reaction was terminated by the addition of detection mix, which is composed of IP1-d2 and anti-IP1-cryptate diluted in lysis buffer as well as 1× stimulation buffer. The plates were allowed to incubate for 1 hour at room temperature and were then read in the EnVision® multimode plate reader, measuring inositol phosphate levels.

Cisbio IP1 is a cell-based functional assay quantifying the accumulation of inositol monophosphate (IP), a metabolite released as a result of orexin 2 receptor activation through the phospholipase C-Gq signaling pathway. This is a competitive immunoassay in which the IP1 produced by the cells upon receptor activation competes with the IP1 analog coupled to the d$_2$ fluorophore (acceptor) for binding to an anti-IP1 monoclonal antibody labeled with Eu cryptate (donor). The measured HTRF-FRET based signal is inversely proportional to the IP1 concentration produced.

The EC$_{50}$ values reported in Table 2 were obtained according to the human OX$_2$R IP1 assay described above. Data are the mean EC$_{50}$ values ±S.E.M. The compound methyl (2R,3S)-3-((methylsulfonyl)amino)-2-(((cis-4-phenylcyclohexyl)oxy)methyl)-piperidine-1-carboxylate is a reference compound which is disclosed in Example 5 of PCT publication no. WO2017/135306.

TABLE 2

| Compound | Compound No. | EC$_{50}$ (nM) |
|---|---|---|
| 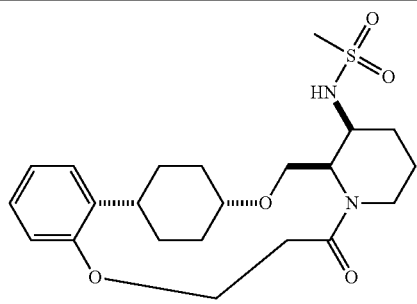 | 1 | *** |
| 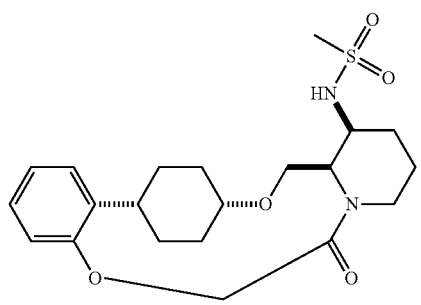 | 2 | *** |

TABLE 2-continued

| Compound | Compound No. | EC$_{50}$ (nM) |
|---|---|---|
| 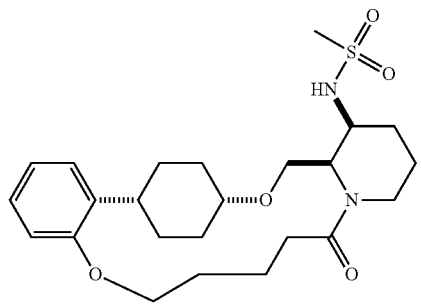 | 3 | * |
| 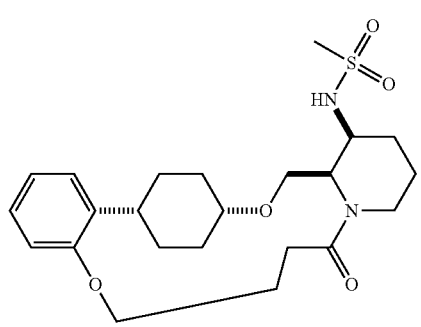 | 4 | *** |
| 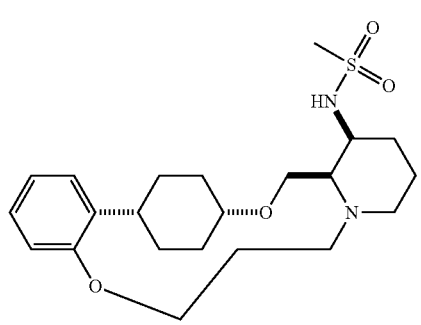 | 5 | * |
| 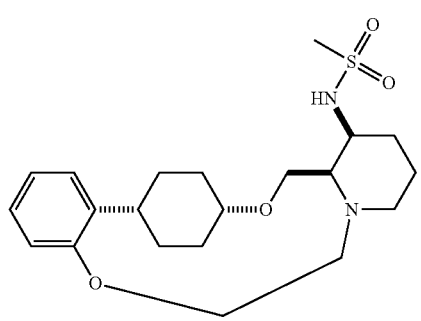 | 6 | *** |
| 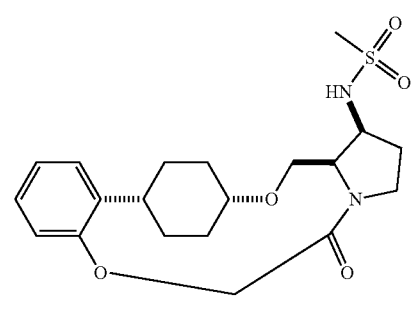 | 7 | *** |

TABLE 2-continued

| Compound | Compound No. | EC$_{50}$ (nM) |
|---|---|---|
| | 8 | *** |
| | 9 | *** |
| | 10 | ** |
| | 11 | *** |
| | 12 | *** |
| | 13 | ** |
| | 14 | * |
| | 15 | **/\ |
| | 18 | ** |
| | 36 | *** |

TABLE 2-continued
| Compound | Compound No. | EC$_{50}$ (nM) |
|---|---|---|
| 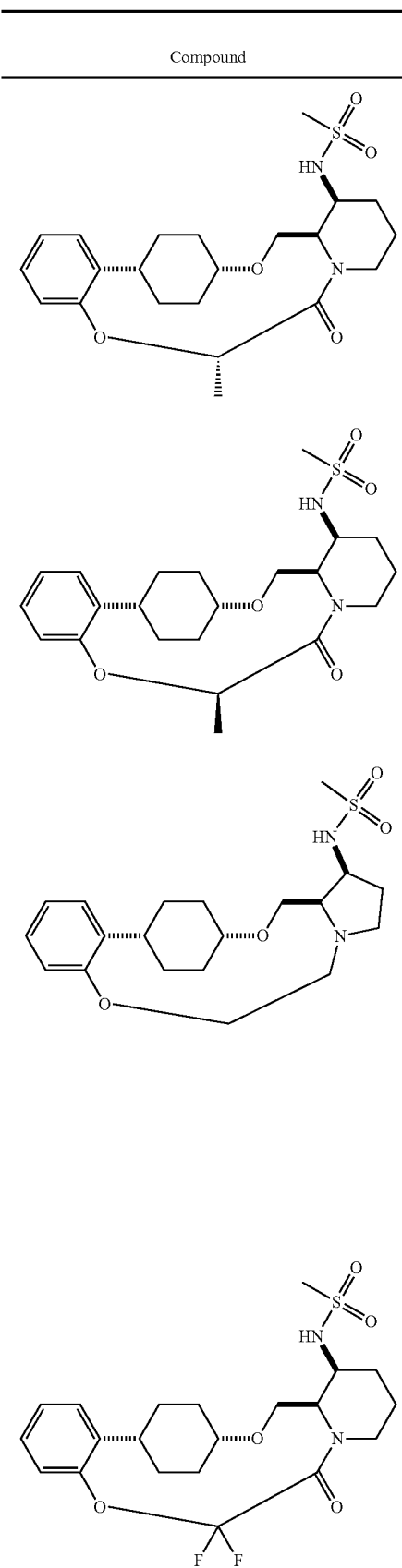 | 37 | *** |
| | 38 | *** |
| | 39 | * |
| | 40 | *** |
TABLE 2-continued
| Compound | Compound No. | EC$_{50}$ (nM) |
|---|---|---|
| 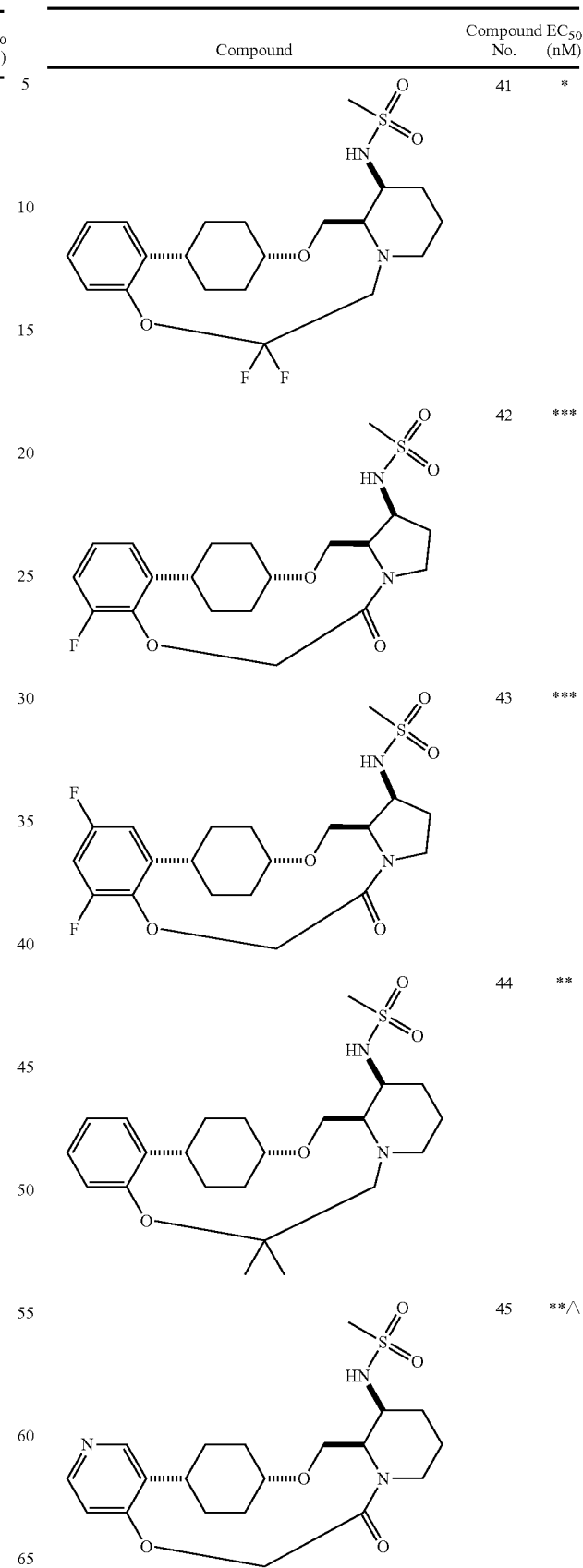 | 41 | * |
| | 42 | *** |
| | 43 | *** |
| | 44 | ** |
| | 45 | **/\ |

TABLE 2-continued

| Compound | Compound No. | EC$_{50}$ (nM) |
|---|---|---|
| | 46 | *** |
| | 47 | ***/\ |
| | 48 | *** |
| | 49 | ***/\ |
| | 50 | *** |
| | 51 | *** |
| | 52 | *** |
| | 53 | *** |
| | 54 | *** |

TABLE 2-continued

| Compound | Compound No. | EC$_{50}$ (nM) |
|---|---|---|
| (structure) | 55 | *** |
| (structure) | 56 | ** |
| (structure) | 57 | *** |
| (structure) | 58 | ** |
| (structure) | 59 | ** |
| (structure) | 60 | ** |
| (structure) | 61 | * |
| (structure) | 62 | * |
| (structure) | 63 | * |
| (structure) | 64 | *** |

TABLE 2-continued

| Compound | Compound No. | EC$_{50}$ (nM) |
|---|---|---|
| [structure] | 65 | ** |
| [structure] | 66 | *** |
| methyl (2R,3S)-3-((methylsulfonyl)amino)-2-(((cis-4-phenylcyclohexyl)oxy)methyl)-piperidine-1-carboxylate | — | *** |

***EC$_{50}$ <100 nM
**EC$_{50}$ 100-1,000 nM
*EC$_{50}$ >1,000 nM
^Racemic mixture

Example 3: MDCK-MDR1 Permeability Assay

The bidirectional permeability (Apical to Basal and Basal to Apical directions) of test compounds in MDCK-MIDR1 cells were evaluated using MDCK-MIDR1 cells seeded in Solvo PreadyPort™ MIDCK 96-well plate. Once the plate was received from ReadyCell (Barcelona, Spain), it was treated as per PreadyPort™ user's manual.

For the Apical to Basolateral (A→B) permeability, 80 µL of test compound (3 µM) co-dosed with LY (Lucifer Yellow) (100 µM) in HBSS (Hank's Balanced Salt Solution) assay buffer was added to the donor side (A) while 250 µL of HBSS buffer was added to the receiver side (B). For the Basolateral to Apical (B→A) permeability, 255 µL of test compound (3 µM) in HBSS assay buffer was added to the donor side (B) while 75 µL of HBSS buffer containing LY (100 µM) was added to the receiver side (A).

The plate was placed in an incubator set at 37 degrees C. After 10 minutes of pre-warming, 5 µL aliquot was taken from donor compartment and set aside as the dosing solution. The MDCK-MDR1 incubation plate was placed back into the incubator for 2 hours of incubation at 37 degrees C. After 2 hours of incubation, 25 µL and 5 µL aliquots were removed from the receiver and donor sides, respectively. To the 5 µL aliquots taken from the donor sides (before and after a 2-hour incubation) were diluted with 20 µL of the HBSS buffer. All samples were mixed with 150 µL with acetonitrile containing internal standard (IS) and 200 µL water, and analyzed by LC-MS/MS.

The apparent permeability ($P_{app}$) was calculated using the following formula:

$$P_{app} = dQ/dt \times 1/A \times C_0$$

where:
dQ/dt: amount of translocated material over incubation time (nmol/s)
A: area of insert (0.14 cm$^2$ for PreadyPort™ MDR1-96)
$C_0$: initial concentration of product applied in apical (A→B) or basal (B→A) compartment (nmol/mL)

The efflux ratio (ER) was measured by dividing the $P_{app}$ (basolateral to apical direction) by $P_{app}$ (apical to basolateral direction). It is a general measure of the involvement of active processes. An ER>2 is considered positive for active transport.

Percent recovery was measured using the following equation:

$$\text{Percent Recovery} = 100 \times \frac{C_R^{final} \times V_R + C_D^{final} \times V_D}{V_D \times C_N}$$

where:
$V_R$: Volume of the receiver compartment (mL)
$V_D$: Volume of the donor compartment (mL)
$C_N$: Concentration of dosing solution (µM) collected after 10 minutes of incubation
$C_R^{final}$: Receiver concentration at the end of the incubation (µM)
$C_D^{final}$: Donor concentration at the end of the incubation (µM)

The data reported in Table 3 were obtained according to the MDCK-MIDR1 permeability assay described above.

TABLE 3

| Compound | Compound No. | $P_{app}$ A→B ($10^{-6}$ cm/s) | Efflux ratio (ER) |
|---|---|---|---|
| [structure] | 1 | 0.15 | >100 |

TABLE 3-continued

| Compound | Compound No. | $P_{app}$ A→B ($10^{-6}$ cm/s) | Efflux ratio (ER) |
|---|---|---|---|
| | 2 | 0.89 | 39 |
| | 3 | 0.80 | 34 |
| | 4 | 0.47 | 97 |
| | 6 | 21 | 0.66 |
| | 7 | 14 | 2.2 |

TABLE 3-continued

| Compound | Compound No. | P$_{app}$ A→B (10$^{-6}$ cm/s) | Efflux ratio (ER) |
|---|---|---|---|
| | 8 | 0.48 | 3.8 |
| | 9 | 0.45 | 2.6 |
| | 10 | 0.29 | 15 |
| | 11 | 2.2 | 5.5 |
| | 12 | 2.3 | 6.2 |

TABLE 3-continued

| Compound | Compound No. | $P_{app}$ A→B ($10^{-6}$ cm/s) | Efflux ratio (ER) |
|---|---|---|---|
| | 13 | 26 | 0.55 |
| | 14 | 0.12 | 4.4 |
| | 15 | 0.08 | 22 |
| | 18 | 3.9 | 2.0 |
| | 36 | 2.0 | 9.5 |

TABLE 3-continued

| Compound | Compound No. | $P_{app}$ A→B ($10^{-6}$ cm/s) | Efflux ratio (ER) |
|---|---|---|---|
| | 37 | 0.91 | 27 |
| | 38 | 0.77 | 18 |
| | 39 | 24 | 0.49 |
| | 40 | 3.6 | 5.1 |

TABLE 3-continued

| Compound | Compound No. | P$_{app}$ A→B (10$^{-6}$ cm/s) | Efflux ratio (ER) |
|---|---|---|---|
| | 42 | 11 | 1.3 |
| | 43 | 12 | 1.1 |
| | 44 | 6.3 | 1.9 |
| | 45 | 0.15 | 12 |
| | 46 | 0.31 | 58 |

TABLE 3-continued

| Compound | Compound No. | P$_{app}$ A→B (10$^{-6}$ cm/s) | Efflux ratio (ER) |
|---|---|---|---|
| | 47 | 0.09 | 49 |
| | 48 | 7.3 | 1.5 |
| | 49 | 0.72 | 36 |
| | 50 | 1.2 | 21 |
| | 51 | 0.59 | 21 |

TABLE 3-continued
| Compound | Compound No. | $P_{app}$ A→B ($10^{-6}$ cm/s) | Efflux ratio (ER) |
|---|---|---|---|
| 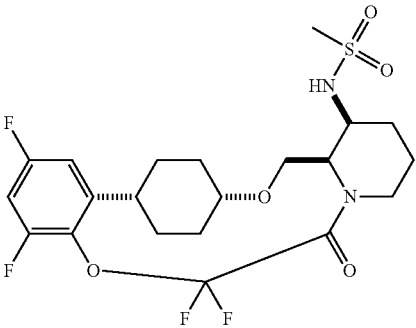 | 52 | 1.2 | 12 |
| 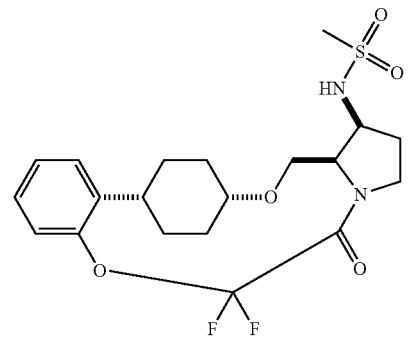 | 53 | 2.8 | 7.9 |
| 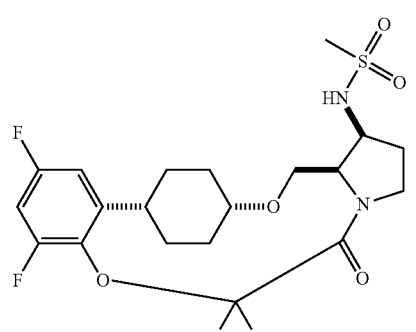 | 54 | 2.6 | 7.3 |
| 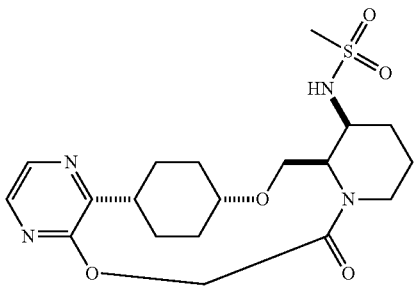 | 55 | 0.092 | 77 |

TABLE 3-continued

| Compound | Compound No. | P$_{app}$ A→B (10$^{-6}$ cm/s) | Efflux ratio (ER) |
|---|---|---|---|
| | 56 | 0.13 | 5.2 |
| | 57 | 0.16 | 51 |
| | 58 | 1.5 | 10 |
| | 60 | 8.8 | 1.4 |
| | 61 | 2.0 | 5.5 |

TABLE 3-continued

| Compound | Compound No. | P$_{app}$ A→B (10$^{-6}$ cm/s) | Efflux ratio (ER) |
|---|---|---|---|
| | 62 | 6.8 | 2.2 |
| | 63 | 9.1 | 0.75 |
| | 64 | 0.83 | 30 |
| | 65 | 15 | 0.5 |

TABLE 3-continued

| Compound | Compound No. | $P_{app}$ A→B ($10^{-6}$ cm/s) | Efflux ratio (ER) |
|---|---|---|---|
| [structure] | 66 | <0.047 | >9.5 |
| methyl (2R,3S)-3-((methylsulfonyl)amino)-2-(((cis-4-phenylcyclohexyl)oxy)methyl)-piperidine-1-carboxylate | — | 5.9 | 4.0 |

Example 4: Hepatocytes Stability Assay

In vitro metabolic stability was assessed using cryopreserved hepatocytes from male Sprague Dawley rats and a pool of 50 mixed gender humans (BioIVT, Baltimore, MD). The incubation mixtures were prepared by mixing 250 µL of pre-warmed KHB (Krebs-Henseleit buffer) containing 2×10⁶ cell/mL of hepatocytes with 250 µL of pre-warmed KHB buffer containing 2 µM of test compounds in a 48-well plate, giving a final concentration of 1 µM test compound (0.1% DMSO) and 1×10⁶ cell/mL of hepatocytes. The reaction mixture was incubated at 37 degrees C. A 50 µL aliquot of incubation mixture was taken at time points (0, 15, 30, 60, 120 and 240 minutes) and transferred into a 96-well plate containing 300 µL ice-cold acetonitrile (containing 30 ng/mL of labetalol and 10 ng/mL of Naltrexone-d3 as internal standards) and immediately placed in ice to terminate the reaction. Samples were centrifuged, and supernatants were transferred into 96-well plates for liquid chromatography with tandem mass spectrometry (LC-MS/MS) analysis to monitor the depletion of the test compound.

Data was calculated as percent remaining by assuming zero-minute time point peak area ratio (analyte/IS) as 100% and dividing remaining time point peak area ratios by zero-minute time point peak area ratio. Data were fitted to a first-order decay model to determine half-life. From a plot of log (ln) peak area against time, the slope of the line was determined. Subsequently, half-life ($T_{1/2}$) and intrinsic clearance ($CL_{int}$) were calculated using the equations below:

Elimination rate constant $(k)=(-\text{slope})$

Half-life $(T_{1/2})\text{min}=0.693/k$

Intrinsic Clearance ($CL_{int}$) (mL/min/million cells)= $(V\times 0.693)/T_{1/2}$ $V$=incubation volume mL/number of cells The in vitro $T_{1/2}$ was converted to in vitro intrinsic clearance ($CL_{int,hep}$) in units of mL/min/kg using the formula shown below:

$$CLint, hep = \frac{0.693}{T1/2} \times \frac{\text{mL incubation}}{\text{million cells}} \times \frac{120 \text{ million cells}}{g \text{ Liver}} \times \frac{g \text{ liver}}{kg \text{ body}}$$

The in vitro intrinsic clearance ($CL_{int,hep}$) was scaled to in vivo hepatic clearance ($CL_{,hep}$) using the following equation which was adapted from a well-stirred model.

$$CL, hep = \frac{Q \times fu \times CLint, hep}{Q + fu \times CLint, hep}$$

where Q is the liver blood flow and fu is the fraction unbound (assumed to be unity in this case). All parameters used in the calculation are shown below (Table 4).

TABLE 4

Physiological Parameters Used in the In Vitro To In Vivo Scaling

|  | Mouse | Rat | Dog | Monkey | Human |
|---|---|---|---|---|---|
| Body Weight (kg) | 0.02 | 0.25 | 10 | 5 | 70 |
| Liver weight (g/kg) | 87.5 | 40 | 32 | 30 | 25.7 |
| Liver Blood Flow (mL/min/kg) | 90 | 55.2 | 30.9 | 43.6 | 20.7 |

Davies B. and Morris T. (1993) Physiological Parameters in Laboratory Animals and Humans.
Pharma Res. 10 (7):1093-1095.

The extraction ratio (ER) was calculated by dividing the hepatic clearance of a compound to the liver blood flow. The data reported in Table 5 were obtained according to the human hepatocytes stability assay described above.

TABLE 5
| Compound | Compound No. | CL$_{int}$ (μL/min/ million cells) | Extraction Ratio (ER) |
|---|---|---|---|
| 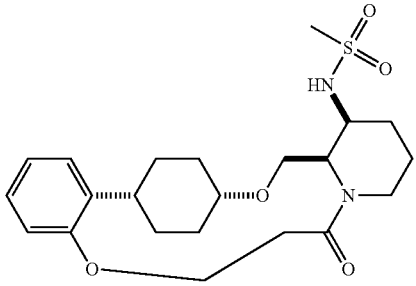 | 1 | 14 | 0.67 |
| 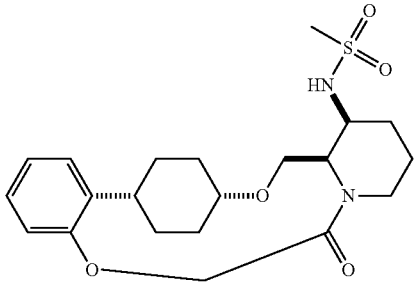 | 2 | 13 | 0.67 |
| 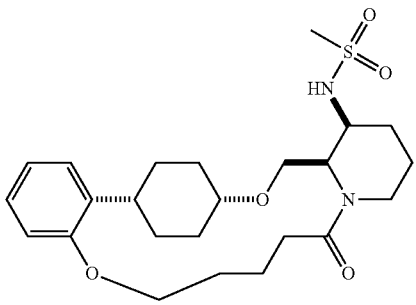 | 3 | 43 | 0.87 |
| 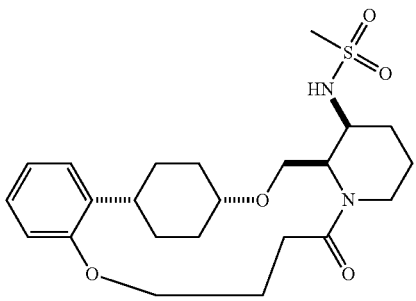 | 4 | 28 | 0.81 |
| 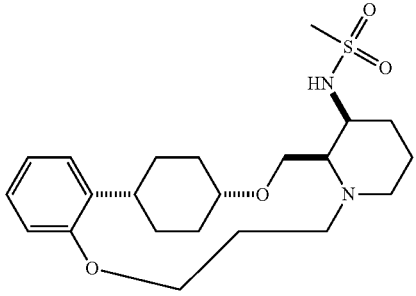 | 5 | 63 | 0.90 |

TABLE 5-continued

| Compound | Compound No. | CL$_{int}$ (μL/min/ million cells) | Extraction Ratio (ER) |
|---|---|---|---|
| | 6 | 45 | 0.87 |
| | 7 | 24 | 0.78 |
| | 8 | 5.8 | 0.46 |
| | 9 | 6.7 | 0.50 |
| | 10 | 8.3 | 0.55 |

TABLE 5-continued

| Compound | Compound No. | CL$_{int}$ (μL/min/ million cells) | Extraction Ratio (ER) |
|---|---|---|---|
| | 11 | 33 | 0.83 |
| | 12 | 13 | 0.66 |
| | 13 | 47 | 0.88 |
| | 14 | <1.9 | <0.22 |
| | 15 | <1.9 | <0.22 |

TABLE 5-continued

| Compound | Compound No. | CL$_{int}$ (μL/min/ million cells) | Extraction Ratio (ER) |
|---|---|---|---|
| | 18 | 23 | 0.77 |
| | 36 | 66 | 0.91 |
| | 37 | 30 | 0.82 |
| | 38 | 30 | 0.82 |

TABLE 5-continued

| Compound | Compound No. | CL$_{int}$ (μL/min/ million cells) | Extraction Ratio (ER) |
|---|---|---|---|
| [structure] | 39 | 47 | 0.88 |
| [structure] | 40 | 65 | 0.91 |
| [structure] | 41 | 60 | 0.90 |
| [structure] | 42 | 52 | 0.89 |

TABLE 5-continued

| Compound | Compound No. | CL$_{int}$ (μL/min/ million cells) | Extraction Ratio (ER) |
|---|---|---|---|
| | 43 | 34 | 0.83 |
| | 44 | 65 | 0.91 |
| | 45 | <1.9 | <0.22 |
| | 46 | 6.9 | 0.51 |
| | 47 | 3.0 | 0.31 |

TABLE 5-continued

| Compound | Compound No. | CL$_{int}$ (μL/min/ million cells) | Extraction Ratio (ER) |
|---|---|---|---|
| (structure) | 48 | 60 | 0.90 |
| (structure) | 49 | 12 | 0.64 |
| (structure) | 50 | 16 | 0.70 |
| (structure) | 51 | 4.6 | 0.41 |

TABLE 5-continued

| Compound | Compound No. | CL$_{int}$ (μL/min/ million cells) | Extraction Ratio (ER) |
| --- | --- | --- | --- |
| (structure) | 52 | 44 | 0.87 |
| (structure) | 53 | 19 | 0.92 |
| (structure) | 54 | 56 | 0.89 |
| (structure) | 55 | <1.9 | <0.22 |

TABLE 5-continued
| Compound | Compound No. | CL$_{int}$ (μL/min/ million cells) | Extraction Ratio (ER) |
|---|---|---|---|
| 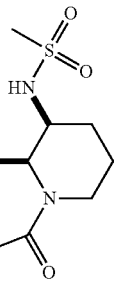 | 56 | <1.9 | <0.22 |
| 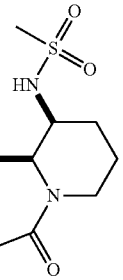 | 57 | 2.1 | 0.24 |
| 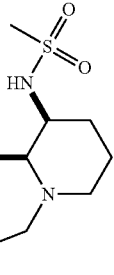 | 58 | 62 | 0.90 |
| 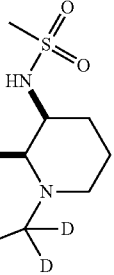 | 60 | 54 | 0.89 |
| 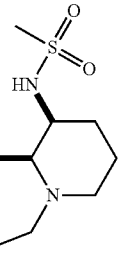 | 61 | 33 | 0.83 |

TABLE 5-continued
| Compound | Compound No. | CL$_{int}$ (μL/min/ million cells) | Extraction Ratio (ER) |
|---|---|---|---|
| 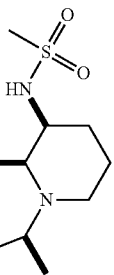 | 62 | 18 | 0.89 |
| 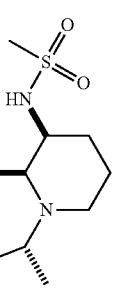 | 63 | 40 | 0.86 |
| 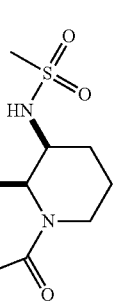 | 64 | 9.0 | 0.57 |
| 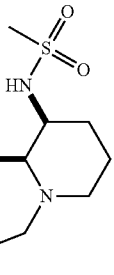 | 65 | 34 | 0.84 |

TABLE 5-continued

| Compound | Compound No. | CL_int (μL/min/ million cells) | Extraction Ratio (ER) |
|---|---|---|---|
| (structure shown) | 66 | <1.9 | <0.22 |
| methyl (2R,3S)-3-((methylsulfonyl)amino)-2-(((cis-4-phenylcyclohexyl)oxy)methyl)-piperidine-1-carboxylate | — | 51 | 0.88 |

Example 5: Assessment of Wake Promotion in Sprague-Dawley Rats

Wake promotion was assessed using electroencephalography (EEG) and electromyography (EMG) in adult male Sprague-Dawley rats (350-600 g). All rats (Charles River Laboratories, Raleigh, NC, USA) were intraperitoneally implanted with telemetry devices (F50-EEE, Data Sciences International Inc., M/N, USA) under isoflurane anesthesia. For EEG, stainless steel screws were implanted over frontal cortex and parietal cortex, and reference screws were placed over cerebellum. Additionally, an electrode was placed in neck muscle for EMG. Rats were given carprofen post-surgery and underwent a 7 to 10-day recovery period. Rats habituated to the experimental room for 7 days and were maintained on a 12-hour light-dark cycle.

EEG and EMG data were recorded using the DSI telemetry system and Ponemah software (Data Sciences International Inc., MN, USA). Sleep-wake stages were scored both manually and with Somnivore, a supervised machine learning software platform, in 10 second epocs. Records were visually inspected as needed post-processing.

All test compounds were dissolved in 5% DMSO and suspended in 95% saline with 0.5% methylcellulose and 0.5% tween. In a cross-over design, rats were dosed during the inactive light phase at zeitgeber time 5 (ZT5) at a dose volume of 3.33 ml/kg body weight. Unless otherwise indicated, all compounds were dosed orally. Recordings for each rat were initiated immediately after dosing and lasted for 6 hours post-dose.

Two key endpoints include wakefulness time and cortical activation time. Wakefulness time is derived from the sleep-wake stage analysis. Cortical activation time is based on the duration in which frontal gamma oscillatory activity (30-100 Hz), a key feature of wakefulness, was elevated relative to a pre-treatment baseline. Mean cortical activation time was computed relative to vehicle treatment for the 6-hour post-dose period. Results are shown in Table 6 below.

TABLE 6

| Compound | Route | Dose (mpk) | Mean cortical activation time (% vehicle treatment) |
|---|---|---|---|
| 2 | PO | 3 | 190.37 |
| 7 | PO | 3 | 164.89 |
| 46 | PO | 3 | 156.92 |
| 12 | PO | 3 | 236.04 |
| 55 | PO | 3 | 145.05 |
| 51 | PO | 3 | 165.83 |
| 49 | PO | 3 | 340.00 |
| methyl (2R,3S)-3-((methylsulfonyl)amino)-2-(((cis-4-phenylcyclohexyl)oxy)methyl)-piperidine-1-carboxylate | SC | 3 | 118.75 |

PO (oral); SC (subcutaneous); mpk (milligram per kilogram);

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound of Formula I-A or a pharmaceutically acceptable salt thereof:

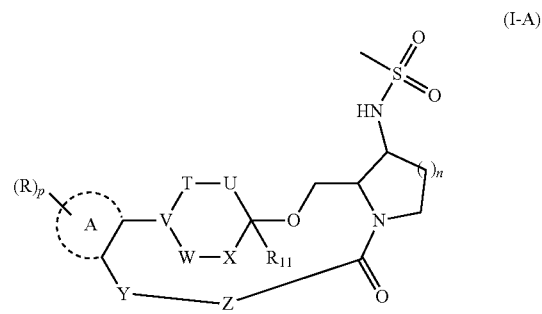

(I-A)

wherein:
  ring A is selected from the group consisting of phenyl, pyridinyl, pyridazinyl, pyrimidinyl, pyrazinyl, and triazinyl;
  n is 1, 2, or 3;
  T is $CR_1R_2$ or O;
  W is $CR_4R_5$ or O;
  U is $CR_6R_7$;
  X is $CR_8R_9$;
  V is $CR_3$ or N;
  Y is $NR_{10}$, O or absent;
  Z is $(CR_{12}R_{13})_m$;
  R is halogen or deuterium; and
  p is 0, 1, 2, 3, or 4;
and further wherein:
  m is 1, 2, 3, or 4;
  $R_1$, $R_2$, $R_4$, and $R_5$ are each, independently, selected from the group consisting of H, halogen, and deuterium;
  or, alternatively, $R_2$ and $R_5$ together with the carbon atoms to which they are attached, form a single bond;
  $R_3$ is selected from the group consisting of H, deuterium, halogen, hydroxyl, and cyano;
  or, alternatively, $R_3$ and $R_1$, together with the carbon atoms to which they are attached, form a $C_3$-$C_5$ cycloalkyl;
  or, alternatively, $R_3$ and $R_4$, together with the carbon atoms to which they are attached, form a $C_3$-$C_5$ cycloalkyl;
  $R_6$, $R_7$, $R_8$, $R_9$, and $R_{11}$ are each, independently, selected from the group consisting of H, halogen, and deuterium;
  $R_{10}$ is selected from the group consisting of H, unsubstituted $C_1$-$C_3$alkyl, and $C_1$-$C_3$alkyl substituted with one or more halogen atoms; and
  each $R_{12}$ and $R_{13}$ is, independently, selected from the group consisting of H, halogen, deuterium, unsubstituted $C_1$-$C_3$alkyl, and $C_1$-$C_3$alkyl substituted with one or more halogen atoms.

2. The compound of claim 1, wherein n is 1 or 2.
3. The compound of claim 1, wherein ring A is phenyl.
4. The compound of claim 1, wherein ring A is pyridinyl.
5. The compound of claim 1, wherein Y is O.
6. The compound of claim 1, wherein Y is absent.
7. The compound of claim 1, wherein T is $CR_1R_2$.
8. The compound of claim 1, wherein T is O.
9. The compound of claim 1, wherein W is $CR_4R_5$.
10. The compound of claim 1, wherein W is O.
11. The compound of claim 1, wherein V is $CR_3$.
12. The compound of claim 1, wherein m is 1 or 2.
13. A pharmaceutical composition comprising a compound of claim 1 or a pharmaceutically acceptable salt thereof, and a pharmaceutically acceptable carrier.
14. A method of treating narcolepsy in a subject in need thereof comprising administering to the subject a compound of claim 1 or a pharmaceutically acceptable salt thereof.
15. A method of treating cataplexy in a subject in need thereof comprising administering to the subject a compound of claim 1 or a pharmaceutically acceptable salt thereof.

16. The compound of claim 1, wherein the compound is:

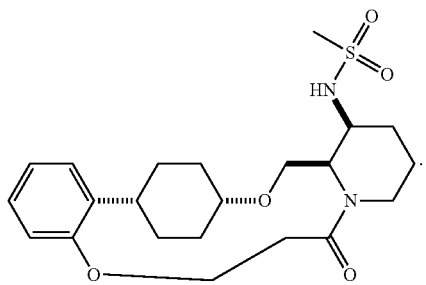

17. The compound of claim 1, wherein the compound is:

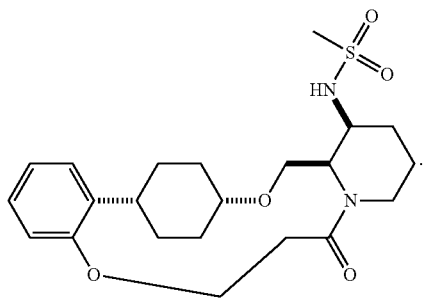

18. The compound of claim 1, wherein the compound is:

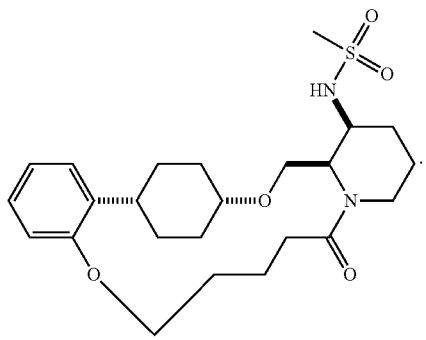

19. The compound of claim 1, wherein the compound is:

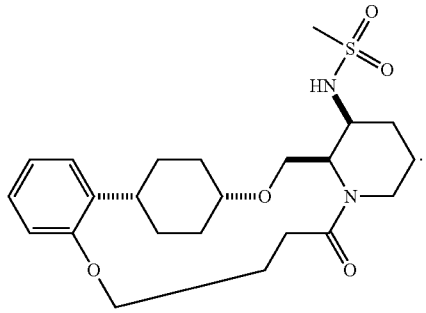

20. The compound of claim 1, wherein the compound is:

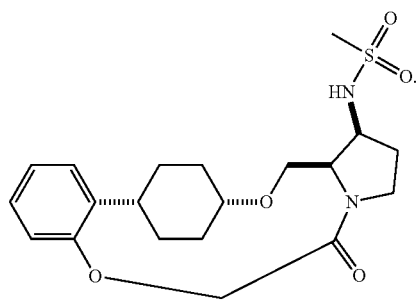

21. The compound of claim 1, wherein the compound is:

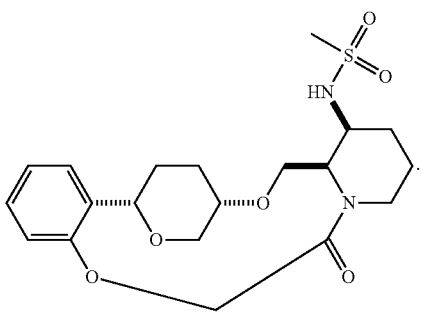

22. The compound of claim 1, wherein the compound is:

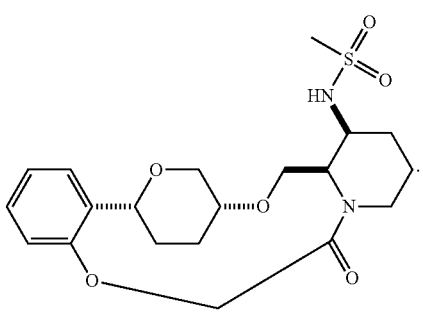

23. The compound of claim 1, wherein the compound is:

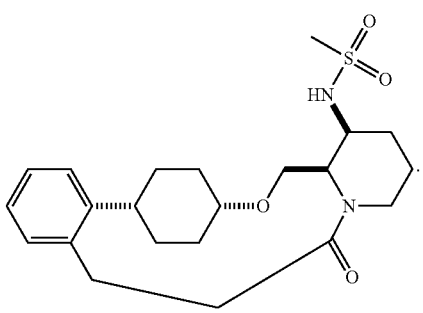

24. The compound of claim 1, wherein the compound is:

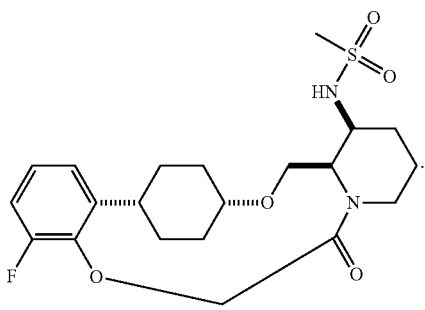

25. The compound of claim 1, wherein the compound is:

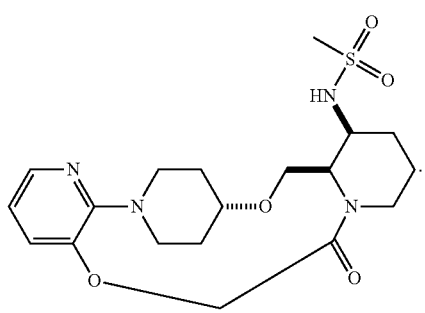

26. The compound of claim 1, wherein the compound is:

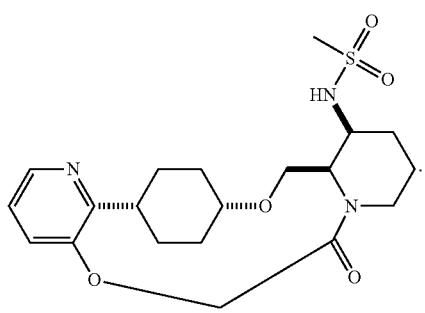

27. The compound of claim 1, wherein the compound is:

28. The compound of claim 1, wherein the compound is:

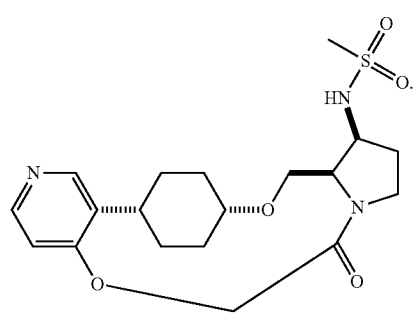

29. The compound of claim 1, wherein the compound is:

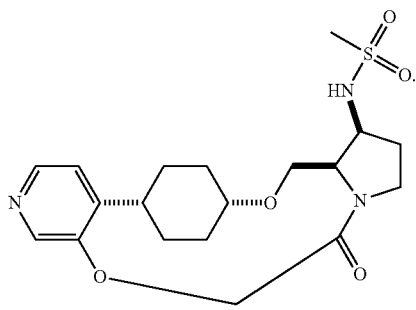

30. The compound of claim 1, wherein the compound is:

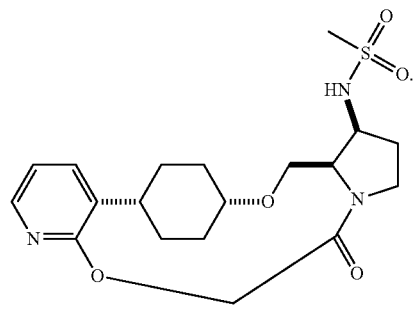

31. The compound of claim 1, wherein the compound is:

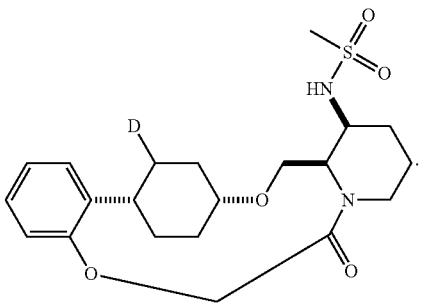

32. The compound of claim 1, wherein the compound is:

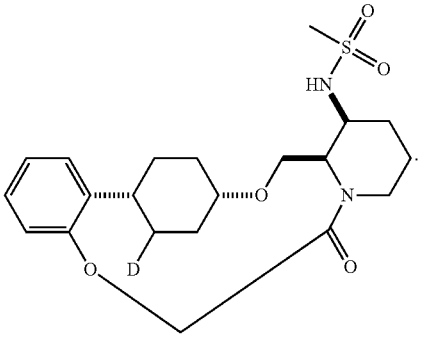

33. The compound of claim 1, wherein the compound is:

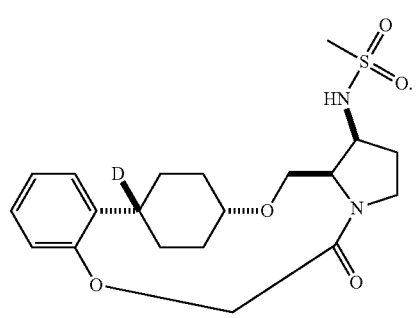

34. The compound of claim 1, wherein the compound is:

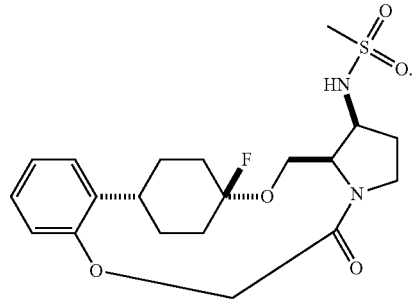

35. The compound of claim 1, wherein the compound is:

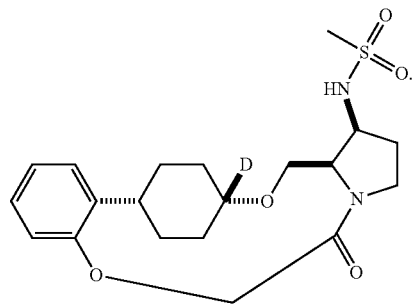

36. The compound of claim 1, wherein the compound is:

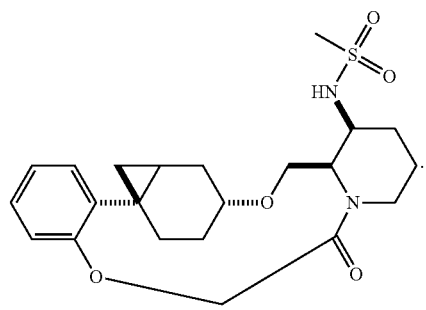

37. The compound of claim 1, wherein the compound is:

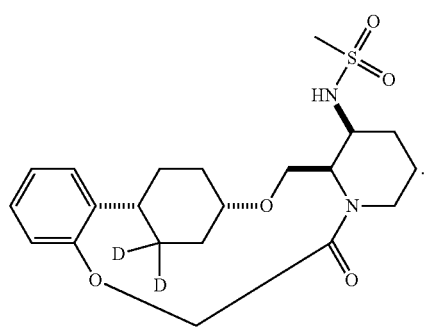

38. The compound of claim 1, wherein the compound is:

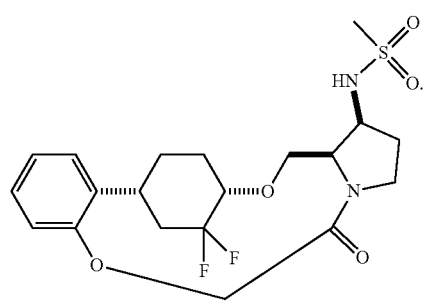

39. The compound of claim 1, wherein the compound is:

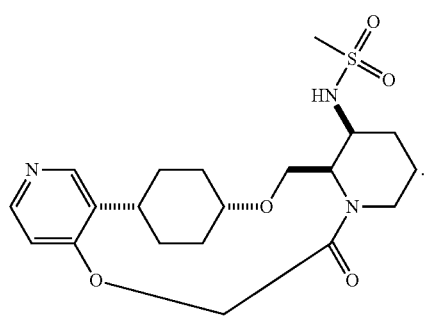

40. The compound of claim 1, wherein the compound is:

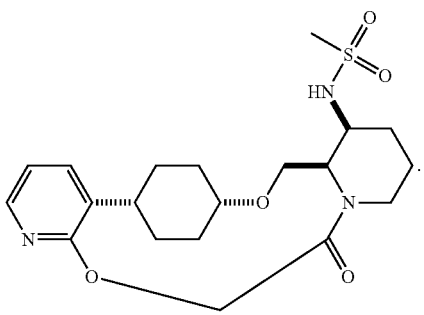

41. The compound of claim 1, wherein the compound is:

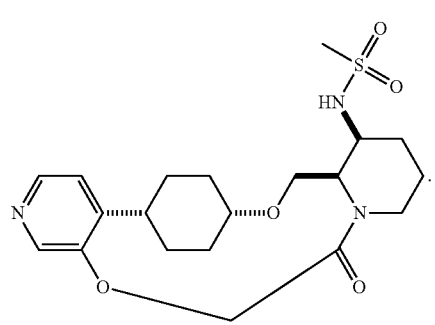

42. The compound of claim 1, wherein the compound is:

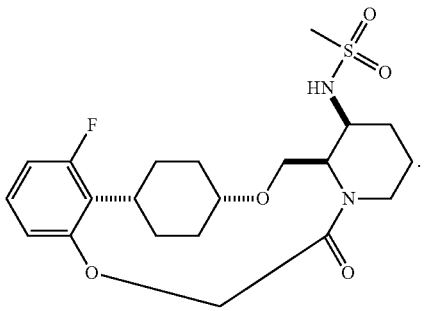

43. The compound of claim 1, wherein the compound is:

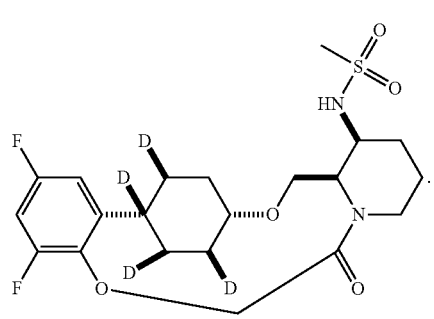

44. The compound of claim 1, wherein the compound is:

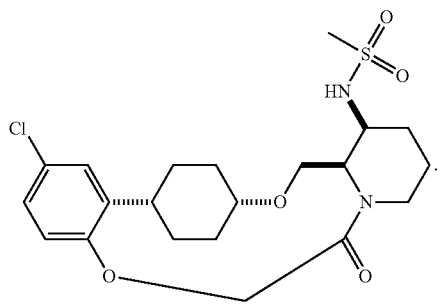

45. The compound of claim 1, wherein the compound is:

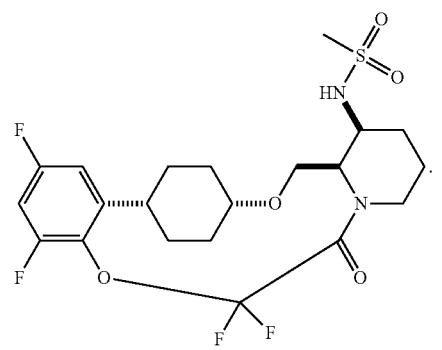

46. The compound of claim 1, wherein the compound is:

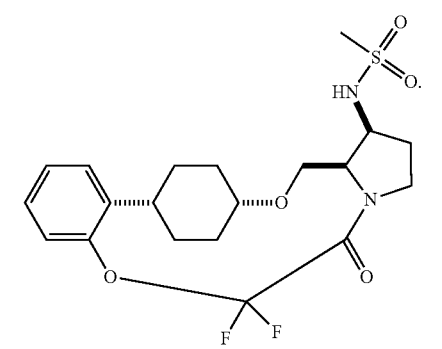

47. The compound of claim 1, wherein the compound is:

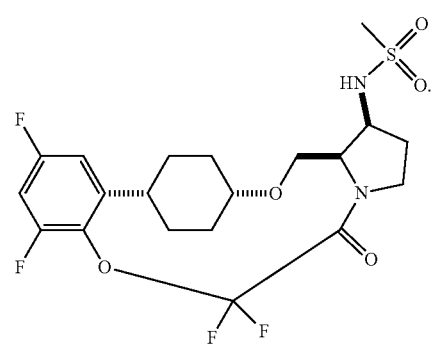

48. The compound of claim 1, wherein the compound is:

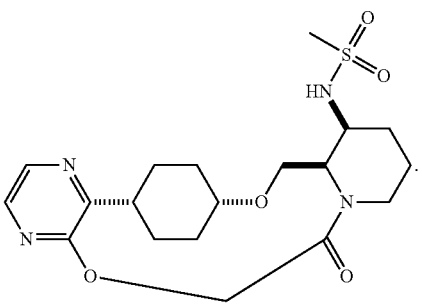

49. The compound of claim 1, wherein the compound is:

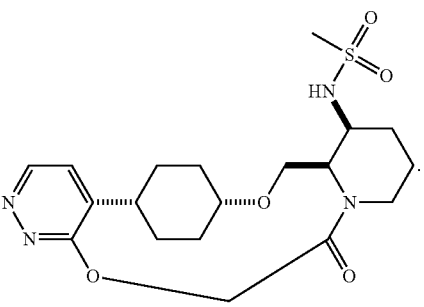

50. The compound of claim 1, wherein the compound is:

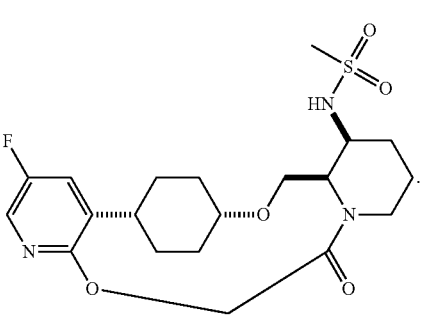

51. The compound of claim 1, wherein the compound is:

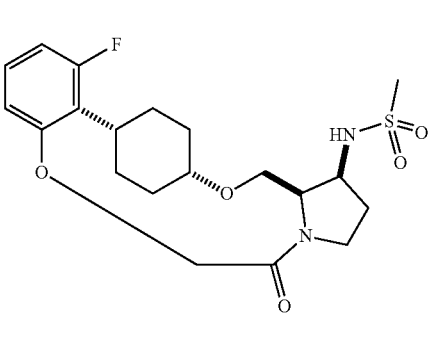

* * * * *